(12) United States Patent
Matozaki et al.

(10) Patent No.: US 12,024,566 B2
(45) Date of Patent: Jul. 2, 2024

(54) ANTI-SIRPALPHA ANTIBODY

(71) Applicants: NATIONAL UNIVERSITY CORPORATION KOBE UNIVERSITY, Kobe (JP); DAIICHI SANKYO COMPANY, LIMITED, Tokyo (JP)

(72) Inventors: Takashi Matozaki, Kobe (JP); Mayumi Sue, Tokyo (JP); Kensuke Nakamura, Tokyo (JP); Chigusa Yoshimura, Tokyo (JP)

(73) Assignees: NATIONAL UNIVERSITY CORPORATION KOBE UNIVERSITY, Kobe (JP); DAIICHI SANKYO COMPANY, LIMITED, Tokyo (JP)

( * ) Notice: Subject to any disclaimer, the term of this patent is extended or adjusted under 35 U.S.C. 154(b) by 783 days.

(21) Appl. No.: 17/258,115

(22) PCT Filed: Jul. 9, 2019

(86) PCT No.: PCT/JP2019/027114
§ 371 (c)(1),
(2) Date: Jan. 5, 2021

(87) PCT Pub. No.: WO2020/013170
PCT Pub. Date: Jan. 16, 2020

(65) Prior Publication Data
US 2021/0155707 A1 May 27, 2021

(30) Foreign Application Priority Data
Jul. 10, 2018 (JP) ................................. 2018-131116

(51) Int. Cl.
*A61K 39/395* (2006.01)
*A61P 35/00* (2006.01)
(Continued)

(52) U.S. Cl.
CPC .... *C07K 16/2896* (2013.01); *A61K 2039/505* (2013.01); *A61P 35/00* (2018.01);
(Continued)

(58) Field of Classification Search
None
See application file for complete search history.

(56) References Cited

U.S. PATENT DOCUMENTS 8,722,587 B2 * 5/2014 Mason ..................... A61P 29/00
506/26
9,518,277 B2 * 12/2016 Franklin ............... C12P 7/6463
(Continued)

FOREIGN PATENT DOCUMENTS

| CO | NC20180010855 | 10/2018 |
|---|---|---|
| CO | NC2019/0005033 | 5/2019 |

(Continued)

OTHER PUBLICATIONS

Holodov, L.E., et al., "Clinical Pharmacokinetics Handbook", Medicine, pp. 83-98, 134-138, 160, 378-380, 1985.
(Continued)

*Primary Examiner* — Daniel E Kolker
*Assistant Examiner* — Brianna K Swartwout
(74) *Attorney, Agent, or Firm* — Foley & Lardner LLP

(57) ABSTRACT

An anti-SIRPα antibody that can be used as a tumor agent and an anti-tumor agent comprising the antibody as an active ingredient. An antibody that binds specifically to human SIRPα to inhibit binding of human SIRPα to CD47.

29 Claims, 41 Drawing Sheets
Specification includes a Sequence Listing.

(51) Int. Cl.
  *C07K 16/28* (2006.01)
  *C07K 16/32* (2006.01)
  *A61K 39/00* (2006.01)
(52) U.S. Cl.
  CPC ...... *C07K 16/2863* (2013.01); *C07K 16/2887* (2013.01); *C07K 16/32* (2013.01); *C07K 2317/21* (2013.01); *C07K 2317/565* (2013.01); *C07K 2317/72* (2013.01); *C07K 2317/732* (2013.01); *C07K 2317/76* (2013.01)

(56) References Cited

U.S. PATENT DOCUMENTS

| | | | |
|---|---|---|---|
| 2004/0010124 A1* | 1/2004 | Johnson | A61P 37/02 530/388.22 |
| 2013/0078234 A1* | 3/2013 | Takahashi | C07K 16/42 435/327 |
| 2014/0141002 A1 | 5/2014 | Clemmons et al. | |
| 2014/0242095 A1* | 8/2014 | Wang | A61P 35/02 530/389.7 |
| 2015/0017130 A1* | 1/2015 | Yang | A61K 35/12 435/325 |
| 2015/0152429 A1* | 6/2015 | Albertsen | C12N 15/8231 536/23.6 |
| 2015/0337053 A1* | 11/2015 | McCarthy | C07K 16/00 435/254.2 |
| 2017/0073414 A1* | 3/2017 | Weiskopf | A61P 19/02 |
| 2017/0342154 A1 | 11/2017 | Igawa et al. | |
| 2019/0153095 A1 | 5/2019 | Matozaki et al. | |
| 2019/0359707 A1 | 11/2019 | Pincetic et al. | |
| 2020/0140565 A1 | 5/2020 | Wang et al. | |

FOREIGN PATENT DOCUMENTS

| | | |
|---|---|---|
| CO | NC2020/0013871 | 11/2020 |
| JP | 2014-525940 A | 10/2014 |
| JP | 2016-169220 A | 9/2016 |
| JP | 2017-510251 A | 4/2017 |
| WO | WO-2010/130053 A1 | 11/2010 |
| WO | WO-2011/076781 A1 | 6/2011 |
| WO | WO-2013/056352 A1 | 4/2013 |
| WO | WO-2013/109752 A1 | 7/2013 |
| WO | WO-2015/042557 A1 | 3/2015 |
| WO | WO-2017/068164 A1 | 4/2017 |
| WO | WO-2017/178653 A2 | 10/2017 |
| WO | WO-2018/008470 A1 | 1/2018 |
| WO | WO-2018/026600 A1 | 2/2018 |
| WO | WO-2018/057669 A1 | 3/2018 |
| WO | WO-2018/107058 A1 | 6/2018 |
| WO | WO-2018/190719 A2 | 10/2018 |

OTHER PUBLICATIONS

Office Action issued in corresponding Russian Patent Application No. 2021102983, dated Jul. 28, 2022.
Sergeev, P.V., "A Short Course in Molecular Pharmacology", Ministry of Health of the Russian Soviet Federative Socialist Republic, p. 10, 1975.
Anonymous, "Engineered Fc Regions," Review InvivoGen, Retrieved from the Internet: URL: https://www.invivogen.com/sites/default/files/invivogen/resources/documents/reviews/review-Engineered-Fc-Regions-invivogen.pdf (2001) (Retrieved Mar. 3, 2020) (2 pages).
Crommelin, D.J.A., et al., Pharmaceutical Biotechnology Fundamentals and Applications, 4th ed., p. 153 (2013).
Ladner, R. C., "Mapping the Epitopes of Antibodies," Biotechnology and Genetic Engineering Reviews, 24:1-30 (2007).
Office Action issued in corresponding Russian Patent Application No. 2021102983 dated Mar. 23, 2022.
Severin, E. S., et al., "Biological Chemistry," Medical Information Agency, Moscow, p. 86 (2008), https://www.iephb.ru/wp-content/uploads/Severin.-Biohimiya.pdf (English translation included).
Supplementary European Search Report issued in corresponding European Patent Application No. 19833586.1 dated Mar. 11, 2022.
Zhao, X. W., et al., "CD47-signal regulatory protein-alpha (SIRPalpha) interactions form a barrier for antibody-mediated tumor cell destruction," PNAS, 108(45):18342-18347 (2011).
Office Action issued in corresponding Colombian Patent Application No. NC2020/0014727, dated Apr. 18, 2023.
Saito, et al. "Regulation by SIRPα of dendritic cell homeostasis in lymphoid tissues," BLOOD vol. 116, No. 18, Nov. 4, 2010, pp. 3517-3525.
International Searching Authority, "International Search Report," issued in connection with International Patent Application No. PCT/JP2019/027114, dated Oct. 8, 2019.
International Searching Authority, "Written Opinion," issued in connection with International Patent Application No. PCT/JP2019/027114, dated Oct. 8, 2019.
Saito et al., "Action mechanism of cancer immunotherapy targeting CD47/SIRPα signal", Journal of Molecular Targeted Therapy for Cancer, (2017), vol. 15, No. 4, 2017, pp. 414-419.
Matozak et al., "Functions and molecular mechanisms of the CD47-SIRPα signalling pathway," Trends in Cell Biology, vol. 19, No. 2, Jan. 12, 2009, pp. 72-80.
Takenaka et al., "Polymorphism in *Sirpa* modulates engraftment of human hematopoietic stem cells," Nature Immunology, vol. 8, No. 12, Dec. 2007, pp. 1313-1323.
Liu et al., "Pre-Clinical Development of a Humanized Anti-CD47 Antibody with Anti-Cancer Therapeutic Potential," PLOS One, vol. 10, No. 9, Sep. 21, 2015, pp. 1-23.
Yanagita et al., "Anti-SIRPα antibodies as a potential new tool for cancer immunotherapy," JCI Insight, vol. 2, No. 1, 2017, pp. 1-15.
Ring et al., "Anti-SIRPα antibody immunotherapy enhances neutrophil and macrophage antitumor activity," PNAS, Nov. 20, 2017, pp. e10578-e10585.
Liu et al. "CD47 blockade triggers T cell-mediated destruction of immunogenic tumors," Nature Medicine, vol. 21, No. 10, Oct. 2015, pp. 1209-1215.
Pai-Scherf et al., "FDA Approval Summary: Pembrolizumab for Treatment of Metastatic Non-Small Cell Lung Cancer: First-Line Therapy and Beyond," The Oncologist, vol. 22, 2017, pp. 1392-1399.
Weinstock et al., "U.S. Food and Drug Administration Approval Summary: Atezolizumab for Metastatic Non-Small Cell Lung Cancer," Clinical Cancer Research, vol. 23, No. 16, Aug. 15, 2017, pp. 4534-4539.
Diamond, et al., "Somatic mutation of the T15 heavy chain gives rise to an antibody with autoantibody specificity", Proc. Natl. Acad. Sci. USA, vol. 81, pp. 5841-5844, (1984).
Lamminmaki, et al., "Crystal Structure of a Recombinant Anti-estradiol Fab Fragment in Complex with 17β-Estradiol", The Journal of Biological Chemistry, vol. 276, No. 39, p. 36687-36694, (2001).
Office Action dated Nov. 23, 2021 issued in a corresponding Russian Patent Application No. 2021102983, (18 pages).
Ohno, et al., "Antigen-binding specificities of antibodies are primarily determined by seven residues of VH", Proc. Natl. Acad. Sci. USA, vol. 82, pp. 2945-2949, (1985).
Ratnikova, Development and testing of miniature single-domain antibodies against the CD47 tumor marker based on the alpaca immunoglobulin heavy chain and their application to the treatment of tumors: Dissertation, Candidate of biology: Ratnikova, Natalia Mikhailovna; [Venue of defense: Engelhardt Institute of Molecular Biology, Russian Academy of Sciences], Moscow 2017, chapter 1, 1.2, with English-language machine translation, (25 pages).
Rudikoff, et al., "Single amino acid substitution of altering antigen-binding specificity", Proc. Natl. Acad. Sci. USA. Immunology, p. 1979-1983, (1982).
Yarilin, "Basics of Immunology: Textbook", Moscow: Medicine, pp. 172-174, (1999), with English-language translation, (10 pages).
Office Action issued in corresponding Columbian Patent Application No. NC2020/0014727, dated Apr. 18, 2023.

(56) References Cited

OTHER PUBLICATIONS

Saito, et al. "Regulation by SIRPα of dendritic cell homeostasis in lymphoid tissues," BLOOD vol. 116, No. 18, Nov. 4, 2010, pp. 3517-3523.

* cited by examiner

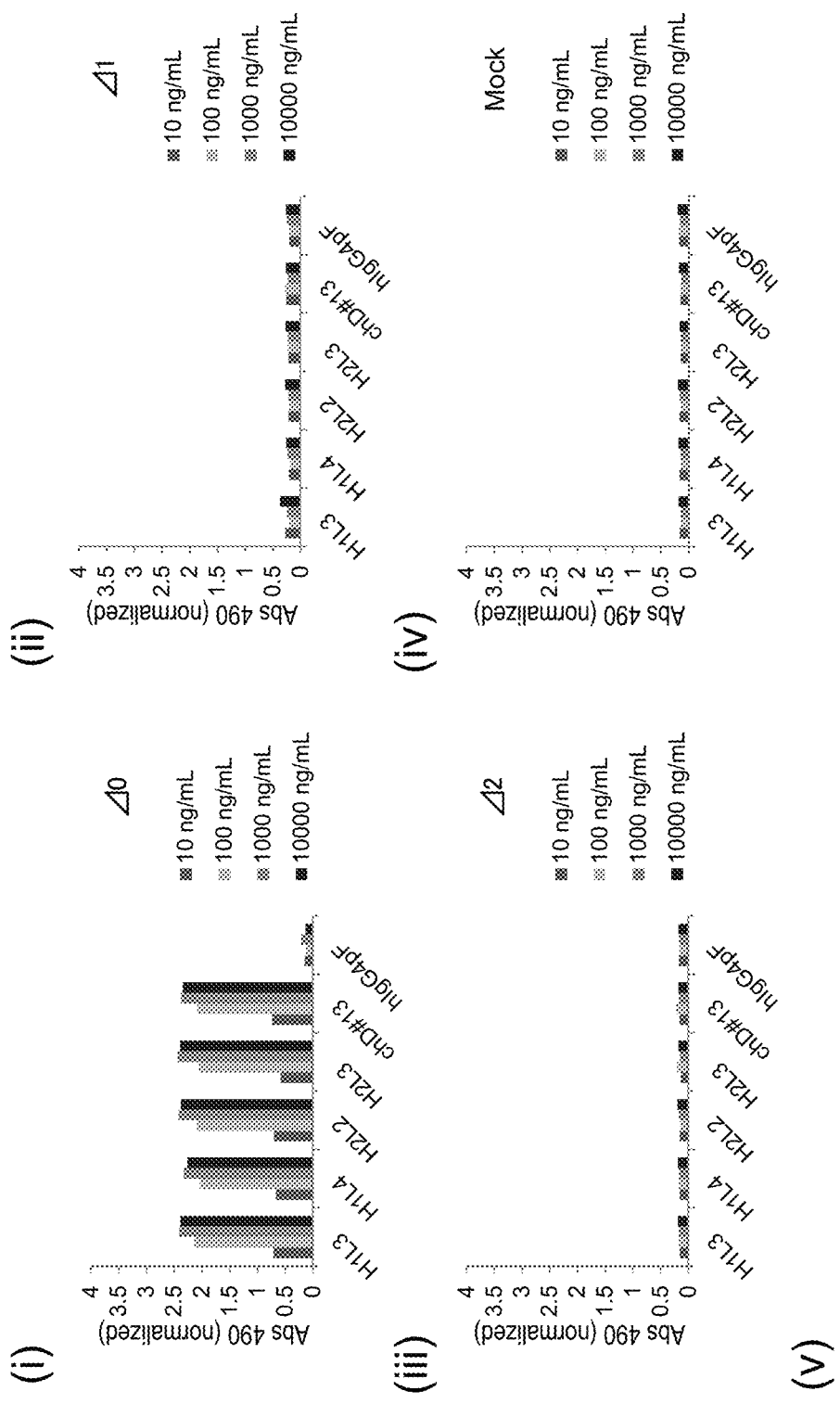

Fig. 4

```
V1   1 MEPAGPAPGRLGPLLCLLLAASCAWSGVAGEEELQVIQPDKSVLVAAGETATLRCTATSL 60
V2   1 ............................................S....S.I.H.V.. 60
V3   1 ............................................S....S.I.L.V.. 60
V4   1 .................................................S.I.L... 60
V5   1 ..........................G.................S....S.I.H... 60
V6   1 ..................F.......................................  60
V7   1 ............................................S....S.I.H.V.. 60
V8   1 ........................................................... 60
V9   1 ........................................................... 60
V10  1 ..................R.........................S....S.I.H.V.. 60

V1   61 IPVGPIQWFRGAGPGRELIYNQKEGHFPRVTTVSDLTKRNNMDFSIRIGNITPADAGTYY 120
V2   61 .........................ES....E......S.S................. 120
V3   61 ..A......................ES....E......S.S................. 120
V4   61 ..A........................................................ 120
V5   61 ........................................................... 120
V6   61 ........................................................... 120
V7   61 .........................ES....E......S.S................. 120
V8   61 ..A......................ES....E......S.S................. 120
V9   61 ..A............................P......S................... 120
V10  61 ..A............................ ......S.S................. 120

V1  121 CVKFRKGSPDDVEFKSGAGTELSVRA 146
V2  121 ...........T-............. 145
V3  121 ...........T-............. 145
V4  121 .......................... 146
V5  121 .......................... 146
V6  121 .......................... 146
V7  121 .....................G.... 146
V8  121 ...........T-............. 145
V9  121 ...........T-............. 145
V10 121 ...........T-............. 145
```

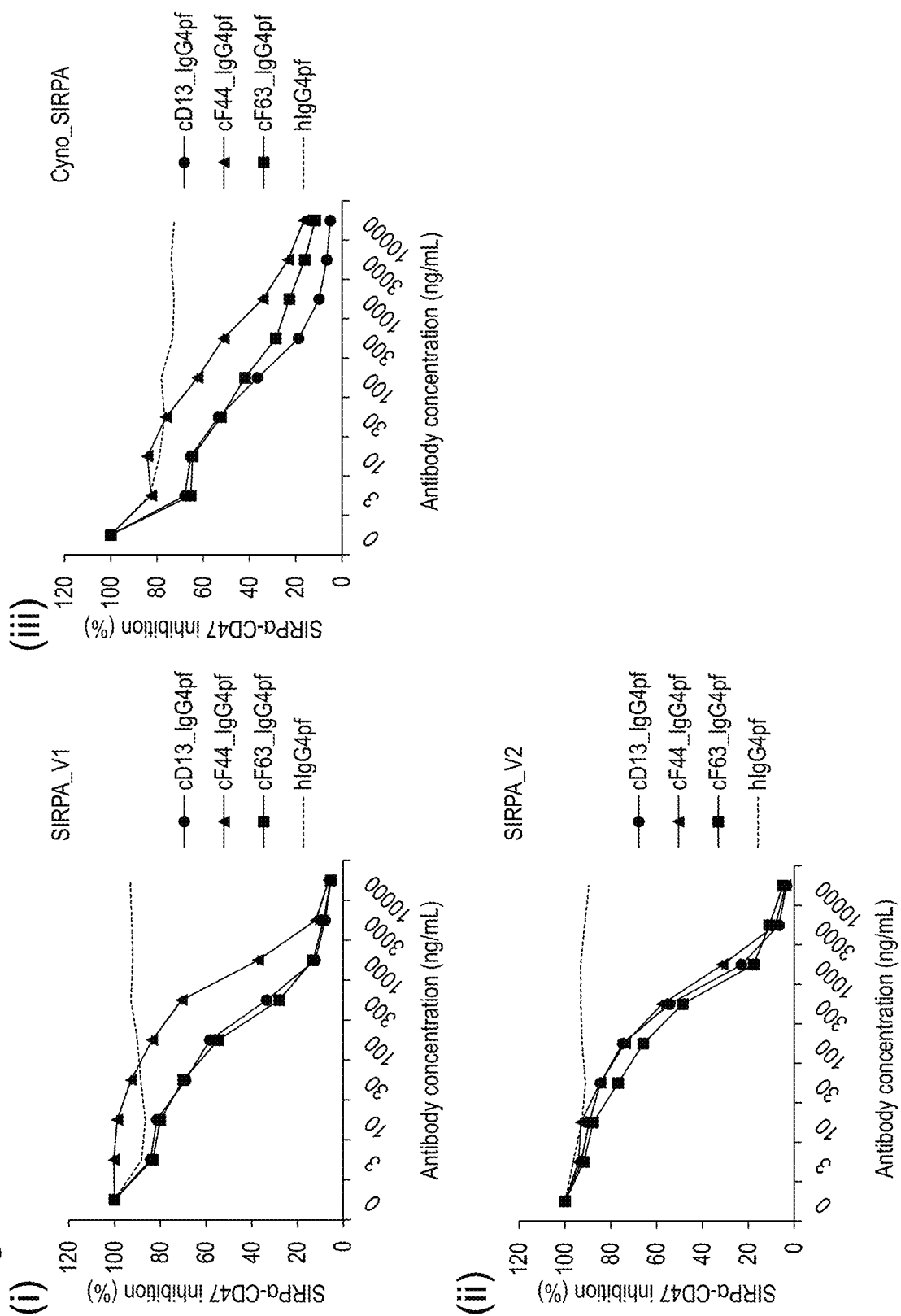

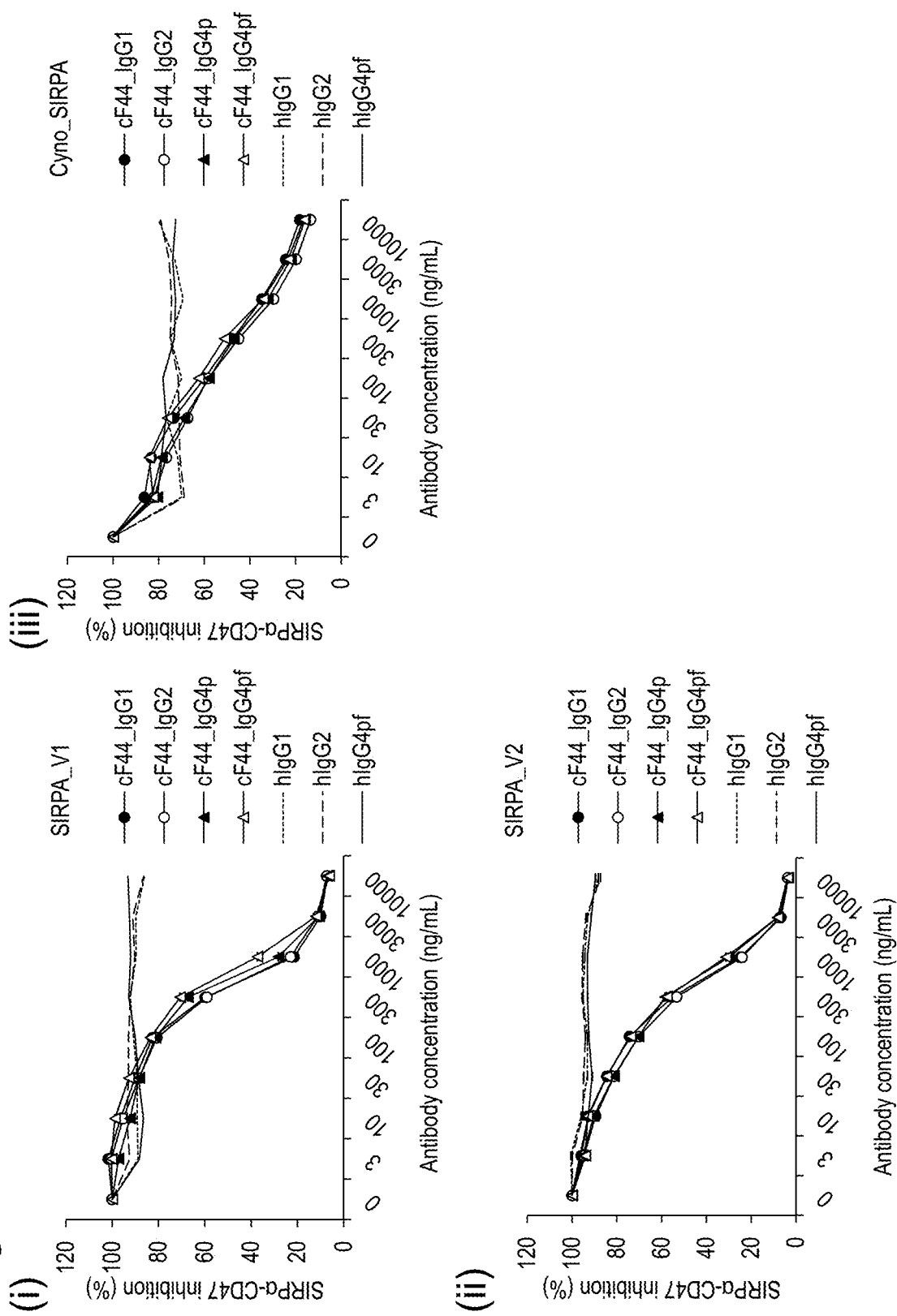

Fig. 9
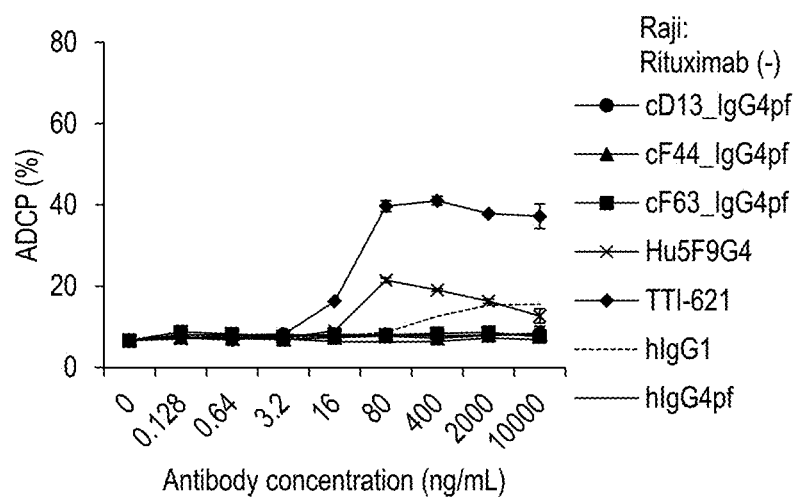
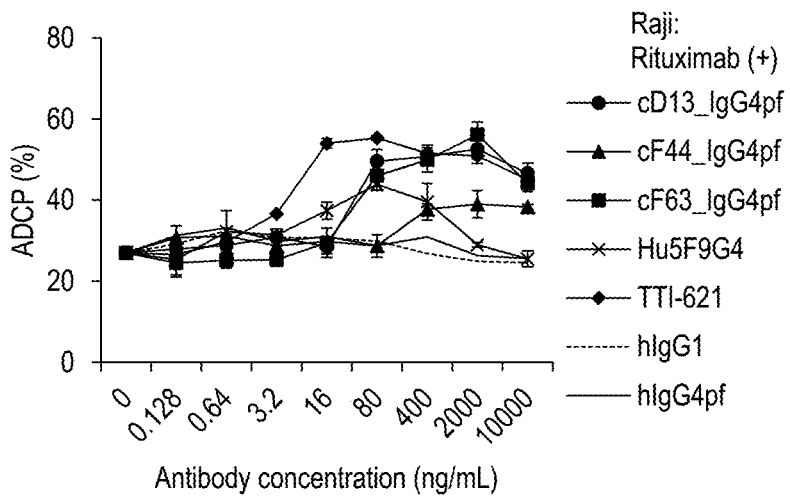

```
cD13_H    1  MKHLWFFLLLVAAPRWVLSEVQLVESGGGLVQPGRSLKLSCLASGFTFSDYGMIWVRQAP   60
hH1       1  ................Q.........V......R...A....................   60
hH2       1  ..........................V......R...A....................   60 cD13_H   61  GKGLEWVASISSSSSYIYYADTVKGRFTISRENAKNTLFLHMTSLRSEDTALYYCARRYY  120
hH1      61  ....................S.......D.S..R.Y.Q.N...A.....V.........  120
hH2      61  ....................S.......D.S....Y.Q.N...A.....V.........  120 cD13_H  121  GFNYPFFDYWGQGVMVTVSS  139
hH1     121  ...........T........  139
hH2     121  ...........T........  139
```

```
cD13_L    1 MVLQTQVFISLLLWISGAYGDTVLTQSP-ALAVSLGQRVTISCGASKSVRTYMHWYQQKS  59
hL2       1 .................AIQ.....SS.SA.V......T.............P      60
hL3       1 ....................Q...SS.SA.V......T.............P      60
hL4       1 .........................DS........A..N............P      60 cD13_L   60 GQQPKLLIYSASNLEAGVPSRFSGSGSGTDFTLTIDPVEADDIANYYCQQSNEPPYTFGA 119
hL2      61 .KA.............................SSLQPE.F.T.............Q   120
hL3      61 .K..............................SSLQPE.F.T.............Q   120
hL4      61 ................................SSLQ.E.V.V.............Q   120 cD13_L  120 GTKLELK 126
hL2     121 .I..... 127
hL3     121 .I..... 127
hL4     121 ...V.I. 127
```

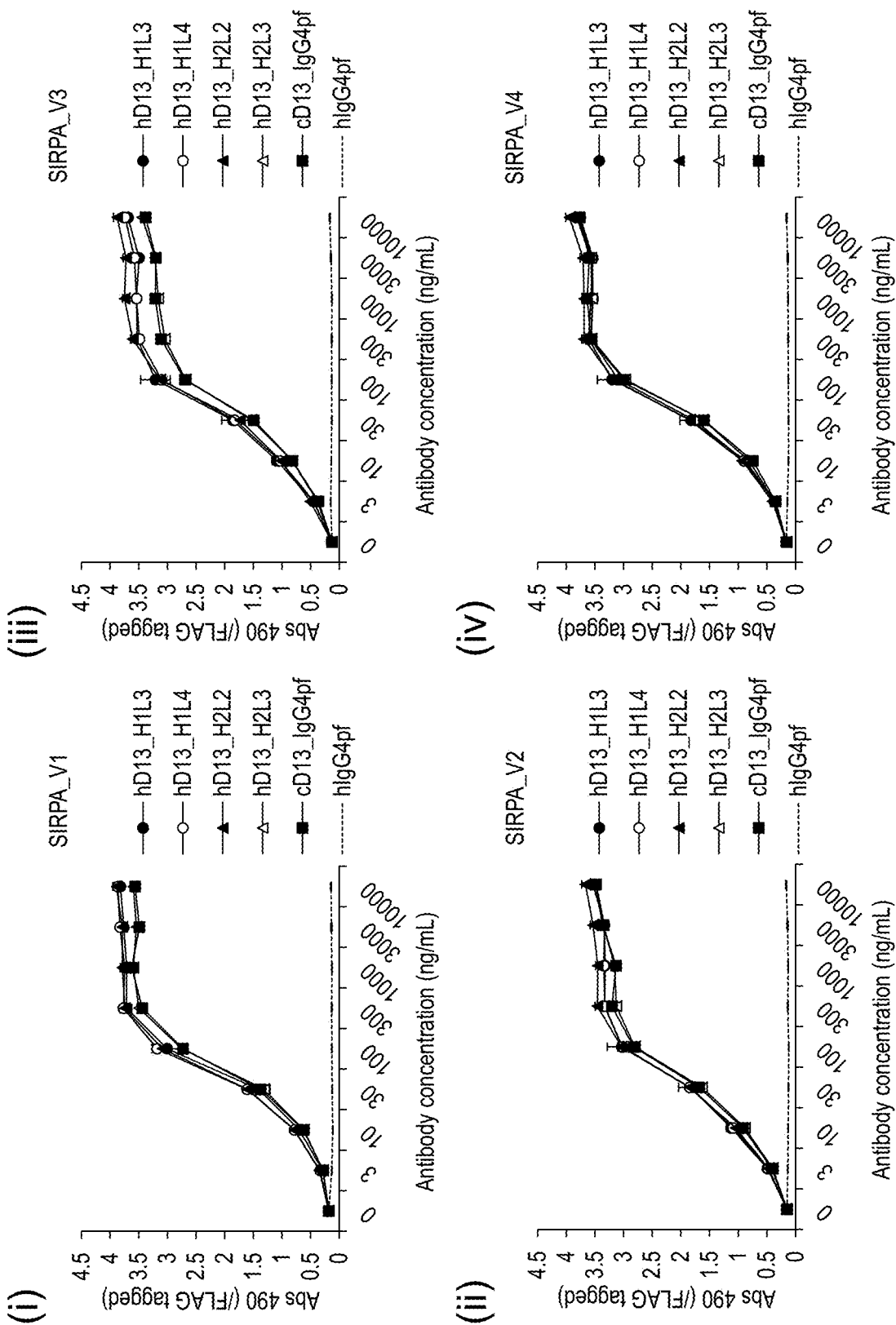

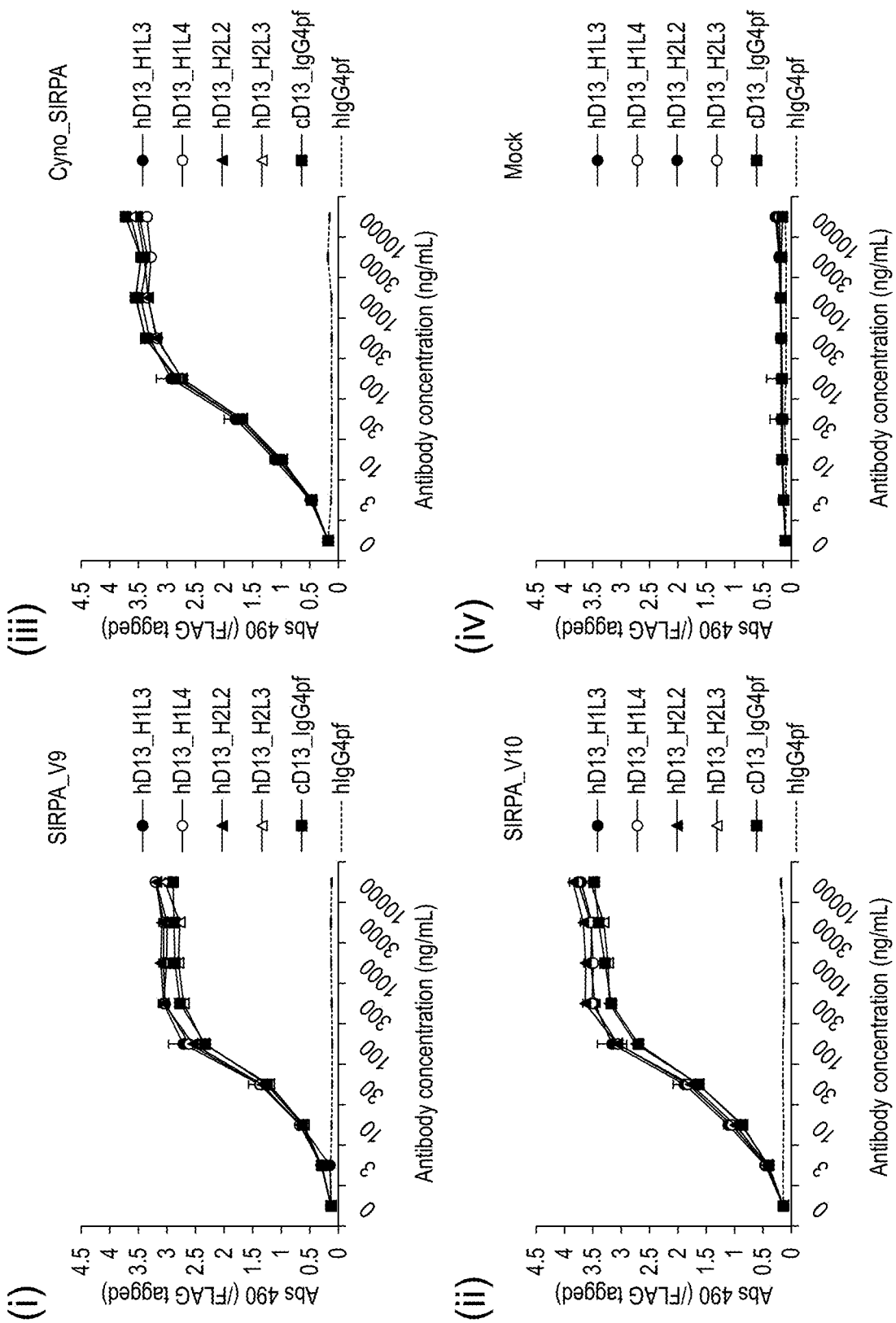

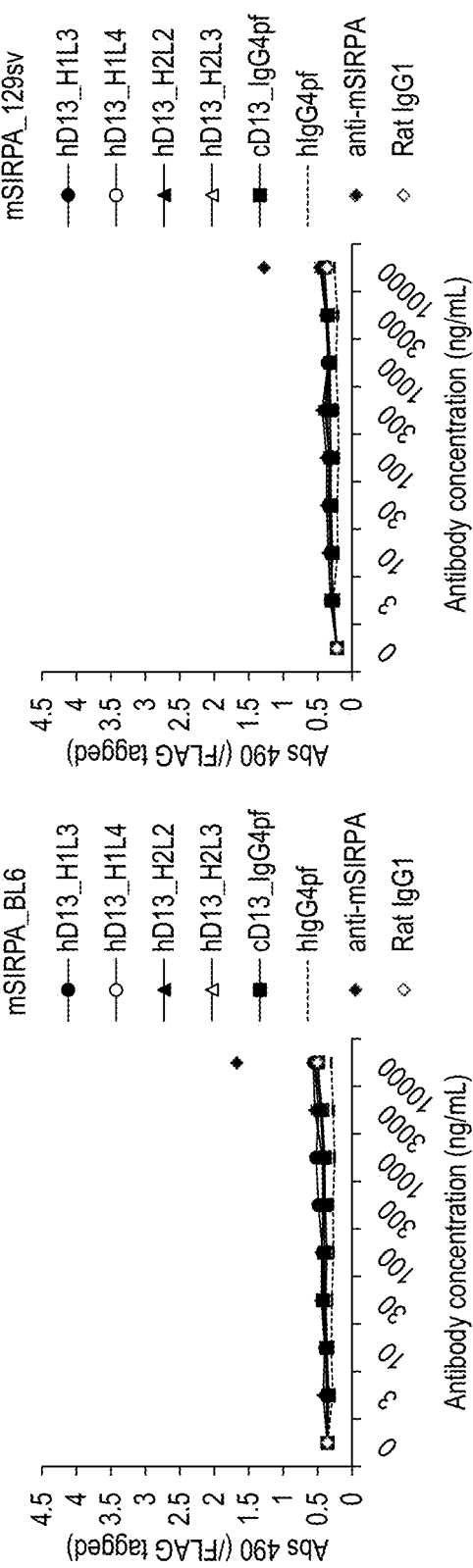
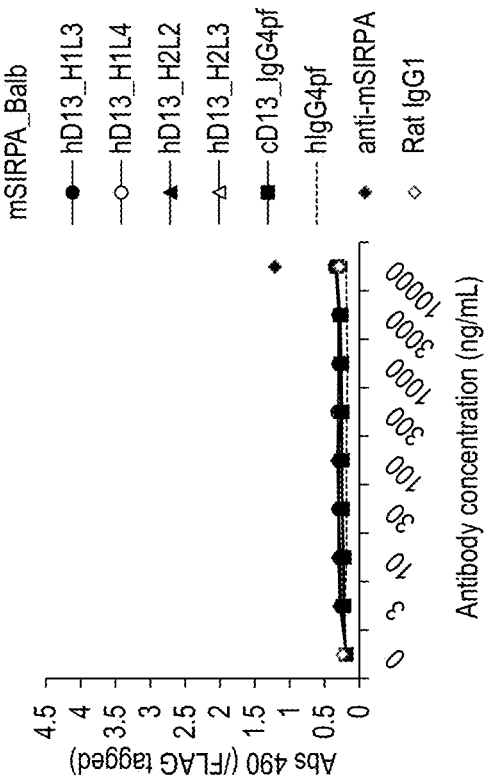
Fig. 14A

Fig. 17

SEQ ID NO: 22: Nucleotide sequence encoding cD13 light
chain
ATGGTGCTGCAGACCCAGGTGTTCATCTCCCTGCTGCTGTGGATCTCCGGCGCGTA
CGGCGACACTGTGCTGACCCAGTCTCCTGCTTTGGCTGTGTCTCTAGGGCAGAGGG
TCACCATCTCTTGTGGGGCCAGCAAAAGTGTCCGTACATATATGCACTGGTACCAA
CAAAAATCGGGACAGCAACCCAAACTCCTGATCTATAGTGCATCCAACCTAGAGGC
TGGAGTCCCTTCCAGGTTCAGTGGGAGTGGGTCTGGGACAGACTTTACCCTCACCA
TAGATCCTGTGGAGGCTGATGACATTGCAAACTATTACTGTCAGCAGAGTAATGAA
CCTCCGTACACGTTTGGAGCTGGGACCAAGCTGGAACTGAAACGGACGGTGGCCGC
CCCCTCCGTGTTCATCTTCCCCCCTCCGACGAGCAGCTGAAGTCCGGCACCGCCT
CCGTGGTGTGCCTGCTGAATAACTTCTACCCCAGAGAGGCCAAGGTGCAGTGGAAG
GTGGACAACGCCCTGCAGTCCGGGAACTCCCAGGAGAGCGTGACCGAGCAGGACAG
CAAGGACAGCACCTACAGCCTGAGCAGCACCCTGACCCTGAGCAAAGCCGACTACG
AGAAGCACAAGGTGTACGCCTGCGAGGTGACCCACCAGGGCCTGAGCTCCCCCGTC
ACCAAGAGCTTCAACAGGGGGGAGTGT Signal sequence (1-60), variable region (61-378),
constant region (379-699)

SEQ ID NO: 23: Amino acid sequence of cD13 light chain
MVLQTQVFISLLLWISGAYGDTVLTQSPALAVSLGQRVTISCGASKSVRTYMHWYQ
QKSGQQPKLLIYSASNLEAGVPSRFSGSGSGTDFTLTIDPVEADDIANYYCQQSNE
PPYTFGAGTKLELKRTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPV
TKSFNRGEC Signal sequence (1-20), variable region (21-126),
constant region (127-233)

Fig. 18

SEQ ID NO: 24: Nucleotide sequence encoding cD13 heavy chain
ATGAAACACCTGTGGTTCTTCCTCCTGCTGGTGGCAGCTCCCAGATGGGTGCTGAG
CGAGGTACAGCTGGTGGAGTCTGGAGGAGGCTTAGTGCAGCCTGGAAGGTCCCTGA
AACTCTCCTGTTTAGCCTCTGGATTCACTTTCAGTGACTATGGAATGATCTGGGTT
CGCCAGGCTCCAGGGAAGGGGCTGGAGTGGGTTGCATCTATTAGTAGTAGTAGCAG
TTACATCTACTATGCAGACACAGTGAAGGGCCGATTCACCATCTCCAGAGAAAATG
CCAAGAACACCCTGTTCCTGCACATGACCAGTCTGAGGTCTGAAGACACTGCCTTG
TATTACTGTGCAAGAAGATACTATGGGTTTAACTACCCTTTTGATTACTGGGGCCA
AGGAGTCATGGTCACAGTCAGCTCAGCCTCCACCAAGGGCCCTAGCGTGTTCCCTC
TGGCCCCTTGTAGCAGAAGCACCAGCGAGTCTACAGCCGCCCTGGGCTGCCTCGTG
AAGGACTACTTTCCCGAGCCCGTGACCGTGTCCTGGAACTCTGGCGCTCTGACAAG
CGGCGTGCACACCTTTCCAGCCGTGCTGCAGAGCAGCGGCCTGTACTCTCTGTCCA
GCGTCGTGACTGTGCCCAGCAGCTCTCTGGGCACCAAGACCTACACCTGTAACGTG
GACCACAAGCCCAGCAACACCAAGGTGGACAAGCGGGTGGAATCTAAGTACGGCCC
TCCCTGCCCTCCTTGCCCAGCCCCTGAAGCCGCGGGCGGACCCTCCGTGTTCCTGT
TCCCCCCAAAGCCCAAGGACACCCTGATGATCAGCCGGACCCCCGAAGTGACCTGC
GTGGTGGTGGATGTGTCCCAGGAAGATCCCGAGGTGCAGTTCAATTGGTACGTGGA
CGGCGTGGAAGTGCACAACGCCAAGACCAAGCCTAGAGAGGAACAGTTCAACAGCA
CCTACCGGGTGGTGTCCGTGCTGACAGTGCTGCACCAGGACTGGCTGAACGGCAAA
GAGTACAAGTGCAAGGTGTCCAACAAGGGCCTGCCCAGCTCCATCGAGAAAACCAT
CAGCAAGGCCAAGGGCCAGCCCCGCGAACCCCAGGTGTACACACTGCCTCCAAGCC
AGGAAGAGATGACCAAGAATCAGGTGTCCCTGACCTGTCTCGTGAAAGGCTTCTAC
CCCTCCGATATCGCCGTGGAATGGGAGAGCAACGGCCAGCCCGAGAACAACTACAA
GACCACCCCCCCTGTGCTGGACTCCGATGGCTCATTCTTCCTGTACAGCAGACTGA
CCGTGGACAAGAGCCGGTGGCAGGAAGGCAACGTGTTCAGCTGCTCCGTGATGCAC
GAGGCCCTGCACAACCACTACACCCAGAAGTCCCTGTCTCTGAGCCTGGGCAAA Signal sequence (1-57), variable region (58-417),
constant region (418-1398)

SEQ ID NO: 25: Amino acid sequence of cD13 heavy chain
MKHLWFFLLLVAAPRWVLSEVQLVESGGGLVQPGRSLKLSCLASGFTFSDYGMIWV
RQAPGKGLEWVASISSSSSYIYYADTVKGRFTISRENAKNTLFLHMTSLRSEDTAL
YYCARRYYGFNYPFDYWGQVMVTVSSASTKGPSVFPLAPCSRSTSESTAALGCLV
KDYFPEPVTVSWNSGALTSGVHTFPAVLQSSGLYSLSSVVTVPSSSLGTKTYTCNV
DHKPSNTKVDKRVESKYGPPCPPCPAPEAAGGPSVFLFPPKPKDTLMISRTPEVTC
VVVDVSQEDPEVQFNWYVDGVEVHNAKTKPREEQFNSTYRVVSVLTVLHQDWLNGK
EYKCKVSNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVFSCSVMH
EALHNHYTQKSLSLSLGK Signal sequence (1-19), variable region (20-139),
constant region (140-466)

Fig. 19

SEQ ID NO: 26: Nucleotide sequence encoding cF44 light chain
ATGGTGCTGCAGACCCAGGTGTTCATCTCCCTGCTGCTGTGGATCTCCGGCGCGTA
CGGCGATGTCCAGATGACCCAGTCTCCATCTAATCTTGCTGCCTCTCCTGGAGAAA
GTGTTTCCATCAATTGCAAGGCAAGTAAGAGCATTAGCAAGTATTTAGCCTGGTAT
CAACAGAAACCTGGGAAAGCAAATAAGCTTCTTATCTACTCTGGGTCAACTTTGCA
ATCTGGAACTCCATCGAGGTTCAGTGGCAGTGGATCTGGTACAGATTTCACTCTCA
CCATCAGAAACCTGGAGCCTGAAGATTTTGGACTCTATTACTGTCAACAGCATAAT
GAATACCCACCCACGTTTGGAGCTGGGACCAAGTTGGAACTGAAACGGACGGTGGC
CGCCCCCTCCGTGTTCATCTTCCCCCCTCCGACGAGCAGCTGAAGTCCGGCACCG
CCTCCGTGGTGTGCCTGCTGAATAACTTCTACCCCAGAGAGGCCAAGGTGCAGTGG
AAGGTGGACAACGCCCTGCAGTCCGGGAACTCCCAGGAGAGCGTGACCGAGCAGGA
CAGCAAGGACAGCACCTACAGCCTGAGCAGCACCCTGACCCTGAGCAAAGCCGACT
ACGAGAAGCACAAGGTGTACGCCTGCGAGGTGACCCACCAGGGCCTGAGCTCCCCC
GTCACCAAGAGCTTCAACAGGGGGGAGTGT Signal sequence (1-60), variable region (61-381),
constant region (382-702)

SEQ ID NO: 27: Amino acid sequence of cF44 light chain
MVLQTQVFISLLLWISGAYGDVQMTQSPSNLAASPGESVSINCKASKSISKYLAWY
QQKPGKANKLLIYSGSTLQSGTPSRFSGSGSGTDFTLTIRNLEPEDFGLYYCQQHN
EYPPTFGAGTKLELKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSP
VTKSFNRGEC Signal sequence (1-20), variable region (21-127),
constant region (128-234)

Fig. 20

SEQ ID NO: 28: Nucleotide sequence encoding cF44 heavy chain
ATGAAACACCTGTGGTTCTTCCTCCTGCTGGTGGCAGCTCCCAGATGGGTGCTGAG
CGAGGTGCAGCTGGTGGAATCTGGGGGAGGCTTAGTGCAGCCTGGAAGGTCCCTGA
AACTCTCCTGTGCAGCCTCAGGATTCACTTTCAGTAACTATTACATGGCCTGGGTC
CGCCAGGCTCCAACGAAGGGTCTGGAGTGGGTCACATACATTACTACTGGTGGTGG
TAGCACTTACTTTCGAGACTCCGTGAAGGGCCGATTCACTATCTCCAGAGATAATG
CAGAAAGCACCCTATACCTGCAAATGGACAGTCTGAGGTCTGAGGACACGGCCACT
TATTACTGTACAGCAGCTAACTACGGAGGGTCCTACTTTGATTACTGGGGCCAAGG
AGTCATGGTCACAGTCAGCTCAGCCTCCACCAAGGGCCCTAGCGTGTTCCCTCTGG
CCCCTTGTAGCAGAAGCACCAGCGAGTCTACAGCCGCCCTGGGCTGCCTCGTGAAG
GACTACTTTCCCGAGCCCGTGACCGTGTCCTGGAACTCTGGCGCTCTGACAAGCGG
CGTGCACACCTTTCCAGCCGTGCTGCAGAGCAGCGGCCTGTACTCTCTGTCCAGCG
TCGTGACTGTGCCCAGCAGCTCTCTGGGCACCAAGACCTACACCTGTAACGTGGAC
CACAAGCCCAGCAACACCAAGGTGGACAAGCGGGTGGAATCTAAGTACGGCCCTCC
CTGCCCTCCTTGCCCAGCCCCTGAAGCCGCGGGCGGACCCTCCGTGTTCCTGTTCC
CCCCAAAGCCCAAGGACACCCTGATGATCAGCCGGACCCCCGAAGTGACCTGCGTG
GTGGTGGATGTGTCCCAGGAAGATCCCGAGGTGCAGTTCAATTGGTACGTGGACGG
CGTGGAAGTGCACAACGCCAAGACCAAGCCTAGAGAGGAACAGTTCAACAGCACCT
ACCGGGTGGTGTCCGTGCTGACAGTGCTGCACCAGGACTGGCTGAACGGCAAAGAG
TACAAGTGCAAGGTGTCCAACAAGGGCCTGCCCAGCTCCATCGAGAAAACCATCAG
CAAGGCCAAGGGCCAGCCCCGCGAACCCCAGGTGTACACACTGCCTCCAAGCCAGG
AAGAGATGACCAAGAATCAGGTGTCCCTGACCTGTCTCGTGAAAGGCTTCTACCCC
TCCGATATCGCCGTGGAATGGGAGAGCAACGGCCAGCCCGAGAACAACTACAAGAC
CACCCCCCCTGTGCTGGACTCCGATGGCTCATTCTTCCTGTACAGCAGACTGACCG
TGGACAAGAGCCGGTGGCAGGAAGGCAACGTGTTCAGCTGCTCCGTGATGCACGAG
GCCCTGCACAACCACTACACCCAGAAGTCCCTGTCTCTGAGCCTGGGCAAA Signal sequence (1-57), variable region (58-414),
constant region (415-1395)

SEQ ID NO: 29: Amino acid sequence of cF44 heavy chain
MKHLWFFLLLVAAPRWVLSEVQLVESGGGLVQPGRSLKLSCAASGFTFSNYYMAWV
RQAPTKGLEWVTYITTGGGSTYFRDSVKGRFTISRDNAESTLYLQMDSLRSEDTAT
YYCTAANYGGSYFDYWGQGVMVTVSSASTKGPSVFPLAPCSRSTSESTAALGCLVK
DYFPEPVTVSWNSGALTSGVHTFPAVLQSSGLYSLSSVVTVPSSSLGTKTYTCNVD
HKPSNTKVDKRVESKYGPPCPPCPAPEAAGGPSVFLFPPKPKDTLMISRTPEVTCV
VVDVSQEDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLVKGFYP
SDIAVEWESNGQPENNYKTTPPVLDSDGSFFLYSRLTVDKSRWQEGNVFSCSVMHE
ALHNHYTQKSLSLSLGK Signal sequence (1-19), variable region (20-138),
constant region (139-465)

Fig. 21

SEQ ID NO: 30: Nucleotide sequence encoding cF63 light chain
ATGGTGCTGCAGACCCAGGTGTTCATCTCCCTGCTGCTGTGGATCTCCGGCGCGTA
CGGCCAGTTCACGCTGACTCAACCAAAGTCCGTGTCAGGAGCTTTAAGAAGCACTA
TCACCATTCCCTGTGAGCGCAGCAGTGGTGACATTGGAGATAGCTATGTGAGCTGG
TACCAGCGACACTTGGGAAGACCCCCCATCAATGTGATCTATGCTGATGATCAAAG
ACCATCTGAAGTGTCTGATCGGTTCTCGGGCTCCATCGACAGCTCCTCTAACTCAG
CCTCACTGACCATCACTAATCTGCAGATGGATGATGAGGCCGACTACTTCTGTCAG
TCTTACGATAGTAAGATTGACATTTTCGGCGGTGGAACCAAGCTCACTGTCCTAGG
CCAGCCTAAGGCTGCCCCTAGCGTGACCCTGTTCCCTCCTTCCAGCGAGGAGCTTC
AAGCTAACAAGGCCACCCTGGTGTGTCTTATCTCTGACTTCTACCCTGGCGCTGTG
ACCGTGGCCTGGAAGGCTGACAGCTCCCCTGTGAAGGCCGGAGTGGAGACCACCAC
ACCTAGCAAGCAGTCTAACAACAAGTACGCTGCCAGCTCCTACCTGAGCCTTACCC
CTGAGCAGTGGAAGTCTCACAGAAGCTACTCCTGTCAAGTGACCCACGAGGGCAGC
ACCGTGGAGAAGACCGTGGCTCCTACCGAGTGTTCC Signal sequence (1-60), variable region (61-390), constant region (391-708)

SEQ ID NO: 31: Amino acid sequence of cF63 light chain
MVLQTQVFISLLLWISGAYGQFTLTQPKSVSGALRSTITIPCERSSGDIGDSYVSW
YQRHLGRPPINVIYADDQRPSEVSDRFSGSIDSSSNSASLTITNLQMDDEADYFCQ
SYDSKIDIFGGGTKLTVLGQPKAAPSVTLFPPSSEELQANKATLVCLISDFYPGAV
TVAWKADSSPVKAGVETTTPSKQSNNKYAASSYLSLTPEQWKSHRSYSCQVTHEGS
TVEKTVAPTECS Signal sequence (1-20), variable region (21-130), constant region (131-236)

Fig. 22

SEQ ID NO: 32: Nucleotide sequence encoding cF63 heavy chain
ATGAAACACCTGTGGTTCTTCCTCCTGCTGGTGGCAGCTCCCAGATGGGTGCTGAG
CCAGGTGCAGCTGAAGGAGTCAGGACCTGGTCTGGTGCAGCCCTCAGAGACCCTGT
CCCTCACCTGCACTGTCTCTGGGTTCTCACTAGCCAGCTATAGTTTAAGTTGGGTT
CGCCAGCCTTCAGGAAAAGGTCCTGAGTGGATGGGAAGAATGTACTATGATGGAGA
CACAGCATATAATTCAGCTCTCAAATCCCGACTGAGCATCAGCAGGGACACCTCCA
AGAACCAAGTTTTCTTAAAAATGAACAGTCTGCAAACTGATGACACAGGCACTTAC
TACTGTACCAGAGATAGGAGTATGTTTGGTACGGATTATCCCCACTGGTACTTTGA
CTTCTGGGGCCCAGGAACCATGGTCACCGTGAGCTCAGCCTCCACCAAGGGCCCTA
GCGTGTTCCCTCTGGCCCCTTGTAGCAGAAGCACCAGCGAGTCTACAGCCGCCCTG
GGCTGCCTCGTGAAGGACTACTTTCCCGAGCCCGTGACCGTGTCCTGGAACTCTGG
CGCTCTGACAAGCGGCGTGCACACCTTCCAGCCGTGCTGCAGAGCAGCGGCCTGT
ACTCTCTGTCCAGCGTCGTGACTGTGCCCAGCAGCTCTCTGGGCACCAAGACCTAC
ACCTGTAACGTGGACCACAAGCCCAGCAACACCAAGGTGGACAAGCGGGTGGAATC
TAAGTACGGCCCTCCCTGCCCTCCTTGCCCAGCCCTGAAGCCGCGGGCGGACCCT
CCGTGTTCCTGTTCCCCCCAAAGCCCAAGGACACCCTGATGATCAGCCGGACCCCC
GAAGTGACCTGCGTGGTGGTGGATGTGTCCCAGGAAGATCCCGAGGTGCAGTTCAA
TTGGTACGTGGACGGCGTGGAAGTGCACAACGCCAAGACCAAGCCTAGAGAGGAAC
AGTTCAACAGCACCTACCGGGTGGTGTCCGTGCTGACAGTGCTGCACCAGGACTGG
CTGAACGGCAAAGAGTACAAGTGCAAGGTGTCCAACAAGGGCCTGCCCAGCTCCAT
CGAGAAAACCATCAGCAAGGCCAAGGGCCAGCCCCGCGAACCCCAGGTGTACACAC
TGCCTCCAAGCCAGGAAGAGATGACCAAGAATCAGGTGTCCCTGACCTGTCTCGTG
AAAGGCTTCTACCCCTCCGATATCGCCGTGGAATGGGAGAGCAACGGCCAGCCCGA
GAACAACTACAAGACCACCCCCCCTGTGCTGGACTCCGATGGCTCATTCTTCCTGT
ACAGCAGACTGACCGTGGACAAGAGCCGGTGGCAGGAAGGCAACGTGTTCAGCTGC
TCCGTGATGCACGAGGCCCTGCACAACCACTACACCCAGAAGTCCCTGTCTCTGAG
CCTGGGCAAA Signal sequence (1-57), variable region (58-429),
constant region (430-1410)

SEQ ID NO: 33: Amino acid sequence of cF63 heavy chain
MKHLWFFLLLVAAPRWVLSQVQLKESGPGLVQPSETLSLTCTVSGFSLASYSLSWV
RQPSGKGPEWMGRMYYDGDTAYNSALKSRLSISRDTSKNQVFLKMNSLQTDDTGTY
YCTRDRSMFGTDYPHWYFDFWGPGTMVTVSSASTKGPSVFPLAPCSRSTSESTAAL
GCLVKDYFPEPVTVSWNSGALTSGVHTFPAVLQSSGLYSLSSVVTVPSSSLGTKTY
TCNVDHKPSNTKVDKRVESKYGPPCPPCPAPEAAGGPSVFLFPPKPKDTLMISRTP
EVTCVVVDVSQEDPEVQFNWYVDGVEVHNAKTKPREEQFNSTYRVVSVLTVLHQDW
LNGKEYKCKVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSRWQEGNVFSC
SVMHEALHNHYTQKSLSLSLGK Signal sequence (1-19), variable region (20-143),
constant region (144-470)

Fig. 23

SEQ ID NO: 34: Nucleotide sequence encoding hL2
ATGGTGCTGCAGACCCAGGTGTTCATCTCCCTGCTGCTGTGGATCTCCGGCGCGTA
CGGCGCCATTCAGCTGACACAGAGCCCTAGCAGCCTGAGCGCCTCTGTGGGCCAGA
GAGTGACCATTACCTGCGGCGCCAGCAAGAGCGTGCGGACCTACATGCACTGGTAT
CAGCAGAAGCCCGGCAAGGCCCCCAAGCTGCTGATCTACAGCGCCTCCAATCTGGA
AGCCGGCGTGCCCAGCAGATTTTCCGGCTCTGGCAGCGGCACCGACTTCACCCTGA
CAATCAGCAGCCTGCAGCCCGAGGACTTCGCCACCTACTACTGCCAGCAGAGCAAC
GAGCCCCCCTACACCTTTGGCCAGGGCACCAAGCTGGAAATCAAGCGTACGGTGGC
CGCCCCCTCCGTGTTCATCTTCCCCCCCTCCGACGAGCAGCTGAAGTCCGGCACCG
CCTCCGTGGTGTGCCTGCTGAATAACTTCTACCCCAGAGAGGCCAAGGTGCAGTGG
AAGGTGGACAACGCCCTGCAGTCCGGGAACTCCCAGGAGAGCGTGACCGAGCAGGA
CAGCAAGGACAGCACCTACAGCCTGAGCAGCACCCTGACCCTGAGCAAAGCCGACT
ACGAGAAGCACAAGGTGTACGCCTGCGAGGTGACCCACCAGGGCCTGAGCTCCCCC
GTCACCAAGAGCTTCAACAGGGGGGAGTGT Signal sequence (1-60), variable region (61-381),
constant region (382-702)

SEQ ID NO: 35: Amino acid sequence of hL2
MVLQTQVFISLLLWISGAYGAIQLTQSPSSLSASVGQRVTITCGASKSVRTYMHWY
QQKPGKAPKLLIYSASNLEAGVPSRFSGSGSGTDFTLTISSLQPEDFATYYCQQSN
EPPYTFGQGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSP
VTKSFNRGEC Signal sequence (1-20), variable region (21-127),
constant region (128-234)

Fig. 24

SEQ ID NO: 36: Nucleotide sequence encoding hL3
ATGGTGCTGCAGACCCAGGTGTTCATCTCCCTGCTGCTGTGGATCTCCGGCGCGTA
CGGCGATACCCAGCTGACACAGAGCCCTAGCAGCCTGTCTGCCAGCGTGGGCCAGA
GAGTGACCATTACCTGCGGCGCCAGCAAGAGCGTGCGGACCTACATGCACTGGTAT
CAGCAGAAGCCCGGCAAGCAGCCCAAGCTGCTGATCTACAGCGCCTCCAACCTGGA
AGCCGGCGTGCCCAGCAGATTTTCTGGCAGCGGCTCCGGCACCGACTTCACCCTGA
CAATCAGCAGCCTGCAGCCCGAGGACTTCGCCACCTACTACTGCCAGCAGAGCAAC
GAGCCCCCTACACCTTTGGCCAGGGCACCAAGCTGGAAATCAAGCGTACGGTGGC
CGCCCCCTCCGTGTTCATCTTCCCCCCCTCCGACGAGCAGCTGAAGTCCGGCACCG
CCTCCGTGGTGTGCCTGCTGAATAACTTCTACCCCAGAGAGGCCAAGGTGCAGTGG
AAGGTGGACAACGCCCTGCAGTCCGGGAACTCCCAGGAGAGCGTGACCGAGCAGGA
CAGCAAGGACAGCACCTACAGCCTGAGCAGCACCCTGACCCTGAGCAAAGCCGACT
ACGAGAAGCACAAGGTGTACGCCTGCGAGGTGACCCACCAGGGCCTGAGCTCCCCC
GTCACCAAGAGCTTCAACAGGGGGGAGTGT Signal sequence (1-60), variable region (61-381),
constant region (382-702)

SEQ ID NO: 37: Amino acid sequence of hL3
MVLQTQVFISLLLWISGAYGDTQLTQSPSSLSASVGQRVTITCGASKSVRTYMHWY
QQKPGKQPKLLIYSASNLEAGVPSRFSGSGSGTDFTLTISSLQPEDFATYYCQQSN
EPPYTFGQGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSP
VTKSFNRGEC Signal sequence (1-20), variable region (21-127),
constant region (128-234)

Fig. 25

SEQ ID NO: 38: Nucleotide sequence encoding hL4
ATGGTGCTGCAGACCCAGGTGTTCATCTCCCTGCTGCTGTGGATCTCCGGCGCGTA
CGGCGATACCGTGCTGACCCAGAGCCCTGATAGCCTGGCCGTGTCCCTGGGACAGA
GAGCCACCATCAATTGCGGCGCCAGCAAGAGCGTGCGGACCTACATGCACTGGTAT
CAGCAGAAGCCCGGCCAGCAGCCCAAGCTGCTGATCTACAGCGCCTCCAACCTGGA
AGCCGGCGTGCCCAGCAGATTTTCTGGCAGCGGCTCCGGCACCGACTTCACCCTGA
CAATCAGCTCCCTGCAGGCCGAGGACGTGGCCGTGTACTACTGCCAGCAGAGCAAC
GAGCCCCCCTACACCTTTGGCCAGGGCACCAAGGTGGAAATCAAGCGTACGGTGGC
CGCCCCCTCCGTGTTCATCTTCCCCCCCTCCGACGAGCAGCTGAAGTCCGGCACCG
CCTCCGTGGTGTGCCTGCTGAATAACTTCTACCCCAGAGAGGCCAAGGTGCAGTGG
AAGGTGGACAACGCCCTGCAGTCCGGGAACTCCCAGGAGAGCGTGACCGAGCAGGA
CAGCAAGGACAGCACCTACAGCCTGAGCAGCACCCTGACCCTGAGCAAAGCCGACT
ACGAGAAGCACAAGGTGTACGCCTGCGAGGTGACCCACCAGGGCCTGAGCTCCCCC
GTCACCAAGAGCTTCAACAGGGGGGAGTGT Signal sequence (1-60), variable region (61-381),
constant region (382-702)

SEQ ID NO: 39: Amino acid sequence of hL4
MVLQTQVFISLLLWISGAYGDTVLTQSPDSLAVSLGQRATINCGASKSVRTYMHWY
QQKPGQQPKLLIYSASNLEAGVPSRFSGSGSGTDFTLTISSLQAEDVAVYYCQQSN
EPPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSP
VTKSFNRGEC Signal sequence (1-20), variable region (21-127),
constant region (128-234)

Fig. 26

SEQ ID NO: 40: Nucleotide sequence encoding hH1
ATGAAACACCTGTGGTTCTTCCTCCTGCTGGTGGCAGCTCCCAGATGGGTGCTGAG
CCAGGTGCAGCTGGTGGAATCTGGCGGCGGAGTGGTGCAGCCTGGCAGAAGCCTGA
GACTGAGCTGTGCCGCCAGCGGCTTCACCTTCAGCGACTACGGCATGATCTGGGTG
CGCCAGGCCCCTGGCAAAGGCCTGGAATGGGTGGCCAGCATCAGCAGCAGCTCCAG
CTACATCTACTACGCCGACAGCGTGAAGGGCCGGTTCACCATCAGCCGGGACAACA
GCAAGAACCGGCTGTACCTGCAGATGAACAGCCTGCGGGCCGAGGACACCGCCGTG
TACTATTGCGCCAGACGGTACTACGGCTTCAACTACCCCTTCGACTACTGGGGCCA
GGGCACAATGGTCACCGTCAGCTCAGCCTCCACCAAGGGCCCTAGCGTGTTCCCTC
TGGCCCCTTGTAGCAGAAGCACCAGCGAGTCTACAGCCGCCCTGGGCTGCCTCGTG
AAGGACTACTTTCCCGAGCCCGTGACCGTGTCCTGGAACTCTGGCGCTCTGACAAG
CGGCGTGCACACCTTTCCAGCCGTGCTGCAGAGCAGCGGCCTGTACTCTCTGTCCA
GCGTCGTGACTGTGCCCAGCAGCTCTCTGGGCACCAAGACCTACACCTGTAACGTG
GACCACAAGCCCAGCAACACCAAGGTGGACAAGCGGGTGGAATCTAAGTACGGCCC
TCCCTGCCCTCCTTGCCCAGCCCCTGAAGCCGCGGGCGGACCCTCCGTGTTCCTGT
TCCCCCCAAAGCCCAAGGACACCCTGATGATCAGCCGGACCCCCGAAGTGACCTGC
GTGGTGGTGGATGTGTCCCAGGAAGATCCCGAGGTGCAGTTCAATTGGTACGTGGA
CGGCGTGGAAGTGCACAACGCCAAGACCAAGCCTAGAGAGGAACAGTTCAACAGCA
CCTACCGGGTGGTGTCCGTGCTGACAGTGCTGCACCAGGACTGGCTGAACGGCAAA
GAGTACAAGTGCAAGGTGTCCAACAAGGGCCTGCCCAGCTCCATCGAGAAAACCAT
CAGCAAGGCCAAGGGCCAGCCCCGCGAACCCCAGGTGTACACACTGCCTCCAAGCC
AGGAAGAGATGACCAAGAATCAGGTGTCCCTGACCTGTCTCGTGAAAGGCTTCTAC
CCCTCCGATATCGCCGTGGAATGGGAGAGCAACGGCCAGCCCGAGAACAACTACAA
GACCACCCCCCCTGTGCTGGACTCCGATGGCTCATTCTTCCTGTACAGCAGACTGA
CCGTGGACAAGAGCCGGTGGCAGGAAGGCAACGTGTTCAGCTGCTCCGTGATGCAC
GAGGCCCTGCACAACCACTACACCCAGAAGTCCCTGTCTCTGAGCCTGGGCAAA Signal sequence (1-57), variable region (58-417),
constant region (418-1398)

SEQ ID NO: 41: Amino acid sequence of hH1
MKHLWFFLLLVAAPRWVLSQVQLVESGGGVVQPGRSLRLSCAASGFTFSDYGMIWV
RQAPGKGLEWVASISSSSSYIYYADSVKGRFTISRDNSKNRLYLQMNSLRAEDTAV
YYCARRYYGFNYPFDYWGQGTMVTVSSASTKGPSVFPLAPCSRSTSESTAALGCLV
KDYFPEPVTVSWNSGALTSGVHTFPAVLQSSGLYSLSSVVTVPSSSLGTKTYTCNV
DHKPSNTKVDKRVESKYGPPCPPCPAPEAAGGPSVFLFPPKPKDTLMISRTPEVTC
VVVDVSQEDPEVQFNWYVDGVEVHNAKTKPREEQFNSTYRVVSVLTVLHQDWLNGK
EYKCKVSNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVFSCSVMH
EALHNHYTQKSLSLSLGK Signal sequence (1-19), variable region (20-139),
constant region (140-466)

Fig. 27

SEQ ID NO: 42: Nucleotide sequence encoding hH2
ATGAAACACCTGTGGTTCTTCCTCCTGCTGGTGGCAGCTCCCAGATGGGTGCTGAG
CGAAGTGCAGCTGGTGGAATCTGGCGGCGGAGTGGTGCAGCCTGGCAGAAGCCTGA
GACTGAGCTGTGCCGCCAGCGGCTTCACCTTCAGCGACTACGGCATGATCTGGGTG
CGCCAGGCCCCTGGCAAAGGCCTGGAATGGGTGGCCAGCATCAGCAGCAGCTCCAG
CTACATCTACTACGCCGACAGCGTGAAGGGCCGGTTCACCATCAGCCGGGACAACA
GCAAGAACACCCTGTACCTGCAGATGAACAGCCTGCGGGCCGAGGACACCGCCGTG
TACTATTGCGCCAGACGGTACTACGGCTTCAACTACCCCTTCGACTACTGGGGCCA
GGGCACAATGGTCACCGTCAGCTCAGCCTCCACCAAGGGCCCTAGCGTGTTCCCTC
TGGCCCCTTGTAGCAGAAGCACCAGCGAGTCTACAGCCGCCCTGGGCTGCCTCGTG
AAGGACTACTTTCCCGAGCCCGTGACCGTGTCCTGGAACTCTGGCGCTCTGACAAG
CGGCGTGCACACCTTTCCAGCCGTGCTGCAGAGCAGCGGCCTGTACTCTCTGTCCA
GCGTCGTGACTGTGCCCAGCAGCTCTCTGGGCACCAAGACCTACACCTGTAACGTG
GACCACAAGCCCAGCAACACCAAGGTGGACAAGCGGGTGGAATCTAAGTACGGCCC
TCCCTGCCCTCCTTGCCCAGCCCCTGAAGCCGCGGGCGGACCCTCCGTGTTCCTGT
TCCCCCCAAAGCCCAAGGACACCCTGATGATCAGCCGGACCCCCGAAGTGACCTGC
GTGGTGGTGGATGTGTCCCAGGAAGATCCCGAGGTGCAGTTCAATTGGTACGTGGA
CGGCGTGGAAGTGCACAACGCCAAGACCAAGCCTAGAGAGGAACAGTTCAACAGCA
CCTACCGGGTGGTGTCCGTGCTGACAGTGCTGCACCAGGACTGGCTGAACGGCAAA
GAGTACAAGTGCAAGGTGTCCAACAAGGGCCTGCCCAGCTCCATCGAGAAAACCAT
CAGCAAGGCCAAGGGCCAGCCCCGCGAACCCCAGGTGTACACACTGCCTCCAAGCC
AGGAAGAGATGACCAAGAATCAGGTGTCCCTGACCTGTCTCGTGAAAGGCTTCTAC
CCCTCCGATATCGCCGTGGAATGGGAGAGCAACGGCCAGCCCGAGAACAACTACAA
GACCACCCCCCTGTGCTGGACTCCGATGGCTCATTCTTCCTGTACAGCAGACTGA
CCGTGGACAAGAGCCGGTGGCAGGAAGGCAACGTGTTCAGCTGCTCCGTGATGCAC
GAGGCCCTGCACAACCACTACACCCAGAAGTCCCTGTCTCTGAGCCTGGGCAAA Signal sequence (1-57), variable region (58-417),
constant region (418-1398)

SEQ ID NO: 43: Amino acid sequence of hH2
MKHLWFFLLLVAAPRWVLSEVQLVESGGGVVQPGRSLRLSCAASGFTFSDYGMIWV
RQAPGKGLEWVASISSSSSYIYYADSVKGRFTISRDNSKNTLYLQMNSLRAEDTAV
YYCARRYYGFNYPFDYWGQGTMVTVSSASTKGPSVFPLAPCSRSTSESTAALGCLV
KDYFPEPVTVSWNSGALTSGVHTFPAVLQSSGLYSLSSVVTVPSSSLGTKTYTCNV
DHKPSNTKVDKRVESKYGPPCPPCPAPEAAGGPSVFLFPPKPKDTLMISRTPEVTC
VVVDVSQEDPEVQFNWYVDGVEVHNAKTKPREEQFNSTYRVVSVLTVLHQDWLNGK
EYKCKVSNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVFSCSVMH
EALHNHYTQKSLSLSLGK Signal sequence (1-19), variable region (20-139),
constant region (140-466)

Fig. 28

SEQ ID NO: 1: D13 CDRL1
GASKSVRTYMH

SEQ ID NO: 2: D13 CDRL2
SASNLEA

SEQ ID NO: 3: D13 CDRL3
QQSNEPPYT

SEQ ID NO: 4: D13 CDRH1
GFTFSDYGMI

SEQ ID NO: 5: D13 CDRH2
SISSSSSYIY

SEQ ID NO: 6: D13 CDRH3
RYYGFNYPFDY

Fig. 29

SEQ ID NO: 7: F44 CDRL1
KASKSISKYLA

SEQ ID NO: 8: F44 CDRL2
SGSTLQS

SEQ ID NO: 9: F44 CDRL3
QQHNEYPPT

SEQ ID NO: 10: F44 CDRH1
GFTFSNYYMA

SEQ ID NO: 11: F44 CDRH2
YITTGGGSTY

SEQ ID NO: 12: F44 CDRH3
ANYGGSYFDY

Fig. 30

SEQ ID NO: 13: F63 CDRL1
ERSSGDIGDSYVS

SEQ ID NO: 14: F63 CDRL2
ADDQRPS

SEQ ID NO: 15: F63 CDRL3
QSYDSKIDI

SEQ ID NO: 16: F63 CDRH1
GFSLASYSLS

SEQ ID NO: 17: F63 CDRH2
RMYYDGDTA

SEQ ID NO: 18: F63 CDRH3
DRSMFGTDYPHWYFDF

Fig. 34

SEQ ID NO: 81: Amino acid sequence of OSE-172 antibody
heavy chain (OSE-172_hG4Pro)
MKHLWFFLLLVAAPRWVLSEVQLVQSGAEVKKPGESLRISCKASGYSFTSYWVHWV
RQMPGKGLEWMGNIDPSDSDTHYSPSFQGHVTLSVDKSISTAYLQLSSLKASDTAM
YYCVRGGTGTLAYFAYWGQGTLVTVSSASTKGPSVFPLAPCSRSTSESTAALGCLV
KDYFPEPVTVSWNSGALTSGVHTFPAVLQSSGLYSLSSVVTVPSSSLGTKTYTCNV
DHKPSNTKVDKRVESKYGPPCPPCPAPEFLGGPSVFLFPPKPKDTLMISRTPEVTC
VVVDVSQEDPEVQFNWYVDGVEVHNAKTKPREEQFNSTYRVVSVLTVLHQDWLNGK
EYKCKVSNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVFSCSVMH
EALHNHYTQKSLSLSPGK*

SEQ ID NO: 82: Amino acid sequence of OSE-172 antibody
light chain (OSE-172_hK)
MVLQTQVFISLLLWISGAYGDVVMTQSPLSLPVTLGQPASISCRSSQSLVHSYGNT
YLYWFQQRPGQSPRLLIYRVSNRFSGVPDRFSGSGSGTDFTLKISRVEAEDVGVYY
CFQGTHVPYTFGGGTKVEIKRTVAAPSVFIFPPSDEQLKSGTASVVCLLNNFYPRE
AKVQWKVDNALQSGNSQESVTEQDSKDSTYSLSSTLTLSKADYEKHKVYACEVTHQ
GLSSPVTKSFNRGEC*

Fig. 35

SEQ ID NO: 83: Amino acid sequence of KWAR23 antibody heavy chain (KWAR23_hG4Pro)
MKHLWFFLLLVAAPRWVLSEVQLQQSGAELVKPGASVKLSCTASGFNIKDYYIHWV
QQRTEQGLEWIGRIDPEDGETKYAPKFQDKATITADTSSNTAYLHLSSLTSEDTAV
YYCARWGAYWGQGTLVTVSAASTKGPSVFPLAPCSRSTSESTAALGCLVKDYFPEP
VTVSWNSGALTSGVHTFPAVLQSSGLYSLSSVVTVPSSSLGTKTYTCNVDHKPSNT
KVDKRVESKYGPPCPPCPAPEFLGGPSVFLFPPKPKDTLMISRTPEVTCVVVDVSQ
EDPEVQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHY
TQKSLSLSLGK*

SEQ ID NO: 84 Amino acid sequence of KWAR23 antibody light chain (KWAR23_hK)
MVLQTQVFISLLLWISGAYGQIVLTQSPAIMSASPGEKVTLTCSASSSVSSSYLYW
YQQKPGSSPKLWIYSTSNLASGVPARFSGSGSGTSYSLTISSMEAEDAASYFCHQW
SSYPRTFGAGTKLELKRTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSS
PVTKSFNRGEC*

Fig. 36

SEQ ID NO: 85: Amino acid sequence of ADU-1805 antibody heavy chain (ADU-1805_hG2)
MKHLWFFLLLVAAPRWVLSEVQLVQSGAEVVKPGASVKLSCKASGSTFTSYWMHWV
KQAPGQGLEWIGAIYPVNSDTTYNQKFKGKATLTVDKSASTAYMELSSLRSEDTAV
YYCTRSFYYSLDAAWFVYWGQGTLVTVSSASTKGPSVFPLAPCSRSTSESTAALGC
LVKDYFPEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMISRTPEVT
CVVVDVSHEDPEVQFNWYVDGVEVHNAKTKPREEQFNSTFRVVSVLTVVHQDWLNG
KEYKCKVSNKGLPAPIEKTISKTKGQPREPQVYTLPPSREEMTKNQVSLTCLVKGF
YPSDIAVEWESNGQPENNYKTTPPMLDSDGSFFLYSKLTVDKSRWQQGNVFSCSVM
HEALHNHYTQKSLSLSPGK*

SEQ ID NO: 86: Amino acid sequence of ADU-1805 antibody light chain (ADU-1805_hK)
MVLQTQVFISLLLWISGAYGDIQMTQSPSSLSASVGDRVTITCRASQDIGSRLNWL
QQKPGKAPKRLIYATSSLDSGVPSRFSGSGSGTEFTLTISSLQPEDFATYYCLQYA
SSPFTFGGGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSP
VTKSFNRGEC*

ANTI-SIRPALPHA ANTIBODY

CROSS-REFERENCE TO RELATED APPLICATIONS

The present application claims priority under 37 U.S.C. § 371 to International Patent Application No. PCT/JP2019/027114, filed Jul. 9, 2019, which claims priority to and the benefit of Japanese Patent Application No. 2018-131116, filed on Jul. 10, 2018. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 127565-0102 Updated SL.txt and is 185 kb in size.

TECHNICAL FIELD

The present invention relates to an anti-SIRPα antibody useful for the treatment of tumors and an anti-tumor agent comprising the antibody.

BACKGROUND ART

SIRPα (SHPS-1) is a single-pass transmembrane molecule belonging to the Ig superfamily, which is present in myeloid cells such as macrophages, dendritic cells, and neutrophils as well as glia cells (Non Patent Literature 1). The extracellular region thereof consists of one IgV domain and two IgC domains, and 10 different variants have been reported for the IgV domain, which is a site for binding to CD47, in humans (Non Patent Literature 2). The intracellular region contains an immunoreceptor tyrosine-based inhibition motif (ITIM), and the binding to CD47 induces the binding to tyrosine phosphatases SHP-1 and SHP-2, leading to transmission of an inhibitory signal.

An example of physiological phenomena resulting from the SIRPα-CD47 interaction that have been shown is that, when CD47 on an erythrocyte binds to SIRPα on a macrophage, a "Don't-eat-me" signal is transmitted to prevent unnecessary phagocytosis of the erythrocyte (Non Patent Literature 3). It has also been suggested that the binding of SIRPα present on macrophages and dendritic cells to CD47 highly expressed in tumor cells inhibits the phagocytic activity against the tumor cells in the tumor microenvironment. Inhibition of the phagocytic activity is expected to lead to subsequent inhibition of tumor antigen-presentation to T cells and further to inhibition of immune responses to tumor. Thus, the immune phenomenon of tumor cell phagocytosis is considered to serve as a checkpoint of tumor antigen uptake (entry).

So far, it has been reported that the phagocytic activity against tumor cells is enhanced when the SIRPα-CD47 interaction is inhibited by an antibody against CD47, which is a ligand for SIRPα (Non Patent Literature 4), and similar phenomena have been reported in the use of an anti-SIRPα antibody in combination with an anti-cancer antibody that has an effector activity of attracting tumor cells to immune cells (Non Patent Literatures 5 and 6). Additionally, it has been suggested that not only anti-tumor effects, but also tumor immunity is induced when an anti-CD47 antibody is used in an allogenic tumor-bearing mouse model (Non Patent Literature 7), and the anti-SIRPα antibody can therefore be expected to have similar effects when it is used in combination with an anti-cancer antibody.

Meanwhile, as immune checkpoint inhibitors, multiple antibodies against immunoinhibitory molecules on T cells, such as PD-1/PD-L1, have been developed and proved to be clinically effective (Non Patent Literatures 8 and 9). Currently, SIRPα-CD47 is the only identified molecule that inhibits phagocytosis, and an antibody that inhibits this molecule is expected as a potential novel checkpoint inhibitor against targets other than T cells and may also be broadly effective in patients who do not respond to conventional immune checkpoint inhibitors.

So far, a study using an anti-mouse SIRPα antibody (MY-1) in a model in which human Burkitt's lymphoma was subcutaneously transplanted has shown that anti-tumor effects are exhibited when the antibody is used in combination with rituximab. In a mouse colon cancer model, anti-tumor effects have been shown in the use in combination with a PD-1 antibody (Non Patent Literature 5). In addition, a study using an anti-mSIRPα antibody (P84) from different clones has shown that the use in combination with an anti-PD-L1 antibody or an anti-4-IBB antibody also exhibits anti-tumor effects and life-prolonging effects in a mouse liver cancer model. Given that further anti-tumor effects and complete remission effects were achieved when the same tumor cells were re-transplanted in mice showing complete remission effects, potent tumor immune responses may be induced by inhibiting different immune checkpoints (Patent Literature 1). These results are examples of effects exhibited by the use of the anti-mouse SIRPα antibody in combination with not only conventional anti-cancer antibodies expected to have the effector activity but also immune checkpoint inhibitors targeting T cells, and an anti-human SIRPα antibody can be expected to have similar effects.

In recent years, patents on anti-SIRPα antibodies have been reported in succession by various companies (Patent Literatures 1, 2, and 3). For example, OSE-172 is an IgG4Pro antibody that binds to SIRPα V1 and SIRPβ1 but does not bind to SIRPα V2 or SIRPγ. KWAR23 is an IgG1N279A antibody that binds to 10 different SIRPα variants, SIRPβ1, and SIRPγ. ADU-1805 is an IgG2 antibody that binds to 10 different SIRPα variants and SIRPγ. The antibody which is most suitable as a medicament among these antibodies remains unknown, and efforts continue to be made to obtain an excellent antibody.

Further, a study using an anti-CD47 antibody has reported that sufficient anti-tumor effects and complete remission effects are also exhibited by the use in combination with chemotherapeutic agents and radiation therapy, which have been used as standard of care (SOC), in addition to the antibody drugs described above. Particularly in cases of the use in combination with chemotherapeutic agents, more potent anti-tumor effects and complete remission effects are exhibited by administering a chemotherapeutic agent prior to an anti-CD47 antibody than by simultaneously administering the chemotherapeutic agent with the anti-CD47 antibody (Non Patent Literature 7). This finding indicates that antigen uptake (immuno-activation) effects by inhibition of the SIRPα-CD47 interaction can be enhanced by pre-administering a chemotherapeutic agent to prepare an environment in which tumor antigens can be easily taken up.

From the above, it can be inferred that an anti-SIRPα antibody is a drug that can induce a more potent tumor immune response when used in combination with various anti-tumor agents.

CITATION LIST

Patent Literature

Patent Literature 1: International Publication No. WO 2017/178653
Patent Literature 2: International Publication No. WO 2018/026600
Patent Literature 3: International Publication No. WO 2018/190719

Non Patent Literature

Non Patent Literature 1: Matozaki et al. Trends Cell Biol. 2009; 19(2), 72-80
Non Patent Literature 2: Takenaka et al. Nat. Immunol. 2007; 8(12), 1313-1323
Non Patent Literature 3: Matozaki et al. Trends in Cell Biol. 2009; 19(2), 72-80
Non Patent Literature 4: Liu et al. PLOS ONE. 2015; 10(9)
Non Patent Literature 5: Yanagita et al. JCI Insight. 2017; 2(1), 1-15
Non Patent Literature 6: Ring et al. PNAS. 2017; 114(49), E10578-E10585
Non Patent Literature 7: Liu et al. Nat. Med. 2015; 21(10), 1209-1215
Non Patent Literature 8: Lee et al. The Oncologist. 2017; 22(11), 1392-1399
Non Patent Literature 9: Weinstock et al. Clin. Can. Res. 2017; 23(16), 4534-4539

SUMMARY OF INVENTION

Technical Problem

The object of the present invention is to provide an anti-SIRPα antibody that can be used as an anti-tumor agent and an anti-tumor agent comprising the antibody as an active ingredient.

Solution to Problem

The present inventors examined a method for enhancing the phagocytic activity of phagocytes against tumor cells by inhibiting the interaction between SIRPα expressed in a phagocyte having the phagocytic activity and CD47 expressed on a tumor cell by an anti-SIRPα antibody to inhibit the transmission of a "Don't-eat-me" signal from the tumor cell to the phagocyte. The present inventors attempted to prepare an antibody having a high affinity for SIRPα and a high effect of inhibiting the interaction between SIRPα and CD47, and they also considered the preparation of an anti-SIRPα antibody not having effector functions, considering a possibility that an anti-SIRPα antibody that has effector functions, such as ADCC and ADCP, may attack immune cells of the self. To reduce the effector functions, a mutation for reducing the effector functions was introduced into the Fc region of an antibody, and the antibody subclass was designated as IgG4. As a result, an anti-SIRPα antibody that inhibits potently the interaction between SIRPα and CD47 but has reduced effector functions could be prepared. This antibody does not have sufficient anti-tumor effects on its own because it does not bind to the Fc receptor of an effector cell and therefore does not have effector functions. Accordingly, the antibody was used in combination with other antibody drugs having effector functions or other antibody drugs having an immune checkpoint inhibitory action. It was demonstrated that the antibody exhibited favorable anti-tumor effects, and thus the present invention was accomplished.

That is, the present invention provides the followings.
[1] An antibody that binds specifically to human SIRPα to inhibit binding of human SIRPα to CD47, the antibody comprising:
  (a) a light chain CDRL1 consisting of an amino acid sequence set forth in SEQ ID NO: 1;
  (b) a light chain CDRL2 consisting of an amino acid sequence set forth in SEQ ID NO: 2;
  (c) a light chain CDRL3 consisting of an amino acid sequence set forth in SEQ ID NO: 3;
  (d) a heavy chain CDRH1 consisting of an amino acid sequence set forth in SEQ ID NO: 4;
  (e) a heavy chain CDRH2 consisting of an amino acid sequence set forth in SEQ ID NO: 5; and
  (f) a heavy chain CDRH3 consisting of an amino acid sequence set forth in SEQ ID NO: 6.
[2] The antibody according to [1], wherein a heavy chain constant region is a heavy chain constant region of human IgG4, and has a mutation that reduces an ADCC and/or ADCP activity.
[3] The antibody according to [1] or [2], wherein the heavy chain constant region is a heavy chain constant region of human IgG4, and phenylalanine at position 234, as numbered according to the EU index as in Kabat et al., is substituted by alanine, leucine at position 235 is substituted by alanine, and serine at position 228 is substituted by proline.
[4] The antibody according to [3], wherein an amino acid sequence of the heavy chain constant region is an amino acid sequence consisting of amino acid residues 140 to 466 in SEQ ID NO: 25.
[5] An antibody that binds specifically to human SIRPα to inhibit binding of human SIRPα to CD47, the antibody comprising:
  (ai) a light chain variable region consisting of an amino acid sequence consisting of amino acid residues 21 to 126 in SEQ ID NO: 23; or
  (aii) a light chain variable region consisting of an amino acid sequence having at least 95% sequence identity with the amino acid sequence consisting of amino acid residues 21 to 126 in SEQ ID NO: 23 and having a binding activity to human SIRPα; and
  (bi) a heavy chain variable region consisting of an amino acid sequence consisting of amino acid residues 20 to 139 in SEQ ID NO: 25; or
  (bii) a heavy chain variable region consisting of an amino acid sequence having at least 95% sequence identity with the amino acid sequence consisting of amino acid residues 20 to 139 in SEQ ID NO: 25 and having a binding activity to human SIRPα, wherein a heavy chain constant region is a heavy chain constant region of human IgG4, and has a mutation that reduces an ADCC and/or ADCP activity.
[6] The antibody according to [5], wherein the heavy chain constant region is the heavy chain constant region of human IgG4, and phenylalanine at position 234, as numbered according to the EU index as in Kabat et al., is substituted by alanine, leucine at position 235 is substituted by alanine, and serine at position 228 is substituted by proline.
[7] The antibody according to [6], wherein an amino acid sequence of the heavy chain constant region is an amino acid sequence consisting of amino acid residues 140 to 466 in SEQ ID NO: 25.

[8] An antibody that binds specifically to human SIRPα to inhibit binding of human SIRPα to CD47, the antibody comprising:
(a) a light chain CDRL1 consisting of an amino acid sequence set forth in SEQ ID NO: 7;
(b) a light chain CDRL2 consisting of an amino acid sequence set forth in SEQ ID NO: 8;
(c) a light chain CDRL3 consisting of an amino acid sequence set forth in SEQ ID NO: 9;
(d) a heavy chain CDRH1 consisting of an amino acid sequence set forth in SEQ ID NO: 10;
(e) a heavy chain CDRH2 consisting of an amino acid sequence set forth in SEQ ID NO: 11; and
(f) a heavy chain CDRH3 consisting of an amino acid sequence set forth in SEQ ID NO: 12.

[9] The antibody according to [8], wherein a heavy chain constant region is a heavy chain constant region of human IgG4, and has a mutation that reduces an ADCC and/or ADCP activity.

[10] The antibody that binds specifically to human SIRPα to inhibit binding of human SIRPα to CD47 according to [8] or [9], wherein a heavy chain constant region is a heavy chain constant region of human IgG4, and phenylalanine at position 234, as numbered according to the EU index as in Kabat et al., is substituted by alanine, leucine at position 235 is substituted by alanine, and serine at position 228 is substituted by proline.

[11] The antibody according to [10], wherein an amino acid sequence of the heavy chain constant region is an amino acid sequence consisting of amino acid residues 139 to 465 in SEQ ID NO: 29.

[12] An antibody that binds specifically to human SIRPα to inhibit binding of human SIRPα to CD47, the antibody comprising:
(ai) a light chain variable region consisting of an amino acid sequence consisting of amino acid residues 21 to 127 in SEQ ID NO: 27; or
(aii) a light chain variable region consisting of an amino acid sequence having at least 95% sequence identity with the amino acid sequence consisting of amino acid residues 21 to 127 in SEQ ID NO: 27 and having a binding activity to human SIRPα; and
(bi) a heavy chain variable region consisting of an amino acid sequence consisting of amino acid residues 20 to 138 in SEQ ID NO: 29; or
(bii) a heavy chain variable region consisting of an amino acid sequence having at least 95% sequence identity with the amino acid sequence consisting of amino acid residues 20 to 138 in SEQ ID NO: 29 and having a binding activity to human SIRPα,
wherein a heavy chain constant region is a heavy chain constant region of human IgG4, and has a mutation that reduces an ADCC and/or ADCP activity.

[13] The antibody that binds specifically to human SIRPα to inhibit binding of human SIRPα to CD47 according to [12], wherein the heavy chain constant region is the heavy chain constant region of human IgG4, and phenylalanine at position 234, as numbered according to the EU index as in Kabat et al., is substituted by alanine, leucine at position 235 is substituted by alanine, and serine at position 228 is substituted by proline.

[14] The antibody according to [13], wherein an amino acid sequence of the heavy chain constant region is an amino acid sequence consisting of amino acid residues 139 to 465 in SEQ ID NO: 29.

[15] An antibody that binds specifically to human SIRPα to inhibit binding of human SIRPα to CD47, the antibody comprising:
(a) a light chain CDRL1 consisting of an amino acid sequence set forth in SEQ ID NO: 13;
(b) a light chain CDRL2 consisting of an amino acid sequence set forth in SEQ ID NO: 14;
(c) a light chain CDRL3 consisting of an amino acid sequence set forth in SEQ ID NO: 15;
(d) a heavy chain CDRH1 consisting of an amino acid sequence set forth in SEQ ID NO: 16;
(e) a heavy chain CDRH2 consisting of an amino acid sequence set forth in SEQ ID NO: 17; and
(f) a heavy chain CDRH3 consisting of an amino acid sequence set forth in SEQ ID NO: 18.

[16] The antibody according to [15], wherein a heavy chain constant region is a heavy chain constant region of human IgG4, and has a mutation that reduces an ADCC and/or ADCP activity.

[17] The antibody that binds specifically to human SIRPα to inhibit binding of human SIRPα to CD47 according to [15] or [16], wherein a heavy chain constant region is a heavy chain constant region of human IgG4, and phenylalanine at position 234, as numbered according to the EU index as in Kabat et al., is substituted by alanine, leucine at position 235 is substituted by alanine, and serine at position 228 is substituted by proline.

[18] The antibody according to [17], wherein an amino acid sequence of the heavy chain constant region is an amino acid sequence consisting of amino acid residues 144 to 470 in SEQ ID NO: 33.

[19] An antibody that binds specifically to human SIRPα to inhibit binding of human SIRPα to CD47 comprising
(ai) a light chain variable region consisting of an amino acid sequence consisting of amino acid residues 21 to 130 in SEQ ID NO: 31 or
(aii) a light chain variable region consisting of an amino acid sequence having at least 95% sequence identity with the amino acid sequence consisting of amino acid residues 21 to 130 in SEQ ID NO: 31 and having a binding activity to human SIRPα and
(bi) a heavy chain variable region consisting of an amino acid sequence consisting of amino acid residues 20 to 143 in SEQ ID NO: 33 or
(bii) a heavy chain variable region consisting of an amino acid sequence having at least 95% sequence identity with the amino acid sequence consisting of amino acid residues 20 to 143 in SEQ ID NO: 33 and having a binding activity to human SIRPα,
wherein a heavy chain constant region is a heavy chain constant region of human IgG4, and has a mutation that reduces an ADCC and/or ADCP activity.

[20] The antibody that binds specifically to human SIRPα to inhibit binding of human SIRPα to CD47 according to [19], wherein the heavy chain constant region is the heavy chain constant region of human IgG4, and phenylalanine at position 234, as numbered according to the EU index as in Kabat et al., is substituted by alanine, leucine at position 235 is substituted by alanine, and serine at position 228 is substituted by proline.

[21] The antibody according to [20], wherein an amino acid sequence of the heavy chain constant region is an amino acid sequence consisting of amino acid residues 144 to 470 in SEQ ID NO: 33.

[22] The antibody according to any one of [1] to [4], which is any of the following (1) to (8):

(1) an antibody that binds specifically to human SIRPα to inhibit binding of human SIRPα to CD47, the antibody consisting of: a heavy chain consisting of an amino acid sequence consisting of amino acid residues 20 to 466 in SEQ ID NO: 41; and a light chain consisting of an amino acid sequence consisting of amino acid residues 21 to 234 in SEQ ID NO: 37;

(2) an antibody that binds specifically to human SIRPα to inhibit binding of human SIRPα to CD47, the antibody consisting of: a heavy chain consisting of an amino acid sequence having at least 95% sequence identity with the amino acid sequence consisting of amino acid residues 20 to 466 in SEQ ID NO: 41 and having a binding activity to human SIRPα; and a light chain consisting of an amino acid sequence having at least 95% sequence identity with amino acid residues 21 to 234 in SEQ ID NO: 37 and having a binding activity to human SIRPα;

(3) an antibody that binds specifically to human SIRPα to inhibit binding of human SIRPα to CD47, the antibody consisting of: a heavy chain consisting of an amino acid sequence consisting of amino acid residues 20 to 466 in SEQ ID NO: 41; and a light chain consisting of an amino acid sequence consisting of amino acid residues 21 to 234 in SEQ ID NO: 39;

(4) an antibody that binds specifically to human SIRPα to inhibit binding of human SIRPα to CD47, the antibody consisting of: a heavy chain consisting of an amino acid sequence having at least 95% sequence identity with the amino acid sequence consisting of amino acid residues 20 to 466 in SEQ ID NO: 41 and having a binding activity to human SIRPα; and a light chain consisting of an amino acid sequence having at least 95% sequence identity with the amino acid sequence consisting of amino acid residues 21 to 234 in SEQ ID NO: 39 and having a binding activity to human SIRPα;

(5) an antibody that binds specifically to human SIRPα to inhibit binding of human SIRPα to CD47, the antibody consisting of: a heavy chain consisting of an amino acid sequence consisting of amino acid residues 20 to 466 in SEQ ID NO: 43; and a light chain consisting of an amino acid sequence consisting of amino acid residues 21 to 234 in SEQ ID NO: 35;

(6) an antibody that binds specifically to human SIRPα to inhibit binding of human SIRPα to CD47, the antibody consisting of: a heavy chain consisting of an amino acid sequence having at least 95% sequence identity with the amino acid sequence consisting of amino acid residues 20 to 466 in SEQ ID NO: 43 and having a binding activity to human SIRPα; and a light chain consisting of an amino acid sequence having at least 95% sequence identity with the amino acid sequence consisting of amino acid residues 21 to 234 in SEQ ID NO: 35 and having a binding activity to human SIRPα;

(7) an antibody that binds specifically to human SIRPα to inhibit binding of human SIRPα to CD47, the antibody consisting of: a heavy chain consisting of an amino acid sequence consisting of amino acid residues 20 to 466 in SEQ ID NO: 43; and a light chain consisting of an amino acid sequence consisting of amino acid residues 21 to 234 in SEQ ID NO: 37; and (8) an antibody that binds specifically to human SIRPα to inhibit binding of human SIRPα to CD47, the antibody consisting of: a heavy chain consisting of an amino acid sequence having at least 95% sequence identity with the amino acid sequence consisting of amino acid residues 20 to 466 in SEQ ID NO: 43 and having a binding activity to human SIRPα; and a light chain consisting of an amino acid sequence having at least 95% sequence identity with the amino acid sequence consisting of amino acid residues 21 to 234 in SEQ ID NO: 37 and having a binding activity to human SIRPα.

[23] The antibody according to [22], wherein the ADCC and/or ADCP activity is reduced.

[24] An antibody that binds specifically to human SIRPα to inhibit binding of human SIRPα to CD47, wherein the antibody binds to an epitope comprising Gln at position 82, Lys at position 83, Glu at position 84, and Gly at position 85 in human SIRPα set forth in SEQ ID NO: 57.

[25] The antibody according to [24], wherein a heavy chain constant region is a heavy chain constant region of human IgG4, and has a mutation that reduces an ADCC and/or ADCP activity.

[26] The antibody according to [24] or [25], wherein a heavy chain constant region is a heavy chain constant region of human IgG4, and phenylalanine at position 234, as numbered according to the EU index as in Kabat et al., is substituted by alanine, leucine at position 235 is substituted by alanine, and serine at position 228 is substituted by proline.

[27] The antibody according to [26], wherein an amino acid sequence of the heavy chain constant region is an amino acid sequence consisting of amino acid residues 140 to 466 in SEQ ID NO: 25.

[28] The antibody according to any of [1] to [27], which enhances a phagocytic activity of a macrophage.

[29] The antibody according to any of [1] to [28], wherein a lysine residue at the carboxyl terminus of the heavy chain is deleted.

[30] An antigen-binding fragment of the antibody according to any of [1] to [29].

[31] The antigen-binding fragment of the antibody according to [30], which is selected from the group consisting of Fab, F(ab')2, Fab', and scFv.

[32] A pharmaceutical composition comprising the antibody according to any of [1] to [29] or the antigen-binding fragment of the antibody according to [30] or [31] as an active ingredient.

[33] The pharmaceutical composition according to [32], which is an anti-tumor agent.

[34] The pharmaceutical composition according to [33], which further comprises an immune checkpoint inhibitor and/or an antibody drug that specifically responds to a cancer antigen to have the ADCC and/or ADCP activity as an active ingredient of the anti-tumor agent.

[35] A pharmaceutical composition, which is used in combination with an immune checkpoint inhibitor and/or an antibody drug that specifically responds to a cancer antigen to have the ADCC and/or ADCP activity, wherein the pharmaceutical composition comprises the antibody according to any of [1] to [29] or the antigen-binding fragment of the antibody according to [30] or [31] as an active ingredient.

[36] The pharmaceutical composition according to [34] or [35], wherein the immune checkpoint inhibitor is an inhibitor of binding of PD-L1 and PD-1 or a CTLA4 inhibitor.

[37] The pharmaceutical composition according to [34] or [35], wherein the antibody drug that specifically responds to a cancer antigen to have the ADCC and/or ADCP activity is selected from the group consisting of an anti-CD20 antibody, an anti-HER2 antibody, and an anti-EGFR antibody.

[38] The pharmaceutical composition according to any of [33] to [37], wherein the tumor is one type or two or more types of tumors selected from the group consisting of carcinoma, sarcoma, lymphoma, leukemia, myeloma, germinoma, brain tumor, carcinoid, neuroblastoma, retinoblastoma, and nephroblastoma.

[39] The pharmaceutical composition according to [38], wherein the tumor is one type or two or more types of tumors selected from the group consisting of kidney cancer, melanoma, squamous cell cancer, basal cell cancer, conjunctival cancer, oral cancer, laryngeal cancer, pharyngeal cancer, thyroid cancer, lung cancer, breast cancer, esophageal cancer, gastric cancer, duodenal cancer, small intestinal cancer, colon cancer, rectal cancer, appendix cancer, anal cancer, liver cancer, gallbladder cancer, biliary cancer, pancreatic cancer, adrenal cancer, bladder cancer, prostate cancer, uterine cancer, vaginal cancer, liposarcoma, angiosarcoma, chondrosarcoma, rhabdomyosarcoma, Ewing's sarcoma, osteosarcoma, undifferentiated pleomorphic sarcoma, myxofibrosarcoma, malignant peripheral neurilemmoma, retroperitoneal sarcoma, synoviosarcoma, uterine sarcoma, gastrointestinal stromal tumor, leiomyosarcoma, epithelioid sarcoma, B-cell lymphoma, NK/T-cell lymphoma, Hodgkin's lymphoma, myeloid leukemia, lymphatic leukemia, myeloproliferative disease, myelodysplastic syndrome, multiple myeloma, testicular cancer, ovarian cancer, neuroglioma, and meningioma.

[40] A polynucleotide consisting of nucleotide sequences encoding amino acid sequences of a heavy chain and a light chain of the antibody according to any of [1] to [29].

[41] A vector comprising the polynucleotide according to [40].

[42] A host cell comprising the polynucleotide according to [40] or the vector according to [41].

[43] A method for producing the antibody according to any of [1] to [29], comprising culturing the host cell according to [42] and purifying an antibody from the culture.

[44] An antibody produced by the method according to [43].

The present specification encompasses the contents disclosed in Japanese Patent Application No. 2018-131116, to which the present application claims a priority.

Advantageous Effects of Invention

The anti-SIRPα antibody of the present invention potently inhibits an interaction between SIRPα expressed in a phagocyte and CD47 expressed on a tumor cell and inhibits transmission of a "Don't-eat-me" signal from the tumor cell to the phagocyte, while the antibody is safe because it does not have effector functions and therefore does not attack immune cells of the self The anti-SIRPα antibody of the present invention can exhibit excellent anti-tumor effects when it is used in combination with other antibody drugs having effector functions or other antibody drugs having an immune checkpoint inhibitory action.

BRIEF DESCRIPTION OF DRAWINGS

FIG. 1B shows the reactivity of humanized anti-human SIRPA antibodies to hmSIRPA constructs used for an epitope analysis of anti-SIRPA antibodies (i) to (iv) and the amino acid sequences of SIRPA constructs used for the epitope analysis of anti-SIRPA antibodies (v).

FIG. 4 shows a comparison of amino acid sequences of variants for the beta 5-6 loop portion of human SIRPA.

FIG. 8A shows the inhibitory activity of human chimeric anti-SIRPA antibodies (cD13, cF44, and cF63) against binding of human or monkey SIRPA and CD47 [(i) SIRPA_V1, (ii) SIRPA_V2, (iii) monkey SIRPA].

FIG. 8B shows the inhibitory activity of human chimeric anti-SIRPA antibodies (isotypes of cF44) against binding of human or monkey SIRPA and CD47 [(i) SIRPA_V1, (ii) SIRPA_V2, (iii) monkey SIRPA].

FIG. 9 shows ADCP activity against a Burkitt's lymphoma cell line when the anti-SIRPA antibody is used as a single agent (A) and when the anti-SIRPA antibody is used in combination with rituximab (B).

FIG. 11 shows a comparison of amino acid sequences of the heavy chain variable region of the D13 antibody, the variable region of a humanized antibody heavy chain hH1, and the variable region of a humanized antibody heavy chain hH2.

FIG. 12 shows a comparison of amino acid sequences of the light chain variable region of the D13 antibody, the variable region of a humanized antibody light chain hL2, the variable region of a humanized antibody heavy chain hL3, and the variable region of a humanized antibody light chain hL4.

FIG. 13A is graphs showing a binding activity of a humanized anti-SIRPA antibody to human SIRPA variants [(i) V1, (ii) V2, (iii) V3, and (iv) V4].

FIG. 13C is graphs showing a binding activity of a humanized anti-SIRPA antibody to human SIRPA variants [(i) V9, (ii) V10, (iii) monkey SIRPA, and (iv) mock].

FIG. 14A is graphs showing a binding activity of a humanized anti-SIRPA antibody to mouse SIRPA [(i) C57BL/6, (ii) BALB/c, and (iii) 1295v].

FIG. 17 shows a nucleotide sequence encoding the cD13 light chain and an amino acid sequence of the cD13 light chain.

FIG. 18 shows a nucleotide sequence encoding the cD13 heavy chain and an amino acid sequence of the cD13 heavy chain.

FIG. 19 shows a nucleotide sequence encoding the cF44 light chain and an amino acid sequence of the cF44 light chain.

FIG. 20 shows a nucleotide sequence encoding the cF44 heavy chain and an amino acid sequence of the cF44 heavy chain.

FIG. 21 shows a nucleotide sequence encoding the cF63 light chain and an amino acid sequence of the cF63 light chain.

FIG. 22 shows a nucleotide sequence encoding the cF63 heavy chain and an amino acid sequence of the cF63 heavy chain.

FIG. 23 shows a nucleotide sequence encoding hL2 and an amino acid sequence of hL2.

FIG. 24 shows a nucleotide sequence encoding hL3 and an amino acid sequence of hL3.

FIG. 25 shows a nucleotide sequence encoding hL4 and an amino acid sequence of hL4.

FIG. 26 shows a nucleotide sequence encoding hH1 and an amino acid sequence of hH1.

FIG. 27 shows a nucleotide sequence encoding hH2 and an amino acid sequence of hH2.

FIG. 28 shows sequences of the D13 antibody CDRs.

FIG. 29 shows sequences of the F44 antibody CDRs.

FIG. 30 shows sequences of the F63 antibody CDRs.

FIG. 34 shows amino acid sequences of the OSE-172 antibody heavy chain (OSE-172 hG4Pro) and light chain (OSE-172 hK).

FIG. 35 shows amino acid sequences of the KWAR23 antibody heavy chain (KWAR23 hG4Pro) and light chain (KWAR23 hK).

FIG. 36 shows amino acid sequences of the ADU-1805 antibody heavy chain (ADU-1805 hG2) and light chain (ADU-1805 hK).

DESCRIPTION OF EMBODIMENTS

Figure 1A:
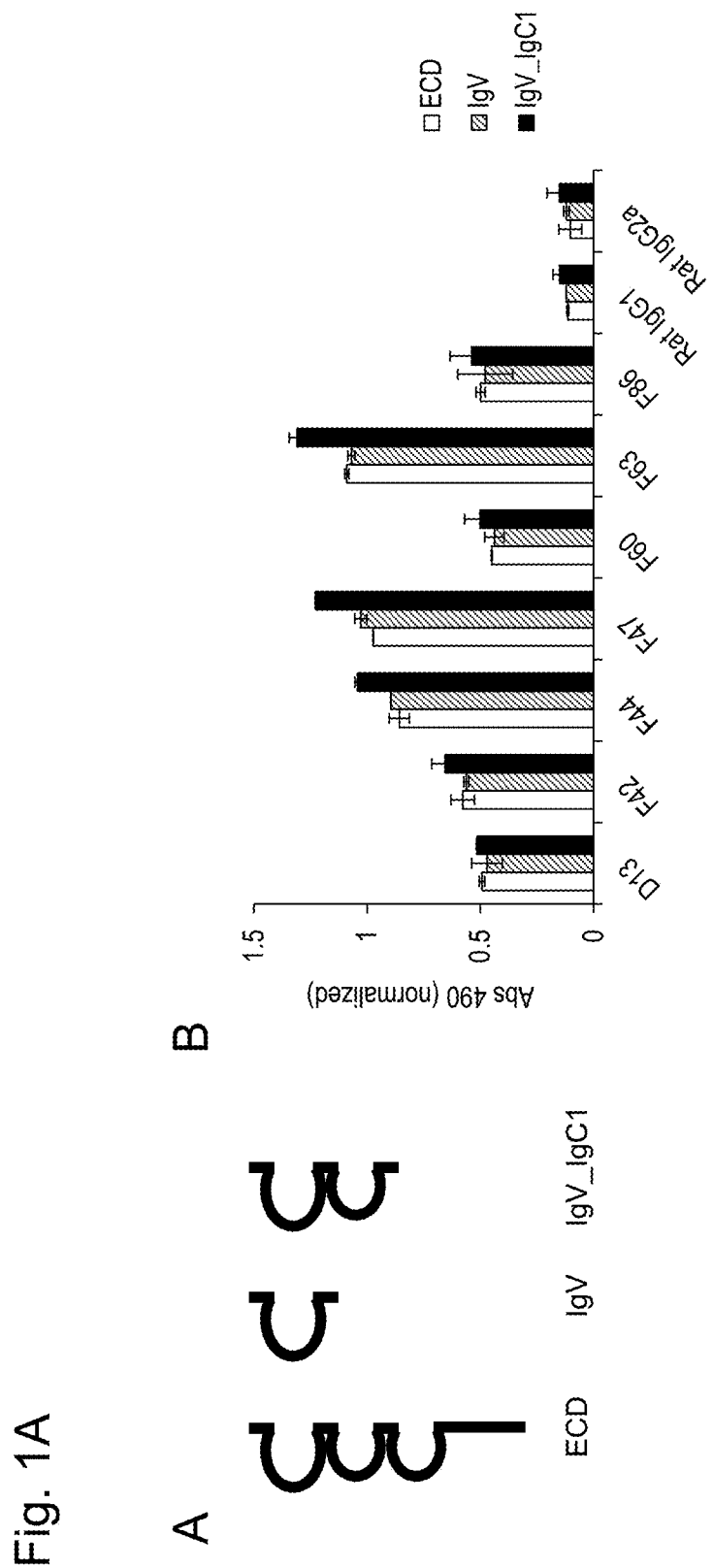
FIG. 1A illustrates structures of SIRPA constructs used for an epitope analysis of an anti-SIRPA antibody (A) and shows the reactivity of rat anti-human SIRPA antibodies to each construct (B).

The present invention is described in detail below.
Characteristics of Anti-SIRPα Antibody The present invention is an anti-SIRPα antibody that recognizes and binds to the extracellular IgV domain of an SIRPα protein.

A signal regulatory protein a (SIRPα) is a single-pass transmembrane molecule belonging to the Ig superfamily that is present in myeloid cells such as macrophages, dendritic cells, and neutrophils as well as glia cells. The extracellular region thereof consists of one IgV domain and two IgC domains, and 10 different variants V1 to V10 have been reported for the IgV domain, which is a CD47 binding site, in humans. The extracellular IgV domain of the SIRPα protein is an IgV domain which is one of three extracellular Ig-like domains constituting the SIRPα protein. Of the variants, V1 and V2 are major variants, and the anti-SIRPα antibody of the present invention binds to all variants including the major variants V1 and V2. In the present invention, "SIRPα" may be referred to as "SIRPA."

The amino acid sequence of the human SIRPα protein is disclosed as GenBank accession number NP_001035111.

A monoclonal antibody used in the present invention can be obtained as an antibody produced and secreted by a hybridoma prepared by immunizing a mammal such as mouse, rat, rabbit, hamster, guinea pig, equine, monkey, dog, swine, bovine, goat, and sheep with SIRPα or a fragment thereof as an immunogen and fusing a spleen cell or the like from the animal and myeloma. A hybridoma can be prepared by a known method.

SIRPα can also be chemically synthesized as an immunogen on the basis of sequence information and can also be obtained as a recombinant protein by a known method based on the sequence information of a DNA encoding the protein.

Screening for an antibody can be performed by an arbitrary method, but it is sufficient to perform screening preferably by cell-based ELISA using animal cells transfected with a DNA encoding SIRPα. An amino acid sequence of the V1 protein of human SIRPα is set forth in SEQ ID NO: 56 in the sequence listing, and an amino acid sequence of the V2 protein of human SIRPα is set forth in SEQ ID NO: 57 in the sequence listing.

The anti-SIRPα antibody of the present invention inhibits binding of SIRPα and CD47.

A tumor cell highly expresses CD47 and escapes from phagocytosis by a phagocyte when SIRPα expressed in the phagocyte having a phagocytic activity and CD47 bind and interact with each other to transmit a "Don't-eat-me" signal to the phagocyte. The anti-SIRPα antibody inhibits the binding of SIRPα and CD47 to inhibit the transmission of a "Don't-eat-me" signal from the tumor cell to the phagocyte and thereby enhances the phagocytic activity of the phagocyte against the tumor cell. As a result, anti-tumor effects can be induced. Examples of phagocytes having the phagocytic activity include macrophages, such as M1 and M2 macrophages, and dendritic cells such as immature dendritic cells (imDC).

At this time, the anti-SIRPα antibody has effector functions, and when it binds to an Fc receptor, such as the Fcγ receptor of a phagocyte, such as a macrophage, or an effector cell, such as a natural killer cell and a T cell, it attacks the effector cell, such as a peripheral blood mononuclear cell (PBMC) and a macrophage, of the self through antibody dependent cellular cytotoxicity (ADCC) or antibody dependent cellular phagocytosis (ADCP).

To prevent attacking cells of the self, the anti-SIRPα antibody of the present invention has reduced effector functions. As a result, the anti-SIRPα antibody of the present invention has only an effect of inhibiting the binding of SIRPα and CD47 and does not exhibit effector functions because it does not bind to the Fc receptor of an effector cell.

The anti-SIRPα antibody of the present invention can be used safely as a medicament without causing adverse drug reactions because it does not attack immune cells of the self However, the anti-SIRPα antibody of the present invention does not exhibit sufficient anti-tumor effects solely because the effector functions thereof are reduced. Therefore, it is used in combination with other anti-tumor agents as described later.

To reduce the effector functions, the Fc portion of the anti-SIRPα antibody needs to be prevented from binding to the Fc receptor of a macrophage or a T cell. Therefore, the anti-SIRPα antibody of the present invention has been replaced with an antibody derived from IgG4 as a subclass. In general, among human IgG subclasses, IgG4 is known as a subclass with low effector functions, such as an ADCC activity, CDC activity, and/or ADCP activity (Bruggemann et al., J. Exp. Med. 1987; 1351-1361). It is used as an IgG format to prevent cytotoxicity through the effector functions when a therapeutic antibody targets a molecule expressed in a normal organ (e.g., Opdivo). However, the low effector functions of the IgG4 subclass do not mean that it has no effector functions at all. Accordingly, the anti-SIRPα antibody of the present invention has a mutation introduced into the heavy chain constant region thereof, so that the effector functions are further reduced, that is, a substitution of one or more amino acids that reduces the ADCC and/or ADCP activity or the like. Examples of such a mutation include a substitution of phenylalanine at position 234, as shown in the EU index in Kabat et al. (Kabat et al., Sequences of proteins of immunological interest Fifth edition [1991]), by alanine (F234A) and a substitution of leucine at position 235 by alanine (L235A) (Parekh et al., mAbs. 2012; 310-318). Such a mutation in an antibody is called FALA mutation. Phenylalanine at position 234, as numbered according to the EU index as in Kabat et al., may be referred to as phenylalanine of EU numbering 234.

Furthermore, because formation of the SS bond between the antibody heavy chains of IgG4 is not stable, a mutation that promotes the formation of the SS bond between antibody heavy chains is introduced to increase stability thereof. Examples of such a mutation include a substitution of serine at position 228, as numbered according to the EU index as in Kabat et al. (Angal et al., Molecular Immunology. 1993; 105-108), by proline (S228P). This antibody mutation is called PRO mutation.

The above-mentioned FALA mutation and PRO mutation may be simultaneously introduced into the constant regions of the antibody of the present invention (Vafa et al., Methods. 2014; 65, 114-126). An IgG4 heavy chain having both the FALA mutation and the PRO mutation is called an "IgG4proFALA" type heavy chain, "IgG4PFALA" type heavy chain, or "IgG4pf" type heavy chain.

The antibody heavy chain constant region consists of CH1, hinge, CH2, and CH3 regions. CH1 is defined as EU index 118 to 215, the hinge is defined as EU index 216 to 230, CH2 is defined as EU index 231 to 340, and CH3 is defined as EU index 341 to 446. Alanine by which phenylalanine at position 234, as numbered according to the EU index as in Kabat et al., is substituted corresponds to alanine at position 253 in SEQ ID NO: 25, which represents an amino acid sequence of the D13 antibody heavy chain, alanine at position 252 in SEQ ID NO: 29, which represents an amino acid sequence of the F44 antibody heavy chain, and alanine at position-257 in SEQ ID NO: 33, which represents an amino acid sequence of the F63 antibody heavy chain; and alanine by which leucine at position 235 is substituted corresponds to alanine at position 254 in SEQ ID NO: 25, alanine at position 253 in SEQ ID NO: 29, and alanine at position 258 in SEQ ID NO: 33. Further, proline by which serine at position 228, as numbered according to the EU index as in Kabat et al., is substituted corresponds to proline at position 247 in SEQ ID NO: 25, proline at position 246 in SEQ ID NO: 29, and proline at position 251 in SEQ ID NO: 33.

Amino acid sequences of the "IgG4proFALA" type heavy chain constant region are an amino acid sequence consisting of amino acid residues 140 to 466 in SEQ ID NO: 25, an amino acid sequence consisting of amino acid residues 139 to 465 in SEQ ID NO: 29, and an amino acid sequence consisting of amino acid residues 144 to 470 in SEQ ID NO: 33.

Among the human IgG subclasses, human IgG1 has very potent effector functions including a CDC activity through complement binding and an antibody-dependent cytotoxic activity (Bruggemann et al., J. Exp. Med. 1987; 1351-1361) and is utilized as an IgG format that exhibits therapeutic effects by inducing cancer cell death due to cell injury through effector functions when a therapeutic antibody is used to target a molecule highly expressed in cancer (e.g., trastuzumab, rituximab). When IgG1 is used as an isotype of the antibody of the present invention, effector functions can be regulated by substituting part of amino acid residues in the constant region (refer to International Publication Nos. WO 88/007089, WO 94/28027, and WO 94/29351). Examples of IgG1mutants having attenuated effector functions include IgG1 LALA (IgG1-L234A, IgG1-L235A) and IgG1 LAGA (IgG1-L235A, IgG1-G237A). The IgG1 heavy chain constant regions into which these mutations are introduced can also be used as a constant region of the antibody of the present invention.

Among the human IgG subclasses, human IgG2 has very weak effector functions including a CDC activity through complement binding and an antibody-dependent cytotoxic activity (Bruggemann et al., J. Exp. Med. 1987; 1351-1361) and is utilized as one of IgG formats to prevent cytotoxicity through effector functions when a therapeutic antibody is used to target a molecule expressed in a normal organ (e.g., denosumab, evolocumab, brodalumab). The IgG2 heavy chain constant region can also be used as the constant region of the antibody of the present invention.

The anti-SIRPα antibody of the present invention has species cross-reactivity, such that it binds to human and monkey (cynomolgus monkey) SIRPα but not to mouse SIRPα.

Human Chimeric Antibodies and Humanized Antibodies

The anti-SIRPα antibody of the present invention includes a human chimeric antibody and a humanized antibody modified to reduce heterogeneous antigenicity against humans. The humanized antibody is also referred to as a CDR transplanted antibody.

Human Chimeric Antibodies

A human chimeric antibody refers to an antibody consisting of a light chain variable region and a heavy chain variable region of an antibody of an animal other than humans and a light chain constant region and a heavy chain constant region of a human antibody. The human chimeric antibody can be prepared by collecting a cDNA encoding the light chain variable region and a cDNA encoding the heavy chain variable region from a hybridoma producing the anti-SIRPα antibody, inserting the cDNAs into an expression vector having cDNAs encoding the light chain constant region and the heavy chain constant region of the human antibody to construct a human chimeric antibody expression vector, and introducing the expression vector into a host cell for expression.

The heavy chain constant region consists of three domains $C_H1$, $C_H2$, and $C_H3$. In the present invention, as described above, the human heavy chain constant region of a chimeric antibody is IgG4proFALA, which is the heavy chain constant region of the IgG4 subclass and has the PRO mutation and the FALA mutation. Further, it is sufficient that the light chain constant region belongs to the human Ig family, and the light chain constant region is a κ or λ constant region.

Examples of a human chimeric antibody of the anti-SIRPα antibody of the present invention include antibodies cD13, cF44, and cF63, which are human chimeric antibodies having the variable region of rat anti-human SIRPα monoclonal antibodies D13, F44, and F63. These three antibodies are antibodies having a high binding property to human SIRPα and having a high inhibitory activity against binding of SIRPα and CD47. Among these, the cD13 and cF63 antibodies having a high activity are preferred.

cD13 Antibodies

The nucleotide sequence of the cDNA encoding the light chain variable region of the cD13 antibody is a nucleotide sequence consisting of nucleotides 61 to 378 in SEQ ID NO: 22 in the sequence listing (FIG. 17), and the amino acid sequence of the light chain variable region of the cD13 antibody is an amino acid sequence consisting of amino acid residues 21 to 126 in SEQ ID NO: 23 in the sequence listing (FIG. 17).

Further, the nucleotide sequence of the cDNA encoding the heavy chain variable region of the cD13 antibody is a nucleotide sequence consisting of nucleotides 58 to 417 in SEQ ID NO: 24 in the sequence listing (FIG. 18), and the amino acid sequence of the heavy chain variable region of the cD13 antibody is an amino acid sequence consisting of amino acid residues 20 to 139 in SEQ ID NO: 25 in the sequence listing (FIG. 18).

That is, the anti-SIRPα antibody of the present invention is an anti-human SIRPα antibody that binds to human SIRPα, comprising: the light chain variable region comprising the amino acid sequence consisting of amino acid residues 21 to 126 in SEQ ID NO: 23; and the heavy chain variable region comprising the amino acid sequence consisting of amino acid residues 20 to 139 in SEQ ID NO: 25.

Further, DNAs consisting of a nucleotide sequence having a sequence identity of at least 85%, preferably at least 90%, more preferably at least 95%, particularly preferably at least 97%, at least 98%, or at least 99% calculated using the above-mentioned nucleotide sequence consisting of nucleotides 61 to 378 in SEQ ID NO: 22 or nucleotide sequence consisting of nucleotides 58 to 417 in SEQ ID NO: 24 and CLUSTAL W (an alignment tool) or the like (using, for example, default, i.e., initially set parameters) and encoding proteins having an activity of a light chain variable region or a heavy chain variable region of an antibody, that is, having a binding activity to human SIRPα are also included in DNAs encoding the light chain variable region or the heavy chain variable region of the antibody of the present invention.

Furthermore, DNAs that can be hybridized with a DNA consisting of a sequence complementary to the above-mentioned nucleotide sequence consisting of nucleotides 61 to 378 in SEQ ID NO: 22 or nucleotide sequence consisting of nucleotides 58 to 417 in SEQ ID NO: 24 under stringent conditions and encoding a protein having an activity of a light chain variable region or a heavy chain variable region of an antibody, that is, having a binding activity to human SIRPα are also included in DNAs encoding the light chain variable region or the heavy chain variable region of the present invention.

Furthermore, the above-mentioned light chain variable region or heavy chain variable region includes not only the light chain variable region or the heavy chain variable region consisting of the amino acid sequence consisting of amino acid residues 21 to 126 in SEQ ID NO: 23 or the amino acid sequence consisting of amino acid residues 20 to 139 in SEQ ID NO: 25, but also a light chain variable region or a heavy chain variable region comprising a protein comprising an amino acid sequence derived from the above amino acid sequence by deletion, substitution, or addition of one or several, for example, one to 10, preferably one to five, more preferably one or two, more preferably one amino acid and having an activity of a heavy chain variable region or a light chain variable region of an antibody, that is, having a binding activity to the human SIRPα.

Examples of such an amino acid sequence derived from the amino acid sequence consisting of amino acid residues 21 to 126 in SEQ ID NO: 23 or the amino acid sequence consisting of amino acid residues 20 to 139 in SEQ ID NO: 25 by deletion, substitution, or addition of one or several amino acids include amino acid sequences having a sequence identity of at least 85%, preferably at least 90%, more preferably at least 95%, particularly preferably at least 97%, 98%, or 99% calculated using the amino acid sequence consisting of amino acid residues 21 to 126 in SEQ ID NO: 23 or the amino acid sequence consisting of amino acid residues 20 to 139 in SEQ ID NO: 25 and CLUSTAL W (an alignment tool) or the like (using, for example, default, i.e., initially set parameters).

Such a protein having an amino acid sequence derived from the amino acid sequence consisting of amino acid residues 21 to 126 in SEQ ID NO: 23 or the amino acid sequence consisting of amino acid residues 20 to 139 in SEQ ID NO: 25 by deletion, substitution, or addition of one or several amino acids is substantially identical to the protein having the amino acid sequence consisting of amino acid residues 21 to 126 in SEQ ID NO: 23 or the amino acid sequence consisting of amino acid residues 20 to 139 in SEQ ID NO: 25.

Further, the cD13 antibody comprises CDRL1 consisting of an amino acid sequence set forth in SEQ ID NO: 1 (GASKSVRTYMH), CDRL2 consisting of an amino acid sequence set forth in SEQ ID NO: 2 (SASNLEA), and CDRL3 consisting of an amino acid sequence set forth in SEQ ID NO: 3 (QQSNEPPYT) as complementarity determining regions (CDRs) of the light chain variable region and further comprises CDRH1 consisting of an amino acid sequence set forth in SEQ ID NO: 4 (GFTFSDYGMI), CDRH2 consisting of an amino acid sequence set forth in SEQ ID NO: 5 (SISSSSSYIY), and CDRH3 consisting of an amino acid sequence set forth in SEQ ID NO: 6 (RYYGFNYPFDY) as CDRs of the heavy chain variable region (FIG. 28).

That is, the anti-SIRPα antibody of the present invention is an antibody that comprises CDRL1 consisting of the amino acid sequence set forth in SEQ ID NO: 1, CDRL2 consisting of the amino acid sequence set forth in SEQ ID NO: 2, and CDRL3 consisting of the amino acid sequence set forth in SEQ ID NO: 3 and further comprises CDRH1 consisting of the amino acid sequence set forth in SEQ ID NO: 4, CDRH2 consisting of the amino acid sequence set forth in SEQ ID NO: 5, and CDRH3 consisting of the amino acid sequence set forth in SEQ ID NO: 6 as CDRs of the heavy chain variable region.

The above-mentioned CDRs include CDRs consisting of an amino acid sequence derived from the amino acid sequence representing each CDR by deletion, substitution, or addition of one or several, preferably one or two, more preferably one amino acid.

The chimeric or humanized D13 antibody binds to a SIRPα variants consisting of an amino acid sequence set forth in SEQ ID NO: 73 but does not bind to a SIRPα variant consisting of an amino acid sequence set forth in SEQ ID NO: 74 or 75. Since the NQKEG sequence (SEQ ID NO: 76) in the amino acid sequence set forth in SEQ ID NO: 73 is substituted by the NQKEE sequence (SEQ ID NO: 77) in SEQ ID NO: 74 and the SFTEG sequence (SEQ ID NO: 80) in SEQ ID NO: 75, it was found that binding of the chimeric or humanized antibody D13 and SIRPα requires the NQKEG sequence (SEQ ID NO: 76). X-ray crystallography has suggested that the cD13 antibody binds to SIRPα via amino acid residues Gln82, Lys83, Glu84, Gly85, His86, and Phe87 (the position of each amino acid residue corresponds to that in SEQ ID NO: 57 in the sequence listing) in SEQ ID NO: 57 representing human SIRPα Variant 2, and a sequence comprising Gln82, Lys83, Glu84, and Gly85 corresponds to the QKEG portion in the above-mentioned NQKEG sequence. Therefore, the NQKEG sequence is an epitope essential for binding of the D13 antibody and human SIRPα. An antibody having an epitope identical to that of the D13 antibody can be selected by selecting an antibody that binds to an antibody that specifically recognizes the NQKEG sequence (SEQ ID NO: 76), that is, an antibody that binds to a SIRPα variant consisting of the amino acid sequence set forth in SEQ ID NO: 73, which has the NQKEG sequence (SEQ ID NO: 76), but does not bind to a SIRPα variant consisting of the amino acid sequence set forth in SEQ ID NO: 74 or 75 and not having the NQKEG sequence.

cF44 Antibodies

The nucleotide sequence of the cDNA encoding the light chain variable region of the cF44 antibody is a nucleotide sequence consisting of nucleotides 61 to 381 in SEQ ID NO: 26 in the sequence listing (FIG. 19), and the amino acid sequence of the light chain variable region of the cF44 antibody is an amino acid sequence consisting of amino acid residues 21 to 127 in SEQ ID NO: 27 in the sequence listing (FIG. 19).

Further, the nucleotide sequence of the cDNA encoding the heavy chain variable region of the cF44 antibody is a nucleotide sequence consisting of nucleotides 58 to 414 in SEQ ID NO: 28 in the sequence listing (FIG. 20), and the amino acid sequence of the heavy chain variable region of the cF44 antibody is an amino acid sequence consisting of amino acid residues 20 to 138 in SEQ ID NO: 29 in the sequence listing (FIG. 20).

That is, the anti-SIRPα antibody of the present invention is an anti-human SIRPα antibody that binds to human SIRPα, comprising: the light chain variable region comprising the amino acid sequence consisting of amino acid residues 21 to 127 in SEQ ID NO: 27; and the heavy chain variable region comprising the amino acid sequence consisting of amino acid residues 20 to 138 in SEQ ID NO: 29.

Further, DNAs consisting of a nucleotide sequence having a sequence identity of at least 85%, preferably at least 90%, more preferably at least 95%, particularly preferably at least 97%, at least 98%, or at least 99% calculated using the above-mentioned nucleotide sequence consisting of nucleotides 61 to 381 in SEQ ID NO: 26 or nucleotide sequence consisting of nucleotides 58 to 414 in SEQ ID NO: 28 and CLUSTAL W (an alignment tool) or the like (using, for example, default, i.e., initially set parameters) and encoding proteins having an activity of a light chain variable region or a heavy chain variable region of an antibody, that is, having a binding activity to human SIRPα are also included in DNAs encoding the light chain variable region or the heavy chain variable region of the antibody of the present invention.

Furthermore, DNAs that can be hybridized with a DNA consisting of a sequence complementary to the above-mentioned nucleotide sequence consisting of nucleotides 61 to 381 in SEQ ID NO: 26 or nucleotide sequence consisting of nucleotides 58 to 414 in SEQ ID NO: 28 under stringent conditions and encoding a protein having an activity of a light chain variable region or a heavy chain variable region of an antibody, that is, having a binding activity to human SIRPα are also included in DNAs encoding the light chain variable region or the heavy chain variable region of the present invention.

Furthermore, the above-mentioned light chain variable region or heavy chain variable region includes not only the light chain variable region or the heavy chain variable region consisting of the amino acid sequence consisting of amino acid residues 21 to 127 in SEQ ID NO: 27 or the amino acid sequence consisting of amino acid residues 20 to 138 in SEQ ID NO: 29, but also a light chain variable region or a heavy chain variable region comprising a protein comprising an amino acid sequence derived from the above amino acid sequence by deletion, substitution, or addition of one or several, for example, one to 10, preferably one to five, more preferably one or two, more preferably one amino acid and having an activity of a heavy chain variable region or a light chain variable region of an antibody, that is, having a binding activity to the human SIRPα.

Examples of such an amino acid sequence derived from the amino acid sequence consisting of amino acid residues 21 to 127 in SEQ ID NO: 27 or the amino acid sequence consisting of amino acid residues 20 to 138 in SEQ ID NO: 29 by deletion, substitution, or addition of one or several amino acids include amino acid sequences having a sequence identity of at least 85%, preferably at least 90%, more preferably at least 95%, particularly preferably at least 97%, at least 98%, or at least 99% calculated using the amino acid sequence consisting of amino acid residues 21 to 127 in SEQ ID NO: 27 or the amino acid sequence consisting of amino acid residues 20 to 138 in SEQ ID NO: 29 and CLUSTAL W (an alignment tool) or the like (using, for example, default, i.e., initially set parameters).

Such a protein having an amino acid sequence derived from the amino acid sequence consisting of amino acid residues 21 to 127 in SEQ ID NO: 27 or the amino acid sequence consisting of amino acid residues 20 to 138 in SEQ ID NO: 29 by deletion, substitution, or addition of one or several amino acids is substantially identical to the protein having the amino acid sequence consisting of amino acid residues 21 to 127 in SEQ ID NO: 27 or the amino acid sequence consisting of amino acid residues 20 to 138 in SEQ ID NO: 29.

Further, the cF44 antibody comprises CDRL1 consisting of an amino acid sequence set forth in SEQ ID NO: 7 (KASKSISKYLA), CDRL2 consisting of an amino acid sequence set forth in SEQ ID NO: 8 (SGSTLQS), and CDRL3 consisting of an amino acid sequence set forth in SEQ ID NO: 9 (QQHNEYPPT) as complementarity determining regions (CDRs) of the light chain variable region and further comprises CDRH1 consisting of an amino acid sequence set forth in SEQ ID NO: 10 (GFTFSNYYMA), CDRH2 consisting of an amino acid sequence set forth in SEQ ID NO: 11 (YITTGGGSTY), and CDRH3 consisting of an amino acid sequence set forth in SEQ ID NO: 12 (ANYGGSYFDY) as CDRs of the heavy chain variable region (FIG. 29).

That is, the anti-SIRPα antibody of the present invention is an antibody that comprises CDRL1 consisting of the amino acid sequence set forth in SEQ ID NO: 7, CDRL2 consisting of the amino acid sequence set forth in SEQ ID NO: 8, and CDRL3 consisting of the amino acid sequence set forth in SEQ ID NO: 9 and further comprises CDRH1 consisting of the amino acid sequence set forth in SEQ ID NO: 10, CDRH2 consisting of the amino acid sequence set forth in SEQ ID NO: 11, and CDRH3 consisting of the amino acid sequence set forth in SEQ ID NO: 12 as CDRs of the heavy chain variable region.

The above-mentioned CDRs include CDRs consisting of an amino acid sequence derived from the amino acid sequence representing each CDR by deletion, substitution, or addition of one or several, preferably one or two, more preferably one amino acid.

cF63 Antibodies

The nucleotide sequence of the cDNA encoding the light chain variable region of the cF63 antibody is a nucleotide sequence consisting of nucleotides 61 to 390 in SEQ ID NO: 30 in the sequence listing (FIG. 21), and the amino acid sequence of the light chain variable region of the cF63 antibody is an amino acid sequence consisting of amino acid residues 21 to 130 in SEQ ID NO: 31 in the sequence listing (FIG. 21).

Further, the nucleotide sequence of the cDNA encoding the heavy chain variable region of the cF63 antibody is a nucleotide sequence consisting of nucleotides 58 to 429 in SEQ ID NO: 32 in the sequence listing (FIG. 22), and the amino acid sequence of the heavy chain variable region of the cF63 antibody is an amino acid sequence consisting of amino acid residues 20 to 143 in SEQ ID NO: 33 in the sequence listing (FIG. 22).

That is, the anti-SIRPα antibody of the present invention is an anti-human SIRPα antibody that binds to human SIRPα, comprising: the light chain variable region comprising the amino acid sequence consisting of amino acid residues 21 to 130 in SEQ ID NO: 31; and the heavy chain variable region comprising the amino acid sequence consisting of amino acid residues 20 to 143 in SEQ ID NO: 33.

Further, DNAs consisting of a nucleotide sequence having a sequence identity of at least 85%, preferably at least 90%, more preferably at least 95%, particularly preferably at least 97%, at least 98%, or at least 99% calculated using the above-mentioned nucleotide sequence consisting of nucleotides 61 to 390 in SEQ ID NO: 30 or nucleotide sequence consisting of nucleotides 58 to 429 in SEQ ID NO: 32 and CLUSTAL W (an alignment tool) or the like (using, for example, default, i.e., initially set parameters) and encoding proteins having an activity of a light chain variable region or a heavy chain variable region of an antibody, that is, having a binding activity to human SIRPα are also included in DNAs encoding the light chain variable region or the heavy chain variable region of the antibody of the present invention.

Furthermore, DNAs that can be hybridized with a DNA consisting of a sequence complementary to the above-mentioned nucleotide sequence consisting of nucleotides 61 to 390 in SEQ ID NO: 30 or nucleotide sequence consisting of nucleotides 58 to 429 in SEQ ID NO: 32 under stringent conditions and encoding a protein having an activity of a light chain variable region or a heavy chain variable region of an antibody, that is, having a binding activity to human SIRPα are also included in DNAs encoding the light chain variable region or the heavy chain variable region of the present invention.

Furthermore, the above-mentioned light chain variable region or heavy chain variable region includes not only the light chain variable region or the heavy chain variable region consisting of the amino acid sequence consisting of amino acid residues 21 to 130 in SEQ ID NO: 31 or the amino acid sequence consisting of amino acid residues 20 to 143 in SEQ ID NO: 33, but also a light chain variable region or a heavy chain variable region comprising a protein comprising an amino acid sequence derived from the above amino acid sequence by deletion, substitution, or addition of one or several, for example, one to 10, preferably one to five, more preferably one or two, more preferably one amino acid and having an activity of a heavy chain variable region or a light chain variable region of an antibody, that is, having a binding activity to the human SIRPα.

Examples of such an amino acid sequence derived from the amino acid sequence consisting of amino acid residues 21 to 130 in SEQ ID NO: 31 or the amino acid sequence consisting of amino acid residues 20 to 143 in SEQ ID NO: 33 by deletion, substitution, or addition of one or several amino acids include amino acid sequences having a sequence identity of at least 85%, preferably at least 90%, more preferably at least 95%, particularly preferably at least 97%, at least 98%, or at least 99% calculated using the amino acid sequence consisting of amino acid residues 21 to 130 in SEQ ID NO: 31 or the amino acid sequence consisting of amino acid residues 20 to 143 in SEQ ID NO: 33 and CLUSTAL W (an alignment tool) or the like (using, for example, default, i.e., initially set parameters).

Such a protein having an amino acid sequence derived from the amino acid sequence consisting of amino acid residues 21 to 130 in SEQ ID NO: 31 or the amino acid sequence consisting of amino acid residues 20 to 143 in SEQ ID NO: 33 by deletion, substitution, or addition of one or several amino acids is substantially identical to the protein having the amino acid sequence consisting of amino acid residues 21 to 130 in SEQ ID NO: 31 or the amino acid sequence consisting of amino acid residues 20 to 143 in SEQ ID NO: 33.

Further, the cF63 antibody comprises CDRL1 consisting of an amino acid sequence set forth in SEQ ID NO: 13 (ERSSGDIGDSYVS), CDRL2 consisting of an amino acid sequence set forth in SEQ ID NO: 14 (ADDQRPS), and CDRL3 consisting of an amino acid sequence set forth in SEQ ID NO: 15 (QSYDSKIDI) as complementarity determining regions (CDRs) of the light chain variable region and further comprises CDRH1 consisting of an amino acid sequence set forth in SEQ ID NO: 16 (GFSLASYSLS), CDRH2 consisting of an amino acid sequence set forth in SEQ ID NO: 17 (RMYYDGDTA), and CDRH3 consisting of an amino acid sequence set forth in SEQ ID NO: 18 (DRSMFGTDYPHWYFDF) as CDRs of the heavy chain variable region (FIG. 30).

That is, the anti-SIRPα antibody of the present invention is an antibody that comprises CDRL1 consisting of the amino acid sequence set forth in SEQ ID NO: 13, CDRL2 consisting of the amino acid sequence set forth in SEQ ID NO: 14, and CDRL3 consisting of the amino acid sequence set forth in SEQ ID NO: 15 and further comprises CDRH1 consisting of the amino acid sequence set forth in SEQ ID NO: 16, CDRH2 consisting of the amino acid sequence set forth in SEQ ID NO: 17, and CDRH3 consisting of the amino acid sequence set forth in SEQ ID NO: 18 as CDRs of the heavy chain variable region.

The above-mentioned CDRs include CDRs consisting of an amino acid sequence derived from the amino acid sequence representing each CDR by deletion, substitution, or addition of one or several, preferably one or two, more preferably one amino acid.

Humanized Antibodies

A humanized antibody (CDR-transplanted antibody) refers to an antibody obtained by transplanting amino acid sequences of CDRs of a light chain variable region and a heavy chain variable region of an antibody of an animal other than humans to a light chain variable region and a heavy chain variable region of a human antibody at appropriate positions.

The humanized anti-SIRPα antibody of the present invention can be produced by constructing cDNAs encoding variable regions obtained by transplanting amino acid sequences of CDRs of the light chain variable region and the heavy chain variable region of an antibody of an animal other than humans produced from a hybridoma producing a monoclonal antibody that enhances the phagocytic activity of a macrophage by binding to human SIRPα to inhibit the binding of SIRPα and CD47 into a framework (FR) region of the light chain variable region and the heavy chain variable region of an arbitrary human antibody, inserting them into an animal cell expression vector carrying genes encoding the light chain constant region and the heavy chain constant region of the human antibody to construct a humanized antibody expression vector, and introducing the expression vector into an animal cell to make expressed.

Specifically, it is sufficient to synthesize a DNA sequence designed so that CDRs of the D13, F44, or F63 antibody and a framework region of a human antibody are joined. The framework region of a human antibody joined through CDRs is selected so that the CDRs form a favorable antigen binding site. Further, if necessary, amino acids in the framework region in the antibody variable region may be substituted so that a CDR of a humanized antibody forms an appropriate antigen binding site. A humanized antibody to which CDRs are transplanted can be prepared by a known CDR grafting technique.

Examples of a heavy chain of a humanized antibody having CDRs in the heavy chain variable region of the D13 antibody (six CDRs consisting of amino acids set forth in SEQ ID NOS: 1 to 6), in which part of amino acids in the framework region in the variable region are substituted by the above-mentioned method, include a humanized antibody heavy chain hH1 and a humanized antibody heavy chain hH2. Further, examples of a light chain of a humanized antibody having CDRs in the light chain variable region of the D13 antibody, in which part of amino acids of the framework region in the variable region are substituted, include a humanized antibody light chain hL2, a humanized antibody light chain hL3, and a humanized antibody light chain hL4.

The full-length nucleotide sequence of the humanized antibody heavy chain hH1 is set forth in SEQ ID NO: 40, and the amino acid sequence thereof is set forth in SEQ ID NO: 41. Further, the full-length nucleotide sequence of the humanized antibody heavy chain hH2 is set forth in SEQ ID NO: 42, and the amino acid sequence thereof is set forth in SEQ ID NO: 43. In SEQ ID NOS: 40 and 42, a nucleotide sequence consisting of nucleotides 1 to 57 encodes the signal sequence, a nucleotide sequence consisting of nucleotides 58 to 417 encodes the variable region, and a nucleotide sequence consisting of nucleotides 418 to 1398 encodes the constant region. Further, in SEQ ID NOS: 41 and 43, an amino acid sequence consisting of amino acid residues 1 to 19 is an amino acid sequence of the signal sequence, an amino acid sequence consisting of amino acid residues 20 to 139 is an amino acid sequence of the variable region, and an amino acid sequence consisting of amino acid residues 140 to 466 is an amino acid sequence of the constant region. FIG. 11 shows a comparison of the amino acid sequences (including the signal sequences) of the variable region of the D13 antibody heavy chain, the variable region of the humanized antibody heavy chain hH1, and the variable region of the humanized antibody heavy chain hH2.

The anti-SIRPα antibody of the present invention includes antibodies having a heavy chain variable region consisting of amino acid residues 20 to 139 and a heavy chain constant region consisting of amino acid residues 140 to 466 in SEQ ID NO: 41 or 43.

The full-length nucleotide sequence of the humanized antibody light chain hL2 is set forth in SEQ ID NO: 34, and the amino acid sequence thereof is set forth in SEQ ID NO: 35. Further, the full-length nucleotide sequence of the humanized antibody light chain hL3 is set forth in SEQ ID NO: 36, and the amino acid sequence thereof is set forth in SEQ ID NO: 37. Further, the full-length nucleotide sequence of the humanized antibody light chain hL4 is set forth in SEQ ID NO: 38, and the amino acid sequence thereof is set forth in SEQ ID NO: 39. In SEQ ID NOS: 34, 36, and, 38, a nucleotide sequence consisting of nucleotides 1 to 60 encodes the signal sequence, a nucleotide sequence consisting of nucleotides 61 to 381 encodes the variable region, and a nucleotide sequence consisting of nucleotides 382 to 702 encodes the constant region. In SEQ ID NOS: 35, 37, and 39, an amino acid sequence consisting of amino acid residues 1 to 20 is an amino acid sequence of the signal sequence, an amino acid sequence consisting of amino acid residues 21 to 127 is an amino acid sequence of the variable region, and an amino acid sequence consisting of amino acid residues 128 to 234 is an amino acid sequence of the constant region. FIG. 12 shows a comparison of amino acid sequences (including the signal sequences) of the variable region of the D13 antibody light chain, the variable region of the humanized antibody light chain hL2, the variable region of the humanized antibody heavy chain hL3, and the variable region of the humanized antibody light chain hL4.

The anti-SIRPα antibody of the present invention includes antibodies comprising: a variable region consisting of amino acid residues 21 to 127; and a light chain constant region consisting of amino acid residues 128 to 234 in SEQ ID NO: 35, 37, or 39.

The heavy chain constant region of the humanized antibody is the heavy chain constant region IgG4proFALA, which is a heavy chain constant region of an IgG4 subclass and has the PRO mutation and the FALA mutation.

Examples of an antibody having a high binding property to human SIRPα and a high inhibitory activity against binding of SIRPα and CD47 include an antibody consisting of the humanized antibody heavy chain hH1 and the humanized antibody light chain hL3 (hD13_H1L3 antibody), an antibody consisting of the humanized antibody heavy chain hH1 and the humanized antibody light chain hL4 (hD13_H1L4 antibody), an antibody consisting of the humanized antibody heavy chain hH2 and the humanized antibody light chain hL2 (hD13_H2L2 antibody), and an antibody consisting of the humanized antibody heavy chain hH2 and humanized antibody light chain hL3 (hD13_H2L3 antibody).

The hD13_H1L3 antibody is an antibody having a heavy chain consisting of amino acid residues 20 to 466 in SEQ ID NO: 41 and a light chain consisting of amino acid residues 21 to 234 in SEQ ID NO: 37.

The hD13_H1L4 antibody is an antibody having a heavy chain consisting of amino acid residues 20 to 466 in SEQ ID NO: 41 and a light chain consisting of amino acid residues 21 to 234 in SEQ ID NO: 39.

The hD13_H2L2 antibody is an antibody having a heavy chain consisting of amino acid residues 20 to 466 in SEQ ID NO: 43 and a light chain consisting of amino acid residues 21 to 234 in SEQ ID NO: 35.

The hD13_H2L3 antibody is an antibody having a heavy chain consisting of amino acid residues 20 to 466 in SEQ ID NO: 43 and a light chain consisting of amino acid residues 21 to 234 in SEQ ID NO: 37.

It is known that a lysine residue at the carboxyl terminus of the heavy chain of an antibody produced in a cultured mammal cell is deleted (Tsubaki et al., Int. J. Biol. Macromol. 2013; 139-147). However, this deletion in the heavy chain sequence does not affect an ability to bind to an antigen or the effector functions (e.g., activation of complements and antibody dependent cytotoxic action) of an antibody. Therefore, the present invention also includes an antibody in which a lysine residue at the carboxyl terminus of the heavy chain is deleted.

Other Antibodies

The antibody of the present invention may be an antigen-binding fragment of an antibody having an antigen binding site of an antibody or a modified fragment thereof. The antibody fragment can be obtained by treating an antibody with a proteolytic enzyme, such as papain or pepsin, or modifying an antibody gene using a genetic engineering technique and expressing the gene in a suitable cultured cell. Among such antibody fragments, a fragment carrying all or part of functions of a full-length antibody molecule can be called an antigen-binding fragment of an antibody. Common examples of functions of an antibody include an antigen-binding activity, an activity to neutralize the antigen activity, an activity to enhance the antigen activity, an antibody-dependent cytotoxic activity, a complement-dependent cytotoxic activity, and a complement-dependent cell-mediated cytotoxic activity. The function of an antigen-binding fragment of an antibody in the present invention is a SIRPα binding activity.

Examples of antibody fragments include Fab, F(ab')2, variable region (Fv), a single chain Fv (scFv) which has Fv of the heavy chain and the light chain joined with a suitable linker, a diabody (diabodies), and a linear antibody, and a polyspecific antibody formed with antibody fragments. Further, Fab' which is a monovalent fragment of the variable region of an antibody obtained by treating F(ab')2 in a reducing condition is also included in the antibody fragments.

Further, the antibody of the present invention may be a polyspecific antibody having specificity to at least two different antigens. Usually, such a molecule binds to two different antigens (i.e., bispecific antibody), and the "polyspecific antibody" in the present invention encompasses an antibody having specificity to more (e.g., three different) antigens.

The polyspecific antibody of the present invention can be a full-length antibody or a fragment of such an antibody [e.g., F(ab')2 of a bispecific antibody]. A bispecific antibody can be produced by binding the heavy chains and the light chains (HL pairs) of two different antibodies or fusing a hybridoma producing different monoclonal antibodies to prepare a bispecific antibody-producing fusion cell (Millstein et al., Nature. 1983; 305, 537-539).

The antibody of the present invention may be a single-chain antibody (also referred to as scFv). The single-chain antibody is obtained by joining the heavy chain variable region and the light chain variable region of an antibody with a polypeptide linker [Pluckthun, The Pharmacology of Monoclonal Antibodies, 113 [Rosenberg and Moore Ed., Springer Verlag, New York, 269-315 (1994)], Nature Biotechnology. 2005; 23, 1126-1136]. Further, a BiscFv fragment prepared by connecting two scFvs with a polypeptide linker can also be used as a bispecific antibody.

Methods for preparing a single-chain antibody are well known in the technical field (for example, refer to U.S. Pat. Nos. 4,946,778, 5,260,203, 5,091,513, 5,455,030, and the like). In this scFv, the heavy chain variable region and the light chain variable region are joined with a linker that does not form a conjugate, preferably a polypeptide linker (Huston, J. S. et al., Proc. Natl. Acad. Sci. U.S.A. 1988; 85, 5879-5883). The heavy chain variable region and the light chain variable region in the scFv may be derived from the same antibody or separate antibodies. As a polypeptide linker that joins variable regions, for example, an arbitrary single-chain peptide consisting of 12 to 19 residues is used.

A DNA encoding scFv is obtained by amplifying a DNA by PCR using the whole sequence or a DNA portion encoding an intended amino acid sequence of a DNA encoding a heavy chain or a heavy chain variable region of the antibody and a DNA encoding a light chain or a light chain variable region as a template and a primer pair that defines both ends and subsequently amplifying the DNA by combining a DNA encoding a polypeptide linker portion and primer pairs that define both ends so that each thereof is joined with the heavy chain or the light chain.

Further, once the DNA encoding scFv is prepared, an expression vector containing the DNA and a host transformed with the expression vector can be obtained according to a usual method, and scFv can be obtained by using the host according to a usual method. These antibody fragments can be produced by the host by obtaining the gene thereof and expressing them in the same manner as described above.

The antibody of the present invention may have an antigen affinity that is increased by polymerization. The antibody to be polymerized may be one kind of antibody or a plurality of antibodies that recognize a plurality of epitopes of the same antigen. Examples of a method for polymerizing an antibody include binding of the IgG CH3 domain and two scFv, binding to streptavidin, and introduction of a helix-turn-helix motif.

The antibody of the present invention may be a polyclonal antibody, which is a mixture of two or more different anti-SIRPα antibodies comprising different amino acid sequences. One example of the polyclonal antibody is a mixture of two or more different antibodies having different CDRs. When a mixture of cells producing different antibodies is cultured, an antibody purified from the culture can be used as such a polyclonal antibody (refer to International Publication WO 2004/061104).

As a modified antibody, an antibody connected to various molecules such as polyethylene glycol (PEG) can be used.

The antibody of the present invention may be an antibody conjugated with another drug (immunoconjugate). Examples of such antibodies include antibodies conjugated to a radioactive substance or a compound having a pharmacological action (Nature Biotechnology. 2005; 23, 1137-1146).

Further, a method of obtaining a single-chain immunoglobulin by joining the full-length sequences of the heavy chain and the light chain of an antibody using an appropriate linker is also known (Lee, H-S. et al., Molecular Immunology. 1999; 36, 61-71; Schirrmann, T. et al., mAbs. 2010; 2(1), 1-4). When dimerized, a single-chain immunoglobulin can have a structure and an activity similar to those of an antibody which is essentially a tetramer. Further, the antibody of the present invention may be an antibody that has a single heavy chain variable region and does not have a light chain sequence. Such an antibody is called a single-domain antibody (sdAb) or a nanobody, and, in fact, it has been reported that such an antibody is observed in camels or llamas, with a maintained ability to bind to an antigen [Muyldemans S. et al., Protein Eng. 1994; 7(9), 1129-35; Hamers-Casterman C. et al., Nature. 1993; 363(6428), 446-8]. The above-mentioned antibody can also be interpreted as one type of the antigen-binding fragment of antibody in the present invention.

Method for Producing Antibody

The antibody of the present invention can be produced in a cell as a recombinant antibody by inserting a DNA encoding a heavy chain variable region or a DNA encoding a light chain variable region into an expression vector, transforming a host cell for expression with the vector, and culturing the host cell.

As a DNA encoding an antibody, a DNA encoding the heavy chain is obtained by ligating a DNA encoding the heavy chain variable region and a DNA encoding the heavy chain constant region, and a DNA encoding the light chain is further obtained by ligating a DNA encoding the light chain variable region and a DNA encoding the light chain constant region.

The anti-SIRPα antibody of the present invention can be produced by inserting the above-mentioned DNA encoding the heavy chain and DNA encoding the light chain into an expression vector, transforming a host cell with the vector, and culturing the host cell. At this time, the above-mentioned DNA encoding the heavy chain and DNA encoding the light chain may be introduced into the same expression vector and the host cell may be transformed with the vector, or the DNA encoding the heavy chain and DNA encoding the light chain may be inserted into separate vectors and the host cell may be transformed with the two vectors. At this time, DNAs encoding the heavy chain variable region and the light chain variable region may be introduced into a vector into which a DNA encoding the heavy chain constant region and the DNA encoding a light chain constant region have been introduced beforehand. Further, the vector may contain a DNA encoding a signal peptide, which promotes secretion of an antibody from a host cell. In this case, the DNA encoding the signal peptide and the DNA encoding the antibody are ligated in-frame beforehand. An antibody can be obtained as a mature protein by removing the signal peptide after an antibody is produced.

At this time, the DNA encoding the heavy chain variable region, the DNA encoding the light chain variable region, the DNA obtained by ligating the DNA encoding the heavy chain variable region and the DNA encoding the heavy chain constant region, or the DNA obtained by ligating the DNA encoding the light chain variable region and the DNA encoding the light chain constant region may be functionally joined with elements such as a promoter, an enhancer, and a polyadenylation signal. The expression "functionally joined" used herein means joining elements so that they perform their functions.

Examples of an expression vector are not particularly limited as long as it can be replicated in a host, such as an animal cell, bacterium, and yeast, and include known plasmids and phages. Examples of a vector used to construct an expression vector include pcDNA (trade name) (Thermo Fisher Scientific Inc.), Flexi (registered trade name) vector (Promega), pUC19, pUEX2 (Amersham Pharmacia Biotech), pGEX-4T, pKK233-2 (Pharmacia), and pMAMneo (Clontech Laboratories, Inc.). As host cells, prokaryotic cells such as *Escherichia coli* and *Bacillus subtilis* and eukaryotic cells such as yeasts and animal cells can be used, but eukaryotic cells are preferably used. Examples of animal cells include HEK293 cell, which is a human embryonic kidney cell line, and Chinese hamster ovary (CHO) cell. It is sufficient to introduce an expression vector into a host cell by a known method to transform the host cell. Examples of the method include an electroporation method, a calcium phosphate precipitation method, and a DEAE-dextran transfection method. The produced antibody can be purified by usual protein isolation or purification methods. For example, affinity chromatography or other chromatography techniques, filtration, ultrafiltration, salting out, dialysis, and the like can be suitably selected and combined.

Anti-Tumor Agents

The present invention encompasses an anti-tumor agent comprising the anti-SIRPα antibody of the present invention as an active ingredient. However, the heavy chain constant region of the anti-SIRPα antibody of the present invention is a heavy chain constant region of the IgG4 subclass, which is the IgG4proFALA heavy chain constant region that has the PRO mutation and the FALA mutation, does not have effector functions, and has only a function of inhibiting transmission of a "Don't-eat-me" signal by inhibiting binding of SIRPα and CD47. Therefore, the anti-SIRPα antibody of the present invention alone cannot damage tumor cells sufficiently. Accordingly, the present invention is used in combination with other anti-tumor agents that have effector functions and can attack and damage tumor cells or with other anti-tumor agents that inhibit an immune checkpoint in an immune cell induced by tumor cells. Other anti-tumor agents for combination use bind to a tumor cell and can bring the tumor cell into contact with a phagocyte, such as macrophage. At this time, the anti-SIRPα antibody of the present invention inhibits binding of CD47 on the tumor cell and SIRPα in the phagocyte, thereby enhancing the phagocytic activity of the phagocyte against the tumor cell, resulting in tumor cell injury. That is, synergistic anti-tumor effects can be exhibited by using the anti-SIRPα antibody of the present invention and other anti-tumor agents in combination.

Examples of the anti-tumor agent to be used in combination with the anti-SIRPα antibody of the present invention include immune checkpoint inhibitors and antibody drugs that binds specifically to a cancer antigen to have the ADCC and/or ADCP activity. Examples of the immune checkpoint inhibitors include inhibitors of binding of PD-1 and PD-L1, a ligand thereof, and CTLA4 inhibitors, and specific examples thereof include anti-PD-1 antibodies (nivolumab, pembrolizumab, cemiplimab, spartalizumab, PDR-001, BI 754091), anti-PD-L1 antibodies (atezolizumab, avelumab, durvalumab), and anti-CTLA4 antibodies (ipilimumab, tremelimumab). Further, examples of antibody drugs that responds specifically to a cancer antigen to have the ADCC and/or ADCP activity include an anti-CD20 antibody (rituximab), an anti-HER2 antibody (trastuzumab), an anti-EGFR antibody (cetuximab), and an anti-CD52 antibody (alemtuzumab).

ADCC refers to a cell-mediated reaction that an Fcγ receptor-expressing nonspecific cytotoxic cell (e.g., NK cell, neutrophil, and macrophage) recognizes an antibody binding onto a target cell and then induces lysis of the target cell. FcγRIIC and FcγRIIIA are expressed in an NK cell, which is the primary cell responsible for ADCC, and FcγRI, FcγRIIA, FcγRIIC, and FcγRIIIA are expressed in a monocyte. Meanwhile, ADCP refers to an Fc receptor-expressing cell-mediated reaction that a phagocyte (e.g., macrophage, neutrophil) recognizes an antibody binding onto the target cell and then induces phagocytosis of the target cell into the cell. FcγRT, FcγRIIA, FcγRIIC, and FcγRIIIA are expressed in a monocyte, which is the primary cell responsible for ADCP.

The present invention includes an anti-tumor agent comprising an anti-SIRPα antibody as an active ingredient, which is used in combination with the above-mentioned other anti-tumor agents.

Further, the present invention includes an anti-tumor agent or a kit containing both an anti-tumor agent comprising an anti-SIRPα antibody as an active ingredient and the above-mentioned other anti-tumor agents.

An anti-tumor agent comprising the anti-SIRPα antibody of the present invention as an active ingredient and the above-mentioned other anti-tumor agents may be administered simultaneously or sequentially. Further, the administration sequence is not limited, and other anti-tumor agents may be administered after an anti-tumor agent comprising the anti-SIRPα antibody of the present invention as an active ingredient has been administered, or an anti-tumor agent comprising the anti-SIRPα antibody of the present invention as an active ingredient may be administered after other anti-tumor agents have been administered.

The anti-tumor agent of the present invention can be used for one type or two or more types of tumors selected from carcinoma, sarcoma, lymphoma, leukemia, myeloma, germinoma, brain tumor, carcinoid, neuroblastoma, retinoblastoma, and nephroblastoma. Specific examples of carcinoma include kidney cancer, melanoma, squamous cell cancer, basal cell cancer, conjunctival cancer, oral cancer, laryngeal cancer, pharyngeal cancer, thyroid cancer, lung cancer, breast cancer, esophageal cancer, gastric cancer, duodenal cancer, small intestinal cancer, colon cancer, rectal cancer, appendix cancer, anal cancer, liver cancer, gallbladder cancer, biliary cancer, pancreatic cancer, adrenal cancer, bladder cancer, prostate cancer, uterine cancer, and vaginal cancer. Specific examples of sarcoma include liposarcoma, angiosarcoma, chondrosarcoma, rhabdomyosarcoma, Ewing's sarcoma, osteosarcoma, undifferentiated pleomorphic sarcoma, myxofibrosarcoma, malignant peripheral neurilemmoma, retroperitoneal sarcoma, synoviosarcoma, uterine sarcoma, gastrointestinal stromal tumor, leiomyosarcoma, and epithelioid sarcoma. Specific examples of lymphoma include B-cell lymphoma, NK/T-cell lymphoma, and Hodgkin's lymphoma. Specific examples of leukemia include myeloid leukemia, lymphatic leukemia, myeloproliferative disease, and myelodysplastic syndrome. Specific examples of myeloma include multiple myeloma. Specific examples of germinoma include testicular cancer and ovarian cancer. Specific examples of brain tumor include neuroglioma and meningioma.

The anti-SIRPα antibody of the present invention enhances cell-mediated immunity when it is used in combination with other anti-tumor agents. The present invention also encompasses a cell-mediated immunity enhancer comprising the anti-SIRPα antibody as an active ingredient. In the cell-mediated immunity enhancer, cell-mediated immunity is enhanced along with enhancement of the functions of natural killer cells and/or T cells.

The anti-tumor agent of the present invention can contain an anti-SIRPα antibody in an amount effective for treatment, as well as pharmaceutically acceptable carriers, diluents, solubilizers, emulsifiers, preservatives, aids, and the like. The "pharmaceutically acceptable carriers" and the like can be suitably selected from a broad range according to the type of a target disease and the dosage form of a drug. An administration method for the anti-tumor agent of the present invention can be suitably selected. For example, the anti-tumor agent can be injected, and local injection, intraperitoneal injection, selective intravenous infusion, intravenous injection, subcutaneous injection, organ perfusate infusion, and the like can be employed. Further, an injection solution can be formulated using a carrier comprising a salt solution, a glucose solution, or a mixture of salt water and a glucose solution, various types of buffer solutions, or the like. Further, a powder may be formulated and mixed with a liquid carrier to prepare an injection solution before use.

Other administration methods can be suitably selected along with development of a formulation. For example, oral solutions, powders, pills, capsules, tablets, and the like can be applied for oral administration. For oral solutions, oral liquid preparations such as suspensions and syrups can be produced using water, saccharides such as sucrose, sorbitol, and fructose, glycols such as polyethylene glycol, oils such as sesame oil and soybean oil, preservatives such as alkyl parahydroxybenzoates, flavors such as strawberry flavor and peppermint, and the like. Powders, pills, capsules, and tablets can be formulated using excipients such as lactose, glucose, sucrose, and mannitol, disintegrating agents such as starch and alginate soda, lubricants such as magnesium stearate and talc, binders such as polyvinyl alcohol, hydroxypropyl cellulose, and gelatin, surfactants such as fatty acid esters, plasticizers such as glycerin, and the like. Tablets and capsules are preferred unit dosage forms for the composition of the present invention in that they are easily administered. Solid production carriers are used to produce tablets and capsules.

The effective dose of an antibody used for treatment can be changed according to characteristics of symptoms to be treated and the patient's age and condition and can be finally determined by a physician. For example, one dose is 0.0001 mg to 100 mg per kg of body weight. The predetermined dose may be administered once every one to 180 days, or the dose may be divided into two doses, three doses, four doses, or more doses per day at appropriate intervals.

EXAMPLES

The present invention is specifically described by the following examples, but these examples are not intended to limit the scope of the present invention.

Example 1. Preparation of Rat Anti-SIRPA Antibody

1)-1 Preparation of Expression Construct
1)-1-1 Construction of SIRPA_V1_ECD Expression Vector A DNA encoding a polypeptide obtained by linking HHHHHH to amino acids 1 to 373 on the C terminal side of the amino acid sequence of human SIRPA_V1 (NCBI Protein Database accession number NP_001035111) and a vector obtained by digesting pcDNA3.3-TOPO/LaxZ (Thermo Fisher Scientific Inc.) with restriction enzymes XbaI and PmeI were bound using In-Fusion HD Cloning Kit (Clontech Laboratories Inc.) to prepare a SIRPA_V1_ECD expression vector. The amino acid sequence of SIRPA_V1_ECD is set forth in SEQ ID NO: 45 in the sequence listing, and the nucleotide sequence encoding SIRPA_V1_ECD is set forth in SEQ ID NO: 44 in the sequence listing.

1)-1-2 Construction of SIRPA_V1_IgV Expression Vector

A SIRPA_V1_IgV expression vector was prepared in the same manner as in 1)-1-1 using a DNA encoding a polypeptide obtained by linking HHHHHH to amino acids 1 to 149 on the C terminal side of the amino acid sequence of SIRPA_V1 (NCBI Protein Database accession number NP_001035111). The amino acid sequence of SIRPA_V1_IgV is set forth in SEQ ID NO: 47 in the sequence listing, and the nucleotide sequence encoding SIRPA_V1_IgV is set forth in SEQ ID NO: 46 in the sequence listing.

1)-1-3 Construction of SIRPA_V2_ECD Expression Vector

A SIRPA_V2_ECD expression vector was prepared in the same manner as in 1)-1-1 using a DNA encoding a polypeptide obtained by linking HHHHHH to amino acids 1 to 372 on the C terminal side of the amino acid sequence of SIRPA_V2 [obtained by modifying the V1 sequence shown in JBC. 2014; 289(14), 10024]. The amino acid sequence of SIRPA_V2_ECD is set forth in SEQ ID NO: 49 in the sequence listing, and the nucleotide sequence encoding SIRPA_V2_ECD is set forth in SEQ ID NO: 48 in the sequence listing.

1)-1-4 Construction of SIRPA_V2_IgV Expression Vector

A SIRPA_V2_IgV expression vector was prepared in the same manner as in 1)-1-1 using a DNA encoding a polypeptide obtained by linking HHHHHH to amino acids 1 to 148 on the C terminal side of the amino acid sequence of SIRPA_V2. The amino acid sequence of SIRPA_V2_IgV is set forth in SEQ ID NO: 51 in the sequence listing, and the nucleotide sequence encoding SIRPA_V2_IgV is set forth in SEQ ID NO: 50 in the sequence listing.

1)-1-5 Construction of cSIRPA_ECD Expression Vector

A cSIRPA_ECD expression vector was prepared in the same manner as in 1)-1-1 using a DNA encoding a polypeptide obtained by linking HHHHHH to amino acids 1 to 372 on the C terminal side of the amino acid sequence of cSIRPA (NCBI Protein Database accession number NP_001271679). The amino acid sequence of cSIRPA_ECD is set forth in SEQ ID NO: 53 in the sequence listing, and the nucleotide sequence encoding cSIRPA_ECD is set forth in SEQ ID NO: 52 in the sequence listing.

1)-1-6 Construction of CD47-Fc Expression Vector

A CD47-Fc expression vector was prepared in the same manner as in 1)-1-1 using a DNA encoding a polypeptide of human CD47 (NCBI Protein Database accession number NP_001768). The amino acid sequence of CD47-Fc is set forth in SEQ ID NO: 55 in the sequence listing, and the nucleotide sequence encoding SIRPA_V1_ECD is set forth in SEQ ID NO: 54 in the sequence listing.

1)-2 Preparation of Recombinant Proteins

1)-2-1 Preparation of SIRPA_V1_ECD

SIRPA_V1_ECD was expressed transiently by transfecting FreeStyle 293F Cells (Thermo Fisher Scientific Inc.) with the SIRPA_V1_ECD expression vector prepared in 1)-1-1. The culture supernatant was added to a HisTrap excel (GE Healthcare Japan) equilibrated with 3×PBS, and the column was washed with 3×PBS. Subsequently, fractions were eluted with 3×PBS containing 500 mM imidazole (pH 7.5). SIRPA_V1_ECD was purified from the collected SIRPA_V1_ECD fractions using HiLoad 26/600 Superdex 75 pg (GE Healthcare Japan).

1)-2-2 Preparation of SIRPA_V1_IgV

SIRPA_V1_IgV was expressed transiently by transfecting FreeStyle 293F Cells (Thermo Fisher Scientific Inc.) with the SIRPA_V1_IgV expression vector prepared in 1)-1-2. The culture supernatant was added to a HisTrap excel (GE Healthcare Japan) equilibrated with 3×PBS, and the column was washed with 3×PBS. Subsequently, fractions were eluted with 3×PBS containing 500 mM imidazole (pH 7.5). SIRPA_V1_IgV was purified from the collected SIRPA_V1_IgV fractions using HiLoad 26/600 Superdex 75 pg (GE Healthcare Japan).

1)-2-3 Preparation of SIRPA_V2_ECD

SIRPA_V2_ECD was purified in the same manner as in 1)-2-1 using the SIRPA_V2_ECD expression vector prepared in 1)-1-3.

1)-2-4 Preparation of SIRPA_V2_IgV

SIRPA_V2_ECD was purified in the same manner as in 1)-2-2 using the SIRPA_V2_ECD expression vector prepared in 1)-1-4.

1)-2-5 Preparation of cSIRPA_ECD cSIRPA_ECD was purified in the same manner as in 1)-2-1 using the cSIRPA_ECD expression vector prepared in 1)-1-5.

1)-2-6 Preparation of CD47-Fc

CD47-Fc was expressed transiently by transfecting FreeStyle 293F Cells (Thermo Fisher Scientific Inc.) with the CD47-Fc expression vector. All the culture supernatant was added to MabSelect SuRe (GE Healthcare Japan) equilibrated with PBS, and then the column was washed with PBS. Subsequently, fractions were eluted with a 2 M arginine hydrochloride solution (pH 4.0) to collect a fraction containing CD47-Fc. CD47-Fc was purified from the collected CD47-Fc fraction using HiLoad 26/600 Superdex 200 pg (GE Healthcare Japan).

1)-3 Immunization

For immunization, female WKY/Izm rats (Japan SLC, Inc.) were used and given a mixture of each of the antigen proteins SIRPA_V1_ECD, SIRPA_V1_IgV, SIRPA_V2_ECD, and SIRPA_V2_IgV prepared in 1)-2 and Freund's Complete Adjuvant (Wako Pure Chemical Industries, Ltd.) to the base of the tail. The lymph nodes and the spleen were collected from the rats and used to prepare a hybridoma.

1)-4 Preparation of Hybridoma

Lymph node cells or spleen cells were electrofused with mouse myeloma SP2/0-ag14 cells (ATCC, CRL-1581) using LF301-Cell Fusion Unit (BEX), and the fused cells were diluted and cultured in ClonaCell-HY Selection Medium D (Stem Cell Technologies Inc.). A monoclonal hybridoma was prepared by collecting emerging hybridoma colonies. The collected hybridoma colonies were each cultured, and the obtained hybridoma culture supernatants were used to screen for an anti-SIRPA antibody-producing hybridoma.

1)-5 Construction of Expression Vector for Screening for Antigen-Binding Antibody 1)-5-1 Construction of Vector Expressing Human SIRPA_V1 and V2 (pcDNA3.2 V5-DEST-SIRPA_V1_ECD and SIRPA_V2_ECD)

The cDNAs encoding a human SIRPA_V1 protein (NP_001035111) or a human SIRPA_V2 protein [obtained by modifying NP_001035111 on the basis of JBC. 2014; 289(14), 10024] were cloned in a vector pcDNA3.2 V5-DEST vector to construct pcDNA3.2 V5-DEST-SIRPA_V1_ECD and V2_ECD (or pcDNA3.2 V5-DEST- SIRPA_V1 and V2), which expressed the respective proteins. The amino acid sequence of the human SIRPA_V1 protein is set forth in SEQ ID NO: 56 in the sequence listing, and the amino acid sequence of the human SIRPA_V2 protein is set forth in SEQ ID NO: 57 in the sequence listing.

1)-5-2 Construction of Vectors Expressing Monkey SIRPA and Mouse SIRPA (pcDNA3.2 V5-DEST-Monkey SIRPA, pFLAG V5-DEST-Monkey SIRPA, and pFLAG V5-DEST-Mouse SIRPA)

The cDNAs encoding a monkey SIRPA protein (NP_001271679) or mouse SIRPA proteins (C57BL/6, NP_031573; BALB/c, BAA20376; 129, P97797; NOD, modified SCID in Immunology. 2014; 143, 61-67) were cloned in a pcDNA3.2 V5-DEST vector or a pFLAG V5-DEST vector to construct vectors pcDNA3.2 V5-DEST-monkey SIRPA, pFLAG V5-DEST-monkey SIRPA, and pFLAG V5-DEST-mouse SIRPA (C57BL/6, BALB/c, 129, NOD), which expressed the respective proteins. The amino acid sequence of monkey SIRPA is set forth in SEQ ID NO: 58 in the sequence listing, the amino acid sequence of mouse SIRPA_C57BL/6 is set forth in SEQ ID NO: 59 in the sequence listing, the amino acid sequence of mouse SIRPA BALB/c is set forth in SEQ ID NO: 60 in the sequence listing, the amino acid sequence of mouse SIRPA 129 is set forth in SEQ ID NO: 61 in the sequence listing, and the amino acid sequence of mouse SIRPA NOD is set forth in SEQ ID NO: 62 in the sequence listing.

1)-6 Hybridoma Screening

1)-6-1 Preparation of Antigen Gene Expressing Cells for Cell-Based ELISA

HEK293α cells (a stably expressing cell line derived from HEK293, which expresses integrin αv and integrin β3) were prepared in a 10% FBS-containing DMEM medium at $7.5 \times 10^5$ cells/mL. According to a transfection procedure using Lipofectamine 2000 (Thermo Fisher Scientific Inc.), pcDNA3.2 V5-DEST-SIRPA_V1 or pcDNA3.2 V5-DEST-SIRPA_V2, or pcDNA3.2 V5-DEST as a control was introduced into the cells, and 50 μL per well was aliquoted into a 96-half area well plate (Corning Incorporated) or 100 μL per well was aliquoted into a 96-well plate (Corning Incorporated), and cells were cultured in a 10% FBS-containing DMEM medium at 37° C. under a 5% $CO_2$ condition for 24 to 27 hours. The obtained introduced cells were used for cell-based ELISA in a state that cells adhered to each other.

1)-6-2 Evaluation of Binding to Human SIRPA (Cell-Based ELISA)

After the culture supernatant of the expression vector-introduced 293α cells prepared in Example 1)-6-1 was removed, the hybridoma culture supernatant was added to each of pcDNA3.2 V5-DEST-SIRPA_V1, pcDNA3.2 V5-DEST-SIRPA_V2, or pcDNA3.2 V5-DEST-introduced 293α cells, and the mixture was allowed to stand at 4° C. for one hour. Cells in the wells were washed twice with 5% FBS-containing PBS, followed by addition of Anti-Rat IgG Peroxidase antibody produced in rabbit (SIGMA) diluted 500-fold with 5% FBS-containing PBS, and the mixture was allowed to stand at 4° C. for one hour. Cells in the wells were washed twice with 5% FBS-containing PBS, followed by addition of 50 μL per well of an OPD coloration solution [o-phenylenediamine dihydrochloride (Wako Pure Chemical Industries, Ltd.) and $H_2O_2$ were dissolved in an OPD solution (0.05 M trisodium citrate, 0.1 M disodium hydrogen phosphate dodecahydrate, pH 4.5) at 0.4 mg/mL and 0.6% (v/v), respectively]. A coloration reaction was performed with stirring occasionally, 50 μL per well of 1 M HCL was added to terminate the coloration reaction, and then absorbance at 490 nm was measured with a plate reader (EnVision: PerkinElmer Inc.). To select a hybridoma producing an antibody that specifically binds to SIRPA expressed on the cell membrane surface, a hybridoma producing a culture supernatant with a higher absorbance with the pcDNA3.2 V5-DEST-SIRPA_V1 or pcDNA3.2 V5-DEST-SIRPA_V2 expression vector-introduced 293α cells than with the control pcDNA3.2 V5-DEST-introduced 293α cells was selected as being positive for production of an anti-SIRPA antibody.

1)-6-3 Evaluation of SIRPA-CD47 Binding Inhibitory Activity

After the culture supernatant of the expression vector-introduced 293α cells prepared in Example 1)-6-1 was removed, the hybridoma culture supernatant was added to each of pcDNA3.2 V5-DEST-SIRPA_V1, pcDNA3.2 V5-DEST-SIRPA_V2, or pcDNA3.2 V5-DEST-introduced 293α cells, immediately followed by addition of 50 μL per well of peroxidase-labeled CD47-Fc prepared with 5% FBS-containing PBS at a final concentration of 10,000 ng/mL, and the mixture was allowed to stand at 4° C. for one hour. The cells in the well were washed twice with 5% FBS-containing PBS, followed by addition of 100 μL per well of an OPD coloration solution [o-phenylenediamine dihydrochloride (Wako Pure Chemical Industries, Ltd.) and $H_2O_2$ were dissolved in an OPD solution (0.05 M trisodium citrate, 0.1 M disodium hydrogen phosphate dodecahydrate, pH 4.5) at 0.4 mg/mL and 0.6% (v/v), respectively]. A coloration reaction was performed with stirring occasionally, 100 μL per well of 1 M HCl was added to terminate the coloration reaction, and then absorbance at 490 nm was measured with a plate reader (SpectraMax: Molecular Devices, LLC). To select a hybridoma producing an antibody that specifically inhibits binding of SIRPA expressed on the cell membrane surface and CD47-Fc, a hybridoma producing a culture supernatant having a lower absorbance with the pcDNA3.2 V5-DEST-SIRPA_V1 or pcDNA3.2 V5-DEST-SIRPA_V2 expression vector-introduced 293α cells than with a group prepared by adding the control medium was selected as being positive for production of an anti-SIRPA antibody that had a ligand-binding inhibitory activity.

1)-6-4 Analysis of Species Cross-Reactivity with Mouse or Monkey SIRPA

After the culture supernatant of the pcDNA3.2 V5-DEST-monkey SIRPA or pcDNA3.2 V5-DEST-mouse SIRPA expression vector-introduced 293α cells or the pcDNA3.2 V5-DEST-introduced 293α cells prepared in Example 1)-5-2 was removed, the binding to monkey or mouse SIRPA was evaluated in the same manner as the method for evaluating the human SIRPA binding activity. A total of seven clones of antibodies D13, F42, F44, F47, F60, F63, and F86 were selected on the basis of the above-mentioned binding activity to SIRPA of humans and other animal species and the SIRPA-CD47 binding inhibitory activity.

1)-7 Isotype Determination of Antibodies

From the obtained rat anti-SIRPA antibody-producing hybridomas, hybridomas producing the D13, F42, F44, F47, F60, F63, and F86 antibodies, which showed a highly specific binding to human SIRPA_V1 and SIRPA_V2 and monkey SIRPA and were therefore suggested to have a high SIRPA-CD47 binding inhibitory activity, were selected, and antibody isotypes thereof were identified. The isotypes were determined using Rat Immunoglobulin Isotyping ELISA Kit (BD Pharmingen). The results demonstrated that the isotype of rat anti-SIRPA monoclonal antibodies D13, F42, F60, and F86 was IgG1/κ chain, the isotype of F44 and F47 was IgG2a/κ chain, and the isotype of F63 was IgG2a/λ chain.

1)-8 Preparation of Monoclonal Antibodies

1)-8-1 Preparation of Culture Supernatants

Seven different rat anti-SIRPA monoclonal antibodies were purified from the hybridoma culture supernatants. First, each antibody-producing hybridoma was proliferated to a sufficient amount using ClonaCell-HY Selection Medium E (STEMCELL Technologies Inc.), and then the medium was exchanged with 5 μg/mL gentamicin (Thermo Fisher Scientific Inc.)-containing Hybridoma SFM (Thermo Fisher Scientific Inc.) to which 20% Ultra Low IgG FBS (Thermo Fisher Scientific Inc.) was added, and hybridoma was cultured for 7 days. The culture supernatant was collected and sterilized through a 0.22-μm filter (Corning Incorporated).

1)-8-2 Purification of Antibodies

Antibodies were purified from the hybridoma culture supernatants prepared in Example 1)-8-1 by protein G affinity chromatography. An antibody was adsorbed in Protein G Column (GE Healthcare Bioscience Corp.), the column was washed with PBS, and then the antibody was eluted with 0.1 M glycine/hydrochloric acid aqueous solution (pH 2.7). The eluate was adjusted to pH 7.0 to 7.5 by adding 1 M Tris-HCl (pH 9.0), the buffer was replaced with PBS using Centrifugal UF Filter Device VIVASPIN20 (molecular weight cutoff for ultrafiltration, 30 kDa: Sartorius AG), and the antibody solution was concentrated to an antibody concentration of 2 mg/mL or higher. Finally, the solution was filtered with a Minisart-Plus filter (Sartorius AG) to obtain a purified sample.

Example 2. In Vitro Evaluation of Seven Different Rat Anti-Human SIRPA Antibodies 2)-1 Construction of Expression Vectors for Screening for Antigen-Binding Antibody 2)-1-1 Construction of FLAG-Human SIRPA Expression Vector (pFLAG V5-DEST-SIRPA_V1-V10)

cDNAs encoding 10 different human SIRPA variant proteins (excerpt from Nature Immunology. 2007; 8, 1313-1323) were cloned in a pFLAG V5-DEST vector to construct pFLAG V5-DEST-SIRPA_V1-V10, a vector expressing these variant proteins.

The amino acid sequence of human SIRPA_V3 is set forth in SEQ ID NO: 63 in the sequence listing, the amino acid sequence of human SIRPA_V4 is set forth in SEQ ID NO: 64 in the sequence listing, the amino acid sequence of human SIRPA_V5 is set forth in SEQ ID NO: 65 in the sequence listing, the amino acid sequence of human SIRPA_V6 is set forth in SEQ ID NO: 66 in the sequence listing, the amino acid sequence of human SIRPA_V7 is set forth in SEQ ID NO: 67 in the sequence listing, the amino acid sequence of human SIRPA_V8 is set forth in SEQ ID NO: 68 in the sequence listing, the amino acid sequence of human SIRPA_V9 is set forth in SEQ ID NO: 69 in the sequence listing, and the amino acid sequence of human SIRPA_V10 is set forth in SEQ ID NO: 70 in the sequence listing.

2)-1-2-1 Construction of Vector Expressing Human SIRPA_ECD, IgV, and IgV_IgC1 (pFLAG V5-DEST-SIRPA_ECD and IgVIgV_IgC1)

cDNAs encoding amino acids 1 to 504 of the full-length human SIRPA_V2, a variant deficient in a region of amino acids 165 to 371 (hereinafter referred to as "IgV variant"), and a variant deficient in a region of amino acids 225 to 371 (hereinafter referred to as "IgV_IgC variant") were cloned in a pFLAG V5-DEST vector to construct a vector expressing the respective variant proteins.

The amino acid sequence of the human SIRPA_V2_IgV variant is set forth in SEQ ID NO: 71 in the sequence listing, and the amino acids of the human SIRPA_V2_IgV_IgC1 variant are set forth in SEQ ID NO: 72 in the sequence listing.

2)-1-2-2 Construction of Vector Expressing hmSIRPA_Δ0, Δ1, and Δ2_Mouse SIRPA (pFLAG V5-DEST-hmSIRPA_Δ0, Δ1, and Δ2)

A SIRPA variant in which the SFTGE sequence (SEQ ID NO: 78) consisting of amino acid residues 81 to 85 set forth in SEQ ID NO: 60 of the mouse SIRPA was substituted by the NQKEG sequence (SEQ ID NO: 76), and the RGSSE sequence consisting of amino acid residues 126 to 130 (SEQ ID NO: 79) was substituted by the KGS sequence was designated as hmSIRPA_Δ0. A SIRPA variant in which the SFTGE sequence (SEQ ID NO: 78) consisting of amino acid residues 81 to 85 set forth in SEQ ID NO: 60 of the mouse SIRPA was substituted by the NQKEE sequence (SEQ ID NO: 77) was designated as hmSIRPA_Δ1. Further, a SIRPA variant in which the SFTGE sequence (SEQ ID NO: 78) consisting of amino acid residues 81 to 85 set forth in SEQ ID NO: 60 of the mouse SIRPA was substituted by the SFTEG sequence (SEQ ID NO: 80) was designated as hmSIRPA_Δ2. The cDNAs encoding these SIRPA variants were cloned in a pFLAG V5-DEST vector to construct a vector expressing the respective SIRPA variants.

The amino acid sequence of hmSIRPA_Δ0 is set forth in SEQ ID NO: 73 in the sequence listing, the amino acids of hmSIRPA_Δ1 are set forth in SEQ ID NO: 74 in the sequence listing, and the amino acids of hmSIRPA_Δ2 are set forth in SEQ ID NO: 75 in the sequence listing.

2)-2 Evaluation of Binding to Human SIRPA Variants V1 to V10

After the culture supernatant of 293α cells into which the vector expressing 10 different variant proteins prepared in Example 2)-1-1 was introduced was removed, 50 μL per well of a purified rat anti-human SIRPA antibody diluted with 5% FBS-containing PBS to a final concentration of 10,000 ng/mL was added to each of pFLAG V5-DEST-SIRPA_V1-V10 and pFLAG V5-DEST-introduced 293α cells, and the mixture was allowed to stand at 4° C. for one hour. Further, 50 μL per well of an anti-FLAG M2 antibody (SIGMA) diluted with 5% FBS-containing PBS to a final concentration of 10,000 ng/mL was added to a well for detecting expression of each SIRPA variant, and the mixture was allowed to stand at 4° C. for one hour. Thereafter, binding to 10 different human SIRPA variants was evaluated in the same manner as in the evaluation of the binding activity of the human SIRPA described in 1)-6-2. Binding of the rat anti-human SIRPA antibodies to each variant was standardized by expression of the FLAG tag.

As shown in Table 1, all the clones showed binding to all the variants.

TABLE 1

Binding of rat anti-human SIPRA antibodies to human SIPRA
variants V1 to V10 hSIRPA-binding activity (variants)

| Clone ID | V1  | V2  | V3  | V4  | V5  | V6  | V7  | V8  | V9  | V10 |
|----------|-----|-----|-----|-----|-----|-----|-----|-----|-----|-----|
| D13      | ++  | ++  | ++  | ++  | ++  | ++  | ++  | ++  | ++  | ++  |
| F42      | ++  | ++  | +   | ++  | ++  | ++  | +++ | ++  | +   | ++  |
| F44      | +++ | +++ | +++ | +++ | +++ | +++ | ++  | +++ | ++  | +++ |
| F47      | +++ | +++ | +++ | +++ | ++  | +++ | +++ | +++ | +++ | +++ |
| F60      | ++  | ++  | ++  | ++  | +   | +   | +   | +   | ++  | ++  |
| F63      | +++ | +++ | +++ | +++ | +++ | +++ | +++ | +++ | +++ | +++ |
| F86      | +   | ++  | ++  | ++  | +   | +   | +   | +   | ++  | ++  |

2)-3 Analysis of Species Cross-Reactivity with Mouse or Monkey SIRPA

After the culture supernatant of 293α cells into which the pFLAG V5-DEST-monkey SIRPA or pFLAG V5-DEST-mouse SIRPA expression vector was introduced and the pFLAG V5-DEST-introduced 293α cells prepared in Example 1)-5-2 was removed, binding to monkey or mouse SIRPA was evaluated in the same manner as for the binding activity of human SIRPA.

As shown in Table 2, all the rat anti-human SIRPA antibodies showed binding to monkey SIRPA but did not show binding to mouse SIRPA.

TABLE 2

Species cross-reactivity of rat anti-human SIPRA antibodies
SIRPA-binding activity (animal species)

| Clone ID | Cynomolgus monkey | BALB/c | C57BL/6 | 129 | NOD SCID |
|----------|-------------------|--------|---------|-----|----------|
| D13      | ++                | −      | −       | −   | −        |
| F42      | ++                | −      | −       | −   | −        |
| F44      | +++               | −      | −       | −   | −        |
| F47      | ++                | −      | −       | −   | −        |
| F60      | ++                | −      | −       | −   | −        |
| F63      | +++               | −      | −       | −   | −        |
| F86      | ++                | −      | −       | −   | −        |

2)-4 Epitope Analysis
2)-4-1 Epitope Analysis by Cell-Based ELISA (1)

After the culture supernatant of 293α cells into which the pFLAG V5-DEST-ECD variant, IgV variant, and IgV_IgC1 variant expression vector prepared in 2)-1-2-1 was introduced or the pFLAG V5-DEST-introduced 293α cells was removed, 50 μL of well of purified rat anti-human SIRPA antibodies diluted with 5% FBS-containing PBS to a final concentration of 10,000 ng/mL were added to the respective cells, and the mixture was allowed to stand at 4° C. for one hour. Further, 50 μL per well of an anti-FLAG M2 antibody (SIGMA) diluted with 5% FBS-containing PBS to a final concentration of 10,000 ng/mL was added to a well for detecting expression of each SIRPA construct, and the mixture was allowed to stand at 4° C. for one hour. Thereafter, binding of the seven purified antibody clones to each domain was evaluated in the same manner as in the evaluation of the binding activity of the human SIRPA. Binding of the rat anti-human SIRPA antibodies to each construct was standardized by expression of the FLAG tag.

Given that the rat anti-human SIRPA antibodies showed binding to all the constructs as shown in FIG. 1A, it was suggested that these antibodies recognized the IgV domain.

2)-4-1-2 Epitope Analysis by Cell-Based ELISA (2)

After the culture supernatant of 293α cells into which the pFLAG V5-DEST-hmSIRPA_Δ0, Δ1, and Δ2 expression vector prepared in 2)-1-2-2 was introduced and the pFLAG V5-DEST-introduced 293α cells was removed, 50 μL per well of four different D13 humanized anti-human SIRPA antibodies and a chimeric anti-human SIRPA antibody diluted with 5% FBS-containing PBS to a final concentration of 10,000 ng/mL were added to these cells, and the mixture was allowed to stand at 4° C. for one hour. Further, 50 μL per well of an anti-FLAG M2 antibody (SIGMA) diluted with 5% FBS-containing PBS to a final concentration of 10,000 ng/mL was added to a well for detecting expression of each SIRPA construct, and the mixture was allowed to stand at 4° C. for one hour. Thereafter, binding to each construct was evaluated in the same manner as in the evaluation of the binding activity of the human SIRPA. Binding of anti-human SIRPA antibodies to each construct was standardized by expression of the FLAG tag.

As shown in FIG. 1B, hD13_H1L3, hD13_H1L4h, hD13_H2L2, hD13_H2L3, and cD13 exhibited a concentration-dependent binding to the added hmSIRPA_Δ0 antibody having the NQKEG sequence but did not exhibit binding to hmSIRPA_Δ1 or hmSIRPA_Δ2 at any concentration.

The above findings indicated that binding of hD13 and cD13 required the NQKEG sequence.

2)-4-2 Epitope Analysis by x-Ray Crystallography
2)-4-2-1 Crystallization of Complex A full-length cD13 antibody was cleaved with Lysyl Endopeptidase (Wako Pure Chemical Industries, Ltd.) to a limited extent under a weak acidic condition, and the Fab fragment of the cD13 antibody was isolated using BioAssist S Cation Exchange Column (Tosoh Corporation). The SIRPA_V2_IgV obtained in Example 1)-2 and the cD13 Fab fragment were mixed in a molar ratio of 1:1, a complex fraction was isolated using a Superdex 75, 10/300 GL gel filtration column (GE Healthcare), followed by buffer replacement with 10 mM Tris HCl (pH 8.2) by ultrafiltration, and the complex was concentrated to 3 g/L. The complex solution was crystallized by a steam diffusion method. A solution obtained by adding an equal volume of a precipitant solution [0.2 M potassium phosphate dibasic, 20% (w/v) Polyethylene Glycol 3350, pH 9.2] to 0.5 μL of the protein solution was placed in a sealed container containing 0.05 mL of a precipitant solution, so that these solutions would not be brought into contact with each other, and the solutions were allowed to stand at 25° C. After one week, 0.2 mm×0.2 mm×0.05 mm rod-like crystals were obtained. The obtained crystals were immersed in a solution obtained by diluting the precipitant solution approximately 1.4-fold with glycol, and subsequently the mixture was frozen with liquid nitrogen. X-ray diffraction data were collected with beam line PF BL-17A of a light source facility Photon Factory (Tsukuba). The diffraction intensity was quantified from the obtained diffraction image using software XDS (Max Plank Institute for Medical Research) to obtain the crystal structure factor. The crystal had a hexagonal crystal system, with the R32 space group and a unit cell of the crystal of a=b=149.61 Å, c=155.61 Å, α=β=90°, and γ=120°.

2)-4-2-2 Structural Analysis of Complex

The phase was determined by performing molecular replacement using a three-dimensional structure coordinate of a homology model of the obtained structure factor and the Fab fragment and a known structure (PDBID: 2JJS) of the human SIRPA IgV domain. A software phaser (CCP4: Collaborative Computational Project No. 4) was used for calculation. The crystal contained one complex in an asymmetric unit. The structure was refined using a software Refmac5 (CCP4: Collaborative Computational Project No. 4), and the model was corrected using a software Coot. This operation was repeated to obtain a final R value of 22% and a free R value of 25% at 2.4 Å resolution. The final model contained amino acid residues 1 to 213 of the L chain and amino acid residues 1 to 225 of the H chain of the cD13 Fab fragment and amino acid residues 33 to 143 of the human SIRPA Variant 2.

2)-4-2-3 Structural Analysis of Complex and Identification of Epitope of D13

Figure 2:
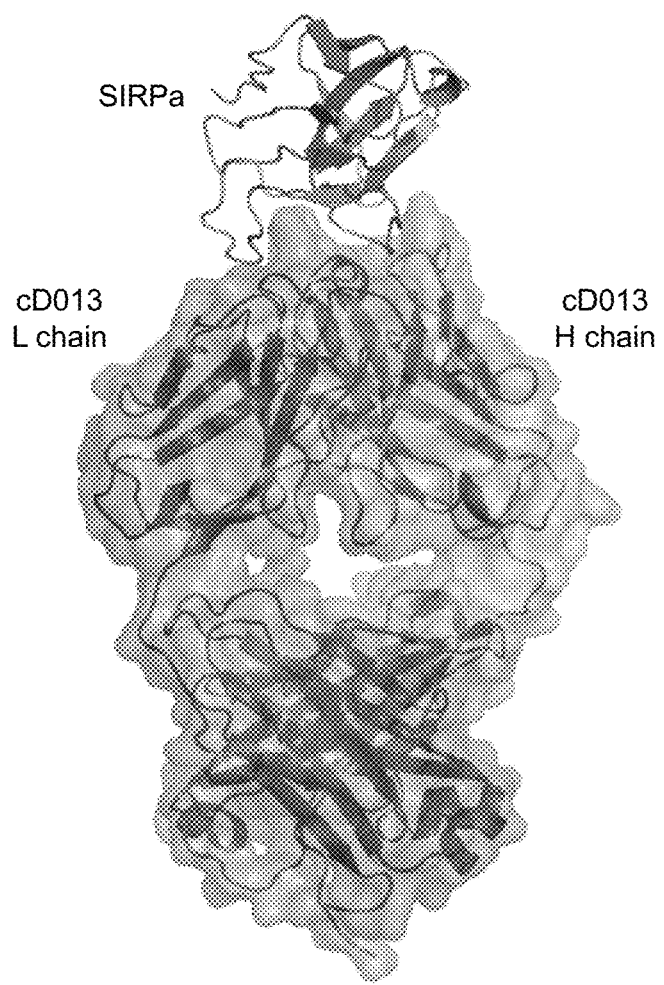
FIG. 2 illustrates a ribbon model of a whole composite of the Fab fragment of an anti-SIRPA antibody and SIRPA_V2_IgV.
Figure 3:
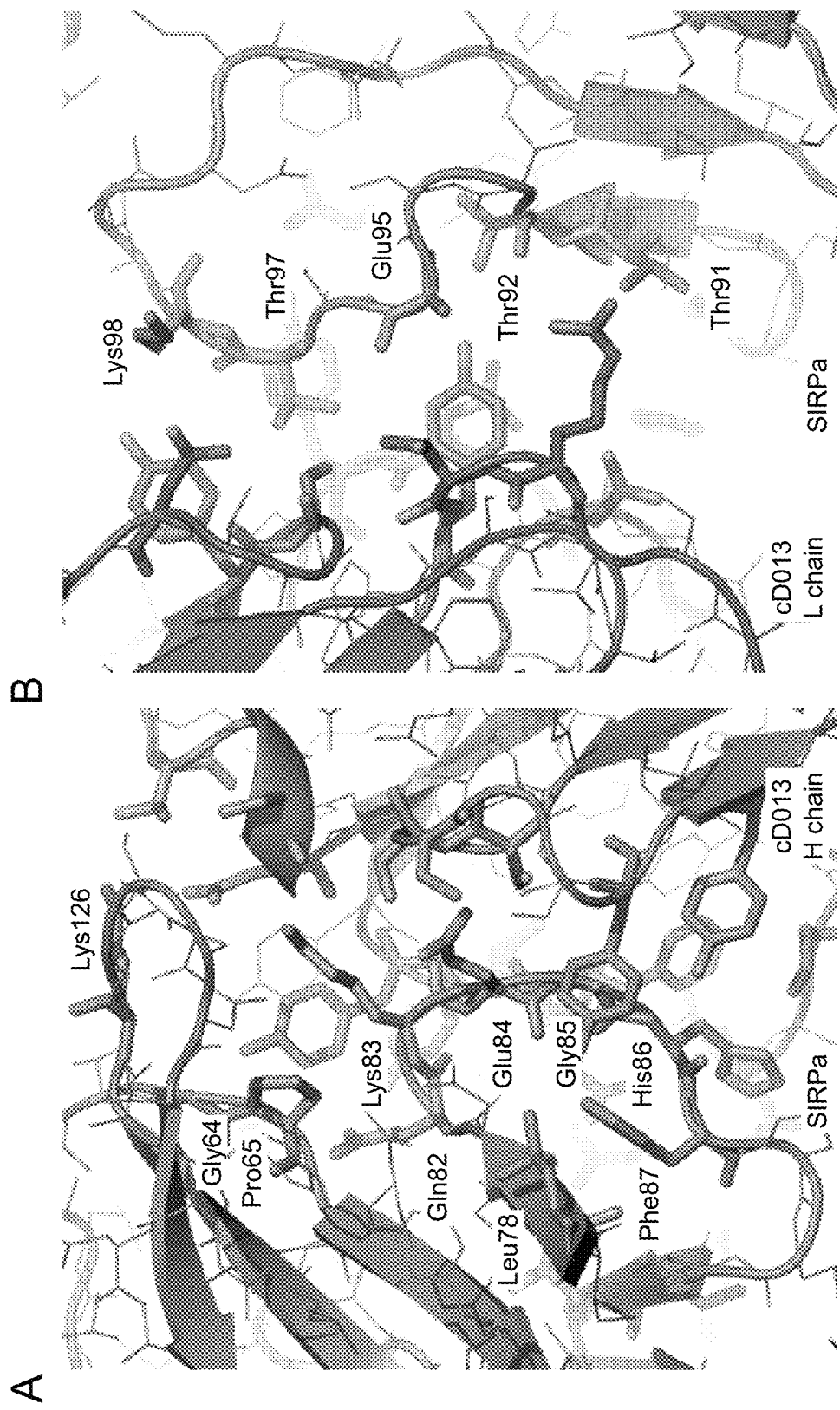
FIG. 3 illustrates interactions between the regions before beta 5 (A) and after beta 5 (B) of human SIRPA and an anti-SIRPA antibody (antibody D13).

The amino acid residues of the human SIRPA within 4 Å from the cD13 Fab fragment (the position of each amino acid residue corresponds to that in SEQ ID NO: 57 in the sequence listing) are as follows: Gly64, Pro65, Leu78, Gln82, Lys83, Glu84, Gly85, His86, Phe87, Thr91, Thr92, Glu95, Thr97, Lys98, and Lys126. FIG. 2 shows a ribbon model of the whole complex and the surface thereof, and FIG. 3 illustrates interactions between the regions before beta 5 (A) and after beta 5 (B) of human SIRPA and cD13. It was indicated that cD13 strongly recognized the beta 4-5 loop, i.e., residue numbers 82 to 87, which has a small sequence variety in human SIRPA, and it enabled a strong binding to various variants (FIG. 4). In contrast, interactions are weak in the beta 5-6 loop, i.e., a region of residue numbers 92 to 105. For example, Glu95, which is substituted by aspartic acid instead of glutamic acid in some variants, is present near Fab, but the electron density of a side chain is not observed, which indicates that Glu95 does not greatly contribute to interactions. Among the sequences in FIG. 4, a black dot "●" indicates that the amino acid residue is identical to the one in SIRPA_V1, and an amino acid residue shown at a site indicates that the amino acid residue is different.

2)-5 Evaluation of Human SIRPA-CD47 Binding Inhibitory Activity

After the culture supernatant of 293α cells into which the human SIRPA expression vector prepared in 1)-5-1 was introduced was removed, 50 μL per well of the purified rat anti-human SIRPA antibodies diluted with 5% FBS-containing PBS to final concentrations of 0 to 10,000 ng/mL were added to each of pcDNA3.2 V5-DEST-SIRPA_V1, pcDNA3.2 V5-DEST-SIRPA_V2, or pcDNA3.2 V5-DEST-introduced 293α cells, immediately followed by addition of 50 μL per well of peroxidase-labeled CD47-Fc prepared in 5% FBS-containing PBS at a final concentration of 10,000 ng/mL, and the mixture was allowed to stand at 4° C. for one hour. Thereafter, the binding inhibitory activity was evaluated in the same manner as in 1)-6-3.

As shown in Table 3, all the rat anti-human SIRPA antibodies showed the binding inhibitory activity against human SIRPA-CD47.

TABLE 3

SIRPA-CD47 binding inhibitory activity of rat anti-human SIRPA antibodies SIRPA-CD47 binding inhibitory activity

| Clone ID | V1-CD47 | V2-CD47 |
|---|---|---|
| D13 | +++ | +++ |
| F42 | +++ | ++ |
| F44 | ++ | ++ |
| F47 | ++ | ++ |
| F60 | ++ | ++ |
| F63 | ++ | ++ |
| F86 | ++ | + |

2)-6 ADCP Activity of Rat Anti-Human SIRPA Antibodies Against Cancer Cell Line

2)-6-1 Preparation of Target Cells

TrypLE Express (Life Technology) was added to human gastric cancer cell line AGS cells, the mixture was allowed to react at 37° C. for five minutes, and then cells were dissociated. A 10% FBS-containing RPMI 1640 medium (Life Technology) was added, cells were washed twice, then cells were washed twice with PBS, and then the viable cell count was obtained by a trypan blue dye exclusion test. A solution of $4 \times 10^7$ cells was collected and centrifuged, and then the cells were suspended in 2 mL of Diluent C provided in PKH26 Red Fluorescent Cell Linker Kit for General Cell Membrane Labeling (Sigma). After 1 mM PKH26 Linker was diluted with Diluent C to 10 μM as a labeling solution, immediately followed by mixing of the cell suspension and an equal volume of a PKH26 Linker solution, and the mixture was allowed to stand at room temperature for five minutes. A volume of 25 mL of a 10% FBS-containing RPMI 1640 medium (Life Technology) was added, cells were washed twice, then the cells were re-suspended to $2 \times 10^6$ cells/mL and used as target cells.

2)-6-2 Preparation of PBMCs

After 25 mL of blood from a normal subject was slowly overlaid on 20 mL of Ficoll-Paque Plus (GE Healthcare), the mixture was centrifuged at 1500 rpm at room temperature for 30 minutes. A cell layer positioned between plasma and Ficoll-Paque Plus was collected with a dropper and suspended in 20 mL of a 10% FBS-containing RPMI 1640 medium (Life Technology). The suspension was centrifuged at 1500 rpm for five minutes, the supernatant was removed, 20 mL of a 10% FBS-containing RPMI 1640 medium was added, and cells were washed twice. After cells were suspended in 1 mL of RoboSep Buffer (STEMCELL Technologies Inc.), the viable cell count was measured by a trypan blue dye exclusion test, and the cells were used as effector cells.

2)-6-3 Preparation of Effector Cells

The PBMCs prepared in Example 2)-6-2 were suspended in RoboSep Buffer (STEMCELL Technologies Inc.) at $5 \times 10^7$ cells/mL. A volume of 50 μL of EasySep Human Monocyte Enrichment Cocktail provided in Human Monocyte Enrichment Kit without CD16 Depletion (STEMCELL Technologies Inc.) was added to 1 mL of the PBMC suspension. After the mixture was allowed to react at 4° C. for 10 minutes, 50 μL of EasySep Magnetic Particles was added to each mL of the PBMC suspension. After the mixture was allowed to react at 4° C. for five minutes, RoboSep Buffer (STEMCELL Technologies Inc.) was added to make 2.5 mL, and the mixture was set in EasySep Magnet. After 2 minutes and 30 seconds, the supernatant was collected and centrifuged at 1200 rpm for five minutes, and monocyte fractions were collected. A 10% FBS-containing RPMI 1640 medium (Life Technology) was added, cells were washed once, followed by addition of a 10% FBS-containing RPMI 1640 medium (Life Technology) containing 10 ng/mL M-CSF (PEPROTEC), and the mixture was seeded in a Suspension Culture Flask 225 (Sumitomo Bakelite Co., Ltd.). The suspension was cultured at 37° C. under a 5% $CO_2$ condition for 10 days. The culture supernatant was removed, followed by addition of a 10% FBS-containing RPMI 1640 medium (Life Technology) containing 10 ng/mL IL-10 and 10 ng/mL M-CSF (PeproTech, Inc.), and the suspension was cultured for further 2 days. After 12 days, TrypLE Express (Life Technology) was added to differentiation-induced macrophages, and the mixture was allowed to react at 37° C. for 40 minutes to dissociate cells. A 10% FBS-containing RPMI 1640 medium (Life Technology) was added, cells were washed twice, and then cells were re-suspended in a 10% FBS-containing RPMI 1640 medium (Life Technology) at $5\times10^5$ cells/mL and used as effector cells.

2)-6-4 Evaluation of ADCP Activity

A volume of 50 µL per well of the target cells prepared by the method of Example 2)-6-1 was added to Ultra-Low Attachment 96-Well U-Shaped Bottom Microplate (Sumitomo Bakelite Co., Ltd.). To the wells, 50 µL per well of seven rat anti-human SIRPA antibody clones, Hu5F9G4 (prepared using an anti-human CD47 antibody: PLOS ONE 10[9]: e0137345, US2015183874), TTI-621 (prepared using a human SIRPA-Fc: International Publication WO 2014/094122), and various control IgG diluted with a 10% FBS-containing RPMI 1640 medium (Life Technology) to final concentrations of 0 to 10,000 ng/mL were added. A volume of 50 µL per well of a 10% FBS-containing RPMI 1640 medium (Life Technology) was added for the single agent group, and 50 µL per well of trastuzumab (Roche) diluted with a 10% FBS-containing RPMI 1640 medium (Life Technology) to a final concentration of 250 ng/mL was added for the combination use group. A volume of 50 µL per well ($1\times10^6$ cells/mL) of the effector cells prepared in Example 2)-6-3 were added, and then the mixture was allowed to stand at 37° C. under a 5% $CO_2$ condition for 16 hours. The mixture was centrifuged at 1200 rpm at 4° C. for five minutes, the supernatant was removed, and cells were washed with 200 µL per well of 5% FBS-containing PBS. A volume of 45 µL per well of 5% FBS-containing PBS and 5 µL per well of APC Mouse Anti-Human CD11b (Becton Dickinson) were added to cells, and the mixture was allowed to stand at 4° C. for 15 minutes. Cells were washed twice with 200 µL per well of 5% FBS-containing PBS. Cells were suspended in 100 µL per well of 1×BD Stabilizing Fixative (Becton Dickinson), and the mixture was allowed to stand overnight at 4° C. On the following day, cells were measured by flow cytometry (FACS Canto II: Becton Dickinson). FlowJo (TreeStar) was used for data analysis. Cells were characterized by detecting forward scattered (FSC) light and side-scattered (SSC) light, and then the numbers of cells positive for PE (A) and cells positive for both APC and PE (B) were obtained. Cells positive for both APC and PE (B) were deemed to be target cells that had been phagocytized by macrophages. The percent cellular phagocytosis by the ADCP activity was calculated by the following equation:

Percent cellular phagocytosis (%)=B/(A+B)×100

Figure 5:
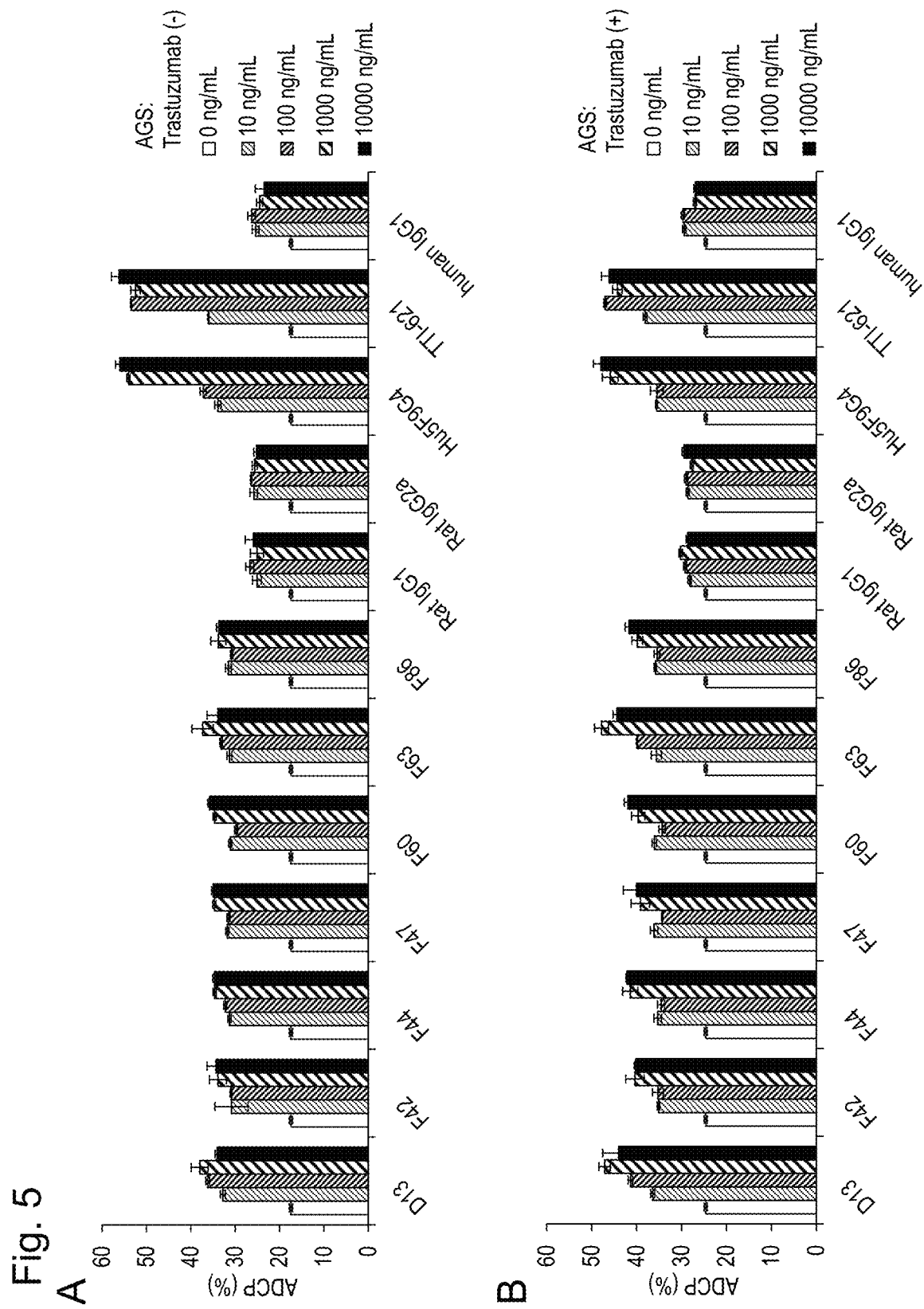
FIG. 5 shows ADCP activity against a gastric cancer cell line when the anti-SIRPA antibody was used as a single agent (A) and when the anti-SIRPA antibody was used in combination with trastuzumab (B).

As shown in FIG. 5, the rat anti-human SIRPA antibodies used alone exhibited a lower ADCP activity against CD47-positive human gastric cancer cell line AGS compared with Hu5F9G4 (anti-human CD47 antibody) and TTI-621 (human SIRPA-Fc) (FIG. 5A). In contrast, the anti-SIRPA antibodies used in combination with trastuzumab exhibited an ADCP activity similar to those of Hu5F9-G4 and TTI-621 (FIG. 5B). These results indicated that inhibition of the SIRPA-CD47 binding by the anti-SIRPA antibodies enhanced the phagocytic activity of macrophages.

Example 3. Nucleotide Sequence Analysis of cDNAs of Variable Regions of Rat Anti-SIRPA Antibodies (D13, F44, and F63) and Determination of Amino Acid Sequences Thereof 3)-1 Nucleotide Sequence Analysis of cDNA of D13 Variable Region and Determination of Amino Acid Sequence Thereof 3)-1-1 Preparation of Total RNA of D13-Producing Hybridoma To amplify the cDNA encoding the D13 variable region, a total RNA was prepared from a D13-producing hybridoma using TRIzol Reagent (Ambion).

3)-1-2 Nucleotide Sequence Analysis of cDNA of D13 Light Chain Variable Region by 5'-RACE PCR and Determination of Amino Acid Sequence Thereof The cDNA encoding the light chain variable region was amplified using approximately 1 µg of the total RNA prepared in Example 3)-1-1 and SMARTer RACE 5'/3' Kit (Clontech Laboratories Inc.). As primers to amplify the cDNA encoding the variable region of the D13 light chain gene by PCR, Universal Primer A Mix (UPM: provided in SMARTer RACE 5'/3' Kit) and primers designed from a known rat light chain constant region sequence were used.

The cDNA encoding the light chain variable region amplified by 5'-RACE PCR was cloned in a plasmid, and subsequently a sequence analysis was performed for the nucleotide sequence of the cDNA encoding the light chain variable region.

The amino acid sequence of the D13 light chain variable region encoded by the determined cDNA nucleotide sequence corresponds to an amino acid sequence consisting of amino acid residues 21 to 126 in SEQ ID NO: 23 in the sequence listing. The amino acid sequences of CDRL1, CDRL2, and CDRL3 of D13 are set forth in SEQ ID NOS: 1 to 3 in the sequence listing. The amino acids of these CDRs are also shown in FIG. 28.

The amino chain sequence of each CDR is based on the definition of AbM (Martin, A. C. R., Cheetham, J. C., and Rees, A. R. Proc. Natl. Acad. Sci. USA. 1989; 86, 9268-9272).

3)-1-3 Nucleotide Sequence Analysis of cDNA of D13 Heavy Chain Variable Region by 5'-RACE PCR and Determination of Amino Acid Sequence Thereof The cDNA encoding the heavy chain variable region was amplified using approximately 1 µg of the total RNA prepared in Example 3)-1-1 and SMARTer RACE 5'/3' Kit (Clontech Laboratories Inc.). As primers to amplify the cDNA encoding the variable region of the D13 heavy chain gene by PCR, Universal Primer A Mix (UPM: provided in SMARTer RACE 5'/3' Kit) and primers designed from a known rat heavy chain constant region sequence were used.

The cDNA encoding the heavy chain variable region amplified by 5'-RACE PCR was cloned in a plasmid, and subsequently a sequence analysis was performed for the nucleotide sequence of the cDNA encoding heavy chain variable region.

The amino acid sequence of the D13 heavy chain variable region encoded by the determined cDNA nucleotide sequence corresponds to an amino acid sequence consisting of amino acid residues 20 to 139 in SEQ ID NO: 25 in the sequence listing. The amino acid sequences of CDRH1, CDRH2, and CDRH3 of D13 are set forth in SEQ ID NOS:

4 to 6 in the sequence listing. The amino acid sequences of these CDRs are also shown in FIG. 28.

3)-2 Nucleotide Sequence Analysis of cDNA of F44 Variable Region and Determination of Amino Acid Sequence Thereof The analysis was performed in the same manner as in Example 3)-1. The amino acid sequence of the F44 light chain variable region encoded by the determined cDNA nucleotide sequence corresponds to an amino acid sequence consisting of amino acid residues 21 to 127 in SEQ ID NO: 27 in the sequence listing. The amino acid sequence of the F44 heavy chain variable region encoded by the determined cDNA nucleotide sequence corresponds to an amino acid sequence consisting of amino acid residues 20 to 138 in SEQ ID NO: 29 in the sequence listing. The amino acid sequences of CDRL1, CDRL2, CDRL3, CDRH1, CDRH2, and CDRH3 of F44 are set forth in SEQ ID NOS: 7 to 12 in the sequence listing. The amino acid sequences of these CDRs are also shown in FIG. 29.

3)-3 Nucleotide Sequence Analysis of cDNA of F63 Variable Region and Determination of Amino Acid Sequence Thereof The analysis was performed in the same manner as in Example 3)-1. The amino acid sequence of the F63 light chain variable region encoded by the determined cDNA nucleotide sequence corresponds to an amino acid sequence consisting of amino acid residues 21 to 130 in SEQ ID NO: 31 in the sequence listing. Further, the amino acid sequence of the F63 heavy chain variable region encoded by the determined cDNA nucleotide sequence corresponds to an amino acid sequence consisting of amino acid residues 20 to 143 in SEQ ID NO: 33. The amino acid sequences of CDRL1, CDRL2, CDRL3, CDRH1, CDRH2, and CDRH3 of F63 are set forth in SEQ ID NOS: 13 to 18 in the sequence listing. The amino acid sequences of these CDRs are also shown in FIG. 30.

Example 4. Preparation of Human Chimeric Anti-SIRPA Antibodies (cD13, cF44, and cF63)

4)-1 Construction of Human Chimeric and Humanized κ Type Light Chain Expression Vector pCMA-LK Approximately 5.4 kb fragment obtained by digesting plasmid pcDNA3.3-TOPO/LacZ (Invitrogen) with restriction enzymes XbaI and PmeI was bound to a DNA fragment set forth in SEQ ID NO: 19 containing a human light chain signal sequence and a DNA sequence encoding a human κ chain constant region using In-Fusion HD PCR Cloning Kit (Clontech Laboratories Inc.) to prepare pcDNA3.3/LK.

pCMA-LK was constructed by removing a neomycin expressing unit from pcDNA3.3/LK.

4)-2 Construction of Human Chimeric and Humanized λ Type Light Chain Expression Vector pCMA-LL A DNA fragment from which the light chain signal sequence and human κ chain constant region were removed by digesting pCMA-LK with XbaI and PmeI was bound to a DNA fragment set forth in SEQ ID NO: 20 containing a DNA sequence encoding a human light chain signal sequence and a human λ chain constant region using In-Fusion HD PCR Cloning Kit (Clontech Laboratories Inc.) to construct pCMA-LL.

4)-3 Construction of Human Chimeric and Humanized IgG4proFALA Type Heavy Chain Expression Vector pCMA-G4PFALA pCMA-G4proFALA was constructed in the same manner as in Example 4)-2 using a DNA fragment set forth in SEQ ID NO: 21 containing a human heavy chain signal sequence and a DNA sequence encoding the amino acids of a human IgG4PFALA constant region.

4)-4 Construction of cD13 Expression Vector

4)-4-1 Construction of cD13 IgG4proFALA Type Heavy Chain Expression Vector

A DNA fragment containing a cDNA encoding a heavy chain variable region was amplified by performing PCR using the cDNA encoding the D13 heavy chain variable region obtained in Example 3)-1 as a template and primers designed for in-fusion cloning. A cD13 heavy chain expression vector was constructed by inserting the amplified DNA fragment at the site where pCMA-G4proFALA was cleaved with a restriction enzyme BlpI using In-Fusion HD PCR Cloning Kit (Clontech Laboratories Inc.). The nucleotide sequence encoding the cD13 heavy chain is set forth in SEQ ID NO: 24 in the sequence listing. A nucleotide sequence consisting of nucleotides 1 to 57 encodes the signal sequence, a nucleotide sequence consisting of nucleotides 58 to 417 encodes the variable region, and a nucleotide sequence consisting of nucleotides 418 to 1398 encodes the constant region. The amino acid sequence of the cD13 heavy chain is set forth in SEQ ID NO: 25 in the sequence listing. An amino acid sequence consisting of amino acid residues 1 to 19 corresponds to the signal sequence, an amino acid sequence consisting of amino acid residues 20 to 139 corresponds to the variable region, and an amino acid sequence consisting of amino acid residues 140 to 466 corresponds to the constant region. The sequences of SEQ ID NOS: 24 and 25 are also shown in FIG. 18.

4)-4-2 Construction of cD13 Light Chain Expression Vector

A DNA fragment containing a cDNA encoding a light chain variable region was amplified by performing PCR using the cDNA encoding the D13 light chain variable region obtained in Example 3)-1 as a template and primers designed for in-fusion cloning. The cD13 light chain expression vector was constructed by inserting the amplified DNA fragment at the site where pCMA-LK was cleaved with a restriction enzyme BsiWI using In-Fusion HD PCR Cloning Kit (Clontech Laboratories Inc.). The nucleotide sequence encoding the cD13 light chain is set forth in SEQ ID NO: 22 in the sequence listing. A nucleotide sequence consisting of nucleotides 1 to 60 encodes the signal sequence, a nucleotide sequence consisting of nucleotides 61 to 378 encodes the variable region, and a nucleotide sequence consisting of nucleotides 379 to 699 encodes the constant region. The amino acid sequence of the cD13 light chain is set forth in SEQ ID NO: 23 in the sequence listing. An amino acid sequence consisting of amino acid residues 1 to 20 corresponds to the signal sequence, an amino acid sequence consisting of amino acid residues 21 to 126 corresponds to the variable region, and an amino acid sequence consisting of amino acid residues 127 to 233 corresponds to the constant region. The sequences of SEQ ID NOS: 22 and 23 are also shown in FIG. 17.

4)-5 Construction of cF44 Expression Vector

4)-5-1 Construction of cF44 IgG4proFALA Type Heavy Chain Expression Vector

A cF44 heavy chain expression vector was constructed in the same manner as in Example 4)-4-1 using the cDNA encoding the F44 heavy chain variable region obtained in Example 3)-2 as a template. The nucleotide sequence encoding the cF44 heavy chain is set forth in SEQ ID NO: 28 in the sequence listing. A nucleotide sequence consisting of nucleotides 1 to 57 encodes the signal sequence, a nucleotide sequence consisting of nucleotides 58 to 414 encodes the variable region, and a nucleotide sequence consisting of nucleotides 415 to 1395 encodes the constant region. The amino acid sequence of the cF44 heavy chain is set forth in SEQ ID NO: 29 in the sequence listing. An amino acid sequence consisting of amino acid residues 1 to 19 corresponds to the signal sequence, an amino acid sequence consisting of amino acid residues 20 to 138 corresponds to the variable region, and an amino acid sequence consisting of amino acid residues 139 to 465 corresponds to the constant region. The sequences of SEQ ID NOS: 28 and 29 are also shown in FIG. 20.

4)-5-2 Construction of cF44 Light Chain Expression Vector

A cF44 light chain expression vector was constructed in the same manner as in Example 4)-4-2 using the cDNA encoding the F44 light chain variable region obtained in Example 3)-2 as a template. The nucleotide sequence encoding the cF44 light chain is set forth in SEQ ID NO: 26 in the sequence listing. A nucleotide sequence consisting of nucleotides 1 to 60 encodes the signal sequence, a nucleotide sequence consisting of nucleotides 61 to 381 encodes the variable region, and a nucleotide sequence consisting of nucleotides 382 to 702 encodes the constant region. The amino acid sequence of the cF44 light chain is set forth in SEQ ID NO: 27 in the sequence listing. An amino acid sequence consisting of amino acid residues 1 to 20 corresponds to the signal sequence, an amino acid sequence consisting of amino acid residues 21 to 127 corresponds to the variable region, and an amino acid sequence consisting of amino acid residues 128 to 234 corresponds to the constant region. The sequences of SEQ ID NOS: 26 and 27 are also shown in FIG. 19.

4)-6 Construction of cF63 Expression Vector

4)-6-1 Construction of cF63 IgG4proFALA Type Heavy Chain Expression Vector

A cF63 heavy chain expression vector was constructed in the same manner as in Example 4)-4-1 using the cDNA encoding the F63 heavy chain variable region obtained in Example 3)-3 as a template. The nucleotide sequence encoding the cF63 heavy chain is set forth in SEQ ID NO: 32 in the sequence listing. A nucleotide sequence consisting of nucleotides 1 to 57 encodes the signal sequence, a nucleotide sequence consisting of nucleotides 58 to 429 encodes the variable region, and a nucleotide sequence consisting of nucleotides 430 to 1410 encodes the constant region. The amino acid sequence of the cF63 heavy chain is set forth in SEQ ID NO: 33 in the sequence listing. An amino acid sequence consisting of amino acid residues 1 to 19 corresponds to the signal sequence, an amino acid sequence consisting of amino acid residues 20 to 143 corresponds to the variable region, and an amino acid sequence consisting of amino acid residues 144 to 470 corresponds to the constant region. The sequences of SEQ ID NOS: 32 and 33 are also shown in FIG. 22.

4)-6-2 Construction of cF63 Light Chain Expression Vector

A DNA fragment containing a cDNA encoding a light chain variable region was amplified by performing PCR using the cDNA encoding the F63 light chain variable region obtained in Example 3)-3 as a template and primers designed for in-fusion cloning. The cF63 light chain expression vector was constructed by inserting the amplified DNA fragment at the site where pCMA-LL was cleaved with restriction enzymes BsiWI and HpaI using In-Fusion HD PCR Cloning Kit (Clontech Laboratories Inc.). The nucleotide sequence encoding the cF63 light chain is set forth in SEQ ID NO: 30 in the sequence listing. A nucleotide sequence consisting of nucleotides 1 to 60 encodes the signal sequence, a nucleotide sequence consisting of nucleotides 61 to 390 encodes the variable region, and a nucleotide sequence consisting of nucleotides 391 to 708 encodes the constant region. The amino acid sequence of the cF63 light chain is set forth in SEQ ID NO: 31 in the sequence listing. An amino acid sequence consisting of amino acid residues 1 to 20 corresponds to the signal sequence, an amino acid sequence consisting of amino acid residues 21 to 130 corresponds to the variable region, and an amino acid sequence consisting of amino acid residues 131 to 236 corresponds to the constant region. The sequences of SEQ ID NOS: 30 and 31 are also shown in FIG. 21.

4)-7 Preparation of cD13, cF44, and cF63

4)-7-1 Production of cD13, cF44, and cF63

FreeStyle 293F Cells (Invitrogen) were cultured according to the manual. In an amount of $1.2 \times 10^9$, FreeStyle 293F Cells (Invitrogen) in a logarithmic growth phase were seeded in a 3-L Fernbach Erlenmeyer Flask (Corning Incorporated) and diluted with FreeStyle 293 Expression Medium (Invitrogen) to $2.0 \times 10^6$ cells/mL. In an amount of 0.24 mg, a heavy chain expression vector, 0.36 mg of a light chain expression vector, and 1.8 mg of Polyethyleneimine (PolyScience #24765) were added to 40 mL of Opti-Pro SFM Medium (Invitrogen), the mixture was stirred gently, further allowed to stand for five minutes, and added to FreeStyle 293F Cells. After cells were cultured with shaking at 90 rpm in an incubator at 37° C. and 8% $CO_2$ for four hours, 600 mL of EX-CELL VPRO Medium (SAFC Bioscience), 18 mL of GlutaMAX I (Gibco), and 30 mL of Yeastolate Ultrafiltrate (Gibco) were added, cells were cultured with shaking at 90 rpm in an incubator at 37° C. and 8% $CO_2$ for 7 days, and the obtained culture supernatant was filtered using Disposable Capsule Filter (Advantec #CCS-045-E1H).

4)-7-2 Purification of cD13, cF44, and cF63

The antibodies were purified from the culture supernatant obtained in Example 4)-7-1 in one step process of rProtein A affinity chromatography. After the culture supernatant was applied to a column filled with MabSelect SuRe equilibrated with PBS (GE Healthcare Bioscience Corp.), the column was washed with PBS in a volume at least 2-fold of the column capacity. Subsequently, the column was eluted with a 2 M arginine hydrochloride solution (pH 4.0) to collect fractions containing the antibodies. The buffer containing the fractions was replaced with PBS (−) by dialysis (Thermo Scientific, Slide-A-Lyzer Dialysis Cassette). The antibodies were concentrated with Centrifugal UF Filter Device VIVASPIN20 (molecular weight cutoff for ultrafiltration, 10 kDa: Sartorius) to an IgG concentration of at least 10 mg/mL. Finally, the solutions were filtered with MinisartPlus Filter (Sartorius) to obtain purified samples.

Example 5. In Vitro Evaluation of Human Chimeric Anti-SIRPA Antibodies (cD13, cF44, and cF63)

5)-1 Evaluation of Binding to Human SIRPA

5)-1-1 Evaluation of Binding to Human SIRPA (Cell-Based ELISA)

The 293α cells [described in Example 1)-6] were prepared in a 10% FBS-containing DMEM medium to $5 \times 10^5$ cells/mL. pFLAG V5-DEST-SIRPA_V1, pFLAG V5-DEST-SIRPA_V2, or pFLAG V5-DEST was introduced into the cells using Lipofectamine LTX (Invitrogen), followed by addition of 100 μL per well to a 96-well plate (Corning Incorporated), and cells were cultured overnight in the 10% FBS-containing DMEM medium at 37° C. under a 5% $CO_2$ condition. The obtained introduced cells were used for cell-based ELISA in a state that they adhered to each other. After the culture supernatant was removed, 50 μL per well of the cD13 (IgG2 and IgG4pf), cF44 (IgG1, IgG2, IgG4p, and IgG4pf), and cF63 (IgG2 and IgG4pf) antibodies prepared in Examples 3 and 4 were added to each of pFLAG V5-DEST-SIRPA_V1, pFLAG V5-DEST-SIRPA_V2, or pFLAG V5-DEST-introduced cells at final concentrations of 0 to 10,000 ng/mL, and the mixture was allowed to stand at 4° C. for one hour. Further, 50 µL per well of anti-FLAG M2 antibody (SIGMA) diluted with 5% FBS-containing PBS to a final concentration of 10,000 ng/mL was added to a well for detecting expression of each SIRPA construct, and the mixture was allowed to stand at 4° C. for one hour. The cells in the well were washed once with 5% FBS-containing PBS, followed by addition of Peroxidase AffiniPure F(ab)$_2$ Fragment Goat Anti-Human IgG, Fcγ Fragment Specific (Jackson ImmunoResearch) diluted 1000-fold with 5% FBS-containing PBS, and the mixture was allowed to stand at 4° C. for one hour. The cells in the well were washed five times with 5% FBS-containing PBS, followed by addition of 100 µL per well of an OPD coloration solution [o-phenylenediamine dihydrochloride (Wako Pure Chemical Industries, Ltd.) and $H_2O_2$ were dissolved in an OPD solution (0.05 M trisodium citrate, 0.1 M disodium hydrogen phosphate dodecahydrate, pH 4.5) at 0.4 mg/mL and 0.6% (v/v), respectively]. A coloration reaction was performed with stirring occasionally, 100 µL per well of 1 M HCl was added to terminate the coloration reaction, and then absorbance at 490 nm was measured with a plate reader ARVO (PerkinElmer Inc.). Binding of the human chimeric anti-human SIRPA antibodies to each construct was standardized by expression of the FLAG tag.

Figure 6:
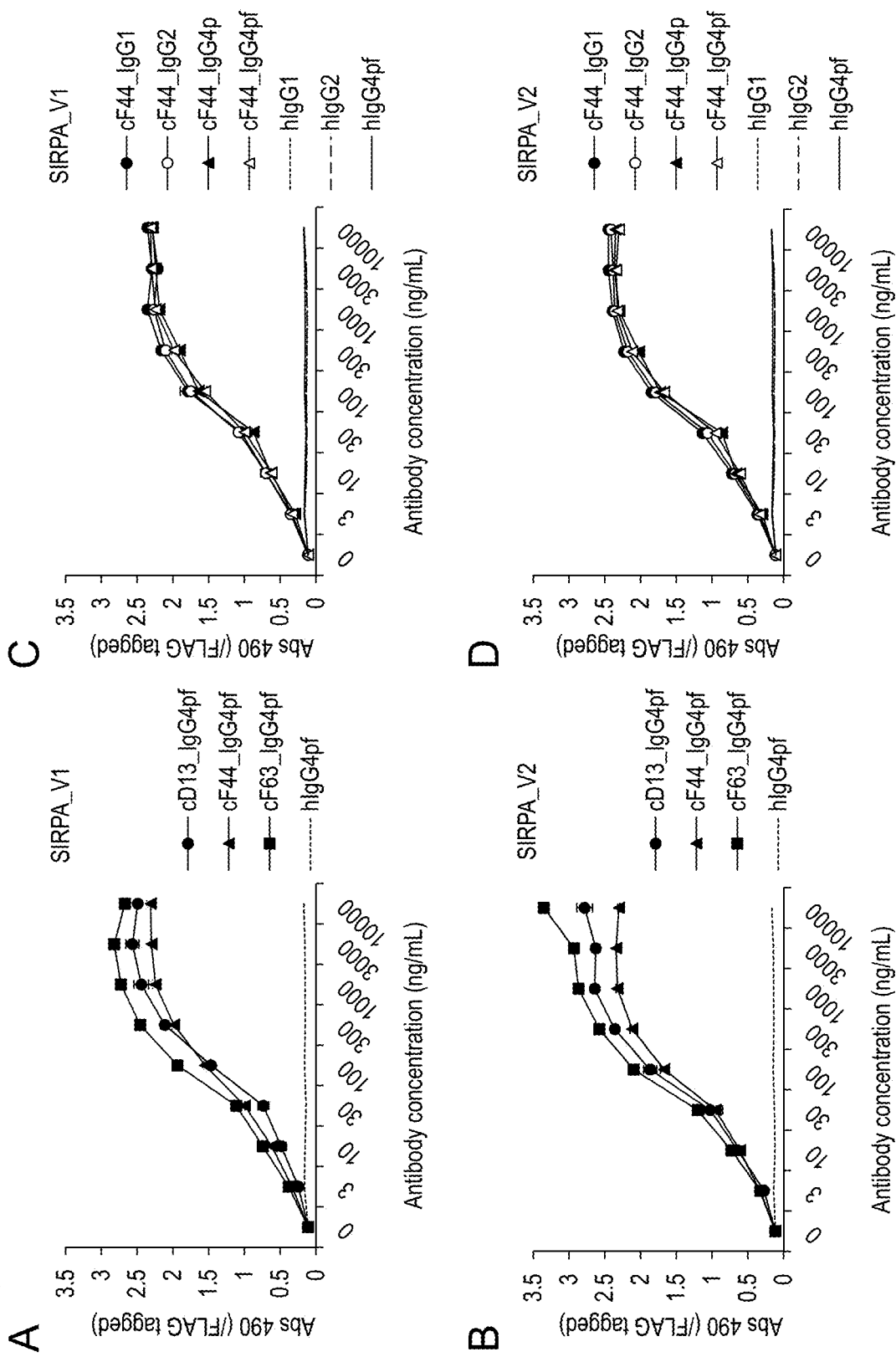
FIG. 6 shows the binding of human chimeric anti-SIRPA antibodies (cD13, cF44, and cF63) to human SIRPA.

As shown in FIG. 6, the cD13, cF44, and cF63 antibodies bound to both SIRPA_V1 and SIRPA_V2 (FIGS. 6A and B), and binding between the isotypes thereof was virtually equivalent (FIGS. 6C and D).

5)-1-2 Evaluation of Binding of Human Chimeric Antibodies to Human SIRPA

The dissociation constants of the cD13, cF44, and cF63 prepared in Example 4 against the human SIRPA_V1_IgV prepared in Example 1 were determined by a capture method comprising capturing a human chimeric antibody as a ligand and measuring an antigen as an analyte, using Biacore T200 (GE Healthcare Bioscience Corp.). HBS-EP+ (GE Healthcare Bioscience Corp.) was used as a running buffer, and CM5 (GE Healthcare Bioscience Corp.) was used as a sensor chip. In an amount of 1 µg/mL human chimeric antibody was added onto a chip at a rate of 10 µL/min for 60 seconds, a serially diluted solution of human SIRPA protein as an antigen (0.5 to 8 µg/mL) was added at a flow rate of 30 µL/min for 120 seconds, and the dissociation phase continued to be monitored for 600 seconds. As a regenerant, 3 M magnesium chloride (GE Healthcare Bioscience Corp.) was added at a flow rate of 20 µL/min for 30 seconds. For data analysis, the binding rate constant (ka), dissociation rate constant (kd), and dissociation constant (KD; KD=kd/ka) were calculated using a 1:1 binding model. The results are shown in Table 4.
[Table 4]

TABLE 4

Dissociation constant of human chimerized antibodies from human SIRPA

| Human chimerized antibody | KD (nM) |
|---|---|
| cD13 | 0.0811 |
| cF44 | 1.72 |
| cF63 | 0.166 |

5)-2 Analysis of Species Cross-Reactivity with Monkey SIRPA

293α cells were prepared in a 10% FBS-containing DMEM medium at 5×10$^5$ cells/mL. pFLAG V5-DEST-monkey SIRPA or pFLAG V5-DEST was introduced into the cells using Lipofectamine LTX (Invitrogen), 100 µL per well was added to a 96-well plate (Corning Incorporated), and cells were cultured overnight in a 10% FBS-containing DMEM medium at 37° C. under a 5% $CO_2$ condition. The obtained introduced cells were used for cell-based ELISA in a state that they adhered to each other. After the culture supernatant was removed, the binding activity against monkey SIRPA was evaluated in the same manner as for the binding activity against human SIRPA.

Figure 7:
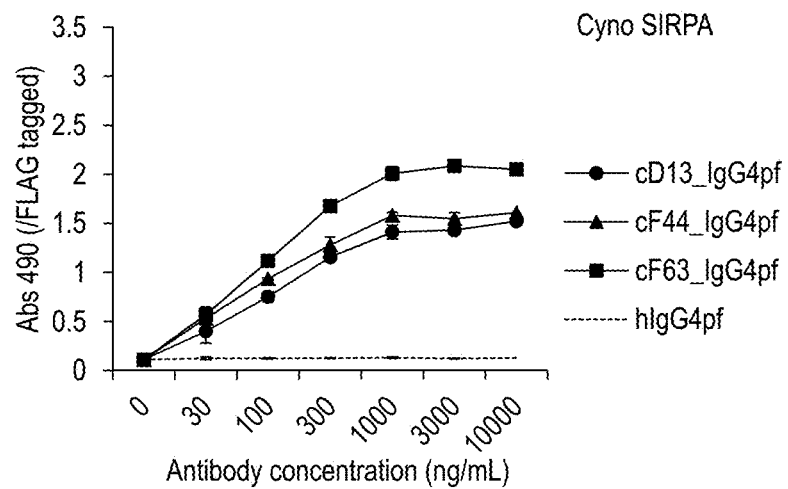
FIG. 7 shows the binding of human chimeric anti-SIRPA antibodies (cD13, cF44, and cF63) to monkey SIRPA.

As shown in FIG. 7, the cD13, cF44, and cF63 antibodies exhibited binding to monkey SIRPA.

5)-3 Evaluation of Human and Monkey SIRPA-CD47 Binding Inhibitory Activity

After the culture supernatant of the human SIRPA and monkey SIRPA expression vector-introduced 293α cells prepared in Examples 5)-1 and 5)-2, respectively, was removed, 50 µL per well of cD13 (IgG2 and IgG4pf), cF44 (four different constant regions IgG1, IgG2, IgG4p, and IgG4pf), and cF63 (IgG2 and IgG4pf) diluted with 5% FBS-containing PBS to final concentrations of 0 to 10,000 ng/mL were added to each of pcDNA3.2 V5-DEST-SIRPA_V1, pcDNA3.2 V5-DEST-monkey SIRPA, and pcDNA3.2 V5-DEST-introduced 293α cells, immediately followed by addition of 50 µL per well of peroxidase-labeled CD47-Fc prepared in 5% FBS-containing PBS at a final concentration of 10,000 ng/mL, and the mixture was allowed to stand at 4° C. for one hour. Thereafter, the SIRPA-CD47 binding inhibitory activity was evaluated in the same manner as in 1)-6-3.

As shown in FIG. 8, cF44, cF63, and cD13 exhibited the inhibitory activity against the binding of human and monkey SIRPA and CD47 [FIG. 8A (i), (ii), and (iii)], and the activity was virtually equivalent between the isotypes thereof [FIG. 8B (i), (ii), and (iii)].

5)-4 ADCP Activity of Human Chimeric Anti-Human SIRPA Antibody Against Cancer Cell Line 5)-4-1 Preparation of Target Cells CD47-positive human Burkitt's lymphoma cell line Raji cells were collected and washed twice with PBS, and then the viable cell count was measured by a trypan blue dye exclusion test. Thereafter, target cells were prepared in the same manner as in 2-6-1.

5)-4-2 Preparation of PBMCs

PBMCs were prepared in the same manner as in 2)-6-2.

5)-4-3 Preparation of Effector Cells

Effector cells were prepared in the same manner as in 2)-6-3.

5)-4-4 Evaluation of ADCP Activity

A volume of 50 µL per well of the target cells prepared by the method of Example 5)-4-1 were added to Ultra-Low Attachment 96-Well U-Shaped Bottom Microplate (Sumitomo Bakelite). A volume of 50 µL per well of cD13, cF44, cF63, Hu5F9G4, TTI-621 and various control Human IgG diluted with a 10% FBS-containing RPMI 1640 medium (Life Technology) to final concentrations of 0 to 10,000 ng/mL were added to the wells. A volume of 50 µL per well of a 10% FBS-containing RPMI 1640 medium (Life Technology) was added for the single agent group, and 50 µL per well of rituximab (Zenyaku Kogyo) diluted with a 10% FBS-containing RPMI 1640 medium (Life Technology) to a final concentration of 400 ng/mL was added for the combination use group. Thereafter, the ADCP activity was evaluated in the same manner as in 2)-6-4.

As shown in FIG. 9, cD13, cF44, and cF63 did not exhibit the ADCP activity against the CD47-positive human Burkitt's lymphoma cell line Raji cells when used as a single agent (FIG. 9A), but exhibited the ADCP activity similar to those of Hu5F9G4 and TTI-621 when used in combination with rituximab (FIG. 9B).

5)-5 Evaluation of Toxicity of Human Chimeric Anti-Human SIRPA Antibody Against PBMCs and Macrophages 5)-5-1 Preparation of PBMCs and Macrophages as Target Cells Target cells were prepared in the same manner as in 2)-6-2 (PBMCs) and 2)-6-3 (macrophages). The collected cells were fluorescence-labeled in the same manner as in 2)-6-1 and used as target cells.

5)-5-2 Preparation of Effector Cells

Effector cells were prepared in the same manner as in 2)-6-3.

5)-5-3 Evaluation of ADCP Activity

A volume of 50 μL per well of PBMCs prepared by the method of Example 5)-4-2 or macrophages were added to Ultra-Low Adhesion Surface 96-Well U-Shaped Bottom Microplate (Sumitomo Bakelite). A volume of 50 μL per well of cD13 (IgG4pf), cF44 (four different constant regions IgG1, IgG2, IgG4p, and IgG4pf), cF63 (IgG4pf), Hu5F9G4, TTI-621, and various control human IgG diluted with a 10% FBS-containing RPMI 1640 medium (Life Technology) to final concentrations of 0.64 to 10,000 ng/mL were added to the wells. A volume of 50 μL per well of a 10% FBS-containing RPMI 1640 medium (Life Technology) was added. Thereafter, the ADCP activity was evaluated in the same manner as in 2)-6-4. The ratio of the ADCP activity against macrophages was calculated by dividing the cell count upon addition of each antibody by the cell count of macrophages upon addition of the control antibody.

Figure 10:
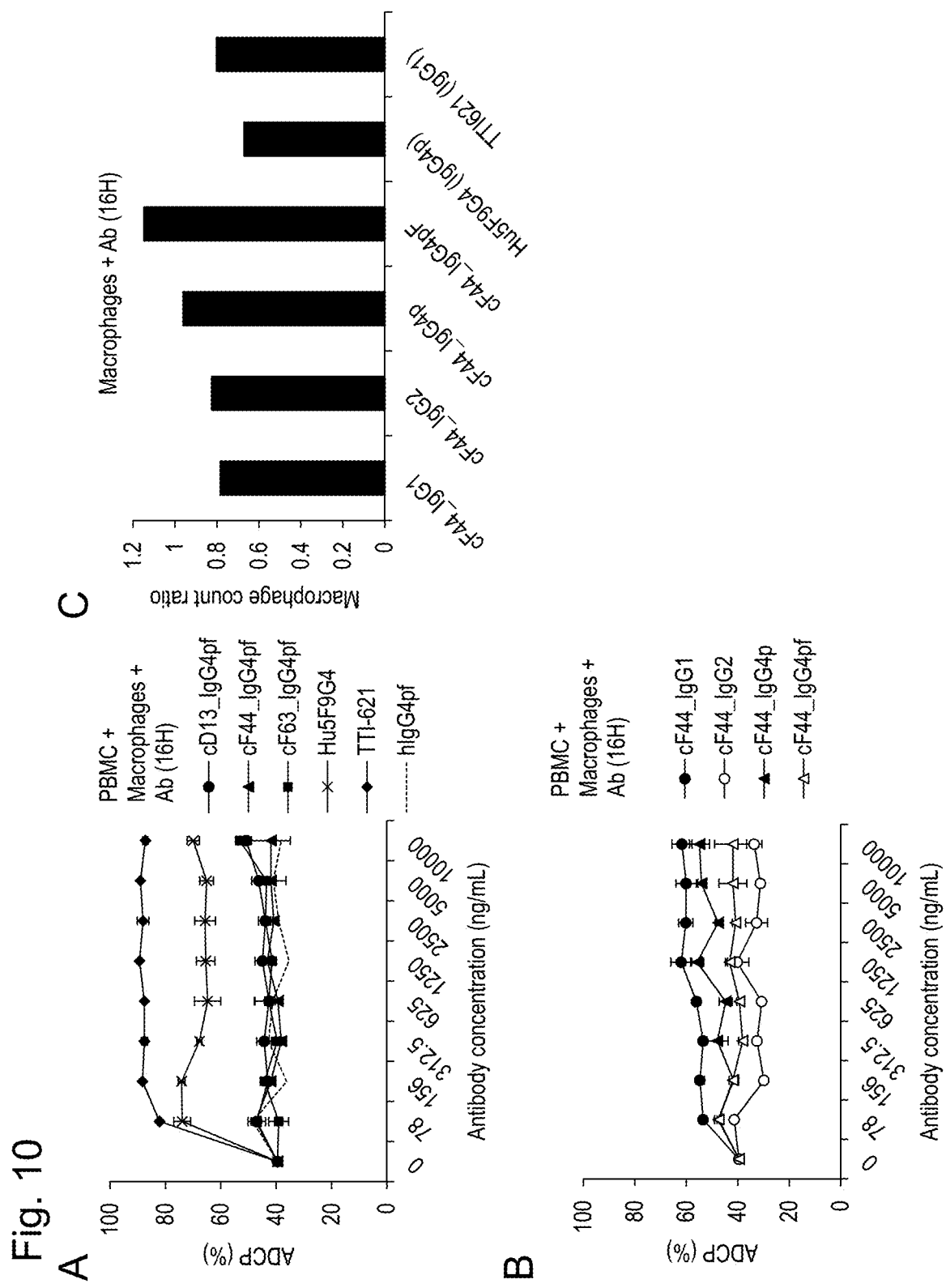
FIG. 10 shows the toxicity of human chimeric anti-human SIRPA antibodies against PBMCs and macrophages. Graph A shows an ADCP activity of cD13, cF44 and cF63 against PBMCs, Graph B shows the ADCP activity of cF44 antibodies with a different constant region, and Graph C shows ratios of macrophages present.

As shown in FIG. 10, the ADCP activity of cD13, cF44, and cF63 against PBMCs was virtually equivalent to that of the control IgG (FIG. 10A). Further, a comparison of cF44 antibodies with a different constant region showed that the IgG1 type and the IgG4p type exhibited the ADCP activity dependently on the concentration of the added antibody, but the IgG2 type and the IgG4pf type did not exhibit the ADCP activity (FIG. 10B).

Meanwhile, when cF44 antibodies with a different constant region were compared for the ratio of macrophages present at 16 hours after adding antibodies, the IgG4pf type showed the lowest percent macrophage reduction, indicating a possibility of the lowest toxicity against SIRPA positive cells induced by adding the antibody (FIG. 10C).

Example 6. Designing Humanized Anti-SIRPA Antibodies

6)-1 Molecular Modeling of Variable Region of Chimeric Antibody cD13

For a molecular modeling of the cD13 variable region, a known method (Methods in Enzymology. 1991; 203, 121-153) was used as a homology modeling. An analysis was performed using the structure (PDB ID: 3CSY) having a high sequence identity with the cD13 heavy chain and light chain variable regions, which is registered in Protein Data Bank (Nuc. Acid. Res. 2007; 35, D301-D303), as a template and a commercially available protein three-dimensional structural analysis program BioLuminate (Schrodinger).

6)-2 Designing Humanized Amino Acid Sequences cD13 was humanized by CDR grafting (Proc. Natl. Acad. Sci. USA. 1989; 86, 10029-10033). IGHV3-30*13 and IGHJ3*01, and IGKV1-6*01 and IGKJ2*01, which are human germline sequences registered in the international ImMunoGeneTics information system (IMGT, http://www.imgt.org), as well as the consensus sequences of human κ chain subgroup 4 established in Kabat et al. [Sequences of Proteins of Immunological Interest, 5th Ed. Public Health Service National Institutes of Health, Bethesda, MD (1991)], were selected as acceptors because they have a high identity to the framework region of cD13. Donor residues transferred onto an acceptor were selected by analyzing a three-dimensional model with reference to the criteria provided by Queen et al. (Proc. Natl. Acad. Sci. USA. 1989; 86, 10029-10033) and the like.

6)-3 Humanization of cD13 Heavy Chains

Two different heavy chains designed were designated as hH1 and hH2. The amino acid sequence of the full-length hH1 heavy chain is set forth in SEQ ID NO: 41 in the sequence listing. The nucleotide sequence encoding the amino acid sequence of SEQ ID NO: 41 is set forth in SEQ ID NO: 40 in the sequence listing. The amino acid sequence of the full-length hH2 heavy chain is set forth in SEQ ID NO: 43 in the sequence listing. The nucleotide sequence encoding the amino acid sequence of SEQ ID NO: 43 is set forth in SEQ ID NO: 42 in the sequence listing. In SEQ ID NOS: 41 and 43, an amino acid sequence consisting of amino acid residues 1 to 19 corresponds to the signal sequence, an amino acid sequence consisting of amino acid residues 20 to 139 corresponds to the variable region, and an amino acid sequence consisting of amino acid residues 140 to 466 corresponds to the constant region. Further, in SEQ ID NOS: 40 and 42, a nucleotide sequence consisting of nucleotides 1 to 57 encodes the signal sequence, a nucleotide sequence consisting of nucleotides 58 to 417 encodes the variable region, and a nucleotide sequence consisting of nucleotides 418 to 1398 encodes the constant region. The sequences of SEQ ID NOS: 40 and 41 are also shown in FIG. 26, and the sequences of SEQ ID NOS: 42 and 43 are also shown in FIG. 27.

A comparison of the amino acid sequences of cD13_H, which is the heavy chain of the human chimeric anti-SIRPA antibody cD13, and hH1 and hH2, which are the heavy chains of the humanized antibody, is shown in FIG. 11. In the sequences of hH1 and hH2, "●" indicates that the amino acid residue is identical to the one in the sequence of c013_H, and the site with an amino acid residue indicates an amino acid residue by which the residue was substituted.

6)-4 Humanization of cD13 Light Chains

Three different light chains designed were designated as hL2, hL3, and hL4. The amino acid sequence of the full-length light chain of hL2 is set forth in SEQ ID NO: 35 in the sequence listing. The nucleotide sequence encoding the amino acid sequence of SEQ ID NO: 35 is set forth in SEQ ID NO: 34 in the sequence listing. The full-length amino acid sequence of the light chain of hL3 is set forth in SEQ ID NO: 37 in the sequence listing. The nucleotide sequence encoding the amino acid sequence of SEQ ID NO: 37 is set forth in SEQ ID NO: 36. The full-length amino acid sequence of the light chain of hL4 is set forth in SEQ ID NO: 39 in the sequence listing. The nucleotide sequence encoding the amino acid sequence of SEQ ID NO: 39 is set forth in SEQ ID NO: 38. In SEQ ID NOS: 35, 37, and 39, an amino acid sequence consisting of amino acid residues 1 to 20 corresponds to the signal sequence, an amino acid sequence consisting of amino acid residues 21 to 127 corresponds to the variable region, and an amino acid sequence consisting of amino acid residues 128 to 234 corresponds to the constant region. Further, in SEQ ID NOS: 34, 36, and 38, a nucleotide sequence consisting of nucleotides 1 to 60 encodes the signal sequence, a nucleotide sequence consisting of nucleotides 61 to 381 encodes the variable region, and a nucleotide sequence consisting of nucleotides 382 to 702 corresponds to the constant region. The sequences of SEQ ID NOS: 34 and 35 are also shown in FIG. 23, and the sequences of SEQ ID NOS: 36 and 37 are also shown in FIG. 24, and the sequences of SEQ ID NOS: 38 and 39 are also shown in FIG. 25.

A comparison of the amino acid sequence of cD13_L, which is the light chain of the human chimeric anti-SIRPA antibody cD13, and those of hL2, hL3, and hL4, which are the light chains of the humanized antibodies, is shown in FIG. 12. In the sequences of hL2, hL3, and hL4, "●" indicates that the amino acid residue is identical to the one in the sequence of cD13_L, and a site with an amino acid residue indicates an amino acid residue by which the residue was substituted.

6)-5 Designing Humanized Antibodies by Combinations of Heavy Chains and Light Chains An antibody comprising hH1 and hL3 is referred to as "H1L3 antibody" or "H1L3." An antibody comprising hH1 and hL4 is referred to as "H1L4 antibody" or "H1L4." An antibody comprising hH2 and hL2 is referred to as "H2L2 antibody" or "H2L2." An antibody comprising hH2 and hL3 is referred to as "H2L3 antibody" or "H2L3."

Example 7. Preparation of Humanized Anti-SIRPA Antibodies

7)-1 Construction of Humanized Antibody Heavy Chain Expression Vectors
7)-1-1 Construction of hH1 Expression Vector A DNA fragment consisting of nucleotides at positions 36 to 434 of the nucleotide sequence of hH1 set forth in SEQ ID NO: 40 in the sequence listing was synthesized (GeneArt). The hH1 expression vector was constructed by inserting the synthesized DNA fragment at a site where pCMA-G4proFALA was cleaved with a restriction enzyme BlpI using In-Fusion HD PCR Cloning Kit (Clontech Laboratories Inc.).

7)-1-2 Construction of hH2 Expression Vector

A DNA fragment consisting of nucleotides at positions 36 to 434 in the nucleotide sequence of hH2 set forth in SEQ ID NO: 42 in the sequence listing was synthesized (GeneArt). The hH2 expression vector was constructed in the same manner as in Example 7)-1-1.

7)-2 Construction of Humanized Antibody Light Chain Expression Vectors
7)-2-1 Construction of hL2 Expression Vector A DNA fragment consisting of nucleotides at positions 37 to 402 in the nucleotide sequence of hL2 of SEQ ID NO: 34 in the sequence listing was synthesized (GeneArt). The hL2 expression vector was constructed by inserting the synthesized DNA fragment at a site where pCMA-LK was cleaved with a restriction enzyme BsiWI using In-Fusion HD PCR Cloning Kit (Clontech Laboratories Inc.).

7)-2-2 Construction of hL3 Expression Vector

A DNA fragment consisting of nucleotides at positions 37 to 402 in the nucleotide sequence of hL3 set forth in SEQ ID NO: 36 in the sequence listing was synthesized (GeneArt). The hL3 expression vector was constructed in the same manner as in Example 7)-2-1.

7)-2-3 Construction of hL4 Expression Vector

A DNA fragment consisting of nucleotides at positions 37 to 402 in the nucleotide sequence of hL4 set forth in SEQ ID NO: 38 in the sequence listing was synthesized (GeneArt). The hL4 expression vector was constructed in the same manner as in Example 7)-2-1.

7)-3 Preparation of Humanized Antibodies
7)-3-1 Production of Humanized Antibodies Humanized antibodies were produced in the same manner as in Example 4)-7-1. Various humanized antibodies were obtained using combinations of the H chain expression vectors and the L chain expression vectors corresponding to the combinations of the H chains and the L chains shown in Example 6)-5.

7)-3-2 Preparation of Humanized Antibodies

The culture supernatant obtained in Example 7)-3-1 was purified by a two-step process of rProtein A affinity chromatography and ceramic hydroxyapatite. After the culture supernatant was applied to a column filled with MabSelect SuRe (GE Healthcare Bioscience Corp.) equilibrated with PBS, the column was washed with PBS in a volume more than two-fold of the column capacity. Subsequently, an antibody was eluted with 2 M arginine hydrochloride solution (pH 4.0). The buffer was replaced with PBS by dialysis of fractions containing the antibody (Thermo Scientific, Slide-A-Lyzer Dialysis Cassette), and the fractions were diluted five-fold with a buffer of 5 mM sodium phosphate/50 mM MES/pH 7.0 and applied to a ceramic hydroxyapatite column (Japan Bio-Rad, Bio-Scale CHT Type-1 Hydroxyapatite Column) equilibrated with a buffer 5 mM NaPi/50 mM MES/30 mM NaCl/pH 7.0. Elution by sodium chloride was performed with a linear concentration gradient to collect fractions containing the antibody. The buffer was replaced with HBSor (25 mM histidine/5% sorbitol, pH 6.0) by dialysis of fractions (Thermo Scientific, Slide-A-Lyzer Dialysis Cassette). The antibody was concentrated with Centrifugal UF Filter Device VIVASPIN20 (molecular weight cutoff for ultrafiltration, 10 kDa: Sartorius AG) and adjusted to an IgG concentration of 50 mg/mL. Finally, the solution was filtered with Minisart-Plus Filter (Sartorius AG) to obtain a purified sample.

Example 8. In Vitro Evaluation of Humanized Anti-SIRPA Antibodies (hD13_H1L3, hD13_H1L4h, hD13_H2L2, and hD13_H2L3)

8)-1 Binding Activity of Humanized Anti-SIRPA Antibodies to Human, Monkey, and Mouse SIRPA
8)-1-1 Binding Activity of Humanized Anti-SIRPA Antibodies to Human, Monkey, and Mouse SIRPA (Cell-Based ELISA)

The 293α cells, described in Example 1)-6, were prepared at $5 \times 10^5$ cells/mL in a 10% FBS-containing DMEM medium. pFLAG V5-DEST-SIRPA_V1-V10, pFLAG V5-DEST-monkey SIRPA, pFLAG V5-DEST-mouse SIRPA, or pFLAG V5-DEST was introduced into the cells using Lipofectamine LTX (Invitrogen), and 100 μL each was aliquoted to a 96-well plate (Corning Incorporated) and cultured overnight in a 10% FBS-containing DMEM medium at 37° C. under a 5% $CO_2$ condition. The obtained introduced cells were used for cell-based ELISA in a state that they adhered. After the culture supernatant was removed, 50 μL per well of hD13_H1L3, hD13_H1L4h, hD13_H2L2, hD13_H2L3, or cD13 prepared in Examples 6 and 7 or a control antibody was added to each of various SIRPA genes-introduced cells at a final concentration of 0 to 10,000 ng/mL, and the mixture was allowed to stand at 4° C.

for one hour. Thereafter, binding to human SIRPA was evaluated in the same manner as in Example 5-1.

Figure 13B:
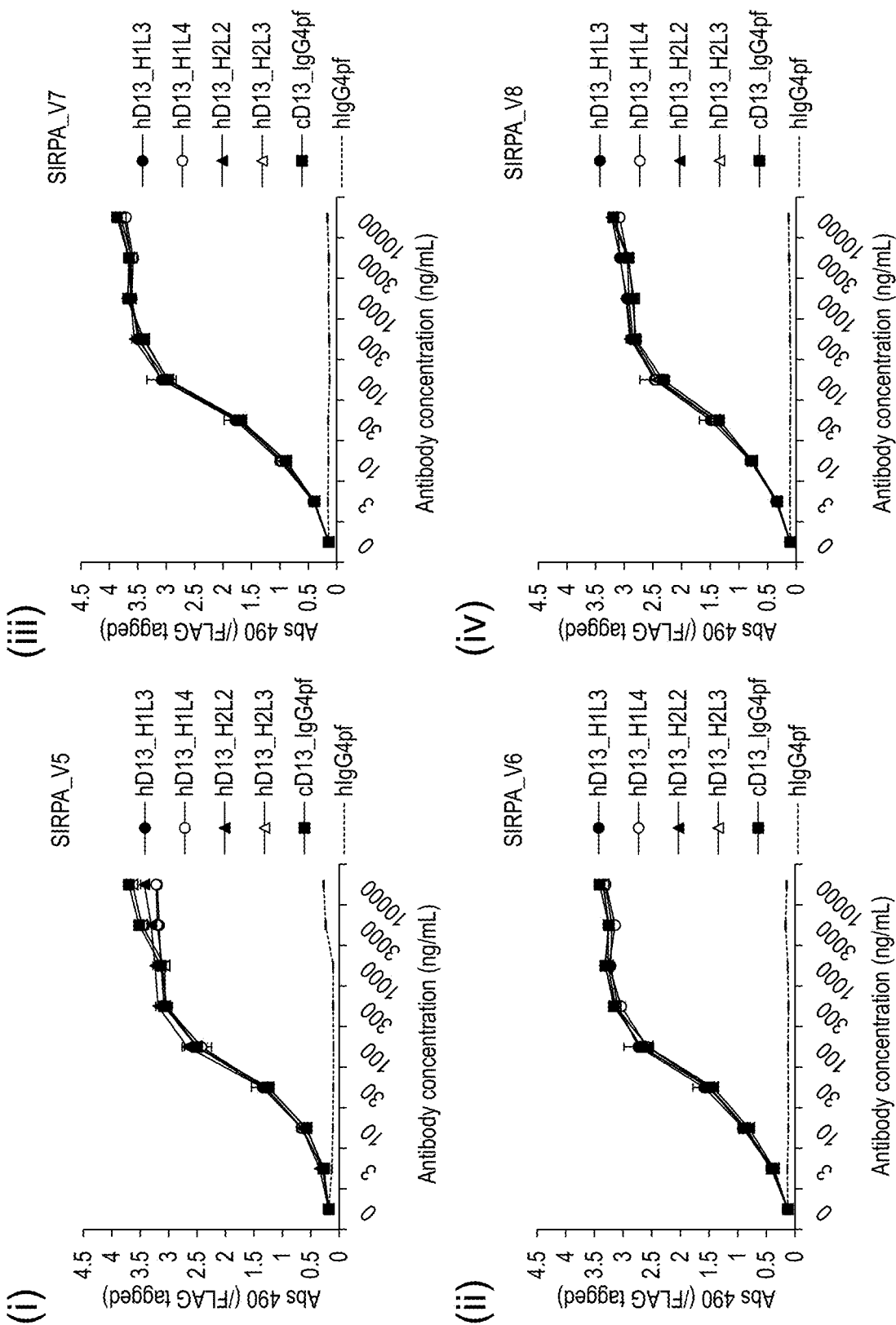
FIG. 13B is graphs showing a binding activity of a humanized anti-SIRPA antibody to human SIRPA variants [(i) V5, (ii) V6, (iii) V7, and (iv) V8].
Figure 14B:
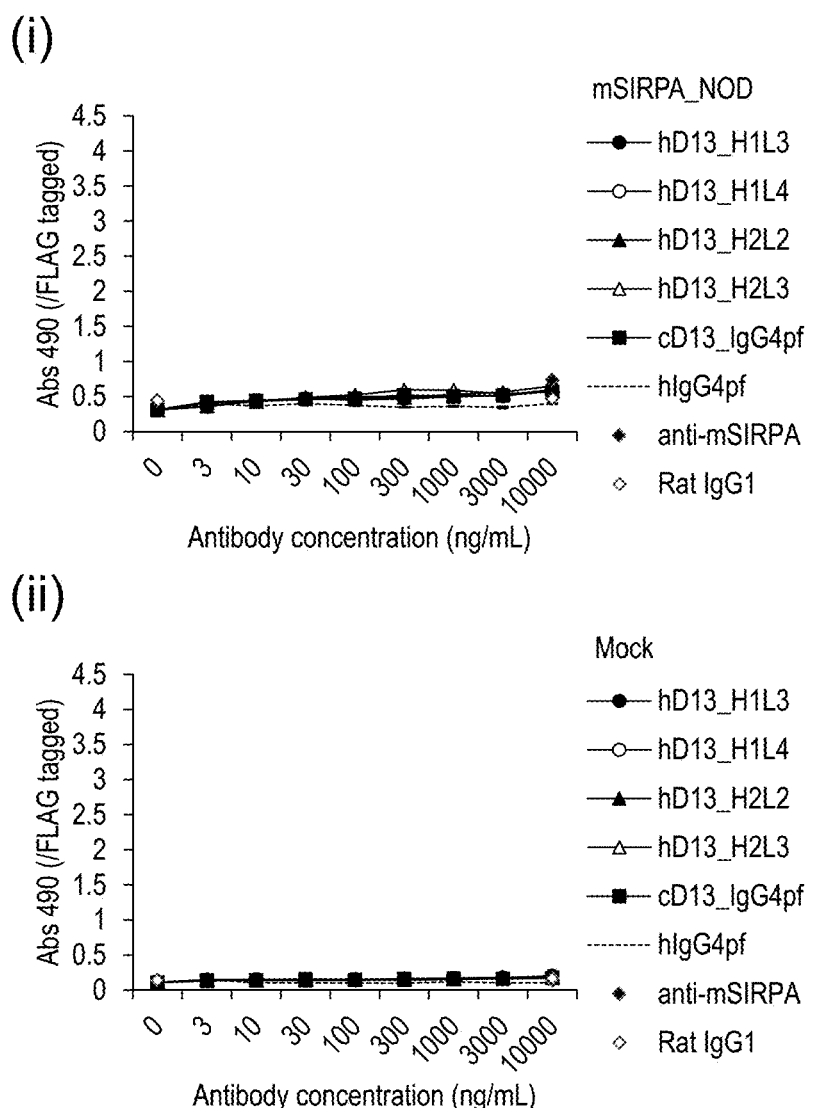
FIG. 14B is graphs showing a binding activity of a humanized anti-SIRPA antibody to mouse SIRPA [(i) NOD, and (ii) mock].

As shown in FIGS. 13A to 13C, the hD13_H1L3, hD13_H1L4h, hD13_H2L2, and hD13_H2L3 antibodies exhibited binding to SIRPA variants V1 to V10 and monkey SIRPA which was equivalent to or higher than that of the cD13 antibody. In contrast, as shown in FIGS. 14A and 14B, neither humanized antibodies nor human chimeric antibody exhibited binding to mouse SIRPA.

8)-1-2 Evaluation of Binding of Humanized Antibodies to SIRPA

The dissociation constants of hD13_H1L3, hD13_H1L4, hD13_H2L2, and hD13_H2L3 prepared in Example 7 against human SIRPA_V1_IgV and monkey SIRPA_ECD prepared in Example 1 were measured by a capture method of capturing a humanized antibody as a ligand to an Anti-Human IgG (Fc) antibody immobilized using Human Antibody Capture Kit (GE Healthcare Bioscience Corp.) and measuring an antigen as an analyte, using Biacore T200 (GE Healthcare Bioscience Corp.). HBS-EP+(GE Healthcare Bioscience Corp.) was used as a running buffer, and CM5 (GE Healthcare Bioscience Corp.) was used as a sensor chip. Onto the chip, 1 µg/mL humanized antibody was added at 10 µL/min for 60 seconds, and then a serially diluted solution (0.5 to 8 µg/mL) of human SIRPA protein or a serially diluted solution (1 to 16 µg/mL) of monkey SIRPA protein was added as an antigen at a flow rate of 30 µL/min for 120 seconds, and subsequently the dissociation phase for 600 seconds was monitored. As a regenerant, 3 M magnesium chloride (GE Healthcare Bioscience Corp.) was added at a flow rate of 20 µL/min for 30 seconds. For data analysis, a binding rate constant (ka), a dissociation rate constant (kd), and a dissociation constant (KD; KD=kd/ka) were calculated using a 1:1 binding model. The results are shown in Table 5.

TABLE 5

Dissociation constants of humanized antibodies against SIRPA

| Humanized antibody | KD (nM) | |
|---|---|---|
| | Human SIRPA | Monkey SIRPA |
| hD13_H1L3 | 0.0785 | 38.6 |
| hD13_H1L4 | 0.107 | 83.9 |
| hD13_H2L2 | 0.131 | 162 |
| hD13_H2L3 | 0.0859 | 54.2 |

8)-2 Evaluation of Inhibitory Activity of Humanized Anti-SIRPA Antibodies Against Binding to Human or Monkey SIRPA-CD47

After the culture supernatant of human SIRPA or monkey SIRPA expression vector-introduced 293α cells prepared in Example 8)-1 was removed, 50 µL per well of hD13_H1L3, hD13_H1L4h, hD13_H2L2, or hD13_H2L3 diluted with 5% FBS-containing PBS to a final concentration of 0 to 10,000 ng/mL was added to each of pcDNA3.2 V5-DEST-SIRPA_V1, pcDNA3.2 V5-DEST-SIRPA_V2, pcDNA3.2 V5-DEST-monkey SIRPA, and pcDNA3.2 V5-DEST-introduced 293α cells, immediately followed by addition of peroxidase-labeled CD47-Fc prepared with 5% FBS-containing PBS at 1 µg/mL, and the mixture was allowed to stand at 4° C. for one hour. Thereafter, the SIRPA-CD47 binding inhibitory activity was evaluated in the same manner as in 1)-6-3.

Figure 15:
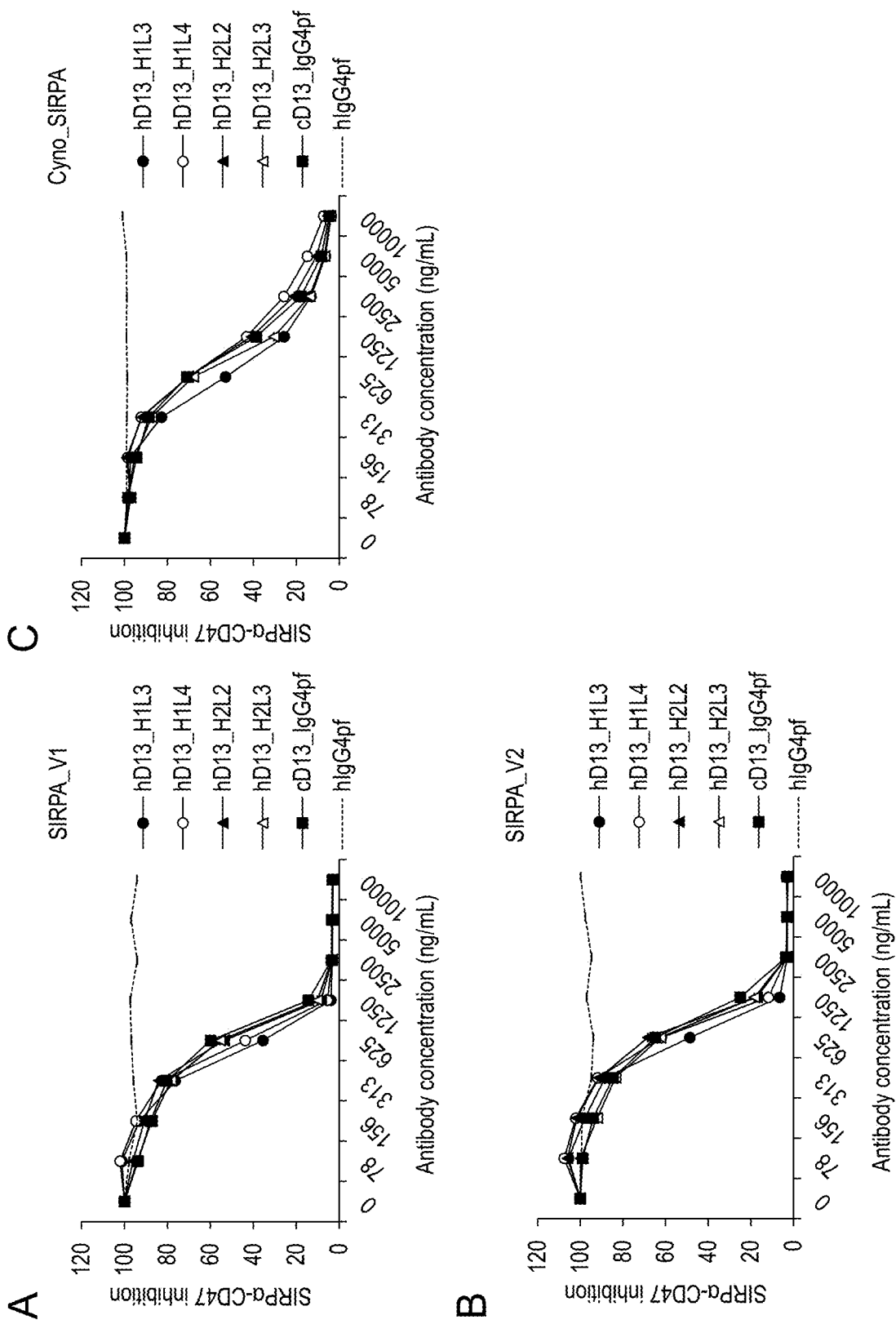
FIG. 15 is graphs showing the results of an evaluation of an inhibitory activity of a humanized anti-SIRPA antibody against binding of human (A and B) or monkey (C) SIRPA and CD47.

As shown in FIG. 15, the hD13_H1L3, hD13_H1L4h, hD13_H2L2, and hD13_H2L3 antibodies exhibited a binding inhibitory activity equivalent to or higher than that of the cD13 antibody against SIRPA_V1 (FIG. 15A), SIRPA_V2 (FIG. 15B), and monkey SIRPA (FIG. 15C).

8)-3 ADCP Activity of Humanized Anti-Human SIRPA Antibodies Against Cancer Cell Line 8)-3-1 Preparation of Target Cells CD47-positive human Burkitt's lymphoma cell line Raji cells or Ramos cells were collected and washed twice with PBS, and the viable cell count was measured by a trypan blue dye exclusion test. Then, $4 \times 10^7$ cells were aliquoted, centrifuged, and suspended in 2 mL of Diluent C included in CellVue Claret Far Red Fluorescent Cell Linker Kit (Sigma). As a labeling solution, 1 mM CellVue Claret Dye was diluted with Diluent C to 10 µM, immediately followed by mixing the cell suspension and an equal volume of the CellVue Claret Dye solution, and the mixture was allowed to stand at room temperature for 15 minutes. A volume of 25 mL of a 10% FBS-containing RPMI 1640 medium (Life Technology) was added, and cells were washed twice and re-suspended at $2 \times 10^6$ cells/mL and used as target cells. Thereafter, the target cells were prepared in the same manner as in 2)-6-1.

8)-3-2 Preparation of PBMCs

PBMCs were prepared in the same manner as in 2)-6-2.

8)-3-3 Preparation of Effector Cells

Effector cells were prepared in the same manner as in 2)-6-3, washed twice with PBS, and re-suspended in PBS to $1 \times 10^6$ cells/mL. Then, 1 µL of a $10^6$ cells/mL CFSE solution (Thermo Fisher) was added as a labeling solution, and the mixture was allowed to stand at room temperature for 10 minutes. A volume of 20 mL of a 10% FBS-containing RPMI 1640 medium (Life Technology) was added, and cells were washed twice, re-suspended to $1 \times 10^6$ cells/mL, and used as effector cells.

8)-3-4 Evaluation of ADCP Activity

A volume of 50 µL per well of the target cells prepared by the method of Example 8)-3-1 were added to Ultra-Low Attachment 96-Well U-Shaped Bottom Microplate (Sumitomo Bakelite). To the wells, 50 µL per well of the hD13_H1L3, hD13_H1L4h, hD13_H2L2, hD13_H2L3, or cD13 antibody, Hu5F9G4, TTI-621, or various control Human IgG diluted with a 10% FBS-containing RPMI 1640 medium (Life Technology) to a final concentration of 0 to 10,000 ng/mL was added. A volume of 50 µL per well of a 10% FBS-containing RPMI 1640 medium (Life Technology) was added for the single agent group, and 50 µL per well of rituximab (Zenyaku Kogyo) diluted with a 10% FBS-containing RPMI 1640 medium (Life Technology) to a final concentration of 400 ng/mL was added for the combination use group. A volume of 50 µL per well of effector cells prepared at $1 \times 10^6$ cells/mL in Example 8-3-3 was added, the mixture was allowed to stand at 37° C. under a 5% $CO_2$ condition for 16 hours. After the mixture was centrifuged at 1200 rpm at 4° C. for five minutes, and the supernatant was removed, cells were washed with 200 µL per well of 5% FBS-containing PBS. The cells were suspended in 100 µL per well of 1×BD Stabilizing Fixative (Becton Dickinson), and the suspension was allowed to stand overnight at 4° C. On the following day, the cell count was measured by flow cytometry (FACS Canto II: Becton Dickinson). For data analysis, FlowJo (TreeStar) was used. Cells were characterized by detecting forward scattered (FSC) light and side-scattered (SSC) light, and then the numbers of cells positive for APC (A) and cells positive for both APC and FITC (B) were obtained. Cells positive for both APC and FITC (B) were deemed to be target cells that had been phagocytized by macrophages. The percent cellular phagocytosis by the ADCP activity was calculated by the following equation:

Percent cellular phagocytosis (%)=$B/(A+B)\times 100$

Figure 16:
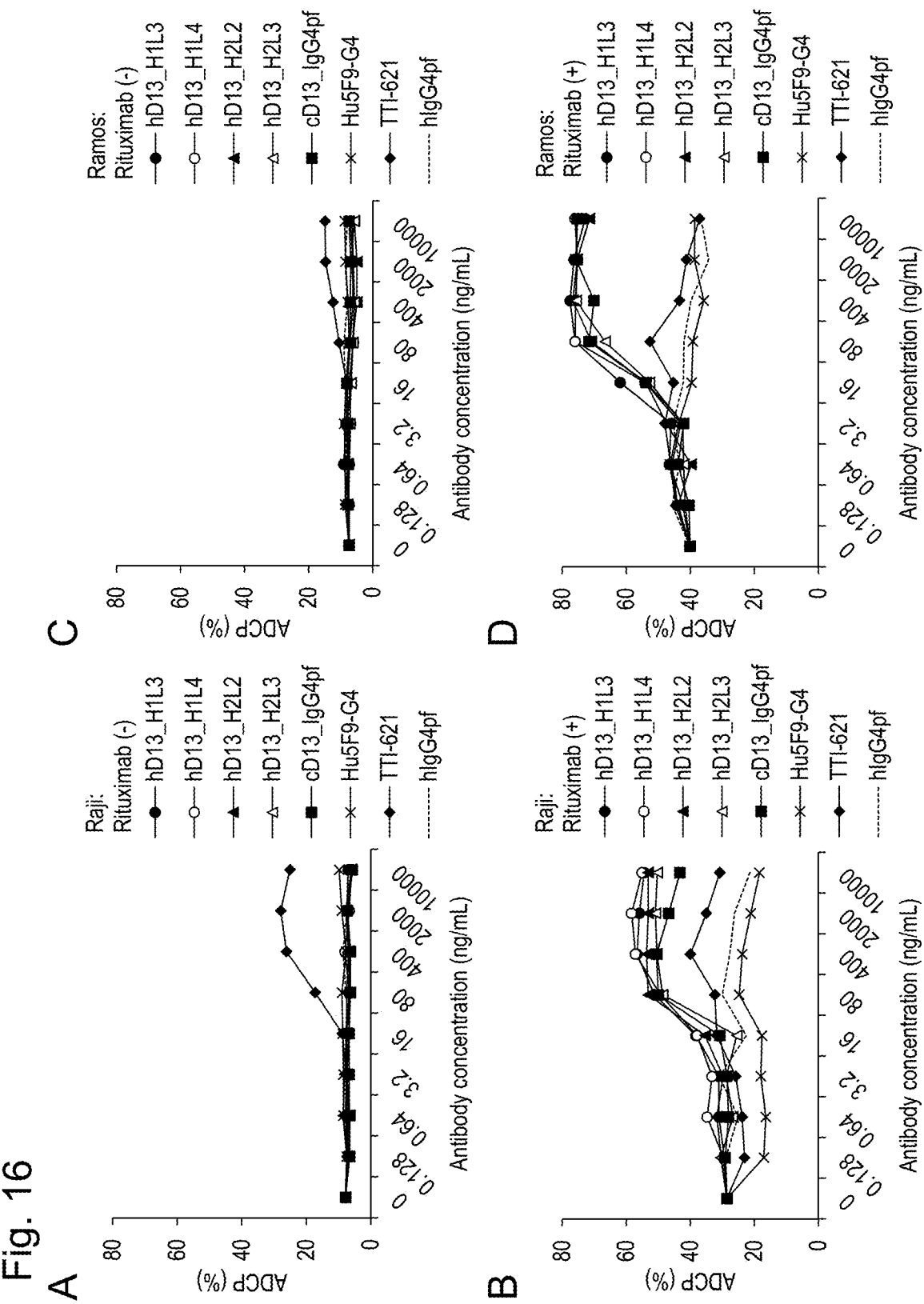
FIG. 16 is graphs showing the ADCP activity against cancer cell lines (A and B, Raji cell line; C and D, Ramos cell line) when a humanized anti-human SIRPA antibody is used as a single agent (A and C) and when the humanized anti-human SIRPA antibody is used in combination with rituximab (B and D).

As shown in FIG. 16, the hD13_H1L3, hD13_H1L4h, hD13_H2L2, hD13_H2L3, and cD13 antibodies did not exhibit the ADCP activity against CD47-positive human Burkitt's lymphoma cell line Raji or Ramos cells when they were used alone (FIGS. 16A and C), and exhibited the ADCP activity dependent on the concentration of the added antibodies when they were used in combination with rituximab (FIGS. 16B and D). The humanized antibody clones exhibited the ADCP activity equivalent to or higher than that of the human chimeric antibody clone.

Example 9. In Vitro Evaluation of Various Anti-SIRPA Antibodies

9)-1 Evaluation of Binding of Various Anti-SIRPA Antibodies to SIRPA

The dissociation constants of the hD13_H1L3 antibody prepared in Example 7, OSE-172 (prepared with reference to International Publication WO 17/178653), KWAR23 (prepared with reference to International Publication WO 18/026600), and ADU-1805 (prepared with reference to International Publication WO 18/190719) were measured against human SIRPA_V1_IgV and human SIRPA_V2_IgV prepared in Example 1. The amino acid sequence of the heavy chain of OSE-172 is set forth in SEQ ID NO: 81, the amino acid sequence of the light chain of OSE-172 is set forth in SEQ ID NO: 82, the amino acid sequence of the heavy chain of KWAR23 is set forth in SEQ ID NO: 83, the amino acid sequence of the light chain of KWAR23 is set forth in SEQ ID NO: 84, the amino acid sequence of the heavy chain of ADU-1805 is set forth in SEQ ID NO: 85, and the amino acid sequence of the light chain of ADU-1805 is set forth in SEQ ID NO: 86 in the sequence listing. The dissociation constants were measured by a capture method comprising capturing each antibody as a ligand to an Anti-Human IgG (Fc) antibody immobilized using Human Antibody Capture Kit (GE Healthcare Bioscience Corp.) and measuring an antigen as an analyte, using Biacore T200 (GE Healthcare Bioscience Corp.). HBS-EP+ (GE Healthcare Bioscience Corp.) was used as a running buffer, and CM5 (GE Healthcare Bioscience Corp.) was used as a sensor chip. Onto the chip, 2 µg/mL of various antibodies were added at 10 µL/min for 30 seconds, then a serially diluted solution (0.25 to 16 nM) of the human SIRPA protein as an antigen was added at a flow rate of 30 µL/min for 120 seconds, and subsequently the dissociation phase for 600 seconds was monitored. As a regenerant, 3 M magnesium chloride (GE Healthcare Bioscience Corp.) was added at a flow rate of 20 µL/min for 30 seconds. For data analysis, a binding rate constant (ka), a dissociation rate constant (kd), and a dissociation constant (KD; KD=kd/ka) were calculated using a 1:1 binding model. The results are shown in Table 6.

TABLE 6

Dissociation constants of various anti-SIRPA antibodies against SIRPA_V1 and V2

| Anti-SIRPAα antibody | KD (nM) | |
|---|---|---|
| | Human SIRPA_V1 | Human SIRPA_V2 |
| hD13_H1L3 | 0.252 | 1.17 |
| OSE-172 | 11.7 | Above quantitation limit |

TABLE 6-continued

Dissociation constants of various anti-SIRPA antibodies against SIRPA_V1 and V2

| Anti-SIRPAα antibody | KD (nM) | |
|---|---|---|
| | Human SIRPA_V1 | Human SIRPA_V2 |
| KWAR23 | 2.55 | 4.46 |
| ADU-1805 | 4.39 | 6.32 |

9)-2 Evaluation of Inhibitory Activity of Various Anti-Human SIRPA Antibodies Against Human SIRPA-CD47 Binding After the culture supernatant of the human SIRPA_V1 or V2 expression vector-introduced 293α cells prepared in Example 9)-1 was removed, 50 µL per well of various anti-SIRPA antibodies or various control Human IgG diluted with 5% FBS-containing PBS to a final concentration of 0 to 10,000 ng/mL was added to each of pcDNA3.2 V5-DEST-SIRPA_V1 or V2-introduced 293α cells, immediately followed by addition of 50 µL per well of peroxidase-labeled CD47-Fc prepared with 5% FBS-containing PBS at 1 µg/mL, and the mixture was allowed to stand at 4° C. for one hour. Thereafter, the SIRPA-CD47 binding inhibitory activity was evaluated in the same manner as in 1)-6-3.

Figure 31:
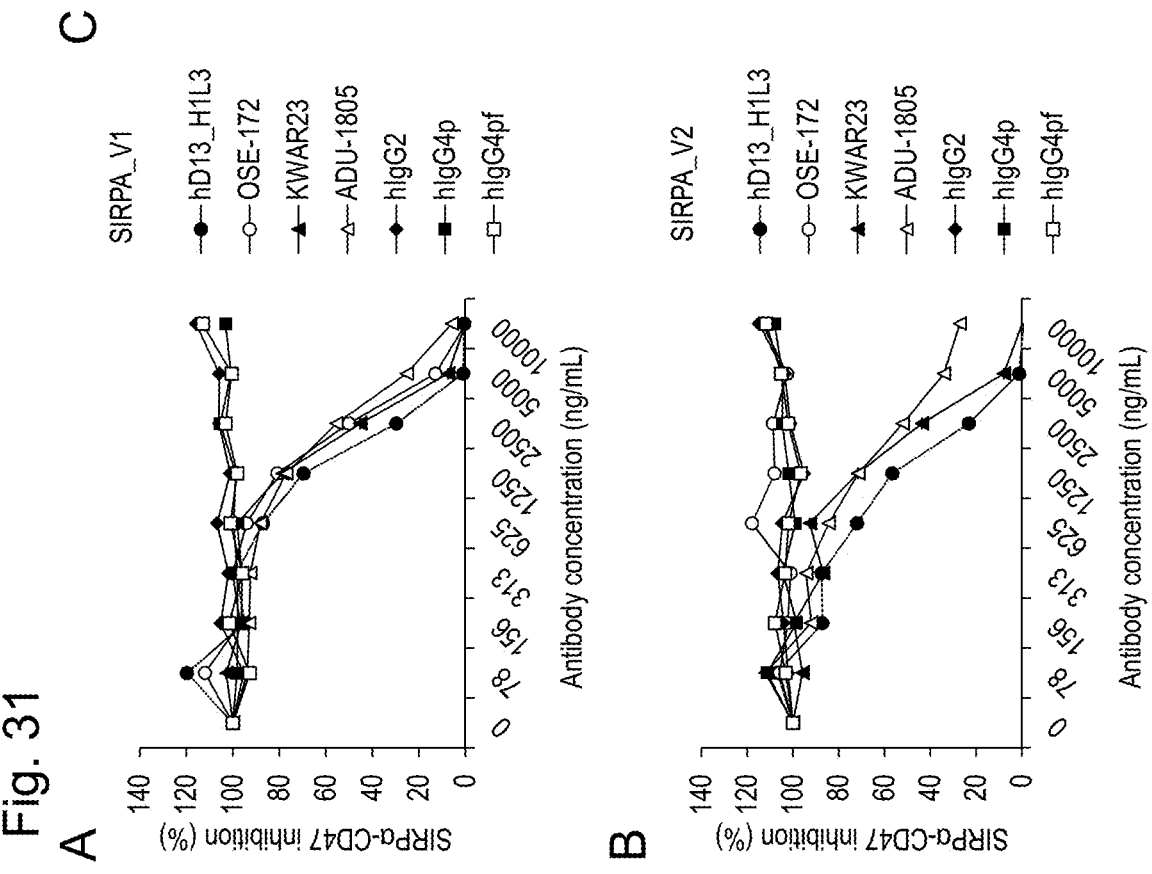
FIG. 31 shows the results of an evaluation of a human SIRPA_V1/CD47 binding inhibitory activity of various anti-human SIRPA antibodies (A), the results of an evaluation of a human SIRPA_V2/CD47 binding inhibitory activity of various anti-human SIRPA antibodies (B), and IC50 values for inhibition of human SIRPA_V1/CD47 or SIRPA_V2/CD47 binding activity by various anti-human SIRPA antibodies.

As shown in FIG. 31A, the hD13_H1L3, OSE-172, KWAR23, and ADU-1805 antibodies exhibited the inhibitory activity against SIRPA_V1-CD47 binding. As shown in FIG. 31B, hD13_H1L3, KWAR23, and ADU-1805 showed binding to human SIRPA_V2-CD47, but OSE-172 did not show the binding inhibitory activity. Further, as shown in FIG. 31C, hD13_H1L3 inhibited binding at the lowest concentration.

9)-3 Evaluation of Binding Activity of Various Anti-Human SIRPA Antibodies to Human SIRPB and Human SIRPG SIRPβ1 (signal regulatory protein 131: the amino acid sequence thereof is published as RefSeq accession number NP_006056) and SIRPγ (signal regulatory protein γ: the amino acid sequence thereof is published as RefSeq accession number NP_061026) are molecules belonging to the SIRPA family. In the present invention, "SIRPα" may be referred to as "SIRPA," "SIRPβ1" may be referred to as "SIRPB1," and "SIRPγ" may be referred to as "SIRPG." CHO-K1 cells were prepared in a 10% FBS-containing Ham's F-12K medium at 3.3×10⁵ cells/mL and cultured overnight at 37° C. under a 5% CO₂ condition. pFLAG V5-DEST-human SIRPB, pFLAG V5-DEST-human SIRPG, or pFLAG V5-DEST was introduced into the cells using Lipofectamine LTX (Invitrogen), and cells were cultured in a 10% FBS-containing Ham's F-12K medium at 37° C. under a 5% CO₂ condition for 24 hours. The obtained introduced cells were collected and seeded on a 96-well plate. After the culture supernatant was removed, 100 µL per well of various anti-human SIRPA antibodies or various control human IgG was added to each of various gene introduced cells at a final concentration of 0 to 10,000 ng/mL, and the mixture was allowed to stand at 4° C. for 25 minutes. After the mixture was centrifuged, the supernatant was removed, and cells were washed twice with 5% FBS-containing PBS. After the mixture was centrifuged, the supernatant was removed, 50 µL per well of a ¹⁄₄₀₀ diluted solution of PE Mouse anti-Human IgG antibody (BioLegend) was added, and the mixture was allowed to stand at 4° C. for 25 minutes. After the mixture was centrifuged, the supernatant was removed, and cells were washed twice with 5% FBS-containing PBS.

After the mixture was centrifuged, and the supernatant was removed, cells were suspended in 100 μL per well of 1×BD Stabilizing Fixative (Becton Dickinson), and the cell count was measured by flow cytometry (FACS Canto II: Becton Dickinson). For data analysis, FlowJo (TreeStar) was used. Cells were characterized by detecting forward scattered (FSC) light and side-scattered (SSC) light, and then the mean fluorescence intensity of PE was calculated. Binding of various antibodies to the family molecules was calculated by standardizing the fluorescence intensity using the mean fluorescence intensity of a sample in which the secondary antibody alone was allowed to react.

Figure 32:
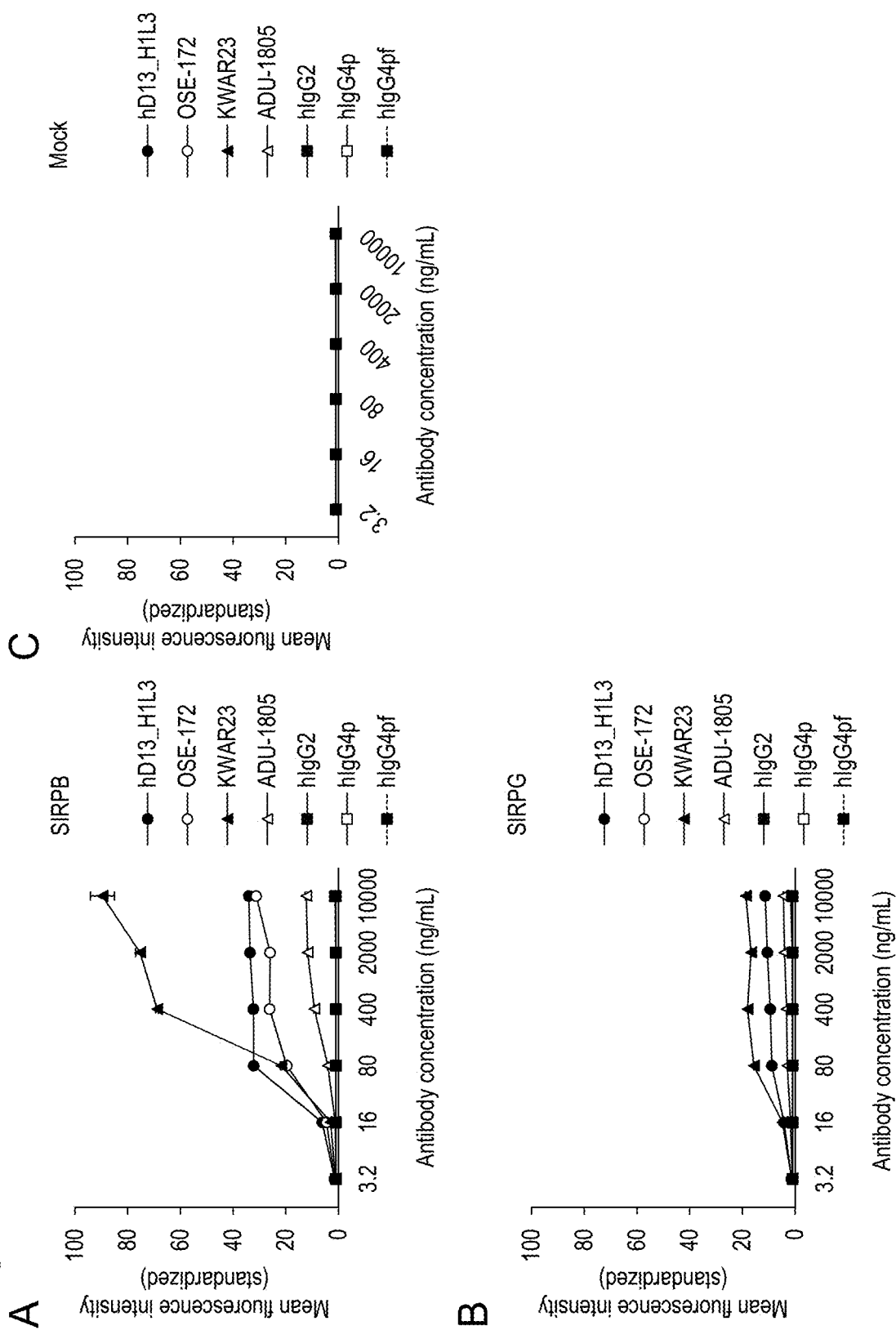
FIG. 32 is graphs showing the results of an evaluation of binding of various anti-human SIRPA antibodies to human SIRPB (A) and human SIRPG (B), and the results of a negative control for A and B (C).

As shown in FIGS. 32A and B, various anti-human SIRPA antibodies exhibited the concentration-dependent binding to human SIRPB and human SIRPG but OSE-172 did not exhibit binding to human SIRPG.

9)-4 ADCP Activity of Various Anti-Human SIRPA Antibodies Against Cancer Cell Line 9)-4-1 Preparation of Target Cells CD47-positive human Burkitt's lymphoma cell line Raji cells were collected and washed twice with PBS, and then the viable cell count was measured by a trypan blue dye exclusion test. Cells were re-suspended in PBS to 1×10⁶ cells/mL. As a labeling solution, 1 μL/10⁶ cells/mL of a Cell Trace Far Red solution (Thermo Fisher) was added, and the mixture was allowed to stand at room temperature for 10 minutes. A volume of 25 mL of a 10% FBS-containing RPMI 1640 medium (Life Technology) was added, and cells were washed twice, then re-suspended to 2×10⁶ cells/mL, and used as target cells. Thereafter, the target cells were prepared in the same manner as in 2)-6-1.

9)-4-2 Preparation of PBMCs

PBMCs were prepared in the same manner as in 2)-6-2.

9)-4-3 Preparation of Effector Cells

Effector cells were prepared in the same manner as in 2)-6-3, washed twice with PBS, and re-suspended in PBS to 1×10⁶ cells/mL. As a labeling solution, 1 μL/10⁶ cells/mL CFSE solution (Thermo Fisher) was added, and the mixture was allowed to stand at room temperature for 10 minutes. A volume of 20 mL of a 10% FBS-containing RPMI 1640 medium (Life Technology) was added, and cells were washed twice, then re-suspended to 1×10⁶ cells/mL, and used as effector cells.

9)-4-4 Evaluation of ADCP Activity

A volume of 50 μL per well of the target cells prepared by the method of Example 8-3-1 was added to Ultra-Low Attachment 96-Well U-Shaped Bottom Microplate (Sumitomo Bakelite). To the wells, 50 μL per well of various anti-SIRPA antibodies or various control Human IgG diluted with a 10% FBS-containing RPMI 1640 medium (Life Technology) to a final concentration of 0 to 10,000 ng/mL was added. For the combination use group, 50 μL per well of rituximab (Zenyaku Kogyo) diluted with a 10% FBS-containing RPMI 1640 medium (Life Technology) to a final concentration of 1000 ng/mL was added. A volume of 50 μL per well of effector cells prepared in Example 8-3-3 were added at 1×10⁶ cells/mL, and the mixture was allowed to stand at 37° C. under a 5% $CO_2$ condition for two to 16 hours. After the mixture was centrifuged at 1200 rpm at 4° C. for 5 minutes, and the supernatant was removed, cells were washed with 200 μL per well of 5% FBS-containing PBS. Cells were suspended in 50 μL per well of 1×BD Stabilizing Fixative (Becton Dickinson), and the cell count was measured by flow cytometry (FACS Canto II: Becton Dickinson). For data analysis, FlowJo (TreeStar) was used. Cells were characterized by detecting forward scattered (FSC) light and side-scattered (SSC) light, and then the numbers of cells positive for APC (A) and cells positive for both APC and FITC (B) were obtained. Cells positive for both APC and FITC (B) were deemed to be target cells that had been phagocytized by macrophages. The percent cellular phagocytosis by the ADCP activity was calculated by the following equation:

Percent cellular phagocytosis (%)=$B/(A+B)\times 100$

Figure 33:
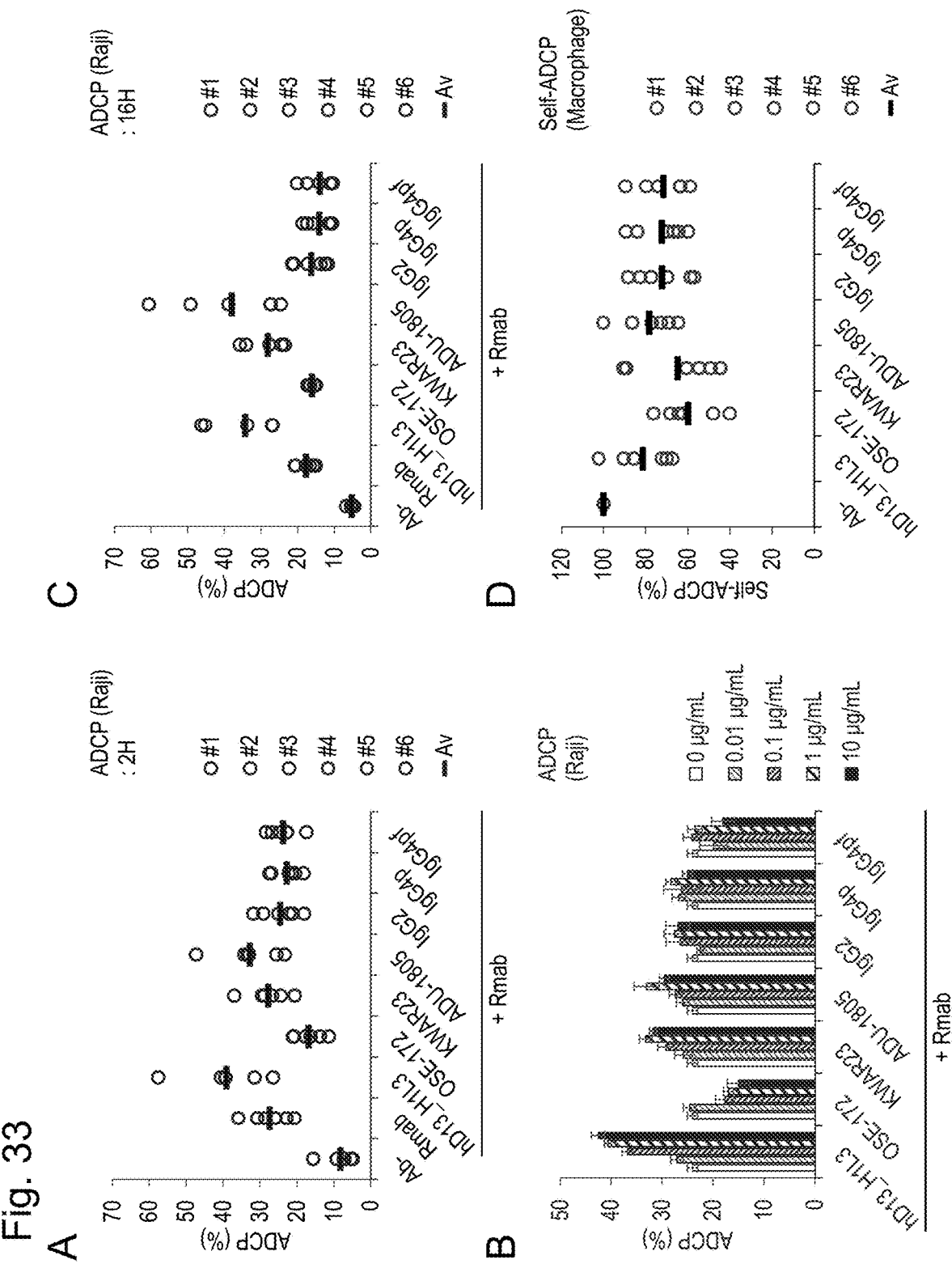
FIG. 33 is graphs showing the ADCP activity against the Burkitt's lymphoma cell line (Raji) when various anti-human SIRPA antibodies were used in combination with rituximab: the reactivity at 10 μg/mL with a reaction time of 2 hours (A) and with a reaction time of 16 hours (B), concentration dependence with a reaction time of 2 hours (C), and a self-ADCP activity, which means phagocytosis between macrophages, of various anti-human SIRPA antibodies (D). In each graph, "Ab-" indicates a negative control to which an antibody was not added, and "+Rmab" indicates that rituximab was simultaneously added.

As shown in FIGS. 33A to C, the hD13_H1L3, OSE-172, KWAR23, and ADU-1805 antibodies in combination with rituximab exhibited the ADCP activity against CD47-positive human Burkitt's lymphoma cell line Raji cells. The ADCP enhancing activity was higher in the order of hD13_H1L3, ADU-1805, KWAR23, and OSE-172 after two hours of reactions (A), and in the order of ADU-1805, hD13_H1L3, KWAR23, and OSE-172 after 16 hours of reactions (B). The reactivity at 16 hours suggests that the phagocytized activity is in a saturated state. A comparison of the concentration-dependent ADCP activity after two hours of reactions showed that hD13_H1L3 exhibited the highest activity from the lowest concentration, followed by ADU-1805 and KWAR23, which exhibited virtually equivalent activities, and OSE-172. The above results indicated that hD13_H1L3 enhanced the ADCP activity in a short time from the lowest concentration.

9)-4-5 Evaluation of Phagocytic Activity Between Macrophages by Various Anti-Human SIRPA Antibodies (Self-ADCP Activity)

A volume of 50 μL per well of effector cells prepared by the method of Example 8-3-3 was added to the Ultra-Low Attachment 96-Well U-Shaped Bottom Microplate (Sumitomo Bakelite). To the wells, 50 μL per well of various anti-SIRPA antibodies or various control Human IgG diluted with a 10% FBS-containing RPMI 1640 medium (Life Technology) to a final concentration of 0 to 5,000 ng/mL was added. A volume of 100 μL per well of a 10% FBS-containing RPMI 1640 medium (Life Technology) was added. The mixture was allowed to stand at 37° C. under a 5% $CO_2$ condition for 16 to 20 hours. The mixture was centrifuged at 1200 rpm at 4° C. for 5 minutes, the supernatant was removed, and cells were washed with 200 μL per well of 5% FBS-containing PBS. Cells were suspended in 100 μL per well of 1×BD Stabilizing Fixative (Becton Dickinson), and the cell count was measured by flow cytometry (FACS Canto II: Becton Dickinson). For data analysis, FlowJo (TreeStar) was used. Cells were characterized by detecting forward scattered (FSC) light and side-scattered (SSC) light, and then the number of FITC positive cells in each well was obtained (A). The extent of reduction in each sample was considered the extent of phagocytosis between macrophages when standardized using the count of FITC positive cells in a well not containing an antibody (B). The self-ADCP activity was calculated by the following equation:

Self-ADCP (%)=$(A/B)\times 100$

As shown in FIG. 33B, macrophages, which are effector cells, exhibited the self-ADCP activity when hD13_H1L3, OSE-172, KWAR23, and ADU-1805 antibodies were added. The percent reduction was higher in the order of OSE-172, KWAR23, ADU-1805, and hD13_H1L3. The high percent reduction indicates a high self-ADCP activity due to the anti-SIRPA antibody. This phenomenon suggests a possibility that SIRPA-positive cells such as macrophages and dendritic cells may be reduced or depleted by administering each of the anti-SIRPA antibodies, thus serving as an indicator of adverse drug reactions to the immune system.

Example 10. In Vivo Evaluation of Various Anti-SIRPA Antibodies

Because SIRPA is a target expressed in immune cells of the host, the anti-tumor effects of human SIRPA antibodies need to be evaluated in mice which express human SIRPA [Ring et al. PNAS. 2017; 114, 49, E10578-E10585]. Meanwhile, to evaluate contribution of the immune system to anti-tumor effects, it is important to use immuno-competent mice, not immuno-compromised mice [Yanagita et al. JCI. 2017; (2)1, 1-15]. A mouse cancer cell line transfected with human CD47 was transplanted to genetically modified mice obtained by introducing human SIRPA alone or both human SIRPA and human CD47 to immuno-competent mice, and the mice are divided into groups when a tumor volume of approximately 100 mm$^3$ is reached. Anti-CD47 biologics, such as various anti-SIRPA antibodies, anti-CD47 antibodies, or SIRPA-Fc fusion proteins, or negative controls such as PBS are administered to these mice groups about once to three times a week for one to three weeks. To evaluate the add-on anti-tumor effects of a combination drug, a chemotherapeutic agent, an antibody drug, a molecular targeted drug, or the like is administered in combination to each of these groups. The tumor size (major diameter/minor diameter) in each treatment group is measured with an electronic caliper or the like every two to three days to calculate the tumor volume. Drug efficacy of each drug can be compared in vivo by calculating the tumor growth inhibition rate from tumor volumes in various antibody treatment groups and the negative control group. The tumor volume and the tumor growth inhibition rate are represented by the following formula:

Tumor volume (mm$^3$)=(major diameter×minor diameter×minor diameter)/2

Tumor growth inhibition rate (%)=(1−tumor volume in each treatment group/tumor volume in the negative control group)×100

INDUSTRIAL APPLICABILITY

The anti-SIRPα antibody of the present invention can be used as an antibody drug that is used in combination with other antibody drugs having other effector functions or other antibody drugs having an immune checkpoint inhibitory action.

SEQUENCE LISTING FREE TEXT

SEQ ID NO: 1: Amino acid sequence of D13 CDR-L1
SEQ ID NO: 2: Amino acid sequence of D13 CDR-L2
SEQ ID NO: 3: Amino acid sequence of D13 CDR-L3
SEQ ID NO: 4: Amino acid sequence of D13 CDR-H1
SEQ ID NO: 5: Amino acid sequence of D13 CDR-H2
SEQ ID NO: 6: Amino acid sequence of D13 CDR-H3
SEQ ID NO: 7: Amino acid sequence of F44 CDR-L1
SEQ ID NO: 8: Amino acid sequence of F44 CDR-L2
SEQ ID NO: 9: Amino acid sequence of F44 CDR-L3
SEQ ID NO: 10: Amino acid sequence of F44 CDR-H1
SEQ ID NO: 11: Amino acid sequence of F44 CDR-H2
SEQ ID NO: 12: Amino acid sequence of F44 CDR-H3
SEQ ID NO: 13: Amino acid sequence of F63 CDR-L1
SEQ ID NO: 14: Amino acid sequence of F63 CDR-L2
SEQ ID NO: 15: Amino acid sequence of F63 CDR-L3
SEQ ID NO: 16: Amino acid sequence of F63 CDR-H1
SEQ ID NO: 17: Amino acid sequence of F63 CDR-H2
SEQ ID NO: 18: Amino acid sequence of F63 CDR-H3
SEQ ID NO: 19: DNA fragment comprising of a human light chain signal sequence and a nucleotide sequence encoding a human κ light chain constant region
SEQ ID NO: 20: DNA fragment comprising of a human light chain signal sequence and a nucleotide sequence encoding a human λ light chain constant region
SEQ ID NO: 21: DNA fragment comprising of a human heavy chain signal sequence and a nucleotide sequence encoding a human IgG4ProFALA heavy chain constant region
SEQ ID NO: 22: Nucleotide sequence encoding a human chimeric antibody D13 light chain
SEQ ID NO: 23: Amino acid sequence of a human chimeric antibody D13 light chain
SEQ ID NO: 24: Nucleotide sequence encoding a human chimeric antibody D13 heavy chain
SEQ ID NO: 25: Amino acid sequence of a human chimeric antibody D13 heavy chain
SEQ ID NO: 26: Nucleotide sequence encoding a human chimeric antibody F44 light chain
SEQ ID NO: 27: Amino acid sequence of a human chimeric antibody F44 light chain
SEQ ID NO: 28: Nucleotide sequence encoding a human chimeric antibody F44 heavy chain
SEQ ID NO: 29: Amino acid sequence of a human chimeric antibody F44 heavy chain
SEQ ID NO: 30: Nucleotide sequence encoding a human chimeric antibody F63 light chain
SEQ ID NO: 31: Amino acid sequence of a human chimeric antibody F63 light chain
SEQ ID NO: 32: Nucleotide sequence encoding a human chimeric antibody F63 heavy chain
SEQ ID NO: 33: Amino acid sequence of a human chimeric antibody F63 heavy chain
SEQ ID NO: 34: Nucleotide sequence encoding the hL2 light chain of humanized D13
SEQ ID NO: 35: Amino acid sequence of the hL2 light chain of humanized D13
SEQ ID NO: 36: Nucleotide sequence encoding the hL3 light chain of humanized D13
SEQ ID NO: 37: Amino acid sequence of the hL3 light chain of humanized D13
SEQ ID NO: 38: Nucleotide sequence encoding the hL4 light chain of humanized D13
SEQ ID NO: 39: Amino acid sequence of the hL4 light chain of humanized D13
SEQ ID NO: 40: Nucleotide sequence encoding the hH1 heavy chain of humanized D13
SEQ ID NO: 41: Amino acid sequence of the hH1 heavy chain of humanized D13
SEQ ID NO: 42: Nucleotide sequence encoding the hH2 heavy chain of humanized D13
SEQ ID NO: 43: Amino acid sequence of the hH2 heavy chain of humanized D13
SEQ ID NO: 44: Nucleotide sequence encoding the ECD of human SIRPA Variant 1
SEQ ID NO: 45: Amino acid sequence of the ECD of human SIRPA Variant 1
SEQ ID NO: 46: Nucleotide sequence encoding the IgV of human SIRPA Variant 1
SEQ ID NO: 47: Amino acid sequence of the IgV of human SIRPA Variant 1
SEQ ID NO: 48: Nucleotide sequence encoding the ECD of human SIRPA Variant 2
SEQ ID NO: 49: Amino acid sequence of the ECD of human SIRPA Variant 2

SEQ ID NO: 50: Nucleotide sequence encoding the IgV of human SIRPA Variant 2
SEQ ID NO: 51: Amino acid sequence of the IgV of human SIRPA Variant 2
SEQ ID NO: 52: Nucleotide sequence encoding the ECD of monkey SIRPA
SEQ ID NO: 53: Amino acid sequence of the ECD of monkey SIRPA
SEQ ID NO: 54: Nucleotide sequence encoding human CD47-Fc
SEQ ID NO: 55: Amino acid sequence of the IgV of human CD47-Fc
SEQ ID NO: 56: Amino acid sequence of human SIRPA Variant 1
SEQ ID NO: 57: Amino acid sequence of human SIRPA Variant 2
SEQ ID NO: 58: Amino acid sequence of monkey SIRPA
SEQ ID NO: 59: Amino acid sequence of C57BL/6 mouse SIRPA
SEQ ID NO: 60: Amino acid sequence of BALB/C mouse SIRPA
SEQ ID NO: 61: Amino acid sequence of 129 mouse SIRPA
SEQ ID NO: 62: Amino acid sequence of NOD mouse SIRPA
SEQ ID NO: 63: Amino acid sequence of human SIRPA Variant 3
SEQ ID NO: 64: Amino acid sequence of human SIRPA Variant 4
SEQ ID NO: 65: Amino acid sequence of human SIRPA Variant 5
SEQ ID NO: 66: Amino acid sequence of human SIRPA Variant 6
SEQ ID NO: 67: Amino acid sequence of human SIRPA Variant 7
SEQ ID NO: 68: Amino acid sequence of human SIRPA Variant 8
SEQ ID NO: 69: Amino acid sequence of human SIRPA Variant 9
SEQ ID NO: 70: Amino acid sequence of human SIRPA Variant 10
SEQ ID NO: 71: Amino acid sequence of human SIRPA_V2_IgV variant
SEQ ID NO: 72: Amino acid sequence of human SIRPA_V2_IgV_IgC1 variant
SEQ ID NO: 73: Amino acid sequence of mouse SIRPA variant hmSIRPA_Δ0
SEQ ID NO: 74: Amino acid sequence of mouse SIRPA variant hmSIRPA_Δ1
SEQ ID NO: 75: Amino acid sequence of mouse SIRPA variant hmSIRPA_Δ2
SEQ ID NO: 76: Sequence consisting of amino acids 81 to 85 in the amino acid sequence of mouse SIRPA variant hmSIRPA_Δ0
SEQ ID NO: 77: Sequence consisting of amino acids 81 to 85 in the amino acid sequence of mouse SIRPA variant hmSIRPA_Δ1
SEQ ID NO: 78: Sequence consisting of amino acids 81 to 85 in the amino acid sequence of BALB/C mouse SIRPA
SEQ ID NO: 79: Sequence consisting of amino acids 126 to 130 in the amino acid sequence of BALB/C mouse SIRPA
SEQ ID NO: 80: Sequence consisting of amino acids 81 to 85 in the amino acid sequence of mouse SIRPA variant hmSIRPA_Δ2
SEQ ID NO: 81: Amino acid sequence of OSE-172 antibody heavy chain (OSE-172 hG4Pro)
SEQ ID NO: 82: Amino acid sequence of OSE-172 antibody light chain (OSE-172 hK)
SEQ ID NO: 83: Amino acid sequence of KWAR23 antibody heavy chain (KWAR23_hG4Pro)
SEQ ID NO: 84: Amino acid sequence of KWAR23 antibody light chain (KWAR23 hK)
SEQ ID NO: 85: Amino acid sequence of ADU-1805 antibody heavy chain (ADU-1805 hG2)
SEQ ID NO: 86: Amino acid sequence of ADU-1805 antibody light chain (ADU-1805 hK)
SEQ ID NO: 87: Partial amino acid sequence of mouse SIRPA mutant hmSIRPA_delta 0
SEQ ID NO: 88: Partial amino acid sequence of mouse SIRPA mutant hmSIRPA_delta 1
SEQ ID NO: 89: Partial amino acid sequence of mouse SIRPA mutant hmSIRPA delta 2

All publications, patents, and patent applications cited in the present specification are incorporated in the present specification in their entirety by reference.

The invention claimed is:

1. An antibody that binds specifically to human SIRPα to inhibit binding of human SIRPα to CD47, the antibody comprising:
(a) a light chain CDRL1 consisting of an amino acid sequence set forth in SEQ ID NO: 1;
(b) a light chain CDRL2 consisting of an amino acid sequence set forth in SEQ ID NO: 2;
(c) a light chain CDRL3 consisting of an amino acid sequence set forth in SEQ ID NO: 3;
(d) a heavy chain CDRH1 consisting of an amino acid sequence set forth in SEQ ID NO: 4;
(e) a heavy chain CDRH2 consisting of an amino acid sequence set forth in SEQ ID NO: 5; and
(f) a heavy chain CDRH3 consisting of an amino acid sequence set forth in SEQ ID NO: 6.

2. The antibody according to claim 1, wherein the antibody comprises a heavy chain constant region of human IgG4, and has a mutation that reduces ADCC and/or ADCP activity.

3. The antibody according to claim 1, wherein the antibody comprises a heavy chain constant region of human IgG4, and, as numbered according to EU index as in Kabat et al., phenylalanine at position 234 is substituted by alanine, leucine at position 235 is substituted by alanine, and serine at position 228 is substituted by a proline.

4. The antibody according to claim 3, wherein the heavy chain constant region consists of the amino acid sequence of residues 140-166 in SEQ ID NO:25.

5. The antibody according to claim 1 comprising:
(ai) a light chain variable region consisting of an amino acid sequence consisting of amino acid residues 21 to 126 in SEQ ID NO: 23; or
(aii) a light chain variable region consisting of an amino acid sequence having at least 95% sequence identity with the amino acid sequence consisting of amino acid residues 21 to 126 in SEQ ID NO: 23 and having a binding activity to human SIRPα; and
(bi) a heavy chain variable region consisting of an amino acid sequence consisting of amino acid residues 20 to 139 in SEQ ID NO: 25; or
(bii) a heavy chain variable region consisting of an amino acid sequence having at least 95% sequence identity with the amino acid sequence consisting of amino acid residues 20 to 139 in SEQ ID NO: 25 and having a binding activity to human SIRPα,
wherein a heavy chain constant region is a heavy chain constant region of human IgG4, and has a mutation that reduces ADCC and/or ADCP activity.

6. The antibody according to claim 5, wherein the antibody comprises a heavy chain constant region of human IgG4, and, as numbered according to EU index as in Kabat et al., phenylalanine at position 234 is substituted by alanine, leucine at position 235 is substituted by alanine, and serine at position 228 is substituted by a proline.

7. The antibody according to claim 6, wherein the heavy chain constant region consists of the amino acid sequence of residues 140-466 in SEQ ID NO: 25.

8. The antibody according to claim 1, which is any of the following (1) to (8):
(1) an antibody that binds specifically to human SIRPα to inhibit binding of human SIRPα to CD47, the antibody consisting of: a heavy chain consisting of an amino acid sequence consisting of amino acid residues 20 to 466 in SEQ ID NO: 41; and a light chain consisting of an amino acid sequence consisting of amino acid residues 21 to 234 in SEQ ID NO: 37;
(2) an antibody that binds specifically to human SIRPα to inhibit binding of human SIRPα to CD47, the antibody consisting of: a heavy chain consisting of an amino acid sequence having at least 95% sequence identity with the amino acid sequence consisting of amino acid residues 20 to 466 in SEQ ID NO: 41; and a light chain consisting of an amino acid sequence having at least 95% sequence identity with amino acid residues 21 to 234 in SEQ ID NO: 37;
(3) an antibody that binds specifically to human SIRPα to inhibit binding of human SIRPα to CD47, the antibody consisting of: a heavy chain consisting of an amino acid sequence consisting of amino acid residues 20 to 466 in SEQ ID NO: 41; and a light chain consisting of an amino acid sequence consisting of amino acid residues 21 to 234 in SEQ ID NO: 39;
(4) an antibody that binds specifically to human SIRPα to inhibit binding of human SIRPα to CD47, the antibody consisting of: a heavy chain consisting of an amino acid sequence having at least 95% sequence identity with the amino acid sequence consisting of amino acid residues 20 to 466 in SEQ ID NO: 41; and a light chain consisting of an amino acid sequence having at least 95% sequence identity with the amino acid sequence consisting of amino acid residues 21 to 234 in SEQ ID NO: 39;
(5) an antibody that binds specifically to human SIRPα to inhibit binding of human SIRPα to CD47, the antibody consisting of: a heavy chain consisting of an amino acid sequence consisting of amino acid residues 20 to 466 in SEQ ID NO: 43; and a light chain consisting of an amino acid sequence consisting of amino acid residues 21 to 234 in SEQ ID NO: 35;
(6) an antibody that binds specifically to human SIRPα to inhibit binding of human SIRPα to CD47, the antibody consisting of: a heavy chain consisting of an amino acid sequence having at least 95% sequence identity with the amino acid sequence consisting of amino acid residues 20 to 466 in SEQ ID NO: 43; and a light chain consisting of an amino acid sequence having at least 95% sequence identity with the amino acid sequence consisting of amino acid residues 21 to 234 in SEQ ID NO: 35;
(7) an antibody that binds specifically to human SIRPα to inhibit binding of human SIRPα to CD47, the antibody consisting of: a heavy chain consisting of an amino acid sequence consisting of amino acid residues 20 to 466 in SEQ ID NO: 43; and a light chain consisting of an amino acid sequence consisting of amino acid residues 21 to 234 in SEQ ID NO: 37; and
(8) an antibody that binds specifically to human SIRPα to inhibit binding of human SIRPα to CD47, the antibody consisting of: a heavy chain consisting of an amino acid sequence having at least 95% sequence identity with the amino acid sequence consisting of amino acid residues 20 to 466 in SEQ ID NO: 43; and a light chain consisting of an amino acid sequence having at least 95% sequence identity with the amino acid sequence consisting of amino acid residues 21 to 234 in SEQ ID NO: 37.

9. The antibody according to claim 8, wherein ADCC and/or ADCP activity is reduced.

10. The antibody according to claim 1, which enhances phagocytic activity of a macrophage.

11. The antibody according to claim 1, wherein a lysine residue at the carboxyl terminus of the heavy chain is deleted.

12. An antigen-binding fragment of the antibody according to claim 1.

13. The antigen-binding fragment of the antibody according to claim 12, wherein the antigen-binding fragment is selected from the group consisting of Fab, F(ab')2, Fab', and scFv.

14. A pharmaceutical composition comprising the antibody according to claim 1 as an active ingredient.

15. The pharmaceutical composition according to claim 14, wherein the pharmaceutical composition is an anti-tumor agent.

16. The pharmaceutical composition according to claim 15, further comprising
an immune checkpoint inhibitor; and/or
an antibody drug that specifically responds to a cancer antigen to have ADCC and/or ADCP activity
as an active ingredient of the anti-tumor agent.

17. A pharmaceutical composition comprising the antibody according to claim 1 to be used in combination with an immune checkpoint inhibitor and/or an antibody drug that specifically responds to a cancer antigen to have the ADCC and/or ADCP activity.

18. The pharmaceutical composition according to claim 16, wherein the immune checkpoint inhibitor inhibits PD-L1 binding to PD-1 or is a CTLA4 inhibitor.

19. The pharmaceutical composition according to claim 16, wherein the antibody drug that specifically responds to a cancer antigen to have ADCC and/or ADCP activity is selected from the group consisting of an anti-CD20 antibody, an anti-HER2 antibody, and an anti-EGFR antibody.

20. The pharmaceutical composition according to claim 15, wherein the tumor is one or more types of tumors selected from the group consisting of carcinoma, sarcoma, lymphoma, leukemia, myeloma, germinoma, brain tumor, carcinoid, neuroblastoma, retinoblastoma, and nephroblastoma.

21. The pharmaceutical composition according to claim 20, wherein the tumor is one or more types of tumors selected from the group consisting of kidney cancer, melanoma, squamous cell cancer, basal cell cancer, conjunctival cancer, oral cancer, laryngeal cancer, pharyngeal cancer, thyroid cancer, lung cancer, breast cancer, esophageal cancer, gastric cancer, duodenal cancer, small intestinal cancer, colon cancer, rectal cancer, appendix cancer, anal cancer, liver cancer, gallbladder cancer, biliary cancer, pancreatic cancer, adrenal cancer, bladder cancer, prostate cancer, uterine cancer, vaginal cancer, liposarcoma, angiosarcoma, chondrosarcoma, rhabdomyosarcoma, Ewing's sarcoma, osteosarcoma, undifferentiated pleomorphic sarcoma, myxofibrosarcoma, malignant peripheral neurilemmoma, retroperitoneal sarcoma, synoviosarcoma, uterine sarcoma, gastrointestinal stromal tumor, leiomyosarcoma, epithelioid sarcoma, B-cell lymphoma, NK/T-cell lymphoma, Hodgkin's lymphoma, myeloid leukemia, lymphatic leukemia, myeloproliferative disease, myelodysplastic syndrome, multiple myeloma, testicular cancer, ovarian cancer, neuroglioma, and meningioma.

22. A polynucleotide consisting of nucleotide sequences encoding a heavy chain and light chain of the antibody according to claim 1.

23. A vector comprising the polynucleotide according to claim 22.

24. A host cell comprising the polynucleotide according to claim 22.

25. A method for producing the antibody according to claim 1, comprising culturing a host cell comprising a polynucleotide encoding a heavy chain and light chain of the antibody according to claim 1 and purifying an antibody from the culture.

26. An antibody produced by the method according to claim 25.

27. A pharmaceutical composition comprising the antigen-binding fragment of claim 12 as an active ingredient.

28. A pharmaceutical composition comprising the antibody according to claim 12 to be used in combination with an immune checkpoint inhibitor and/or an antibody drug that specifically responds to a cancer antigen to have the ADCC and/or ADCP activity.

29. A host cell comprising the vector according to claim 23.

* * * * *

UNITED STATES PATENT AND TRADEMARK OFFICE
CERTIFICATE OF CORRECTION

PATENT NO. : 12,024,566 B2
APPLICATION NO. : 17/258115
DATED : July 2, 2024
INVENTOR(S) : Takashi Matozaki et al.

It is certified that error appears in the above-identified patent and that said Letters Patent is hereby corrected as shown below:

In the Claims

In Claim 4, Column 187, Line 31, please replace "166" and insert -- 466 --

Signed and Sealed this
Twelfth Day of November, 2024

Katherine Kelly Vidal
*Director of the United States Patent and Trademark Office*

SEQUENCE LISTING

```
<160> NUMBER OF SEQ ID NOS: 89

<210> SEQ ID NO 1
<211> LENGTH: 11
<212> TYPE: PRT
<213> ORGANISM: Artificial
<220> FEATURE:
<223> OTHER INFORMATION: amino acid sequence of D13 CDR-L1

<400> SEQUENCE: 1

Gly Ala Ser Lys Ser Val Arg Thr Tyr Met His
1               5                   10

<210> SEQ ID NO 2
<211> LENGTH: 7
<212> TYPE: PRT
<213> ORGANISM: Artificial
<220> FEATURE:
<223> OTHER INFORMATION: amino acid sequence of D13 CDR-L2

<400> SEQUENCE: 2
```

```
Ser Ala Ser Asn Leu Glu Ala
1               5

<210> SEQ ID NO 3
<211> LENGTH: 9
<212> TYPE: PRT
<213> ORGANISM: Artificial
<220> FEATURE:
<223> OTHER INFORMATION: amino acid sequence of D13 CDR-L3

<400> SEQUENCE: 3

Gln Gln Ser Asn Glu Pro Pro Tyr Thr
1               5

<210> SEQ ID NO 4
<211> LENGTH: 10
<212> TYPE: PRT
<213> ORGANISM: Artificial
<220> FEATURE:
<223> OTHER INFORMATION: amino acid sequence of D13 CDR-H1

<400> SEQUENCE: 4

Gly Phe Thr Phe Ser Asp Tyr Gly Met Ile
1               5                   10

<210> SEQ ID NO 5
<211> LENGTH: 10
<212> TYPE: PRT
<213> ORGANISM: Artificial
<220> FEATURE:
<223> OTHER INFORMATION: amino acid sequence of D13 CDR-H2

<400> SEQUENCE: 5

Ser Ile Ser Ser Ser Ser Ser Tyr Ile Tyr
1               5                   10

<210> SEQ ID NO 6
<211> LENGTH: 11
<212> TYPE: PRT
<213> ORGANISM: Artificial
<220> FEATURE:
<223> OTHER INFORMATION: amino acid sequence of D13 CDR-H3

<400> SEQUENCE: 6

Arg Tyr Tyr Gly Phe Asn Tyr Pro Phe Asp Tyr
1               5                   10

<210> SEQ ID NO 7
<211> LENGTH: 11
<212> TYPE: PRT
<213> ORGANISM: Artificial
<220> FEATURE:
<223> OTHER INFORMATION: amino acid sequence of F44 CDR-L1

<400> SEQUENCE: 7

Lys Ala Ser Lys Ser Ile Ser Lys Tyr Leu Ala
1               5                   10

<210> SEQ ID NO 8
<211> LENGTH: 7
<212> TYPE: PRT
<213> ORGANISM: Artificial
<220> FEATURE:
<223> OTHER INFORMATION: amino acid sequence of F44 CDR-L2

<400> SEQUENCE: 8
```

-continued

Ser Gly Ser Thr Leu Gln Ser
1               5

<210> SEQ ID NO 9
<211> LENGTH: 9
<212> TYPE: PRT
<213> ORGANISM: Artificial
<220> FEATURE:
<223> OTHER INFORMATION: amino acid sequence of F44 CDR-L3

<400> SEQUENCE: 9

Gln Gln His Asn Glu Tyr Pro Pro Thr
1               5

<210> SEQ ID NO 10
<211> LENGTH: 10
<212> TYPE: PRT
<213> ORGANISM: Artificial
<220> FEATURE:
<223> OTHER INFORMATION: amino acid sequence of F44 CDR-H1

<400> SEQUENCE: 10

Gly Phe Thr Phe Ser Asn Tyr Tyr Met Ala
1               5                   10

<210> SEQ ID NO 11
<211> LENGTH: 10
<212> TYPE: PRT
<213> ORGANISM: Artificial
<220> FEATURE:
<223> OTHER INFORMATION: amino acid sequence of F44 CDR-H2

<400> SEQUENCE: 11

Tyr Ile Thr Thr Gly Gly Gly Ser Thr Tyr
1               5                   10

<210> SEQ ID NO 12
<211> LENGTH: 10
<212> TYPE: PRT
<213> ORGANISM: Artificial
<220> FEATURE:
<223> OTHER INFORMATION: amino acid sequence of F44 CDR-H3

<400> SEQUENCE: 12

Ala Asn Tyr Gly Gly Ser Tyr Phe Asp Tyr
1               5                   10

<210> SEQ ID NO 13
<211> LENGTH: 13
<212> TYPE: PRT
<213> ORGANISM: Artificial
<220> FEATURE:
<223> OTHER INFORMATION: amino acid sequence of F63 CDR-L1

<400> SEQUENCE: 13

Glu Arg Ser Ser Gly Asp Ile Gly Asp Ser Tyr Val Ser
1               5                   10

<210> SEQ ID NO 14
<211> LENGTH: 7
<212> TYPE: PRT
<213> ORGANISM: Artificial
<220> FEATURE:
<223> OTHER INFORMATION: amino acid sequence of F63 CDR-L2

<400> SEQUENCE: 14

Ala Asp Asp Gln Arg Pro Ser

```
<210> SEQ ID NO 15
<211> LENGTH: 9
<212> TYPE: PRT
<213> ORGANISM: Artificial
<220> FEATURE:
<223> OTHER INFORMATION: amino acid sequence of F63 CDR-L3

<400> SEQUENCE: 15

Gln Ser Tyr Asp Ser Lys Ile Asp Ile
1               5

<210> SEQ ID NO 16
<211> LENGTH: 10
<212> TYPE: PRT
<213> ORGANISM: Artificial
<220> FEATURE:
<223> OTHER INFORMATION: amino acid sequence of F63 CDR-H1

<400> SEQUENCE: 16

Gly Phe Ser Leu Ala Ser Tyr Ser Leu Ser
1               5                   10

<210> SEQ ID NO 17
<211> LENGTH: 9
<212> TYPE: PRT
<213> ORGANISM: Artificial
<220> FEATURE:
<223> OTHER INFORMATION: amino acid sequence of F63 CDR-H2

<400> SEQUENCE: 17

Arg Met Tyr Tyr Asp Gly Asp Thr Ala
1               5

<210> SEQ ID NO 18
<211> LENGTH: 16
<212> TYPE: PRT
<213> ORGANISM: Artificial
<220> FEATURE:
<223> OTHER INFORMATION: amino acid sequence of F63 CDR-H3

<400> SEQUENCE: 18

Asp Arg Ser Met Phe Gly Thr Asp Tyr Pro His Trp Tyr Phe Asp Phe
1               5                   10                  15

<210> SEQ ID NO 19
<211> LENGTH: 449
<212> TYPE: DNA
<213> ORGANISM: Artificial
<220> FEATURE:
<223> OTHER INFORMATION: DNA fragment comprising nucleotide sequences
      coding human light chain signal sequence and human kappa light
      chain constant region

<400> SEQUENCE: 19
gcctccggac tctagagcca ccatggtgct gcagacccag gtgttcatct ccctgctgct      60
gtggatctcc ggcgcgtacg gcgatatcgt gatgattaaa cgtacggtgg ccgccccctc     120
cgtgttcatc ttcccccccct ccgacgagca gctgaagtcc ggcaccgcct ccgtggtgtg    180
cctgctgaat aacttctacc cagagaggc caaggtgcag tggaaggtgg acaacgccct      240
gcagtccggg aactcccagg agagcgtgac cgagcaggac agcaaggaca gcacctacag    300
cctgagcagc accctgaccc tgagcaaagc cgactacgag aagcacaagg tgtacgcctg    360
cgaggtgacc caccagggcc tgagctcccc cgtcaccaag agcttcaaca ggggggagtg    420
```

```
ttaggggccc gtttaaacgg gggaggcta                              449
```

<210> SEQ ID NO 20
<211> LENGTH: 462
<212> TYPE: DNA
<213> ORGANISM: Artificial
<220> FEATURE:
<223> OTHER INFORMATION: DNA fragment comprising nucleotide sequences
      coding human light chain signal sequence and human lambda light
      chain constant region

<400> SEQUENCE: 20

```
cagcctccgg actctagagc caccatggtg ctgcagaccc aggtgttcat ctccctgctg    60
ctgtggatct ccggcgcgta cggctagagc ggcggaacca agttaactgt gcttggccag   120
cctaaggctg cccctagcgt gaccctgttc cctccttcca gcgaggagct tcaagctaac   180
aaggccaccc tggtgtgtct tatctctgac ttctaccctg gcgctgtgac cgtggcctgg   240
aaggctgaca gctcccctgt gaaggccgga gtggagacca ccacacctag caagcagtct   300
aacaacaagt acgctgccag ctcctacctg agccttaccc ctgagcagtg gaagtctcac   360
agaagctact cctgtcaagt gacccacgag ggcagcaccg tggagaagac cgtggctcct   420
accgagtgtt cctaggggcc cgtttaaacg gggaggcta ac                       462
```

<210> SEQ ID NO 21
<211> LENGTH: 1117
<212> TYPE: DNA
<213> ORGANISM: Artificial
<220> FEATURE:
<223> OTHER INFORMATION: DNA fragment comprising nucleotide sequences
      coding human heavy chain signal sequence and human IgG4 Pro FALA
      heavy chain constant region

<400> SEQUENCE: 21

```
ccagcctccg gactctagag ccaccatgaa cacctgtgg ttcttcctcc tgctggtggc    60
agctcccaga tgggtgctga gccaggtgca attgtgcagg cggttagctc agcctccacc   120
aagggcccta gcgtgttccc tctggcccct gtagcagaa gcaccagcga gtctacagcc   180
gccctgggct gcctcgtgaa ggactacttt cccgagcccg tgaccgtgtc ctggaactct   240
ggcgctctga caagcggcgt gcacaccttt ccagccgtgc tgcagagcag cggcctgtac   300
tctctgtcca gcgtcgtgac tgtgcccagc agctctctgg caccaagac ctacacctgt    360 aacgtggacc acaagcccag caacaccaag gtggacaagc gggtggaatc taagtacggc   420 cctcctgcc ctccttgccc agcccctgaa gccgcgggcg accctccgt gttcctgttc     480 cccccaaagc ccaaggacac cctgatgatc agccggaccc ccgaagtgac ctgcgtggtg   540
gtggatgtgt cccaggaaga tcccgaggtg cagttcaatt ggtacgtgga cggcgtggaa   600
gtgcacaacg ccaagaccaa gcctagagag gaacagttca acagcaccta ccgggtggtg   660
tccgtgctga cagtgctgca ccaggactgg ctgaacggca agagtacaa gtgcaaggtg    720 tccaacaagg gcctgcccag ctccatcgag aaaaccatca gcaaggccaa gggccagccc   780
cgcgaacccc aggtgtacac actgcctcca agccaggaag atgaccaa gaatcaggtg     840 tccctgacct gtctcgtgaa aggcttctac ccctccgata tcgccgtgga atgggagagc   900
aacggccagc cgagaacaa ctacaagacc ccccccctg tgctggactc cgatggctca    960
ttcttcctgt acagcagact gaccgtggac aagagccggt ggcaggaagg caacgtgttc  1020
agctgctccg tgatgcacga ggccctgcac aaccactaca cccagaagtc cctgtctctg  1080
```
agcctgggca aatgagttta aacggggag gctaact         1117

<210> SEQ ID NO 22
<211> LENGTH: 699
<212> TYPE: DNA
<213> ORGANISM: Artificial
<220> FEATURE:
<223> OTHER INFORMATION: nucleotide sequence coding human chimeric
      antibody D13 light chain

<400> SEQUENCE: 22
atggtgctgc agacccaggt gttcatctcc ctgctgctgt ggatctccgg cgcgtacggc      60
gacactgtgc tgacccagtc tcctgctttg gctgtgtctc tagggcagag ggtcaccatc     120
tcttgtgggg ccagcaaaag tgtccgtaca tatatgcact ggtaccaaca aaaatcggga     180
cagcaaccca aactcctgat ctatagtgca tccaacctag aggctggagt cccttccagg     240
ttcagtggga gtgggtctgg gacagacttt accctcacca tagatcctgt ggaggctgat     300
gacattgcaa actattactg tcagcagagt aatgaacctc cgtacacgtt tggagctggg     360
accaagctgg aactgaaacg acggtggcc gccccctccg tgttcatctt ccccccctcc     420
gacgagcagc tgaagtccgg caccgcctcc gtggtgtgcc tgctgaataa cttctacccc     480
agagaggcca aggtgcagtg gaaggtggac aacgccctgc agtccgggaa ctcccaggag     540
agcgtgaccg agcaggacag caaggacagc acctacagcc tgagcagcac cctgaccctg     600
agcaaagccg actacgagaa gcacaaggtg tacgcctgcg aggtgaccca ccagggcctg     660 agctccccg tcaccaagag cttcaacagg ggggagtgt                           699

<210> SEQ ID NO 23
<211> LENGTH: 233
<212> TYPE: PRT
<213> ORGANISM: Artificial
<220> FEATURE:
<223> OTHER INFORMATION: amino acid sequence of human chimeric antibody
      D13 light chain

<400> SEQUENCE: 23

Met Val Leu Gln Thr Gln Val Phe Ile Ser Leu Leu Leu Trp Ile Ser
1               5                   10                  15

Gly Ala Tyr Gly Asp Thr Val Leu Thr Gln Ser Pro Ala Leu Ala Val
                20                  25                  30

Ser Leu Gly Gln Arg Val Thr Ile Ser Cys Gly Ala Ser Lys Ser Val
            35                  40                  45

Arg Thr Tyr Met His Trp Tyr Gln Gln Lys Ser Gly Gln Gln Pro Lys
        50                  55                  60

Leu Leu Ile Tyr Ser Ala Ser Asn Leu Glu Ala Gly Val Pro Ser Arg
65                  70                  75                  80

Phe Ser Gly Ser Gly Ser Gly Thr Asp Phe Thr Leu Thr Ile Asp Pro
                85                  90                  95

Val Glu Ala Asp Asp Ile Ala Asn Tyr Tyr Cys Gln Gln Ser Asn Glu
            100                 105                 110

Pro Pro Tyr Thr Phe Gly Ala Gly Thr Lys Leu Glu Leu Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly 165                 170                 175
Asn Ser Gln Glu Ser Val Thr Glu Gln Asp Ser Lys Asp Ser Thr Tyr
                180                 185                 190
Ser Leu Ser Ser Thr Leu Thr Leu Ser Lys Ala Asp Tyr Glu Lys His
            195                 200                 205
Lys Val Tyr Ala Cys Glu Val Thr His Gln Gly Leu Ser Ser Pro Val
        210                 215                 220
Thr Lys Ser Phe Asn Arg Gly Glu Cys
225                 230

<210> SEQ ID NO 24
<211> LENGTH: 1398
<212> TYPE: DNA
<213> ORGANISM: Artificial
<220> FEATURE:
<223> OTHER INFORMATION: nucleotide sequence coding human chimeric
      antibody D13 heavy chain

<400> SEQUENCE: 24

| | |
|---|---:|
| atgaaacacc tgtggttctt cctcctgctg gtggcagctc ccagatgggt gctgagcgag | 60 |
| gtacagctgg tggagtctgg aggaggctta gtgcagcctg aaggtccct gaaactctcc | 120 |
| tgtttagcct ctggattcac tttcagtgac tatggaatga tctgggttcg ccaggctcca | 180 |
| gggaaggggc tggagtgggt tgcatctatt agtagtagta gcagttacat ctactatgca | 240 |
| gacacagtga agggccgatt caccatctcc agagaaaatg ccaagaacac cctgttcctg | 300 |
| cacatgacca gtctgaggtc tgaagacact gccttgtatt actgtgcaag aagatactat | 360 |
| gggtttaact acccttttga ttactggggc caaggagtca tggtcacagt cagctcagcc | 420 |
| tccaccaagg gcctagcgt gttccctctg gccccttgta gcagaagcac cagcgagtct | 480 |
| acagccgccc tgggctgcct cgtgaaggac tactttccg agcccgtgac cgtgtcctgg | 540 |
| aactctggcg ctctgacaag cggcgtgcac acctttccag ccgtgctgca gagcagcggc | 600 |
| ctgtactctc tgtccagcgt cgtgactgtg cccagcagct ctctgggcac caagacctac | 660 |
| acctgtaacg tggaccacaa gcccagcaac accaaggtgg acaagcgggt ggaatctaag | 720 |
| tacggccctc cctgccctcc ttgcccagcc cctgaagccg cgggcggacc ctccgtgttc | 780 |
| ctgttccccc caaagcccaa ggacaccctg atgatcagcc ggacccccga agtgacctgc | 840 |
| gtggtggtgg atgtgtccca ggaagatccc gaggtgcagt tcaattggta cgtggacggc | 900 |
| gtggaagtgc acaacgccaa gaccaagcct agagaggaac agttcaacag cacctaccgg | 960 |
| gtggtgtccg tgctgacagt gctgcaccag gactggctga acggcaaaga gtacaagtgc | 1020 |
| aaggtgtcca acaagggcct gcccagctcc atcgagaaaa ccatcagcaa ggccaagggc | 1080 |
| cagccccgcg aacccaggt gtacacactg cctccaagcc aggaagagat gaccaagaat | 1140 |
| caggtgtccc tgacctgtct cgtgaaaggc ttctaccccct ccgatatcgc cgtggaatgg | 1200 |
| gagagcaacg gccagcccga gaacaactac aagaccaccc ccctgtgct ggactccgat | 1260 |
| ggctcattct tcctgtacag cagactgacc gtggacaaga gccgtggca ggaaggcaac | 1320 |
| gtgttcagct gctccgtgat gcacgaggcc ctgcacaacc actacaccca gaagtccctg | 1380 |
| tctctgagcc tgggcaaa | 1398 |

<210> SEQ ID NO 25
<211> LENGTH: 466
<212> TYPE: PRT
<213> ORGANISM: Artificial
<220> FEATURE:

<223> OTHER INFORMATION: amino acid sequence of human chimeric antibody
     D13 heavy chain

<400> SEQUENCE: 25

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Lys Leu Ser Cys Leu Ala Ser Gly Phe Thr Phe
        35                  40                  45

Ser Asp Tyr Gly Met Ile Trp Val Arg Gln Ala Pro Gly Lys Gly Leu
    50                  55                  60

Glu Trp Val Ala Ser Ile Ser Ser Ser Ser Tyr Ile Tyr Tyr Ala
65                  70                  75                  80

Asp Thr Val Lys Gly Arg Phe Thr Ile Ser Arg Glu Asn Ala Lys Asn
                85                  90                  95

Thr Leu Phe Leu His Met Thr Ser Leu Arg Ser Glu Asp Thr Ala Leu
            100                 105                 110

Tyr Tyr Cys Ala Arg Arg Tyr Tyr Gly Phe Asn Tyr Pro Phe Asp Tyr
        115                 120                 125

Trp Gly Gln Gly Val Met Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Ala Ala Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465

<210> SEQ ID NO 26
<211> LENGTH: 702
<212> TYPE: DNA
<213> ORGANISM: Artificial
<220> FEATURE:
<223> OTHER INFORMATION: nucleotide sequence coding human chimeric
      antibody F44 light chain

<400> SEQUENCE: 26
atggtgctgc agacccaggt gttcatctcc ctgctgctgt ggatctccgg cgcgtacggc    60
gatgtccaga tgacccagtc tccatctaat cttgctgcct ctcctggaga aagtgtttcc   120
atcaattgca aggcaagtaa gagcattagc aagtatttag cctggtatca acagaaacct   180
gggaaagcaa ataagcttct tatctactct gggtcaactt tgcaatctgg aactccatcg   240
aggttcagtg gcagtggatc tggtacagat ttcactctca ccatcagaaa cctggagcct   300
gaagattttg gactctatta ctgtcaacag cataatgaat acccacccac gtttggagct   360
gggaccaagt tggaactgaa acggacggtg gccgccccct ccgtgttcat cttccccccc   420
tccgacgagc agctgaagtc cggcaccgcc tccgtggtgt gcctgctgaa taacttctac   480
cccagagagg ccaaggtgca gtggaaggtg gacaacgccc tgcagtccgg gaactcccag   540
gagagcgtga ccgagcagga cagcaaggac agcacctaca gcctgagcag caccctgacc   600
ctgagcaaag ccgactacga gaagcacaag gtgtacgcct gcgaggtgac ccaccagggc   660
ctgagctccc ccgtcaccaa gagcttcaac agggggagt gt                      702

<210> SEQ ID NO 27
<211> LENGTH: 234
<212> TYPE: PRT
<213> ORGANISM: Artificial
<220> FEATURE:
<223> OTHER INFORMATION: amino acid sequence of human chimeric antibody
      F44 light chain

<400> SEQUENCE: 27

Met Val Leu Gln Thr Gln Val Phe Ile Ser Leu Leu Leu Trp Ile Ser
1               5                   10                  15

Gly Ala Tyr Gly Asp Val Gln Met Thr Gln Ser Pro Ser Asn Leu Ala
            20                  25                  30

Ala Ser Pro Gly Glu Ser Val Ser Ile Asn Cys Lys Ala Ser Lys Ser
        35                  40                  45

Ile Ser Lys Tyr Leu Ala Trp Tyr Gln Gln Lys Pro Gly Lys Ala Asn
    50                  55                  60

Lys Leu Leu Ile Tyr Ser Gly Ser Thr Leu Gln Ser Gly Thr Pro Ser
65                  70                  75                  80

Arg Phe Ser Gly Ser Gly Ser Gly Thr Asp Phe Thr Leu Thr Ile Arg
                85                  90                  95

Asn Leu Glu Pro Glu Asp Phe Gly Leu Tyr Tyr Cys Gln Gln His Asn
            100                 105                 110

Glu Tyr Pro Pro Thr Phe Gly Ala Gly Thr Lys Leu Glu Leu Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 28
<211> LENGTH: 1395
<212> TYPE: DNA
<213> ORGANISM: Artificial
<220> FEATURE:
<223> OTHER INFORMATION: nucleotide sequence coding human chimeric
      antibody F44 heavy chain

<400> SEQUENCE: 28

```
atgaaacacc tgtggttctt cctcctgctg gtggcagctc ccagatgggt gctgagcgag      60
gtgcagctgg tggaatctgg gggaggctta gtgcagcctg aaggtccct gaaactctcc      120 tgtgcagcct caggattcac tttcagtaac tattacatgg cctgggtccg ccaggctcca     180
acgaagggtc tggagtgggt cacatacatt actactggtg gtggtagcac ttactttcga     240
gactccgtga agggccgatt cactatctcc agagataatg cagaaagcac cctatacctg     300
caaatggaca gtctgaggtc tgaggacacg gccacttatt actgtacagc agctaactac     360
ggagggtcct actttgatta ctggggccaa ggagtcatgg tcacagtcag ctcagcctcc     420
accaagggcc ctagcgtgtt ccctctggcc cttgtagca aagcaccag cgagtctaca      480 gccgccctgg gctgcctcgt gaaggactac tttcccgagc ccgtgaccgt gcctggaac     540 tctggcgctc tgacaagcgg cgtgcacacc tttccagccg tgctgcagag cagcggcctg     600
tactctctgt ccagcgtcgt gactgtgccc agcagctctc tgggcaccaa gacctacacc     660
tgtaacgtgg accacaagcc cagcaacacc aaggtggaca gcgggtgga atctaagtac     720 ggccctccct gcctccttg cccagcccct gaagccgcgg gcggaccctc cgtgttcctg     780
ttccccccaa agcccaagga caccctgatg atcagccgga ccccgaagt gacctgcgtg     840 gtggtggatg tgtcccagga agatcccgag gtgcagttca attggtacgt ggacggcgtg     900
gaagtgcaca acgccaagac caagcctaga gaggaacagt tcaacagcac ctaccgggtg     960
gtgtccgtgc tgacagtgct gcaccaggac tggctgaacg gcaaagagta caagtgcaag     1020
gtgtccaaca agggcctgcc cagctccatc gagaaaacca tcagcaaggc caagggccag     1080
ccccgcgaac cccaggtgta cactgctgcc ccaagccagg aagagatgac caagaatcag     1140
gtgtccctga cctgtctcgt gaaaggcttc taccctccg atatcgccgt ggaatgggag     1200
```

```
agcaacggcc agcccgagaa caactacaag accacccccc ctgtgctgga ctccgatggc   1260
tcattcttcc tgtacagcag actgaccgtg gacaagagcc ggtggcagga aggcaacgtg   1320
ttcagctgct ccgtgatgca cgaggccctg cacaaccact acacccagaa gtccctgtct   1380
ctgagcctgg gcaaa                                                    1395
```

```
<210> SEQ ID NO 29
<211> LENGTH: 465
<212> TYPE: PRT
<213> ORGANISM: Artificial
<220> FEATURE:
<223> OTHER INFORMATION: amino acid sequence of human chimeric antibody
      F44 heavy chain

<400> SEQUENCE: 29
```

| Met | Lys | His | Leu | Trp | Phe | Phe | Leu | Leu | Val | Ala | Ala | Pro | Arg | Trp |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Val | Leu | Ser | Glu | Val | Gln | Leu | Val | Glu | Ser | Gly | Gly | Gly | Leu | Val | Gln |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Pro | Gly | Arg | Ser | Leu | Lys | Leu | Ser | Cys | Ala | Ala | Ser | Gly | Phe | Thr | Phe |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Ser | Asn | Tyr | Tyr | Met | Ala | Trp | Val | Arg | Gln | Ala | Pro | Thr | Lys | Gly | Leu |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Glu | Trp | Val | Thr | Tyr | Ile | Thr | Thr | Gly | Gly | Ser | Thr | Tyr | Phe | Arg |
|-----|-----|-----|-----|-----|-----|-----|-----|-----|-----|-----|-----|-----|-----|-----|
| 65  |     |     |     |     | 70  |     |     |     |     | 75  |     |     |     | 80  |

| Asp | Ser | Val | Lys | Gly | Arg | Phe | Thr | Ile | Ser | Arg | Asp | Asn | Ala | Glu | Ser |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Thr | Leu | Tyr | Leu | Gln | Met | Asp | Ser | Leu | Arg | Ser | Glu | Asp | Thr | Ala | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Tyr | Tyr | Cys | Thr | Ala | Ala | Asn | Tyr | Gly | Gly | Ser | Tyr | Phe | Asp | Tyr | Trp |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Gly | Gln | Gly | Val | Met | Val | Thr | Val | Ser | Ser | Ala | Ser | Thr | Lys | Gly | Pro |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ser | Val | Phe | Pro | Leu | Ala | Pro | Cys | Ser | Arg | Ser | Thr | Ser | Glu | Ser | Thr |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ala | Ala | Leu | Gly | Cys | Leu | Val | Lys | Asp | Tyr | Phe | Pro | Glu | Pro | Val | Thr |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Val | Ser | Trp | Asn | Ser | Gly | Ala | Leu | Thr | Ser | Gly | Val | His | Thr | Phe | Pro |
|-----|-----|-----|-----|-----|-----|-----|-----|-----|-----|-----|-----|-----|-----|-----|-----|
|     |     |     |     | 180 |     |     |     |     | 185 |     |     |     |     | 190 |     |

| Ala | Val | Leu | Gln | Ser | Ser | Gly | Leu | Tyr | Ser | Leu | Ser | Ser | Val | Val | Thr |
|-----|-----|-----|-----|-----|-----|-----|-----|-----|-----|-----|-----|-----|-----|-----|-----|
|     |     |     | 195 |     |     |     |     | 200 |     |     |     |     | 205 |     |     |

| Val | Pro | Ser | Ser | Ser | Leu | Gly | Thr | Lys | Thr | Tyr | Thr | Cys | Asn | Val | Asp |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| His | Lys | Pro | Ser | Asn | Thr | Lys | Val | Asp | Lys | Arg | Val | Glu | Ser | Lys | Tyr |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Gly | Pro | Pro | Cys | Pro | Pro | Cys | Pro | Ala | Pro | Glu | Ala | Ala | Gly | Gly | Pro |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Ser | Val | Phe | Leu | Phe | Pro | Pro | Lys | Pro | Lys | Asp | Thr | Leu | Met | Ile | Ser |
|-----|-----|-----|-----|-----|-----|-----|-----|-----|-----|-----|-----|-----|-----|-----|-----|
|     |     |     |     | 260 |     |     |     |     | 265 |     |     |     |     | 270 |     |

| Arg | Thr | Pro | Glu | Val | Thr | Cys | Val | Val | Val | Asp | Val | Ser | Gln | Glu | Asp |
|-----|-----|-----|-----|-----|-----|-----|-----|-----|-----|-----|-----|-----|-----|-----|-----|
|     |     |     | 275 |     |     |     |     | 280 |     |     |     |     | 285 |     |     |

| Pro | Glu | Val | Gln | Phe | Asn | Trp | Tyr | Val | Asp | Gly | Val | Glu | Val | His | Asn |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Ala | Lys | Thr | Lys | Pro | Arg | Glu | Glu | Gln | Phe | Asn | Ser | Thr | Tyr | Arg | Val |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

```
Val Ser Val Leu Thr Val Leu His Gln Asp Trp Leu Asn Gly Lys Glu
            325                 330                 335
Tyr Lys Cys Lys Val Ser Asn Lys Gly Leu Pro Ser Ser Ile Glu Lys
        340                 345                 350
Thr Ile Ser Lys Ala Lys Gly Gln Pro Arg Glu Pro Gln Val Tyr Thr
    355                 360                 365
Leu Pro Pro Ser Gln Glu Glu Met Thr Lys Asn Gln Val Ser Leu Thr
370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Arg Leu Thr Val Asp Lys
            420                 425                 430
Ser Arg Trp Gln Glu Gly Asn Val Phe Ser Cys Ser Val Met His Glu
        435                 440                 445
Ala Leu His Asn His Tyr Thr Gln Lys Ser Leu Ser Leu Ser Leu Gly
    450                 455                 460
Lys
465

<210> SEQ ID NO 30
<211> LENGTH: 708
<212> TYPE: DNA
<213> ORGANISM: Artificial
<220> FEATURE:
<223> OTHER INFORMATION: nucleotide sequence coding human chimeric
      antibody F63 light chain

<400> SEQUENCE: 30
atggtgctgc agacccaggt gttcatctcc ctgctgctgt ggatctccgg cgcgtacggc      60
cagttcacgc tgactcaacc aaagtccgtg tcaggagctt taagaagcac tatcaccatt     120
ccctgtgagc gcagcagtgg tgacattgga gatagctatg tgagctggta ccagcgacac     180
ttgggaagac cccccatcaa tgtgatctat gctgatgatc aaagaccatc tgaagtgtct     240
gatcggttct cgggctccat cgacagctcc tctaactcag cctcactgac catcactaat     300
ctgcagatgg atgatgaggc cgactacttc tgtcagtctt acgatagtaa gattgacatt     360
ttcggcggtg gaaccaagct cactgtccta ggccagccta aggctgcccc tagcgtgacc     420
ctgttccctc cttccagcga ggagcttcaa gctaacaagg ccaccctggt gtgtcttatc     480
tctgacttct accctggcgc tgtgaccgtg gcctggaagg ctgacagctc ccctgtgaag     540
gccggagtgg agaccaccac acctagcaag cagtctaaca acaagtacgc tgccagctcc     600
tacctgagcc ttacccctga gcagtggaag tctcacagaa gctactcctg tcaagtgacc     660
cacgagggca gcaccgtgga agagaccgtg gctcctaccg agtgttcc                  708

<210> SEQ ID NO 31
<211> LENGTH: 236
<212> TYPE: PRT
<213> ORGANISM: Artificial
<220> FEATURE:
<223> OTHER INFORMATION: amino acid sequence of human chimeric antibody
      F63 light chain

<400> SEQUENCE: 31

Met Val Leu Gln Thr Gln Val Phe Ile Ser Leu Leu Leu Trp Ile Ser
1               5                   10                  15
```

Gly Ala Tyr Gly Gln Phe Thr Leu Thr Gln Pro Lys Ser Val Ser Gly
                20                  25                  30

Ala Leu Arg Ser Thr Ile Thr Ile Pro Cys Glu Arg Ser Ser Gly Asp
            35                  40                  45

Ile Gly Asp Ser Tyr Val Ser Trp Tyr Gln Arg His Leu Gly Arg Pro
        50                  55                  60

Pro Ile Asn Val Ile Tyr Ala Asp Asp Gln Arg Pro Ser Glu Val Ser
65                  70                  75                  80

Asp Arg Phe Ser Gly Ser Ile Asp Ser Ser Asn Ser Ala Ser Leu
                85                  90                  95

Thr Ile Thr Asn Leu Gln Met Asp Asp Glu Ala Asp Tyr Phe Cys Gln
                100                 105                 110

Ser Tyr Asp Ser Lys Ile Asp Ile Phe Gly Gly Gly Thr Lys Leu Thr
                115                 120                 125

Val Leu Gly Gln Pro Lys Ala Ala Pro Ser Val Thr Leu Phe Pro Pro
            130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
            195                 200                 205

Trp Lys Ser His Arg Ser Tyr Ser Cys Gln Val Thr His Glu Gly Ser
210                 215                 220

Thr Val Glu Lys Thr Val Ala Pro Thr Glu Cys Ser
225                 230                 235

<210> SEQ ID NO 32
<211> LENGTH: 1410
<212> TYPE: DNA
<213> ORGANISM: Artificial
<220> FEATURE:
<223> OTHER INFORMATION: nucleotide sequence coding human chimeric
      antibody F63 heavy chain

<400> SEQUENCE: 32
atgaaacacc tgtggttctt cctcctgctg gtggcagctc ccagatgggt gctgagccag      60
gtgcagctga aggagtcagg acctggtctg gtgcagccct cagagaccct gtccctcacc     120
tgcactgtct ctgggttctc actagccagc tatagtttaa gttgggttcg ccagccttca     180
ggaaaaggtc tgagtggat gggaagaatg tactatgatg agacacagc atataattca      240 gctctcaaat cccgactgag catcagcagg acacctcca agaaccaagt tttcttaaaa      300
atgaacagtc tgcaaactga tgacacaggc acttactact gtaccagaga taggagtatg     360
tttggtacgg attatccca ctggtacttt gacttctggg gccaggaac catggtcacc      420 gtgagctcag cctccaccaa gggcctagc gtgttccctc tggcccttg tagcagaagc      480 accagcgagt ctacagccgc cctgggctgc ctcgtgaagg actactttcc gagcccgtg      540 accgtgtcct ggaactctgg cgctctgaca agcggcgtgc acacctttcc agccgtgctg     600
cagagcagcg gcctgtactc tctgtccagc gtcgtgactg tgcccagcag ctctctgggc     660
accaagacct acacctgtaa cgtggaccac aagcccagca acaccaaggt ggacaagcgg     720
gtggaatcta agtacggccc tcctgccct ccttgcccag ccctgaagc cgcgggcgga       780

```
ccctccgtgt tcctgttccc cccaaagccc aaggacaccc tgatgatcag ccggacccccc    840 gaagtgacct gcgtggtggt ggatgtgtcc caggaagatc ccgaggtgca gttcaattgg    900
tacgtggacg gcgtggaagt gcacaacgcc aagaccaagc ctagagagga acagttcaac    960
agcacctacc gggtggtgtc cgtgctgaca gtgctgcacc aggactggct gaacggcaaa    1020
gagtacaagt gcaaggtgtc caacaagggc ctgcccagct ccatcgagaa aaccatcagc    1080
aaggccaagg ccagccccg cgaacccag gtgtacacac tgcctccaag ccaggaagag    1140
atgaccaaga atcaggtgtc cctgacctgt ctcgtgaaag gcttctaccc ctccgatatc    1200
gccgtggaat gggagagcaa cggccagccc gagaacaact acaagaccac ccccctgtg    1260 ctggactccg atggctcatt cttcctgtac agcagactga ccgtggacaa gagccggtgg    1320
caggaaggca acgtgttcag ctgctccgtg atgcacgagg ccctgcacaa ccactacacc    1380
cagaagtccc tgtctctgag cctgggcaaa                                      1410
```

<210> SEQ ID NO 33
<211> LENGTH: 470
<212> TYPE: PRT
<213> ORGANISM: Artificial
<220> FEATURE:
<223> OTHER INFORMATION: amino acid sequence of human chimeric antibody F63 heavy chain

<400> SEQUENCE: 33

```
Met Lys His Leu Trp Phe Phe Leu Leu Leu Val Ala Ala Pro Arg Trp
1               5                   10                  15

Val Leu Ser Gln Val Gln Leu Lys Glu Ser Gly Pro Gly Leu Val Gln
            20                  25                  30

Pro Ser Glu Thr Leu Ser Leu Thr Cys Thr Val Ser Gly Phe Ser Leu
        35                  40                  45

Ala Ser Tyr Ser Leu Ser Trp Val Arg Gln Pro Ser Gly Lys Gly Pro
    50                  55                  60

Glu Trp Met Gly Arg Met Tyr Tyr Asp Gly Asp Thr Ala Tyr Asn Ser
65                  70                  75                  80

Ala Leu Lys Ser Arg Leu Ser Ile Ser Arg Asp Thr Ser Lys Asn Gln
                85                  90                  95

Val Phe Leu Lys Met Asn Ser Leu Gln Thr Asp Asp Thr Gly Thr Tyr
            100                 105                 110

Tyr Cys Thr Arg Asp Arg Ser Met Phe Gly Thr Asp Tyr Pro His Trp
        115                 120                 125

Tyr Phe Asp Phe Trp Gly Pro Gly Thr Met Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Lys Thr Tyr
    210                 215                 220

Thr Cys Asn Val Asp His Lys Pro Ser Asn Thr Lys Val Asp Lys Arg
225                 230                 235                 240

Val Glu Ser Lys Tyr Gly Pro Pro Cys Pro Pro Cys Pro Ala Pro Glu
```

|     |     |     |     |     | 245 |     |     |     | 250 |     |     |     |     | 255 |
|-----|-----|-----|-----|-----|-----|-----|-----|-----|-----|-----|-----|-----|-----|-----|
| Ala | Ala | Gly | Gly | Pro | Ser | Val | Phe | Leu | Phe | Pro | Pro | Lys | Pro | Lys | Asp |
|     |     |     | 260 |     |     |     |     | 265 |     |     |     |     | 270 |     |     |

Ala Ala Gly Gly Pro Ser Val Phe Leu Phe Pro Pro Lys Pro Lys Asp
          260              265           270

Thr Leu Met Ile Ser Arg Thr Pro Glu Val Thr Cys Val Val Asp
    275              280           285

Val Ser Gln Glu Asp Pro Glu Val Gln Phe Asn Trp Tyr Val Asp Gly
    290              295           300

Val Glu Val His Asn Ala Lys Thr Lys Pro Arg Glu Glu Gln Phe Asn
305              310           315           320

Ser Thr Tyr Arg Val Val Ser Val Leu Thr Val Leu His Gln Asp Trp
          325              330           335

Leu Asn Gly Lys Glu Tyr Lys Cys Lys Val Ser Asn Lys Gly Leu Pro
        340            345           350

Ser Ser Ile Glu Lys Thr Ile Ser Lys Ala Lys Gly Gln Pro Arg Glu
        355            360           365

Pro Gln Val Tyr Thr Leu Pro Pro Ser Gln Glu Met Thr Lys Asn
370              375           380

Gln Val Ser Leu Thr Cys Leu Val Lys Gly Phe Tyr Pro Ser Asp Ile
385              390           395           400

Ala Val Glu Trp Glu Ser Asn Gly Gln Pro Glu Asn Asn Tyr Lys Thr
        405            410           415

Thr Pro Pro Val Leu Asp Ser Asp Gly Ser Phe Phe Leu Tyr Ser Arg
        420            425           430

Leu Thr Val Asp Lys Ser Arg Trp Gln Glu Gly Asn Val Phe Ser Cys
        435            440           445

Ser Val Met His Glu Ala Leu His Asn His Tyr Thr Gln Lys Ser Leu
    450              455           460

Ser Leu Ser Leu Gly Lys
465              470

<210> SEQ ID NO 34
<211> LENGTH: 702
<212> TYPE: DNA
<213> ORGANISM: Artificial
<220> FEATURE:
<223> OTHER INFORMATION: nucleotide sequence coding hL2 light chain of
    humanized D13

<400> SEQUENCE: 34

```
atggtgctgc agacccaggt gttcatctcc ctgctgctgt ggatctccgg cgcgtacggc      60
gccattcagc tgacacagag ccctagcagc ctgagcgcct tgtgggcca gagagtgacc     120
attacctgcg cgccagcaa gagcgtgcgg acctacatgc actggtatca gcagaagccc     180
ggcaaggccc ccaagctgct gatctacagc gcctccaatc tggaagccgg cgtgcccagc    240
agattttccg gctctggcag cggcaccgac ttcaccctga caatcagcag cctgcagccc    300
gaggacttcg ccacctacta ctgccagcag agcaacgagc cccctacac ctttggccag     360
ggcaccaagc tggaaatcaa gcgtacggtg gccgcccct ccgtgttcat cttcccccc      420
tccgacgagc agctgaagtc cggcaccgcc tccgtggtgt gcctgctgaa taacttctac    480
cccagagagg ccaaggtgca gtggaaggtg gacaacgccc tgcagtccgg aactcccag    540
agagcgtga ccgagcagga cagcaaggac agcacctaca gcctgagcag caccctgacc    600
ctgagcaaag ccgactacga gaagcacaag gtgtacgcct gcgaggtgac ccaccaggge    660
ctgagctccc ccgtcaccaa gagcttcaac agggggagt gt                        702
```

<210> SEQ ID NO 35
<211> LENGTH: 234
<212> TYPE: PRT
<213> ORGANISM: Artificial
<220> FEATURE:
<223> OTHER INFORMATION: amino acid sequence of hL2 light chain of humanized D13

<400> SEQUENCE: 35

```
Met Val Leu Gln Thr Gln Val Phe Ile Ser Leu Leu Trp Ile Ser
1               5                   10                  15

Gly Ala Tyr Gly Ala Ile Gln Leu Thr Gln Ser Pro Ser Ser Leu Ser
            20                  25                  30

Ala Ser Val Gly Gln Arg Val Thr Ile Thr Cys Gly Ala Ser Lys Ser
        35                  40                  45

Val Arg Thr Tyr Met His Trp Tyr Gln Gln Lys Pro Gly Lys Ala Pro
50                  55                  60

Lys Leu Leu Ile Tyr Ser Ala Ser Asn Leu Glu Ala Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ser Asn
            100                 105                 110

Glu Pro Pro Tyr Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230
```

<210> SEQ ID NO 36
<211> LENGTH: 702
<212> TYPE: DNA
<213> ORGANISM: Artificial
<220> FEATURE:
<223> OTHER INFORMATION: nucleotide sequence coding hL3 light chain of humanized D13

<400> SEQUENCE: 36

```
atggtgctgc agacccaggt gttcatctcc ctgctgctgt ggatctccgg cgcgtacggc      60
gatacccagc tgacacagag ccctagcagc ctgtctgcca gcgtgggcca gagagtgacc     120
attacctgcg gcgccagcaa gagcgtgcgg acctacatgc actggtatca gcagaagccc     180
ggcaagcagc ccaagctgct gatctacagc gcctccaacc tggaagccgg cgtgcccagc     240
agattttctg gcagcggctc cggcaccgac ttcaccctga caatcagcag cctgcagccc     300
gaggacttcg ccacctacta ctgccagcag agcaacgagc cccctacac ctttggccag     360
```

```
ggcaccaagc tggaaatcaa gcgtacggtg gccgccccct ccgtgttcat cttccccccc    420
tccgacgagc agctgaagtc cggcaccgcc tccgtggtgt gcctgctgaa taacttctac    480
cccagagagg ccaaggtgca gtggaaggtg acaacgccc tgcagtccgg gaactcccag     540
gagagcgtga ccgagcagga cagcaaggac agcacctaca gcctgagcag caccctgacc    600
ctgagcaaag ccgactacga gaagcacaag gtgtacgcct gcgaggtgac ccaccagggc    660
ctgagctccc ccgtcaccaa gagcttcaac agggggagt gt                        702
```

<210> SEQ ID NO 37
<211> LENGTH: 234
<212> TYPE: PRT
<213> ORGANISM: Artificial
<220> FEATURE:
<223> OTHER INFORMATION: amino acid sequence of hL3 light chain of humanized D13

<400> SEQUENCE: 37

```
Met Val Leu Gln Thr Gln Val Phe Ile Ser Leu Leu Trp Ile Ser
1               5                  10                  15

Gly Ala Tyr Gly Asp Thr Gln Leu Thr Gln Ser Pro Ser Leu Ser
            20                  25                  30

Ala Ser Val Gly Gln Arg Val Thr Ile Thr Cys Gly Ala Ser Lys Ser
        35                  40                  45

Val Arg Thr Tyr Met His Trp Tyr Gln Gln Lys Pro Gly Lys Gln Pro
50                  55                  60

Lys Leu Leu Ile Tyr Ser Ala Ser Asn Leu Glu Ala Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ser Asn
            100                 105                 110

Glu Pro Pro Tyr Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 38
<211> LENGTH: 702
<212> TYPE: DNA
<213> ORGANISM: Artificial
<220> FEATURE:
<223> OTHER INFORMATION: nucleotide sequence coding hL4 light chain of humanized D13

<400> SEQUENCE: 38

```
atggtgctgc agacccaggt gttcatctcc ctgctgctgt ggatctccgg cgcgtacggc      60
gataccgtgc tgacccagag ccctgatagc ctggccgtgt ccctgggaca gagagccacc     120
atcaattgcg gcgccagcaa gagcgtgcgg acctacatgc actggtatca gcagaagccc     180
ggccagcagc ccaagctgct gatctacagc gcctccaacc tggaagccgg cgtgcccagc     240 agatttctg gcagcggctc cggcaccgac ttcaccctga caatcagctc cctgcaggcc      300
gaggacgtgg ccgtgtacta ctgccagcag agcaacgagc cccctacac ctttggccag      360 ggcaccaagg tggaaatcaa agcgtacggtg ccgcccct ccgtgttcat cttcccccc       420 tccgacgagc agctgaagtc cggcaccgcc tccgtggtgt gcctgctgaa taacttctac     480
cccagagagg ccaaggtgca gtggaaggtg acaacgccc tgcagtccgg gaactcccag     540
gagagcgtga ccgagcagga cagcaaggac agcacctaca gcctgagcag cacccctgacc    600 ctgagcaaag ccgactacga gaagcacaag gtgtacgcct gcgaggtgac ccaccagggc     660
ctgagctccc ccgtcaccaa gagcttcaac agggggagt gt                         702
```

<210> SEQ ID NO 39
<211> LENGTH: 234
<212> TYPE: PRT
<213> ORGANISM: Artificial
<220> FEATURE:
<223> OTHER INFORMATION: amino acid sequence of hL4 light chain of humanized D13

<400> SEQUENCE: 39

```
Met Val Leu Gln Thr Gln Val Phe Ile Ser Leu Leu Leu Trp Ile Ser
1               5                   10                  15

Gly Ala Tyr Gly Asp Thr Val Leu Thr Gln Ser Pro Asp Ser Leu Ala
            20                  25                  30

Val Ser Leu Gly Gln Arg Ala Thr Ile Asn Cys Gly Ala Ser Lys Ser
        35                  40                  45

Val Arg Thr Tyr Met His Trp Tyr Gln Gln Lys Pro Gly Gln Gln Pro
    50                  55                  60

Lys Leu Leu Ile Tyr Ser Ala Ser Asn Leu Glu Ala Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Tyr Cys Gln Gln Ser Asn
            100                 105                 110

Glu Pro Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 40
<211> LENGTH: 1398
<212> TYPE: DNA
<213> ORGANISM: Artificial
<220> FEATURE:
<223> OTHER INFORMATION: nucleotide sequence coding hH1 heavy chain of humanized D13

<400> SEQUENCE: 40

```
atgaaacacc tgtggttctt cctcctgctg gtggcagctc ccagatgggt gctgagccag      60
gtgcagctgg tggaatctgg cggcggagtg gtgcagcctg gcagaagcct gagactgagc     120
tgtgccgcca gcggcttcac cttcagcgac tacggcatga tctgggtgcg ccaggcccct     180
ggcaaaggcc tggaatgggt ggccagcatc agcagcagct ccagctacat ctactacgcc     240
gacagcgtga agggccggtt caccatcagc cgggacaaca gcaagaaccg gctgtacctg     300
cagatgaaca gcctgcgggc cgaggacacc gccgtgtact attgcgccag acggtactac     360
ggcttcaact accccttcga ctactggggc cagggcacaa tggtcaccgt cagctcagcc     420
tccaccaagg gcctagcgt gttccctctg gccccttgta gcagaagcac cagcgagtct     480
acagccgccc tgggctgcct cgtgaaggac tactttcccg agcccgtgac cgtgtcctgg     540
aactctggcg ctctgacaag cggcgtgcac accttccag ccgtgctgca gagcagcggc     600
ctgtactctc tgtccagcgt cgtgactgtg cccagcagct ctctgggcac caagacctac     660
acctgtaacg tggaccacaa gcccagcaac accaaggtgg acaagcgggt ggaatctaag     720
tacggccctc cctgccctcc ttgcccagcc cctgaagccg cggcggacc ctccgtgttc     780
ctgttccccc caaagcccaa ggacaccctg atgatcagcc ggacccccga agtgacctgc     840
gtggtggtgg atgtgtccca ggaagatccc gaggtgcagt tcaattggta cgtggacggc     900
gtggaagtgc acaacgccaa gaccaagcct agagaggaac agttcaacag cacctaccgg     960
gtggtgtccg tgctgacagt gctgcaccag gactggctga acggcaaaga gtacaagtgc    1020
aaggtgtcca acaagggcct gcccagctcc atcgagaaaa ccatcagcaa ggccaagggc    1080
cagccccgcg aacccaggt gtacacactg cctccaagcc aggaagagat gaccaagaat    1140
caggtgtccc tgacctgtct cgtgaaaggc ttctacccct ccgatatcgc cgtggaatgg    1200
gagagcaacg gccagcccga gaacaactac aagaccaccc cccctgtgct ggactccgat    1260
ggctcattct tcctgtacag cagactgacc gtggacaaga ccggtggca ggaaggcaac    1320
gtgttcagct gctccgtgat gcacgaggcc ctgcacaacc actacaccca gaagtccctg    1380
tctctgagcc tgggcaaa                                                  1398
```

<210> SEQ ID NO 41
<211> LENGTH: 466
<212> TYPE: PRT
<213> ORGANISM: Artificial
<220> FEATURE:
<223> OTHER INFORMATION: amino acid sequence of hH1 heavy chain of humanized D13

<400> SEQUENCE: 41

```
Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45
```

-continued

```
Ser Asp Tyr Gly Met Ile Trp Val Arg Gln Ala Pro Gly Lys Gly Leu
 50                  55                  60
Glu Trp Val Ala Ser Ile Ser Ser Ser Ser Tyr Ile Tyr Tyr Ala
 65                  70                  75                  80
Asp Ser Val Lys Gly Arg Phe Thr Ile Ser Arg Asp Asn Ser Lys Asn
                     85                  90                  95
Arg Leu Tyr Leu Gln Met Asn Ser Leu Arg Ala Glu Asp Thr Ala Val
                100                 105                 110
Tyr Tyr Cys Ala Arg Arg Tyr Tyr Gly Phe Asn Tyr Pro Phe Asp Tyr
            115                 120                 125
Trp Gly Gln Gly Thr Met Val Thr Val Ser Ser Ala Ser Thr Lys Gly
130                 135                 140
Pro Ser Val Phe Pro Leu Ala Pro Cys Ser Arg Ser Thr Ser Glu Ser
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
                180                 185                 190
Pro Ala Val Leu Gln Ser Ser Gly Leu Tyr Ser Leu Ser Ser Val Val
            195                 200                 205
Thr Val Pro Ser Ser Ser Leu Gly Thr Lys Thr Tyr Thr Cys Asn Val
210                 215                 220
Asp His Lys Pro Ser Asn Thr Lys Val Asp Lys Arg Val Glu Ser Lys
225                 230                 235                 240
Tyr Gly Pro Pro Cys Pro Pro Cys Pro Ala Pro Glu Ala Ala Gly Gly
                245                 250                 255
Pro Ser Val Phe Leu Phe Pro Pro Lys Pro Lys Asp Thr Leu Met Ile
                260                 265                 270
Ser Arg Thr Pro Glu Val Thr Cys Val Val Val Asp Val Ser Gln Glu
            275                 280                 285
Asp Pro Glu Val Gln Phe Asn Trp Tyr Val Asp Gly Val Glu Val His
290                 295                 300
Asn Ala Lys Thr Lys Pro Arg Glu Glu Gln Phe Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Gly Leu Pro Ser Ser Ile Glu
                340                 345                 350
Lys Thr Ile Ser Lys Ala Lys Gly Gln Pro Arg Glu Pro Gln Val Tyr
            355                 360                 365
Thr Leu Pro Pro Ser Gln Glu Glu Met Thr Lys Asn Gln Val Ser Leu
370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Arg Leu Thr Val Asp
                420                 425                 430
Lys Ser Arg Trp Gln Glu Gly Asn Val Phe Ser Cys Ser Val Met His
            435                 440                 445
Glu Ala Leu His Asn His Tyr Thr Gln Lys Ser Leu Ser Leu Ser Leu
450                 455                 460
```

Gly Lys
465

<210> SEQ ID NO 42
<211> LENGTH: 1398
<212> TYPE: DNA
<213> ORGANISM: Artificial
<220> FEATURE:
<223> OTHER INFORMATION: nucleotide sequence coding hH2 heavy chain of humanized D13

<400> SEQUENCE: 42

| | |
|---|---:|
| atgaaacacc tgtggttctt cctcctgctg gtggcagctc ccagatgggt gctgagcgaa | 60 |
| gtgcagctgg tggaatctgg cggcggagtg gtgcagcctg gcagaagcct gagactgagc | 120 |
| tgtgccgcca gcggcttcac cttcagcgac tacggcatga tctgggtgcg ccaggcccct | 180 |
| ggcaaaggcc tggaatgggt ggccagcatc agcagcagct ccagctacat ctactacgcc | 240 |
| gacagcgtga agggccggtt caccatcagc cgggacaaca gcaagaacac cctgtacctg | 300 |
| cagatgaaca gcctgcgggc cgaggacacc gccgtgtact attgcgccag acggtactac | 360 |
| ggcttcaact acccccttcga ctactggggc cagggcacaa tggtcaccgt cagctcagcc | 420 |
| tccaccaagg gcccctagcgt gttccctctg gccccttgta gcaagcac cagcgagtct | 480 |
| acagccgccc tgggctgcct cgtgaaggac tactttcccg agcccgtgac cgtgtcctgg | 540 |
| aactctggcg ctctgacaag cggcgtgcac acctttccag ccgtgctgca gagcagcggc | 600 |
| ctgtactctc tgtccagcgt cgtgactgtg cccagcagct ctctgggcac caagacctac | 660 |
| acctgtaacg tggaccacaa gcccagcaac accaaggtgg acaagcgggt ggaatctaag | 720 |
| tacggcccctc cctgccctcc ttgcccagcc cctgaagccg cgggcggacc ctccgtgttc | 780 |
| ctgttccccc caaagcccaa ggacaccctg atgatcagcc ggacccccga agtgacctgc | 840 |
| gtggtggtgg atgtgtccca ggaagatccc gaggtgcagt tcaattggta cgtggacggc | 900 |
| gtggaagtgc acaacgccaa gaccaagcct agagaggaac agttcaacag cacctaccgg | 960 |
| gtggtgtccg tgctgacagt gctgcaccag gactggctga acggcaaaga gtacaagtgc | 1020 |
| aaggtgtcca acaagggcct gcccagctcc atcgagaaaa ccatcagcaa ggccaagggc | 1080 |
| cagccccgcg aaccccaggt gtacacactg cctccaagcc aggaagagat gaccaagaat | 1140 |
| caggtgtccc tgacctgtct cgtgaaaggc ttctaccccct ccgatatcgc cgtggaatgg | 1200 |
| gagagcaacg gccagcccga gaacaactac aagaccaccc ccctgtgct ggactccgat | 1260 |
| ggctcattct cctgtacag cagactgacc gtggacaaga gccggtggca ggaaggcaac | 1320 |
| gtgttcagct gctccgtgat gcacgaggcc ctgcacaacc actacaccca gaagtccctg | 1380 |
| tctctgagcc tgggcaaa | 1398 |

<210> SEQ ID NO 43
<211> LENGTH: 466
<212> TYPE: PRT
<213> ORGANISM: Artificial
<220> FEATURE:
<223> OTHER INFORMATION: amino acid sequence of hH2 heavy chain of humanized D13

<400> SEQUENCE: 43

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Val Val Gln
            20                  25                  30

-continued

Pro Gly Arg Ser Leu Arg Leu Ser Cys Ala Ala Ser Gly Phe Thr Phe
            35                  40                  45

Ser Asp Tyr Gly Met Ile Trp Val Arg Gln Ala Pro Gly Lys Gly Leu
 50                  55                  60

Glu Trp Val Ala Ser Ile Ser Ser Ser Ser Tyr Ile Tyr Tyr Ala
 65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
                100                 105                 110

Tyr Tyr Cys Ala Arg Arg Tyr Tyr Gly Phe Asn Tyr Pro Phe Asp Tyr
            115                 120                 125

Trp Gly Gln Gly Thr Met Val Thr Val Ser Ser Ala Ser Thr Lys Gly
            130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Lys Thr Tyr Thr Cys Asn Val
                210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Ala Ala Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser Gln Glu
                275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
                340                 345                 350

Lys Thr Ile Ser Lys Ala Lys Gly Gln Pro Arg Glu Pro Gln Val Tyr
                355                 360                 365

Thr Leu Pro Pro Ser Gln Glu Glu Met Thr Lys Asn Gln Val Ser Leu
                370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
                420                 425                 430

Lys Ser Arg Trp Gln Glu Gly Asn Val Phe Ser Cys Ser Val Met His
                435                 440                 445

Glu Ala Leu His Asn His Tyr Thr Gln Lys Ser Leu Ser Leu Ser Leu

Gly Lys
465

<210> SEQ ID NO 44
<211> LENGTH: 1140
<212> TYPE: DNA
<213> ORGANISM: Artificial
<220> FEATURE:
<223> OTHER INFORMATION: nucleotide sequence coding human SIRPA variant 1 ECD

<400> SEQUENCE: 44

```
atggaacctg ccggacctgc ccctggcaga ctgggacctc tgctgtgtct gctgctggcc      60
gcctcttgtg cttggagcgg agtggctggc gaagaggaac tgcaagtgat ccagcccgac     120
aagagcgtgc tggtggccgc tggcgaaacc gccaccctga gatgtacagc caccagcctg     180
atccccgtgg gccccatcca gtggtttaga ggcgctggcc ctggccgcga gctgatctac     240
aatcagaaag agggccactt ccccagagtg accaccgtgt ccgacctgac caagcggaac     300
aacatggact tcagcatccg gatcggcaac atcaccctg ccgatgccgg cacctactac     360
tgcgtgaagt tccggaaggg cagccccgac gacgtggaat caaaagcgg agccggcacc     420
gagctgagcg tgcgggctaa accttctgcc cctgtggtgt ctggacctgc cgccagagct     480
acacctcagc acaccgtgtc ttttacctgc gagagccacg gcttcagccc agagacatc     540
accctgaagt ggttcaagaa cggcaacgag ctgtccgact ccagaccaa cgtggaccct     600
gtgggcgaga gcgtgtccta cagcatccac agcaccgcca aggtggtgct gacccgcgaa     660
gatgtgcaca gccaagtgat ctgcgaggtg gcccacgtga cactgcaggg cgatcctctg     720
agaggaaccg ccaacctgtc cgagacaatc agagtgcccc ccaccctgga agtgacccag     780
cagcctgtgc gggccgagaa ccaagtgaac gtgacctgcc aagtgcggaa gttctacccc     840
cagcggctgc agctgacctg gctggaaaac ggcaatgtgt cccggaccga cagccagc     900
accgtgaccg agaacaagga tggcacctac aattggatga gctggctgct cgtgaacgtg     960
tccgcccacc gggacgatgt gaagctgaca tgccaggtgg aacacgacgg ccagcctgcc    1020
gtgtccaaga gccacgatct gaaggtgtca gcccatccca agagcagggg ctccaacaca    1080
gccgccgaga acaccggcag caacgagcgg aacatctacc accaccatca ccaccactga    1140
```

<210> SEQ ID NO 45
<211> LENGTH: 379
<212> TYPE: PRT
<213> ORGANISM: Artificial
<220> FEATURE:
<223> OTHER INFORMATION: amino acid sequence of human SIRPA variant 1 ECD

<400> SEQUENCE: 45

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

```
Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr His His His His His
    370                 375

<210> SEQ ID NO 46
<211> LENGTH: 468
<212> TYPE: DNA
<213> ORGANISM: Artificial
<220> FEATURE:
<223> OTHER INFORMATION: nucleotide sequence coding human SIRPA variant
      1 IgV

<400> SEQUENCE: 46
atggaacctg ccggacctgc ccctggcaga ctgggacctc tgctgtgtct gctgctggcc      60
gcctcttgtg cttggagcgg agtggctggc gaagaggaac tgcaagtgat ccagcccgac     120
aagagcgtgc tggtggccgc tggcgaaacc gccaccctga gatgtacagc caccagcctg     180
atccccgtgg gccccatcca gtggtttaga ggcgctggcc ctggccgcga gctgatctac     240
aatcagaaag agggccactt ccccagagtg accaccgtgt ccgacctgac caagcggaac     300
```

```
aacatggact tcagcatccg gatcggcaac atcacccctg ccgatgccgg cacctactac    360
tgcgtgaagt tccggaaggg cagccccgac gacgtggaat tcaaaagcgg agccggcacc    420
gagctgagcg tgcgggctaa acctagccac caccaccatc accactga                 468
```

<210> SEQ ID NO 47
<211> LENGTH: 155
<212> TYPE: PRT
<213> ORGANISM: Artificial
<220> FEATURE:
<223> OTHER INFORMATION: amino acid sequence of human SIRPA variant 1
      IgV

<400> SEQUENCE: 47

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser His His His His His
145                 150                 155
```

<210> SEQ ID NO 48
<211> LENGTH: 1137
<212> TYPE: DNA
<213> ORGANISM: Artificial
<220> FEATURE:
<223> OTHER INFORMATION: nucleotide sequence coding human SIRPA variant
      2 ECD

<400> SEQUENCE: 48

```
atggaacctg ccggacctgc ccctggcaga ctgggacctc tgctgtgtct gctgctggcc    60
gcctcttgtg cttggagcgg agtggctggc gaagaggaac tgcaagtgat ccagcccgac    120
aagagcgtgt cagtggccgc tggcgagtct gccatcctgc actgtaccgt gaccagcctg    180
atccccgtgg gccccatcca gtggtttaga ggcgctggac tgccagagag ctgatctac    240 aaccagaaag agggccactt ccccagagtg accaccgtgt ccgagagcac caagcgcgag    300
aacatggact tcagcatcag catctccaac atcacccctg ccgacgccgg cacctactac    360
tgcgtgaagt tcagaaaggg cagccccgac accgagttca gagcggagc cggcacagag    420 ctgtctgtgc gggccaaacc ttctgcccct gtggtgtctg accagccgc cagagctaca    480 cctcagcaca ccgtgtcttt tacctgcgag agccacggct tcagcccag agacatcacc    540 ctgaagtggt tcaagaacgg caacgagctg agcgacttcc agaccaacgt ggaccctgtg    600
ggcgagtccg tgtcctacag catccacagc accgccaagg tggtgctgac ccgcgaagat    660
```

```
gtgcacagcc aagtgatctg cgaggtggcc cacgtgacac tgcagggcga tcctctgaga      720
ggaaccgcca acctgagcga gacaatcaga gtgcccccca ccctggaagt gacccagcag      780
ccagtgcggg ccgagaacca agtgaacgtg acctgtcaag tgcggaagtt ctaccccag       840 cggctgcagc tgacctggct ggaaaacggc aatgtgtccc ggaccgagac agccagcacc      900
gtgacagaga caaggatgg cacctacaat tggatgtctt ggctgctcgt gaacgtgtcc       960
gcccaccggg acgatgtgaa gctgacatgc caggtggaac acgacggcca gcctgccgtg     1020
tctaagagcc acgacctgaa ggtgtcagcc catcccaaag agcagggctc caacacagcc     1080
gccgagaaca ccggcagcaa cgagcggaac atctaccacc accatcacca ccactga        1137
```

<210> SEQ ID NO 49
<211> LENGTH: 378
<212> TYPE: PRT
<213> ORGANISM: Artificial
<220> FEATURE:
<223> OTHER INFORMATION: amino acid sequence of human SIRPA variant 2
      ECD

<400> SEQUENCE: 49

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Ser Val Ala Ala Gly
        35                  40                  45

Glu Ser Ala Ile Leu His Cys Thr Val Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
            260                 265                 270
```

-continued

Gln Val Arg Lys Phe Tyr Pro Gln Arg Leu Gln Leu Thr Trp Leu Glu
            275                 280                 285

Asn Gly Asn Val Ser Arg Thr Glu Thr Ala Ser Thr Val Thr Glu Asn
        290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
            340                 345                 350

Lys Glu Gln Gly Ser Asn Thr Ala Ala Glu Asn Thr Gly Ser Asn Glu
        355                 360                 365

Arg Asn Ile Tyr His His His His His His
        370                 375

<210> SEQ ID NO 50
<211> LENGTH: 465
<212> TYPE: DNA
<213> ORGANISM: Artificial
<220> FEATURE:
<223> OTHER INFORMATION: nucleotide sequence coding human SIRPA variant
      2 IgV

<400> SEQUENCE: 50
atggaacctg ccggacctgc ccctggcaga ctgggaccte tgctgtgtct gctgctggcc     60
gcctcttgtg cttggagcgg agtggctggc gaagaggaac tgcaagtgat ccagcccgac    120
aagagcgtgt cagtggccgc tggcgagtct gccatcctgc actgtaccgt gaccagcctg    180
atccccgtgg gccccatcca gtggtttaga ggcgctggac ctgccagaga gctgatctac    240
aaccagaaag agggccactt ccccagagtg accaccgtgt ccgagagcac caagcgcgag    300
aacatggact tcagcatcag catctccaac atcacccctg ccgacgccgg cacctactac    360
tgcgtgaagt tcgagaaggg cagccccgac accgagttca gagcggagc cggcacagag    420 ctgtctgtgc gggccaagcc tagccaccac caccatcacc attga                   465

<210> SEQ ID NO 51
<211> LENGTH: 154
<212> TYPE: PRT
<213> ORGANISM: Artificial
<220> FEATURE:
<223> OTHER INFORMATION: amino acid sequence of human SIRPA variant 2
      IgV

<400> SEQUENCE: 51

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Ser Val Ala Ala Gly
        35                  40                  45

Glu Ser Ala Ile Leu His Cys Thr Val Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
            115                 120                 125

Pro Asp Thr Glu Phe Lys Ser Gly Ala Gly Thr Glu Leu Ser Val Arg
        130                 135                 140

Ala Lys Pro Ser His His His His His His
145                 150

<210> SEQ ID NO 52
<211> LENGTH: 1137
<212> TYPE: DNA
<213> ORGANISM: Artificial
<220> FEATURE:
<223> OTHER INFORMATION: nucleotide sequence coding monkey SIRPA ECD

<400> SEQUENCE: 52
atggaacccg ccggacctgc tcctggcaga ctgggacctc tgctgtgtct gctgctgacc      60
gccagctgtg cttggagcgg agtgctgggc gaagaggaac tgcaagtgat ccagcccgag     120
aagtccgtgt ctgtggccgc tggcgatagc gccacccctg aattgcaccgt gtccagcctg    180 atccccgtgg gccctatcca gtggtttaga ggcgctggcc ctggcagaga gctgatctac    240
aacctgaaag agggccactt ccccagagtg accgccgtgt ccgaccccac caagcggaac    300
aacatggact tcagcatccg gatcagcaac atcacccctg ccgacgccgg cacctactac    360
tgcgtgaagt tcagaaaggg cagccccgac gtggaactga gtctggcgc cggaacagag    420 ctgagcgtgc gggccaaacc ttctgcccct gtggtgtctg acctgccgt gcgggctaca    480 gccgagcaca ccgtgtcttt tacctgcgag agccacggct tcagcccag agacatcacc    540 ctgaagtggt tcaagaacgg caacgagctg tccgacgtgc agaccaacgt ggaccctgcc    600
ggcaagagcg tgtcctacag catcagatcc accgccagag tgctgctgac aagacgggac    660
gtgcacagcc aagtgatctg cgaggtggcc acgtgacac tgcagggcga tcctctgaga    720
ggcaccgcca atctgagcga ggctatccgg gtgcccccat tcctggaagt gacccagcag    780
agcatgcggg ccgacaacca gtgaacgtg acctgccaag tgaccaagtt ctaccccag    840 cggctgcagc tgacctggct ggaaaacggc aatgtgtccc ggaccgagat ggcctctgcc    900
ctgcccgaga caaggatgg cacctacaat tggaccagct ggctgctcgt gaacgtgtcc    960
gcccaccggg acgatgtgaa gctgacatgc caggtggaac acgacggcca gcccgccgtg   1020
aacaagagct tcagcgtgaa agtgtctgct caccccaaag agcagggcag caacactgcc   1080
gccgagaaca ccggcaccaa cgagcggaac atctaccatc accaccatca tcactga      1137

<210> SEQ ID NO 53
<211> LENGTH: 378
<212> TYPE: PRT
<213> ORGANISM: Artificial
<220> FEATURE:
<223> OTHER INFORMATION: amino acid sequence of monkey SIRPA ECD

<400> SEQUENCE: 53

Met Glu Pro Ala Gly Pro Ala Pro Gly Arg Leu Gly Pro Leu Leu Cys
1               5                   10                  15

Leu Leu Leu Thr Ala Ser Cys Ala Trp Ser Gly Val Leu Gly Glu Glu
            20                  25                  30

Glu Leu Gln Val Ile Gln Pro Glu Lys Ser Val Ser Val Ala Ala Gly
        35                  40                  45

Asp Ser Ala Thr Leu Asn Cys Thr Val Ser Ser Leu Ile Pro Val Gly
    50                  55                  60

```
Pro Ile Gln Trp Phe Arg Gly Ala Gly Pro Gly Arg Glu Leu Ile Tyr
 65                  70                  75                  80

Asn Leu Lys Glu Gly His Phe Pro Arg Val Thr Ala Val Ser Asp Pro
             85                  90                  95

Thr Lys Arg Asn Asn Met Asp Phe Ser Ile Arg Ile Ser Asn Ile Thr
        100                 105                 110

Pro Ala Asp Ala Gly Thr Tyr Tyr Cys Val Lys Phe Arg Lys Gly Ser
        115                 120                 125

Pro Asp Val Glu Leu Lys Ser Gly Ala Gly Thr Glu Leu Ser Val Arg
        130                 135                 140

Ala Lys Pro Ser Ala Pro Val Val Ser Gly Pro Ala Val Arg Ala Thr
145                 150                 155                 160

Ala Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Val Gln Thr Asn Val Asp Pro Ala Gly Lys Ser Val Ser Tyr Ser Ile
        195                 200                 205

Arg Ser Thr Ala Arg Val Leu Leu Thr Arg Arg Asp Val His Ser Gln
210                 215                 220

Val Ile Cys Glu Val Ala His Val Thr Leu Gln Gly Asp Pro Leu Arg
225                 230                 235                 240

Gly Thr Ala Asn Leu Ser Glu Ala Ile Arg Val Pro Pro Phe Leu Glu
            245                 250                 255

Val Thr Gln Gln Ser Met Arg Ala Asp Asn Gln Val Asn Val Thr Cys
        260                 265                 270

Gln Val Thr Lys Phe Tyr Pro Gln Arg Leu Gln Leu Thr Trp Leu Glu
        275                 280                 285

Asn Gly Asn Val Ser Arg Thr Glu Met Ala Ser Ala Leu Pro Glu Asn
290                 295                 300

Lys Asp Gly Thr Tyr Asn Trp Thr Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Asn Lys Ser Phe Ser Val Lys Val Ser Ala His Pro
            340                 345                 350

Lys Glu Gln Gly Ser Asn Thr Ala Ala Glu Asn Thr Gly Thr Asn Glu
        355                 360                 365

Arg Asn Ile Tyr His His His His His His
        370                 375

<210> SEQ ID NO 54
<211> LENGTH: 1107
<212> TYPE: DNA
<213> ORGANISM: Artificial
<220> FEATURE:
<223> OTHER INFORMATION: nucleotide sequence coding human CD47-Fc

<400> SEQUENCE: 54
atgtggcccc tggtagcggc gctgttgctg ggctcggcgt gctgcggatc agctcagcta      60
ctatttaata aaacaaaatc tgtagaattc acgttttgta atgacactgt cgtcattcca     120
tgctttgtta ctaatatgga ggcacaaaac actactgaag tatacgtaaa gtggaaattt     180
aaaggaagag atatttacac ctttgatgga gctctaaaca agtccactgt ccccactgac     240
```

```
tttagtagtg caaaaattga agtctcacaa ttactaaaag gagatgcctc tttgaagatg      300
gataagagtg atgctgtctc acacacagga aactacactt gtgaagtaac agaattaacc      360
agagaaggtg aaacgatcat cgagctaaaa tatcgtgttg tttcatggtt ttctccaaat      420
gaagacaaaa ctcacacatg cccaccctgc ccagcacctg aactcctggg gggaccctca      480
gtcttcctct tccccccaaa acccaaggac accctcatga tctcccggac ccctgaggtc      540
acatgcgtgg tggtggacgt gagccacgaa gaccctgagg tcaagttcaa ctggtacgtg      600
gacggcgtgg aggtgcataa tgccaagaca aagccccggg aggagcagta caacagcacg      660
taccgggtgg tcagcgtcct caccgtcctg caccaggact ggctgaatgg caaggagtac      720
aagtgcaagg tctccaacaa agccctccca gcccccatcg agaaaaccat ctccaaagcc      780
aaaggccagc cccgggaacc acaggtgtac accctgcccc catcccggga ggagatgacc      840
aagaaccagg tcagcctgac ctgcctggtc aaaggcttct atcccagcga catcgccgtg      900
gagtgggaga gcaatggcca gcccgagaac aactacaaga ccaccccctcc cgtgctggac      960 tccgacggct ccttcttcct ctacagcaag ctcaccgtgg acaagagcag gtggcagcag     1020
ggcaacgtct tctcatgctc cgtgatgcat gaggctctgc acaaccacta cacccagaag     1080
agcctctccc tgtctcccgg caaatga                                         1107
```

<210> SEQ ID NO 55
<211> LENGTH: 368
<212> TYPE: PRT
<213> ORGANISM: Artificial
<220> FEATURE:
<223> OTHER INFORMATION: amino acid sequence of human CD47-Fc

<400> SEQUENCE: 55

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asp Lys Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205
```

```
Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 56
<211> LENGTH: 504
<212> TYPE: PRT
<213> ORGANISM: Homo sapiens

<400> SEQUENCE: 56

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220
```

```
Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500

<210> SEQ ID NO 57
<211> LENGTH: 503
<212> TYPE: PRT
<213> ORGANISM: Homo sapiens

<400> SEQUENCE: 57

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Ser Val Ala Ala Gly
            35                  40                  45

Glu Ser Ala Ile Leu His Cys Thr Val Thr Ser Leu Ile Pro Val Gly
        50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
```

```
                          85                  90                    95
Thr Lys Arg Glu Asn Met Asp Phe Ser Ile Ser Ile Ser Asn Ile Thr
                100                 105                 110
Pro Ala Asp Ala Gly Thr Tyr Tyr Cys Val Lys Phe Arg Lys Gly Ser
                115                 120                 125
Pro Asp Thr Glu Phe Lys Ser Gly Ala Gly Thr Glu Leu Ser Val Arg
                130                 135                 140
Ala Lys Pro Ser Ala Pro Val Val Ser Gly Pro Ala Ala Arg Ala Thr
145                 150                 155                 160
Pro Gln His Thr Val Ser Phe Thr Cys Glu Ser His Gly Phe Ser Pro
                165                 170                 175
Arg Asp Ile Thr Leu Lys Trp Phe Lys Asn Gly Asn Glu Leu Ser Asp
                180                 185                 190
Phe Gln Thr Asn Val Asp Pro Val Gly Glu Ser Val Ser Tyr Ser Ile
                195                 200                 205
His Ser Thr Ala Lys Val Val Leu Thr Arg Glu Asp Val His Ser Gln
                210                 215                 220
Val Ile Cys Glu Val Ala His Val Thr Leu Gln Gly Asp Pro Leu Arg
225                 230                 235                 240
Gly Thr Ala Asn Leu Ser Glu Thr Ile Arg Val Pro Pro Thr Leu Glu
                245                 250                 255
Val Thr Gln Gln Pro Val Arg Ala Glu Asn Gln Val Asn Val Thr Cys
                260                 265                 270
Gln Val Arg Lys Phe Tyr Pro Gln Arg Leu Gln Leu Thr Trp Leu Glu
                275                 280                 285
Asn Gly Asn Val Ser Arg Thr Glu Thr Ala Ser Thr Val Thr Glu Asn
                290                 295                 300
Lys Asp Gly Thr Tyr Asn Trp Met Ser Trp Leu Leu Val Asn Val Ser
305                 310                 315                 320
Ala His Arg Asp Asp Val Lys Leu Thr Cys Gln Val Glu His Asp Gly
                325                 330                 335
Gln Pro Ala Val Ser Lys Ser His Asp Leu Lys Val Ser Ala His Pro
                340                 345                 350
Lys Glu Gln Gly Ser Asn Thr Ala Ala Glu Asn Thr Gly Ser Asn Glu
                355                 360                 365
Arg Asn Ile Tyr Ile Val Val Gly Val Val Cys Thr Leu Leu Val Ala
                370                 375                 380
Leu Leu Met Ala Ala Leu Tyr Leu Val Arg Ile Arg Gln Lys Lys Ala
385                 390                 395                 400
Gln Gly Ser Thr Ser Ser Thr Arg Leu His Glu Pro Glu Lys Asn Ala
                405                 410                 415
Arg Glu Ile Thr Gln Asp Thr Asn Asp Ile Thr Tyr Ala Asp Leu Asn
                420                 425                 430
Leu Pro Lys Gly Lys Lys Pro Ala Pro Gln Ala Ala Glu Pro Asn Asn
                435                 440                 445
His Thr Glu Tyr Ala Ser Ile Gln Thr Ser Pro Gln Pro Ala Ser Glu
                450                 455                 460
Asp Thr Leu Thr Tyr Ala Asp Leu Asp Met Val His Leu Asn Arg Thr
465                 470                 475                 480
Pro Lys Gln Pro Ala Pro Lys Pro Glu Pro Ser Phe Ser Glu Tyr Ala
                485                 490                 495
Ser Val Gln Val Pro Arg Lys
                500
```

<210> SEQ ID NO 58
<211> LENGTH: 503
<212> TYPE: PRT
<213> ORGANISM: Macaca fascicularis

<400> SEQUENCE: 58

```
Met Glu Pro Ala Gly Pro Ala Pro Gly Arg Leu Gly Pro Leu Leu Cys
1               5                   10                  15

Leu Leu Leu Thr Ala Ser Cys Ala Trp Ser Gly Val Leu Gly Glu Glu
            20                  25                  30

Glu Leu Gln Val Ile Gln Pro Glu Lys Ser Val Ser Val Ala Ala Gly
        35                  40                  45

Asp Ser Ala Thr Leu Asn Cys Thr Val Ser Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Leu Lys Glu Gly His Phe Pro Arg Val Thr Ala Val Ser Asp Pro
                85                  90                  95

Thr Lys Arg Asn Asn Met Asp Phe Ser Ile Arg Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Val Glu Leu Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160

Ala Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Val Gln Thr Asn Val Asp Pro Ala Gly Lys Ser Val Ser Tyr Ser Ile
        195                 200                 205

Arg Ser Thr Ala Arg Val Leu Leu Thr Arg Arg Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Ala Ile Arg Val Pro Pro Phe Leu Glu
                245                 250                 255

Val Thr Gln Gln Ser Met Arg Ala Asp Asn Gln Val Asn Val Thr Cys
            260                 265                 270

Gln Val Thr Lys Phe Tyr Pro Gln Arg Leu Gln Leu Thr Trp Leu Glu
        275                 280                 285

Asn Gly Asn Val Ser Arg Thr Glu Met Ala Ser Ala Leu Pro Glu Asn
    290                 295                 300

Lys Asp Gly Thr Tyr Asn Trp Thr Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Asn Lys Ser Phe Ser Val Lys Val Ser Ala His Pro
            340                 345                 350

Lys Glu Gln Gly Ser Asn Thr Ala Ala Glu Asn Thr Gly Thr Asn Glu
        355                 360                 365

Arg Asn Ile Tyr Ile Val Val Gly Val Val Cys Thr Leu Leu Val Ala
```

```
                    370                 375                 380
Leu Leu Met Ala Ala Leu Tyr Leu Val Arg Ile Arg Gln Lys Lys Ala
385                 390                 395                 400

Gln Gly Ser Thr Ser Thr Arg Leu His Glu Pro Glu Lys Asn Ala
                405                 410                 415

Arg Glu Ile Thr Gln Asp Thr Asn Asp Ile Thr Tyr Ala Asp Leu Asn
                420                 425                 430

Leu Pro Lys Gly Lys Lys Pro Ala Pro Arg Ala Ala Glu Pro Asn Asn
                435                 440                 445

His Thr Glu Gly Ala Ser Ile Gln Thr Ser Pro Gln Pro Ala Ser Glu
    450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
                500

<210> SEQ ID NO 59
<211> LENGTH: 509
<212> TYPE: PRT
<213> ORGANISM: Mus musculus

<400> SEQUENCE: 59

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
                20                  25                  30

Glu Leu Lys Val Thr Gln Pro Glu Lys Ser Val Ser Val Ala Ala Gly
            35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
        115                 120                 125

Ser Glu Pro Asp Thr Glu Ile Gln Ser Gly Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
    210                 215                 220

Ser Lys Val Ile Cys Glu Val Ala His Ile Thr Leu Asp Arg Ser Pro
225                 230                 235                 240
```

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
            275                 280                 285

Leu Glu Asn Gly Asn Val Ser Arg Asn Asp Thr Pro Lys Asn Leu Thr
            290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
            355                 360                 365

Thr His Asn Trp Asn Val Phe Ile Gly Val Gly Val Ala Cys Ala Leu
            370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
            405                 410                 415

Lys Asn Ala Arg Glu Ile Thr Gln Ile Gln Asp Thr Asn Asp Ile Asn
            420                 425                 430

Asp Ile Thr Tyr Ala Asp Leu Asn Leu Pro Lys Glu Lys Lys Pro Ala
            435                 440                 445

Pro Arg Ala Pro Glu Pro Asn Asn His Thr Glu Tyr Ala Ser Ile Glu
450                 455                 460

Thr Gly Lys Val Pro Arg Pro Glu Asp Thr Leu Thr Tyr Ala Asp Leu
465                 470                 475                 480

Asp Met Val His Leu Ser Arg Ala Gln Pro Ala Pro Lys Pro Glu Pro
            485                 490                 495

Ser Phe Ser Glu Tyr Ala Ser Val Gln Val Gln Arg Lys
            500                 505

<210> SEQ ID NO 60
<211> LENGTH: 509
<212> TYPE: PRT
<213> ORGANISM: Mus musculus

<400> SEQUENCE: 60

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Thr
            20                  25                  30

Glu Val Lys Val Thr Gln Pro Glu Lys Ser Val Ser Val Ala Ala Gly
            35                  40                  45

Asp Ser Thr Ile Leu Asn Cys Thr Val Thr Ser Leu Leu Pro Val Gly
        50                  55                  60

Pro Ile Arg Trp Tyr Arg Gly Val Gly Gln Ser Arg Leu Leu Ile Tyr
65                  70                  75                  80

Ser Phe Thr Gly Glu His Phe Pro Arg Val Arg Asn Val Ser Asp Thr
                85                  90                  95

Thr Lys Arg Asn Asn Met Asp Phe Ser Ile Arg Ile Ser Asn Val Thr
            100                 105                 110

Pro Glu Asp Ala Gly Thr Tyr Tyr Cys Val Lys Phe Gln Arg Gly Ser
        115                 120                 125

Ser Glu Pro Asp Thr Glu Ile Gln Ser Gly Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
                260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
        290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
                340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
        370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Thr Arg Leu His Glu Pro Glu
                405                 410                 415

Lys Asn Ala Arg Glu Ile Thr Gln Ile Gln Asp Thr Asn Asp Ile Asn
                420                 425                 430

Asp Ile Thr Tyr Ala Asp Leu Asn Leu Pro Lys Glu Lys Lys Pro Ala
                435                 440                 445

Pro Arg Ala Pro Glu Pro Asn Asn His Thr Glu Tyr Ala Ser Ile Glu
    450                 455                 460

Thr Gly Lys Val Pro Arg Pro Glu Asp Thr Leu Thr Tyr Ala Asp Leu
465                 470                 475                 480

Asp Met Val His Leu Ser Arg Ala Gln Pro Ala Pro Lys Pro Glu Pro
                485                 490                 495

Ser Phe Ser Glu Tyr Ala Ser Val Gln Val Gln Arg Lys
                500                 505

<210> SEQ ID NO 61
<211> LENGTH: 513

<212> TYPE: PRT
<213> ORGANISM: Mus musculus

<400> SEQUENCE: 61

```
Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Val Thr Gly Lys
            20                  25                  30

Glu Leu Lys Val Thr Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Lys Trp Tyr Arg Gly Val Gly Gln Ser Arg Leu Leu Ile Tyr
65                  70                  75                  80

Ser Phe Thr Gly Glu His Phe Pro Arg Val Thr Asn Val Ser Asp Ala
                85                  90                  95

Thr Lys Arg Asn Asn Met Asp Phe Ser Ile Arg Ile Ser Asn Val Thr
            100                 105                 110

Pro Glu Asp Ala Gly Thr Tyr Tyr Cys Val Lys Phe Gln Lys Gly Pro
        115                 120                 125

Ser Glu Pro Asp Thr Glu Ile Gln Ser Gly Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His His Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val His
    210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
    290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Leu Ala
            340                 345                 350

His Ser Ser Asp Gln Gly Ser Met Gln Thr Phe Pro Gly Asn Asn Ala
        355                 360                 365

Thr His Asn Trp Asn Val Phe Ile Gly Val Gly Val Ala Cys Ala Leu
    370                 375                 380

Leu Val Val Leu Leu Met Ala Ala Leu Tyr Leu Leu Arg Ile Lys Gln
385                 390                 395                 400
```

```
Lys Lys Ala Lys Gly Ser Thr Ser Thr Arg Leu His Glu Pro Glu
            405                 410                 415

Lys Asn Ala Arg Glu Ile Thr Gln Val Gln Ser Leu Ile Gln Asp Thr
            420                 425                 430

Asp Asp Ile Asn Asp Ile Thr Tyr Ala Asp Leu Asn Leu Pro Lys Glu
            435                 440                 445

Lys Lys Pro Ala Pro Arg Ala Pro Glu Pro Asn Asn His Thr Glu Tyr
        450                 455                 460

Ala Ser Ile Glu Thr Gly Lys Val Pro Arg Pro Glu Asp Thr Leu Thr
465                 470                 475                 480

Tyr Ala Asp Leu Asp Met Val His Leu Ser Arg Ala Gln Pro Ala Pro
                485                 490                 495

Lys Pro Glu Pro Ser Phe Ser Glu Tyr Ala Ser Val Gln Val Gln Arg
            500                 505                 510

Lys

<210> SEQ ID NO 62
<211> LENGTH: 507
<212> TYPE: PRT
<213> ORGANISM: Mus musculus

<400> SEQUENCE: 62

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Arg Thr
                20                  25                  30

Glu Val Lys Val Ile Gln Pro Glu Lys Ser Val Ser Val Ala Ala Gly
            35                  40                  45

Asp Ser Thr Val Leu Asn Cys Thr Leu Thr Ser Leu Leu Pro Val Gly
        50                  55                  60

Pro Ile Arg Trp Tyr Arg Gly Val Gly Gln Ser Arg Gln Leu Ile Tyr
65                  70                  75                  80

Ser Phe Thr Thr Glu His Phe Pro Arg Val Thr Asn Val Ser Asp Ala
                85                  90                  95

Thr Lys Arg Ser Asn Leu Asp Phe Ser Ile Arg Ile Ser Asn Val Thr
            100                 105                 110

Pro Glu Asp Ala Gly Thr Tyr Tyr Cys Val Lys Phe Gln Arg Gly Ser
            115                 120                 125

Pro Asp Thr Glu Ile Gln Ser Gly Gly Thr Glu Val Tyr Val Leu
        130                 135                 140

Ala Lys Pro Ser Pro Pro Glu Val Ser Gly Pro Ala Asp Arg Gly Ile
145                 150                 155                 160

Pro Asp Gln Lys Val Asn Phe Thr Cys Lys Ser His Gly Phe Ser Pro
                165                 170                 175

Arg Asn Ile Thr Leu Lys Trp Phe Lys Asp Gly Gln Glu Leu His Pro
            180                 185                 190

Leu Glu Thr Thr Val Asn Pro Ser Gly Lys Asn Val Ser Tyr Asn Ile
        195                 200                 205

Ser Ser Thr Val Arg Val Val Leu Asn Ser Met Asp Val His Ser Lys
    210                 215                 220

Val Ile Cys Glu Val Ala His Ile Thr Leu Asp Arg Ser Pro Leu Arg
225                 230                 235                 240

Gly Ile Ala Asn Leu Ser Asn Phe Ile Arg Val Ser Pro Thr Val Lys
                245                 250                 255
```

Val Thr Gln Gln Ser Pro Thr Ser Met Ser Gln Val Asn Leu Thr Cys
            260                 265                 270

Arg Ala Glu Arg Phe Tyr Pro Glu Asp Leu Gln Leu Ile Trp Leu Glu
        275                 280                 285

Asn Gly Asn Val Ser Arg Asn Asp Thr Pro Lys Asn Leu Thr Lys Asn
    290                 295                 300

Thr Asp Gly Thr Tyr Asn Tyr Thr Ser Leu Phe Leu Val Asn Ser Ser
305                 310                 315                 320

Ala His Arg Glu Asp Val Val Phe Thr Cys Gln Val Lys His Asp Gln
                325                 330                 335

Gln Pro Ala Ile Thr Arg Asn His Thr Val Leu Gly Leu Ala His Ser
            340                 345                 350

Ser Asp Gln Gly Ser Met Gln Thr Phe Pro Gly Asn Asn Ala Thr His
        355                 360                 365

Asn Trp Asn Val Phe Ile Gly Val Gly Val Ala Cys Ala Leu Leu Val
    370                 375                 380

Val Leu Leu Met Ala Ala Leu Tyr Leu Leu Arg Ile Lys Gln Lys Lys
385                 390                 395                 400

Ala Lys Gly Ser Thr Ser Ser Thr Arg Leu His Glu Pro Glu Lys Asn
                405                 410                 415

Ala Arg Glu Ile Thr Gln Ile Gln Asp Thr Asn Asp Ile Asn Asp Ile
            420                 425                 430

Thr Tyr Ala Asp Leu Asn Leu Pro Lys Glu Lys Lys Pro Ala Pro Arg
        435                 440                 445

Ala Pro Glu Pro Asn Asn His Thr Glu Tyr Ala Ser Ile Glu Thr Gly
    450                 455                 460

Lys Val Pro Arg Pro Glu Asp Thr Leu Thr Tyr Ala Asp Leu Asp Met
465                 470                 475                 480

Val His Leu Ser Arg Ala Gln Pro Ala Pro Lys Pro Glu Pro Ser Phe
                485                 490                 495

Ser Glu Tyr Ala Ser Val Gln Val Gln Arg Lys
            500                 505

<210> SEQ ID NO 63
<211> LENGTH: 503
<212> TYPE: PRT
<213> ORGANISM: Homo sapiens

<400> SEQUENCE: 63

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Ser Val Ala Ala Gly
        35                  40                  45

Glu Ser Ala Ile Leu Leu Cys Thr Val Thr Ser Leu Ile Pro Val Gly
    50                  55                  60

Pro Ile Gln Trp Phe Arg Gly Ala Gly Pro Ala Arg Glu Leu Ile Tyr
65              70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser

```
                    115                 120                 125
Pro Asp Thr Glu Phe Lys Ser Gly Ala Gly Thr Glu Leu Ser Val Arg
130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                    165                 170                 175

Arg Asp Ile Thr Leu Lys Trp Phe Lys Asn Gly Asn Glu Leu Ser Asp
                180                 185                 190

Phe Gln Thr Asn Val Asp Pro Val Gly Glu Ser Val Ser Tyr Ser Ile
                195                 200                 205

His Ser Thr Ala Lys Val Val Leu Thr Arg Glu Asp Val His Ser Gln
210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
                260                 265                 270

Gln Val Arg Lys Phe Tyr Pro Gln Arg Leu Gln Leu Thr Trp Leu Glu
            275                 280                 285

Asn Gly Asn Val Ser Arg Thr Glu Thr Ala Ser Thr Val Thr Glu Asn
290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
                340                 345                 350

Lys Glu Gln Gly Ser Asn Thr Ala Ala Glu Asn Thr Gly Ser Asn Glu
            355                 360                 365

Arg Asn Ile Tyr Ile Val Val Gly Val Val Cys Thr Leu Leu Val Ala
370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
                405                 410                 415

Arg Glu Ile Thr Gln Asp Thr Asn Asp Ile Thr Tyr Ala Asp Leu Asn
                420                 425                 430

Leu Pro Lys Gly Lys Lys Pro Ala Pro Gln Ala Ala Glu Pro Asn Asn
            435                 440                 445

His Thr Glu Tyr Ala Ser Ile Gln Thr Ser Pro Gln Pro Ala Ser Glu
450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
            500

<210> SEQ ID NO 64
<211> LENGTH: 504
<212> TYPE: PRT
<213> ORGANISM: Homo sapiens
```

<400> SEQUENCE: 64

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Gly Leu Gln Val Ile Gln Pro Asp Lys Ser Val Ser Val Ala Ala Gly
        35                  40                  45

Glu Ser Ala Ile Leu His Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
```

```
                        405                 410                 415
Ala Arg Glu Ile Thr Gln Asp Thr Asn Asp Ile Thr Tyr Ala Asp Leu
            420                 425                 430

Asn Leu Pro Lys Gly Lys Pro Ala Pro Gln Ala Ala Glu Pro Asn
            435                 440                 445

Asn His Thr Glu Tyr Ala Ser Ile Gln Thr Ser Pro Gln Pro Ala Ser
            450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                    485                 490                 495

Ala Ser Val Gln Val Pro Arg Lys
                500

<210> SEQ ID NO 65
<211> LENGTH: 504
<212> TYPE: PRT
<213> ORGANISM: Homo sapiens

<400> SEQUENCE: 65

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Phe Val Leu Ala Ala Gly
        35                  40                  45

Glu Thr Ala Thr Leu Arg Cys Thr Ala Thr Ser Leu Ile Pro Val Gly
50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
            115                 120                 125

Pro Asp Asp Val Glu Phe Lys Ser Gly Ala Gly Thr Glu Leu Ser Val
        130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270
```

-continued

```
Cys Gln Val Arg Lys Phe Tyr Pro Gln Arg Leu Gln Leu Thr Trp Leu
            275                 280                 285

Glu Asn Gly Asn Val Ser Arg Thr Glu Thr Ala Ser Thr Val Thr Glu
290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500
```

<210> SEQ ID NO 66
<211> LENGTH: 504
<212> TYPE: PRT
<213> ORGANISM: Homo sapiens

<400> SEQUENCE: 66

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
        50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Pro Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
130                 135                 140
```

Arg Ala Lys Pro Ser Ala Pro Val Val Ser Gly Pro Ala Arg Ala
145                 150                 155                 160

Thr Pro Gln His Thr Val Ser Phe Thr Cys Glu Ser His Gly Phe Ser
            165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
            195                 200                 205

Ile His Ser Thr Ala Lys Val Val Leu Thr Arg Glu Asp Val His Ser
210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
            245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
            275                 280                 285

Glu Asn Gly Asn Val Ser Arg Thr Glu Thr Ala Ser Thr Val Thr Glu
290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
            325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
            355                 360                 365

Glu Arg Asn Ile Tyr Ile Val Val Gly Val Val Cys Thr Leu Leu Val
370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
            405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
            435                 440                 445

Asn His Thr Glu Tyr Ala Ser Ile Gln Thr Ser Pro Gln Pro Ala Ser
            450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
            485                 490                 495

Ala Ser Val Gln Val Pro Arg Lys
            500

<210> SEQ ID NO 67
<211> LENGTH: 503
<212> TYPE: PRT
<213> ORGANISM: Homo sapiens

<400> SEQUENCE: 67

Met Glu Pro Ala Gly Pro Ala Pro Gly Arg Leu Gly Pro Leu Leu Cys

-continued

```
  1               5                  10                 15
Leu Leu Leu Ala Ala Ser Cys Ala Trp Ser Gly Val Ala Gly Glu Glu
              20                  25                 30

Glu Leu Gln Val Ile Gln Pro Asp Lys Ser Val Ser Val Ala Ala Gly
              35                  40                 45

Glu Ser Ala Ile Leu His Cys Thr Val Thr Ser Leu Ile Pro Val Gly
              50                  55                 60

Pro Ile Gln Trp Phe Arg Gly Ala Gly Pro Ala Arg Glu Leu Ile Tyr
 65                  70                  75                 80

Asn Gln Lys Glu Gly His Phe Pro Arg Val Thr Thr Val Ser Glu Ser
                  85                  90                 95

Thr Lys Arg Glu Asn Met Asp Phe Ser Ile Ser Ile Ser Asn Ile Thr
                 100                 105                110

Pro Ala Asp Ala Gly Thr Tyr Tyr Cys Val Lys Phe Arg Lys Gly Ser
                 115                 120                125

Pro Asp Thr Glu Phe Lys Ser Gly Ala Gly Thr Glu Leu Ser Val Arg
                 130                 135                140

Gly Lys Pro Ser Ala Pro Val Val Ser Gly Pro Ala Ala Arg Ala Thr
145                  150                 155                160

Pro Gln His Thr Val Ser Phe Thr Cys Glu Ser His Gly Phe Ser Pro
                 165                 170                175

Arg Asp Ile Thr Leu Lys Trp Phe Lys Asn Gly Asn Glu Leu Ser Asp
                 180                 185                190

Phe Gln Thr Asn Val Asp Pro Val Gly Glu Ser Val Ser Tyr Ser Ile
                 195                 200                205

His Ser Thr Ala Lys Val Val Leu Thr Arg Glu Asp Val His Ser Gln
                 210                 215                220

Val Ile Cys Glu Val Ala His Val Thr Leu Gln Gly Asp Pro Leu Arg
225                  230                 235                240

Gly Thr Ala Asn Leu Ser Glu Thr Ile Arg Val Pro Pro Thr Leu Glu
                 245                 250                255

Val Thr Gln Gln Pro Val Arg Ala Glu Asn Gln Val Asn Val Thr Cys
                 260                 265                270

Gln Val Arg Lys Phe Tyr Pro Gln Arg Leu Gln Leu Thr Trp Leu Glu
                 275                 280                285

Asn Gly Asn Val Ser Arg Thr Glu Thr Ala Ser Thr Val Thr Glu Asn
                 290                 295                300

Lys Asp Gly Thr Tyr Asn Trp Met Ser Trp Leu Leu Val Asn Val Ser
305                  310                 315                320

Ala His Arg Asp Asp Val Lys Leu Thr Cys Gln Val Glu His Asp Gly
                 325                 330                335

Gln Pro Ala Val Ser Lys Ser His Asp Leu Lys Val Ser Ala His Pro
                 340                 345                350

Lys Glu Gln Gly Ser Asn Thr Ala Ala Glu Asn Thr Gly Ser Asn Glu
                 355                 360                365

Arg Asn Ile Tyr Ile Val Val Gly Val Val Cys Thr Leu Leu Val Ala
                 370                 375                380

Leu Leu Met Ala Ala Leu Tyr Leu Val Arg Ile Arg Gln Lys Lys Ala
385                  390                 395                400

Gln Gly Ser Thr Ser Ser Thr Arg Leu His Glu Pro Glu Lys Asn Ala
                 405                 410                415

Arg Glu Ile Thr Gln Asp Thr Asn Asp Ile Thr Tyr Ala Asp Leu Asn
                 420                 425                430
```

```
Leu Pro Lys Gly Lys Pro Ala Pro Gln Ala Ala Glu Pro Asn Asn
        435                 440                 445

His Thr Glu Tyr Ala Ser Ile Gln Thr Ser Pro Gln Pro Ala Ser Glu
    450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
                500

<210> SEQ ID NO 68
<211> LENGTH: 503
<212> TYPE: PRT
<213> ORGANISM: Homo sapiens

<400> SEQUENCE: 68

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
            260                 265                 270

Gln Val Arg Lys Phe Tyr Pro Gln Arg Leu Gln Leu Thr Trp Leu Glu
        275                 280                 285

Asn Gly Asn Val Ser Arg Thr Glu Thr Ala Ser Thr Val Thr Glu Asn
```

```
                    290                 295                 300
Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
            340                 345                 350

Lys Glu Gln Gly Ser Asn Thr Ala Ala Glu Asn Thr Gly Ser Asn Glu
        355                 360                 365

Arg Asn Ile Tyr Ile Val Val Gly Val Val Cys Thr Leu Leu Val Ala
    370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
                405                 410                 415

Arg Glu Ile Thr Gln Asp Thr Asn Asp Ile Thr Tyr Ala Asp Leu Asn
            420                 425                 430

Leu Pro Lys Gly Lys Lys Pro Ala Pro Gln Ala Ala Glu Pro Asn Asn
        435                 440                 445

His Thr Glu Tyr Ala Ser Ile Gln Thr Ser Pro Gln Pro Ala Ser Glu
    450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
            500

<210> SEQ ID NO 69
<211> LENGTH: 504
<212> TYPE: PRT
<213> ORGANISM: Homo sapiens

<400> SEQUENCE: 69

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
        50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160
```

```
Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500

<210> SEQ ID NO 70
<211> LENGTH: 503
<212> TYPE: PRT
<213> ORGANISM: Homo sapiens

<400> SEQUENCE: 70

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Arg Val Ala Gly Glu Glu
            20                  25                  30
```

-continued

```
Glu Leu Gln Val Ile Gln Pro Asp Lys Ser Val Ser Val Ala Ala Gly
             35                  40                  45

Glu Ser Ala Ile Leu His Cys Thr Val Thr Ser Leu Ile Pro Val Gly
         50                  55                  60

Pro Ile Gln Trp Phe Arg Gly Ala Gly Pro Ala Arg Glu Leu Ile Tyr
 65                  70                  75                  80

Asn Gln Lys Glu Gly His Phe Pro Arg Val Thr Thr Val Ser Glu Ser
                 85                  90                  95

Thr Lys Arg Glu Asn Met Asp Phe Ser Ile Ser Ile Ser Asn Ile Thr
                100                 105                 110

Pro Ala Asp Ala Gly Thr Tyr Tyr Cys Val Lys Phe Arg Lys Gly Ser
                115                 120                 125

Pro Asp Thr Glu Phe Lys Ser Gly Ala Gly Thr Glu Leu Ser Val Arg
                130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
                180                 185                 190

Phe Gln Thr Asn Val Asp Pro Val Gly Glu Ser Val Ser Tyr Ser Ile
                195                 200                 205

His Ser Thr Ala Lys Val Val Leu Thr Arg Glu Asp Val His Ser Gln
                210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
                260                 265                 270

Gln Val Arg Lys Phe Tyr Pro Gln Arg Leu Gln Leu Thr Trp Leu Glu
                275                 280                 285

Asn Gly Asn Val Ser Arg Thr Glu Thr Ala Ser Thr Val Thr Glu Asn
                290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
                340                 345                 350

Lys Glu Gln Gly Ser Asn Thr Ala Ala Glu Asn Thr Gly Ser Asn Glu
                355                 360                 365

Arg Asn Ile Tyr Ile Val Val Gly Val Val Cys Thr Leu Leu Val Ala
                370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
                405                 410                 415

Arg Glu Ile Thr Gln Asp Thr Asn Asp Ile Thr Tyr Ala Asp Leu Asn
                420                 425                 430

Leu Pro Lys Gly Lys Lys Pro Ala Pro Gln Ala Ala Glu Pro Asn Asn
                435                 440                 445
```

```
His Thr Glu Tyr Ala Ser Ile Gln Thr Ser Pro Gln Pro Ala Ser Glu
    450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
                500

<210> SEQ ID NO 71
<211> LENGTH: 296
<212> TYPE: PRT
<213> ORGANISM: Artificial
<220> FEATURE:
<223> OTHER INFORMATION: amino acid sequence of human SIRPA_V2_IgV form

<400> SEQUENCE: 71

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Ser Val Ala Ala Gly
            35                  40                  45

Glu Ser Ala Ile Leu His Cys Thr Val Thr Ser Leu Ile Pro Val Gly
50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Ile Tyr Ile Val Val Gly Val Val Cys Thr Leu Leu Val
                165                 170                 175

Ala Leu Leu Met Ala Ala Leu Tyr Leu Val Arg Ile Arg Gln Lys Lys
            180                 185                 190

Ala Gln Gly Ser Thr Ser Ser Thr Arg Leu His Glu Pro Glu Lys Asn
        195                 200                 205

Ala Arg Glu Ile Thr Gln Asp Thr Asn Asp Ile Thr Tyr Ala Asp Leu
    210                 215                 220

Asn Leu Pro Lys Gly Lys Lys Pro Ala Pro Gln Ala Ala Glu Pro Asn
225                 230                 235                 240

Asn His Thr Glu Tyr Ala Ser Ile Gln Thr Ser Pro Gln Pro Ala Ser
                245                 250                 255

Glu Asp Thr Leu Thr Tyr Ala Asp Leu Asp Met Val His Leu Asn Arg
            260                 265                 270

Thr Pro Lys Gln Pro Ala Pro Lys Pro Glu Pro Ser Phe Ser Glu Tyr
        275                 280                 285

Ala Ser Val Gln Val Pro Arg Lys
    290                 295
```

```
<210> SEQ ID NO 72
<211> LENGTH: 397
<212> TYPE: PRT
<213> ORGANISM: Artificial
<220> FEATURE:
<223> OTHER INFORMATION: amino acid sequence of human SIRPA V2_IgV_IgC1
      form

<400> SEQUENCE: 72
```

| | | | | | | | | | | | | | | |
|---|---|---|---|---|---|---|---|---|---|---|---|---|---|---|
| Met | Glu | Pro | Ala | Gly | Pro | Ala | Pro | Gly | Arg | Leu | Gly | Pro | Leu | Cys |
| 1 | | | | 5 | | | | | 10 | | | | | 15 |
| Leu | Leu | Leu | Ala | Ala | Ser | Cys | Ala | Trp | Ser | Gly | Val | Ala | Gly | Glu |
| | | | | 20 | | | | | 25 | | | | | 30 |
| Glu | Leu | Gln | Val | Ile | Gln | Pro | Asp | Lys | Ser | Val | Ser | Val | Ala | Ala |
| | | | | 35 | | | | | 40 | | | | | 45 |
| Gly | Glu | Ser | Ala | Ile | Leu | His | Cys | Thr | Val | Thr | Ser | Leu | Ile | Pro |
| | | | 50 | | | | | 55 | | | | | 60 | |
| Val | Gly | Pro | Ile | Gln | Trp | Phe | Arg | Gly | Ala | Gly | Pro | Ala | Arg | Glu |
| 65 | | | | | 70 | | | | | 75 | | | | |
| Leu | Ile | Tyr | Asn | Gln | Lys | Glu | Gly | His | Phe | Pro | Arg | Val | Thr | Thr |
| | | 80 | | | | | 85 | | | | | 90 | | |
| Val | Ser | Glu | Ser | Thr | Lys | Arg | Glu | Asn | Met | Asp | Phe | Ser | Ile | Ser |
| | | | 95 | | | | | 100 | | | | | 105 | |
| Ile | Ser | Asn | Ile | Thr | Pro | Ala | Asp | Ala | Gly | Thr | Tyr | Tyr | Cys | Val |
| | | | 110 | | | | | 115 | | | | | 120 | |
| Lys | Phe | Arg | Lys | Gly | Ser | Pro | Asp | Thr | Glu | Phe | Lys | Ser | Gly | Ala |
| | | 125 | | | | | 130 | | | | | 135 | | |
| Gly | Thr | Glu | Leu | Ser | Val | Arg | Ala | Lys | Pro | Ser | Ala | Pro | Val | Val |
| | 140 | | | | | 145 | | | | | 150 | | | |
| Ser | Gly | Pro | Ala | Ala | Arg | Ala | Thr | Pro | Gln | His | Thr | Val | Ser | Phe |
| | 155 | | | | | 160 | | | | | 165 | | | |
| Thr | Cys | Glu | Ser | His | Gly | Phe | Ser | Pro | Arg | Asp | Ile | Thr | Leu | Lys |
| | | 170 | | | | | 175 | | | | | 180 | | |
| Trp | Phe | Lys | Asn | Gly | Asn | Glu | Leu | Ser | Asp | Phe | Gln | Thr | Asn | Val |
| | | 185 | | | | | 190 | | | | | 195 | | |
| Asp | Pro | Val | Gly | Glu | Ser | Val | Ser | Tyr | Ser | Ile | His | Ser | Thr | Ala |
| | | | 200 | | | | | 205 | | | | | 210 | |
| Lys | Val | Val | Leu | Thr | Arg | Glu | Asp | Val | His | Ser | Gln | Val | Ile | Cys |
| | 215 | | | | | 220 | | | | | 225 | | | |
| Glu | Val | Ala | His | Val | Thr | Leu | Gln | Gly | Asp | Pro | Leu | Arg | Gly | Thr |
| | | 230 | | | | | 235 | | | | | 240 | | |
| Ala | Asn | Leu | Ser | Glu | Thr | Ile | Arg | Val | Pro | Pro | Thr | Leu | Glu | Val |
| | | 245 | | | | | 250 | | | | | 255 | | |
| Thr | Gln | Gln | Pro | Val | Arg | Ala | Ile | Tyr | Ile | Val | Val | Gly | Val | Val |
| | | 260 | | | | | 265 | | | | | 270 | | |
| Cys | Thr | Leu | Leu | Val | Ala | Leu | Leu | Met | Ala | Ala | Leu | Tyr | Leu | Val |
| | | 275 | | | | | 280 | | | | | 285 | | |
| Arg | Ile | Arg | Gln | Lys | Lys | Ala | Gln | Gly | Ser | Thr | Ser | Ser | Thr | Arg |
| | | 290 | | | | | 295 | | | | | 300 | | |
| Leu | His | Glu | Pro | Glu | Lys | Asn | Ala | Arg | Glu | Ile | Thr | Gln | Asp | Thr |
| | | | | 305 | | | | | 310 | | | | | 315 | |
| Asn | Asp | Ile | Thr | Tyr | Ala | Asp | Leu | Asn | Leu | Pro | Lys | Gly | Lys | Lys |
| | | 320 | | | | | 325 | | | | | 330 | | |
| Pro | Ala | Pro | Gln | Ala | Ala | Glu | Pro | Asn | Asn | His | Thr | Glu | Tyr | Ala |
| | | 335 | | | | | 340 | | | | | 345 | | |
| Ser | Ile | Gln | Thr | Ser | Pro | Gln | Pro | Ala | Ser | Glu | Asp | Thr | Leu | Thr |
| | | 350 | | | | | 355 | | | | | 360 | | |
| Tyr | Ala | Asp | Leu | Asp | Met | | | | | | | | | |
| | | 365 | | | | | | | | | | | | |

```
Val His Leu Asn Arg Thr Pro Lys Gln Pro Ala Pro Lys Pro Glu Pro
        370                 375                 380

Ser Phe Ser Glu Tyr Ala Ser Val Gln Val Pro Arg Lys
385                 390                 395

<210> SEQ ID NO 73
<211> LENGTH: 507
<212> TYPE: PRT
<213> ORGANISM: Artificial
<220> FEATURE:
<223> OTHER INFORMATION: amino acid sequence of mouse SIRPA mutant
      hmSIRPA_delta 0

<400> SEQUENCE: 73

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Thr
            20                  25                  30

Glu Val Lys Val Thr Gln Pro Glu Lys Ser Val Ser Val Ala Ala Gly
        35                  40                  45

Asp Ser Thr Ile Leu Asn Cys Thr Val Thr Ser Leu Leu Pro Val Gly
    50                  55                  60

Pro Ile Arg Trp Tyr Arg Gly Val Gly Gln Ser Arg Leu Leu Ile Tyr
65                  70                  75                  80

Asn Gln Lys Glu Gly His Phe Pro Arg Val Arg Asn Val Ser Asp Thr
                85                  90                  95

Thr Lys Arg Asn Asn Met Asp Phe Ser Ile Arg Ile Ser Asn Val Thr
            100                 105                 110

Pro Glu Asp Ala Gly Thr Tyr Tyr Cys Val Lys Phe Gln Lys Gly Ser
        115                 120                 125

Pro Asp Thr Glu Ile Gln Ser Gly Gly Gly Thr Glu Val Tyr Val Leu
    130                 135                 140

Ala Lys Pro Ser Pro Pro Glu Val Ser Gly Pro Ala Asp Arg Gly Ile
145                 150                 155                 160

Pro Asp Gln Lys Val Asn Phe Thr Cys Lys Ser His Gly Phe Ser Pro
                165                 170                 175

Arg Asn Ile Thr Leu Lys Trp Phe Lys Asp Gly Gln Glu Leu His Pro
            180                 185                 190

Leu Glu Thr Thr Val Asn Pro Ser Gly Lys Asn Val Ser Tyr Asn Ile
        195                 200                 205

Ser Ser Thr Val Arg Val Val Leu Asn Ser Met Asp Val Asn Ser Lys
    210                 215                 220

Val Ile Cys Glu Val Ala His Ile Thr Leu Asp Arg Ser Pro Leu Arg
225                 230                 235                 240

Gly Ile Ala Asn Leu Ser Asn Phe Ile Arg Val Ser Pro Thr Val Lys
                245                 250                 255

Val Thr Gln Gln Ser Pro Thr Ser Met Asn Gln Val Asn Leu Thr Cys
            260                 265                 270

Arg Ala Glu Arg Phe Tyr Pro Glu Asp Leu Gln Leu Ile Trp Leu Glu
        275                 280                 285

Asn Gly Asn Val Ser Arg Asn Asp Thr Pro Lys Asn Leu Thr Lys Asn
    290                 295                 300

Thr Asp Gly Thr Tyr Asn Tyr Thr Ser Leu Phe Leu Val Asn Ser Ser
305                 310                 315                 320

Ala His Arg Glu Asp Val Val Phe Thr Cys Gln Val Lys His Asp Gln
```

```
                    325                 330                 335
Gln Pro Ala Ile Thr Arg Asn His Thr Val Leu Gly Phe Ala His Ser
                340                 345                 350

Ser Asp Gln Gly Ser Met Gln Thr Phe Pro Asp Asn Asn Ala Thr His
            355                 360                 365

Asn Trp Asn Val Phe Ile Gly Val Gly Val Ala Cys Ala Leu Leu Val
        370                 375                 380

Val Leu Leu Met Ala Ala Leu Tyr Leu Leu Arg Ile Lys Gln Lys Lys
385                 390                 395                 400

Ala Lys Gly Ser Thr Ser Ser Thr Arg Leu His Glu Pro Glu Lys Asn
                405                 410                 415

Ala Arg Glu Ile Thr Gln Ile Gln Asp Thr Asn Asp Ile Asn Asp Ile
            420                 425                 430

Thr Tyr Ala Asp Leu Asn Leu Pro Lys Glu Lys Pro Ala Pro Arg
        435                 440                 445

Ala Pro Glu Pro Asn Asn His Thr Glu Tyr Ala Ser Ile Glu Thr Gly
    450                 455                 460

Lys Val Pro Arg Pro Glu Asp Thr Leu Thr Tyr Ala Asp Leu Asp Met
465                 470                 475                 480

Val His Leu Ser Arg Ala Gln Pro Ala Pro Lys Pro Glu Pro Ser Phe
                485                 490                 495

Ser Glu Tyr Ala Ser Val Gln Val Gln Arg Lys
            500                 505
```

<210> SEQ ID NO 74
<211> LENGTH: 509
<212> TYPE: PRT
<213> ORGANISM: Artificial
<220> FEATURE:
<223> OTHER INFORMATION: amino acid sequence of mouse SIRPA mutant
      hmSIRPA_delta 1

<400> SEQUENCE: 74

```
Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Thr
            20                  25                  30

Glu Val Lys Val Thr Gln Pro Glu Lys Ser Val Ser Val Ala Ala Gly
        35                  40                  45

Asp Ser Thr Ile Leu Asn Cys Thr Val Thr Ser Leu Leu Pro Val Gly
    50                  55                  60

Pro Ile Arg Trp Tyr Arg Gly Val Gly Gln Ser Arg Leu Leu Ile Tyr
65                  70                  75                  80

Asn Gln Lys Glu Glu His Phe Pro Arg Val Arg Asn Val Ser Asp Thr
                85                  90                  95

Thr Lys Arg Asn Asn Met Asp Phe Ser Ile Arg Ile Ser Asn Val Thr
            100                 105                 110

Pro Glu Asp Ala Gly Thr Tyr Tyr Cys Val Lys Phe Gln Arg Gly Ser
        115                 120                 125

Ser Glu Pro Asp Thr Glu Ile Gln Ser Gly Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175
```

```
Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
        195                 200                 205

Asn Ile Ser Ser Thr Val Arg Val Val Leu Asn Ser Met Asp Val Asn
    210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
    290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
    370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Ile Gln Asp Thr Asn Asp Ile Asn
            420                 425                 430

Asp Ile Thr Tyr Ala Asp Leu Asn Leu Pro Lys Glu Lys Lys Pro Ala
        435                 440                 445

Pro Arg Ala Pro Glu Pro Asn Asn His Thr Glu Tyr Ala Ser Ile Glu
    450                 455                 460

Thr Gly Lys Val Pro Arg Pro Glu Asp Thr Leu Thr Tyr Ala Asp Leu
465                 470                 475                 480

Asp Met Val His Leu Ser Arg Ala Gln Pro Ala Pro Lys Pro Glu Pro
                485                 490                 495

Ser Phe Ser Glu Tyr Ala Ser Val Gln Val Gln Arg Lys
            500                 505

<210> SEQ ID NO 75
<211> LENGTH: 509
<212> TYPE: PRT
<213> ORGANISM: Artificial
<220> FEATURE:
<223> OTHER INFORMATION: amino acid sequence of mouse SIRPA mutant
      hmSIRPA_delta 2

<400> SEQUENCE: 75

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Thr
            20                  25                  30
```

-continued

```
Glu Val Lys Val Thr Gln Pro Glu Lys Ser Val Ser Val Ala Ala Gly
             35                  40                  45

Asp Ser Thr Ile Leu Asn Cys Thr Val Thr Ser Leu Leu Pro Val Gly
             50                  55                  60

Pro Ile Arg Trp Tyr Arg Gly Val Gly Gln Ser Arg Leu Leu Ile Tyr
 65                  70                  75                  80

Ser Phe Thr Glu Gly His Phe Pro Arg Val Arg Asn Val Ser Asp Thr
                 85                  90                  95

Thr Lys Arg Asn Asn Met Asp Phe Ser Ile Arg Ile Ser Asn Val Thr
            100                 105                 110

Pro Glu Asp Ala Gly Thr Tyr Tyr Cys Val Lys Phe Gln Arg Gly Ser
            115                 120                 125

Ser Glu Pro Asp Thr Glu Ile Gln Ser Gly Gly Thr Glu Val Tyr
            130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
            180                 185                 190

His Pro Leu Glu Thr Thr Val Asn Pro Ser Gly Lys Asn Val Ser Tyr
            195                 200                 205

Asn Ile Ser Ser Thr Val Arg Val Val Leu Asn Ser Met Asp Val Asn
210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
            275                 280                 285

Leu Glu Asn Gly Asn Val Ser Arg Asn Asp Thr Pro Lys Asn Leu Thr
290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
            355                 360                 365

Thr His Asn Trp Asn Val Phe Ile Gly Val Gly Val Ala Cys Ala Leu
370                 375                 380

Leu Val Val Leu Leu Met Ala Ala Leu Tyr Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Ile Gln Asp Thr Asn Asp Ile Asn
            420                 425                 430

Asp Ile Thr Tyr Ala Asp Leu Asn Leu Pro Lys Glu Lys Lys Pro Ala
            435                 440                 445
```

```
Pro Arg Ala Pro Glu Pro Asn Asn His Thr Glu Tyr Ala Ser Ile Glu
    450                 455                 460

Thr Gly Lys Val Pro Arg Pro Glu Asp Thr Leu Thr Tyr Ala Asp Leu
465                 470                 475                 480

Asp Met Val His Leu Ser Arg Ala Gln Pro Ala Pro Lys Glu Pro
                485                 490                 495

Ser Phe Ser Glu Tyr Ala Ser Val Gln Val Gln Arg Lys
            500                 505
```

```
<210> SEQ ID NO 76
<211> LENGTH: 5
<212> TYPE: PRT
<213> ORGANISM: Artificial
<220> FEATURE:
<223> OTHER INFORMATION: amino acid sequence of 81st to 85th amino acids
      in amino acid sequence of mouse SIRPA mutant hmSIRPA_delta 0

<400> SEQUENCE: 76

Asn Gln Lys Glu Gly
1               5

<210> SEQ ID NO 77
<211> LENGTH: 5
<212> TYPE: PRT
<213> ORGANISM: Artificial
<220> FEATURE:
<223> OTHER INFORMATION: amino acid sequence of 81st to 85th amino acids
      in amino acid sequence of mouse SIRPA mutant hmSIRPA_delta 1

<400> SEQUENCE: 77

Asn Gln Lys Glu Glu
1               5

<210> SEQ ID NO 78
<211> LENGTH: 5
<212> TYPE: PRT
<213> ORGANISM: Artificial
<220> FEATURE:
<223> OTHER INFORMATION: amino acid sequence of 81st to 85th amino acids
      in amino acid sequence of BALB/C mouse SIRPA

<400> SEQUENCE: 78

Ser Phe Thr Gly Glu
1               5

<210> SEQ ID NO 79
<211> LENGTH: 5
<212> TYPE: PRT
<213> ORGANISM: Artificial
<220> FEATURE:
<223> OTHER INFORMATION: amino acid sequence of 126th to 130th amino
      acids in amino acid sequence of BALB/C mouse SIRPA

<400> SEQUENCE: 79

Arg Gly Ser Ser Glu
1               5

<210> SEQ ID NO 80
<211> LENGTH: 5
<212> TYPE: PRT
<213> ORGANISM: Artificial
<220> FEATURE:
<223> OTHER INFORMATION: amino acid sequence of 81st to 85th amino acids
      in amino acid sequence of mouse SIRPA mutant hmSIRPA_delta 2

<400> SEQUENCE: 80
```

Ser Phe Thr Glu Gly
1               5

<210> SEQ ID NO 81
<211> LENGTH: 466
<212> TYPE: PRT
<213> ORGANISM: Artificial
<220> FEATURE:
<223> OTHER INFORMATION: amino acid sequence of OSE-172 antibody heavy
      chain (OSE-172_hG4Pro)

<400> SEQUENCE: 81

Met Lys His Leu Trp Phe Phe Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Glu Ser Leu Arg Ile Ser Cys Lys Ala Ser Gly Tyr Ser Phe
        35                  40                  45

Thr Ser Tyr Trp Val His Trp Val Arg Gln Met Pro Gly Lys Gly Leu
    50                  55                  60

Glu Trp Met Gly Asn Ile Asp Pro Ser Asp Ser Asp Thr His Tyr Ser
65              70                  75                  80

Pro Ser Phe Gln Gly His Val Thr Leu Ser Val Asp Lys Ser Ile Ser
                85                  90                  95

Thr Ala Tyr Leu Gln Leu Ser Ser Leu Lys Ala Ser Asp Thr Ala Met
            100                 105                 110

Tyr Tyr Cys Val Arg Gly Gly Thr Gly Thr Leu Ala Tyr Phe Ala Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

```
Lys Thr Ile Ser Lys Ala Lys Gly Gln Pro Arg Glu Pro Gln Val Tyr
            355                 360                 365

Thr Leu Pro Pro Ser Gln Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
                420                 425                 430

Lys Ser Arg Trp Gln Glu Gly Asn Val Phe Ser Cys Ser Val Met His
                435                 440                 445

Glu Ala Leu His Asn His Tyr Thr Gln Lys Ser Leu Ser Leu Ser Pro
450                 455                 460

Gly Lys
465
```

<210> SEQ ID NO 82
<211> LENGTH: 239
<212> TYPE: PRT
<213> ORGANISM: Artificial
<220> FEATURE:
<223> OTHER INFORMATION: amino acid sequence of OSE-172 antibody light
      chain (OSE-172_hK)

<400> SEQUENCE: 82

```
Met Val Leu Gln Thr Gln Val Phe Ile Ser Leu Leu Leu Trp Ile Ser
1               5                   10                  15

Gly Ala Tyr Gly Asp Val Val Met Thr Gln Ser Pro Leu Ser Leu Pro
                20                  25                  30

Val Thr Leu Gly Gln Pro Ala Ser Ile Ser Cys Arg Ser Ser Gln Ser
            35                  40                  45

Leu Val His Ser Tyr Gly Asn Thr Tyr Leu Tyr Trp Phe Gln Gln Arg
        50                  55                  60

Pro Gly Gln Ser Pro Arg Leu Leu Ile Tyr Arg Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Gly Thr His Val Pro Tyr Thr Phe Gly Gly Gly Thr Lys
        115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
                180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
```

<210> SEQ ID NO 83
<211> LENGTH: 459
<212> TYPE: PRT
<213> ORGANISM: Artificial
<220> FEATURE:
<223> OTHER INFORMATION: amino acid sequence of KWAR23 antibody heavy
      chain (KWAR23_hG4Pro)

<400> SEQUENCE: 83

Met Lys His Leu Trp Phe Phe Leu Leu Leu Val Ala Ala Pro Arg Trp
1               5                   10                  15

Val Leu Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Tyr Tyr Ile His Trp Val Gln Gln Arg Thr Glu Gln Gly Leu
    50                  55                  60

Glu Trp Ile Gly Arg Ile Asp Pro Glu Asp Gly Glu Thr Lys Tyr Ala
65                  70                  75                  80

Pro Lys Phe Gln Asp Lys Ala Thr Ile Thr Ala Asp Thr Ser Ser Asn
                85                  90                  95

Thr Ala Tyr Leu His Leu Ser Ser Leu Thr Ser Glu Asp Thr Ala Val
            100                 105                 110

Tyr Tyr Cys Ala Arg Trp Gly Ala Tyr Trp Gly Gln Gly Thr Leu Val
        115                 120                 125

Thr Val Ser Ala Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

```
Gly Gln Pro Arg Glu Pro Gln Val Tyr Thr Leu Pro Pro Ser Gln Glu
            355                 360                 365

Glu Met Thr Lys Asn Gln Val Ser Leu Thr Cys Leu Val Lys Gly Phe
        370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
            435                 440                 445

Thr Gln Lys Ser Leu Ser Leu Ser Leu Gly Lys
    450                 455

<210> SEQ ID NO 84
<211> LENGTH: 235
<212> TYPE: PRT
<213> ORGANISM: Artificial
<220> FEATURE:
<223> OTHER INFORMATION: amino acid sequence of KWAR23 antibody light
      chain (KWAR23_hK)

<400> SEQUENCE: 84

Met Val Leu Gln Thr Gln Val Phe Ile Ser Leu Leu Leu Trp Ile Ser
1               5                   10                  15

Gly Ala Tyr Gly Gln Ile Val Leu Thr Gln Ser Pro Ala Ile Met Ser
            20                  25                  30

Ala Ser Pro Gly Glu Lys Val Thr Leu Thr Cys Ser Ala Ser Ser Ser
        35                  40                  45

Val Ser Ser Ser Tyr Leu Tyr Trp Tyr Gln Gln Lys Pro Gly Ser Ser
    50                  55                  60

Pro Lys Leu Trp Ile Tyr Ser Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Ser Tyr Phe Cys His Gln Trp
            100                 105                 110

Ser Ser Tyr Pro Arg Thr Phe Gly Ala Gly Thr Lys Leu Glu Leu Lys
            115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 85
```

<211> LENGTH: 467
<212> TYPE: PRT
<213> ORGANISM: Artificial
<220> FEATURE:
<223> OTHER INFORMATION: amino acid sequence of ADU-1805 antibody heavy
      chain (ADU-1805_hG2)

<400> SEQUENCE: 85

Met Lys His Leu Trp Phe Phe Leu Leu Val Ala Ala Pro Arg Trp
1               5                   10                  15

Val Leu Ser Glu Val Gln Leu Val Gln Ser Gly Ala Glu Val Lys
                20                  25                  30

Pro Gly Ala Ser Val Lys Leu Ser Cys Lys Ala Ser Gly Ser Thr Phe
            35                  40                  45

Thr Ser Tyr Trp Met His Trp Val Lys Gln Ala Pro Gly Gln Gly Leu
        50                  55                  60

Glu Trp Ile Gly Ala Ile Tyr Pro Val Asn Ser Asp Thr Thr Tyr Asn
65                  70                  75                  80

Gln Lys Phe Lys Gly Lys Ala Thr Leu Thr Val Asp Lys Ser Ala Ser
                85                  90                  95

Thr Ala Tyr Met Glu Leu Ser Ser Leu Arg Ser Glu Asp Thr Ala Val
                100                 105                 110

Tyr Tyr Cys Thr Arg Ser Phe Tyr Tyr Ser Leu Asp Ala Ala Trp Phe
            115                 120                 125

Val Tyr Trp Gly Gln Gly Thr Leu Val Thr Val Ser Ser Ala Ser Thr
        130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
        210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
        290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
                340                 345                 350

Glu Lys Thr Ile Ser Lys Thr Lys Gly Gln Pro Arg Glu Pro Gln Val
                355                 360                 365

Tyr Thr Leu Pro Pro Ser Arg Glu Glu Met Thr Lys Asn Gln Val Ser

```
                   370                 375                 380
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
450                 455                 460

Pro Gly Lys
465

<210> SEQ ID NO 86
<211> LENGTH: 234
<212> TYPE: PRT
<213> ORGANISM: Artificial
<220> FEATURE:
<223> OTHER INFORMATION: amino acid sequence of ADU-1805 antibody light
      chain (ADU-1805_hK)

<400> SEQUENCE: 86

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Ile Gly Ser Arg Leu Asn Trp Leu Gln Gln Lys Pro Gly Lys Ala Pro
        50                  55                  60

Lys Arg Leu Ile Tyr Ala Thr Ser Ser Leu Asp Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Tyr Cys Leu Gln Tyr Ala
                100                 105                 110

Ser Ser Pro Phe Thr Phe Gly Gly Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 87
<211> LENGTH: 68
```

```
<212> TYPE: PRT
<213> ORGANISM: Artificial
<220> FEATURE:
<223> OTHER INFORMATION: Partial amino acid sequence of mouse SIRPA
      mutant hmSIRPA_delta 0

<400> SEQUENCE: 87

Gly Val Gly Gln Ser Arg Leu Leu Ile Tyr Asn Gln Lys Glu Gly His
1               5                   10                  15

Phe Pro Arg Val Arg Asn Val Ser Asp Thr Thr Lys Arg Asn Asn Met
            20                  25                  30

Asp Phe Ser Ile Arg Ile Ser Asn Val Thr Pro Glu Asp Ala Gly Thr
        35                  40                  45

Tyr Tyr Cys Val Lys Phe Gln Lys Gly Ser Pro Asp Thr Glu Ile Gln
    50                  55                  60

Ser Gly Gly Gly
65

<210> SEQ ID NO 88
<211> LENGTH: 70
<212> TYPE: PRT
<213> ORGANISM: Artificial
<220> FEATURE:
<223> OTHER INFORMATION: Partial amino acid sequence of mouse SIRPA
      mutant hmSIRPA_delta 1

<400> SEQUENCE: 88

Gly Val Gly Gln Ser Arg Leu Leu Ile Tyr Asn Gln Lys Glu Gly His
1               5                   10                  15

Phe Pro Arg Val Arg Asn Val Ser Asp Thr Thr Lys Arg Asn Asn Met
            20                  25                  30

Asp Phe Ser Ile Arg Ile Ser Asn Val Thr Pro Glu Asp Ala Gly Thr
        35                  40                  45

Tyr Tyr Cys Val Lys Phe Gln Arg Gly Ser Ser Glu Pro Asp Thr Glu
    50                  55                  60

Ile Gln Ser Gly Gly Gly
65                  70

<210> SEQ ID NO 89
<211> LENGTH: 70
<212> TYPE: PRT
<213> ORGANISM: Artificial
<220> FEATURE:
<223> OTHER INFORMATION: Partial amino acid sequence of mouse SIRPA
      mutant hmSIRPA_delta 2

<400> SEQUENCE: 89

Gly Val Gly Gln Ser Arg Leu Leu Ile Tyr Ser Phe Thr Glu Gly His
1               5                   10                  15

Phe Pro Arg Val Arg Asn Val Ser Asp Thr Thr Lys Arg Asn Asn Met
            20                  25                  30

Asp Phe Ser Ile Arg Ile Ser Asn Val Thr Pro Glu Asp Ala Gly Thr
        35                  40                  45

Tyr Tyr Cys Val Lys Phe Gln Arg Gly Ser Ser Glu Pro Asp Thr Glu
    50                  55                  60

Ile Gln Ser Gly Gly Gly
65                  70
```